United States Patent
Posner et al.

(10) Patent No.: US 7,417,156 B2
(45) Date of Patent: Aug. 26, 2008

(54) ORALLY ACTIVE, ANTIMALARIAL, ANTICANCER, ARTEMISININ-DERIVED TRIOXANE DIMERS

(75) Inventors: Gary H. Posner, Baltimore, MD (US); Theresa A. Shapiro, Towson, MD (US); Surojit Sur, Baltimore, MD (US); Tanzina Labonte, Baltimore, MD (US); Kristina Borstnik, State College, PA (US); Ik-Hyeon Paik, Baltimore, MD (US); Andrew J. McRiner, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/529,513

(22) PCT Filed: Sep. 26, 2003

(86) PCT No.: PCT/US03/30612

§ 371 (c)(1),
(2), (4) Date: Mar. 3, 2006

(87) PCT Pub. No.: WO2004/028476

PCT Pub. Date: Apr. 8, 2004

(65) Prior Publication Data

US 2006/0142377 A1 Jun. 29, 2006

Related U.S. Application Data

(60) Provisional application No. 60/414,786, filed on Sep. 27, 2002, provisional application No. 60/445,526, filed on Feb. 6, 2003.

(51) Int. Cl.
*A61K 31/357* (2006.01)
*C07D 321/10* (2006.01)

(52) U.S. Cl. .......... 549/348; 549/34; 549/220; 548/232; 514/100; 514/376; 514/439; 514/462; 514/463

(58) Field of Classification Search .......... 549/348, 549/34, 220; 548/232; 514/100, 376, 439, 514/462, 463
See application file for complete search history.

(56) References Cited

U.S. PATENT DOCUMENTS 5,726,203 A 3/1998 Li et al.

FOREIGN PATENT DOCUMENTS

EP 0 974 594 A1 1/2000

OTHER PUBLICATIONS

International Search Report PCT/US03/30612; May 11, 2004; Johns Hopkins University.

*Primary Examiner*—Bernard Dentz
(74) *Attorney, Agent, or Firm*—Townsend and Townsend and Crew LLP

(57) ABSTRACT

In only two steps and in 65% overall yield, natural trioxane artemisinin (I) was converted on gram scale into C-10-carba trioxane dimer (3). This new, very stable dimer was then transformed easily in one additional step into four different dimers (4-7). Alcohol and diol dimers (4 and 5) and ketone dimer (7) are 10 times more antimalarially potent in vitro than artemisinin (I), and alcohol and diol dimers (4 and 5) are strongly inhibitory but not cytotoxic toward several human cancer cell lines. Water-soluble carboxylic acid derivatives (8a-10c and 12) were easily prepared from dimers (4-6); they are thermally stable even at 60° C. for 24 hours, are more orally efficacious as antimalarials than either artelinic acid or sodium artesunate, and have potent and selective anticancer activities. Further derivitization of the alcohol dimers (4 and 17), diol dimer (5) and ketone (7) has produced a number of analogs also antimalarially active in vitro at sub-nanomolar concentrations (most notably: pyridine N-oxides (13, 15, 18, 23, 24 and 25), phosphoric acid triesters (26 and 27), sulfonamide (40) and cyclic carbonate (41)). In addition, dimers (13 and 19) are more efficacious (when administered both orally and i.v.) and less toxic (when administered intraperitoneally to mice as a single dose) than clinically-used sodium artesunate, thereby giving them a better antimalarial therapeutic index than sodium artesunate.

85 Claims, 85 Drawing Sheets

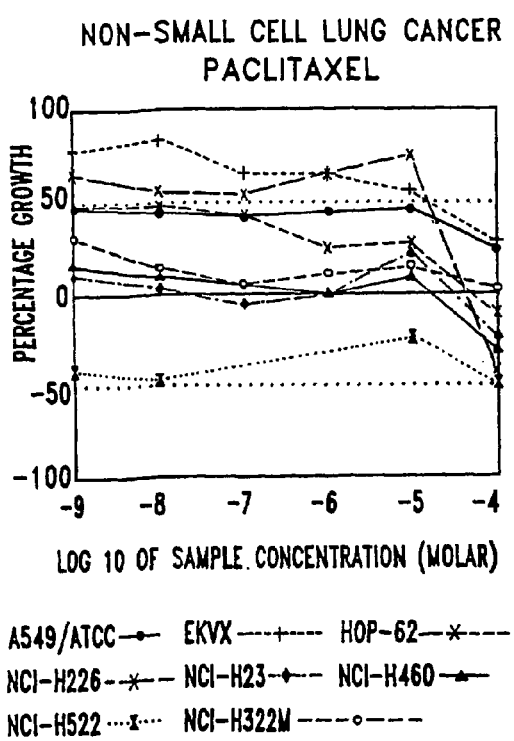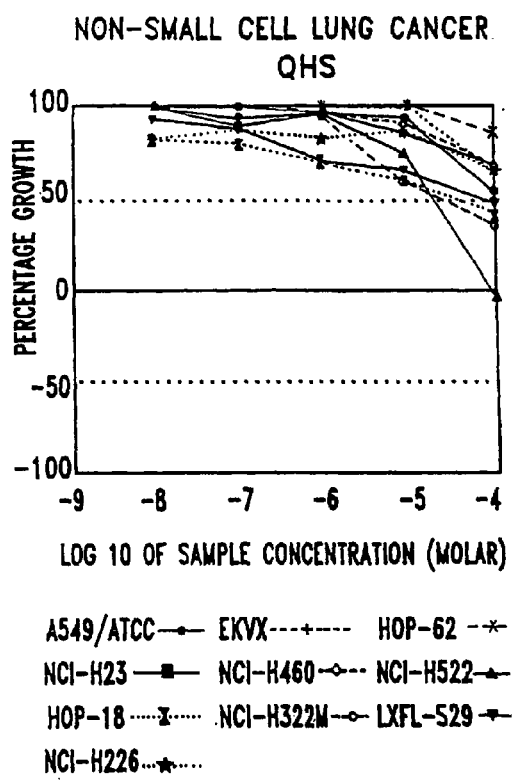
Fig 8a
Fig. 8b

Fib. 9c

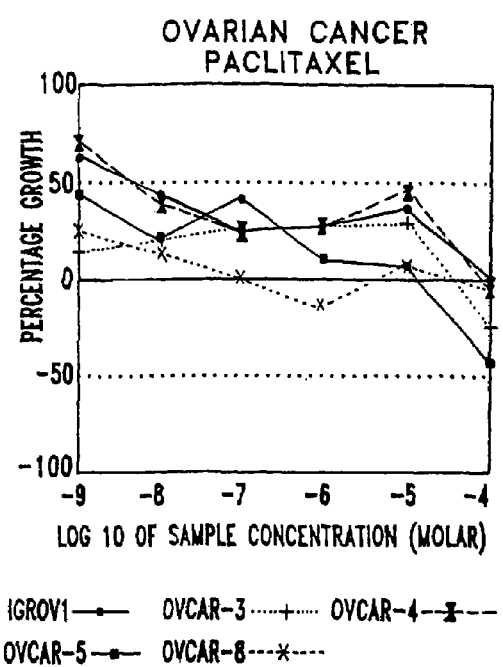
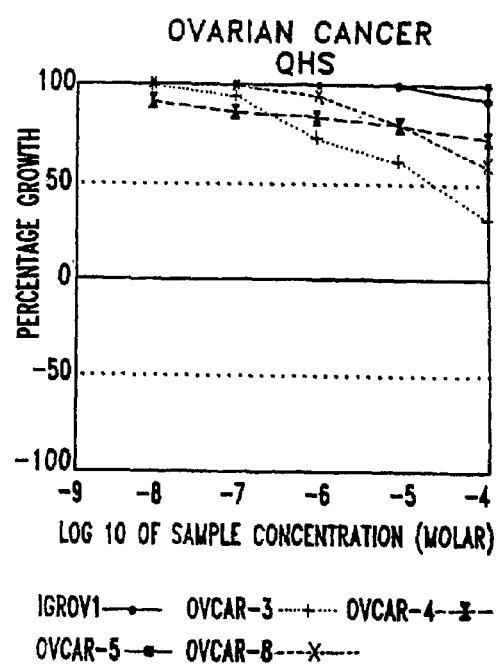
Fig. 12a
Fig. 12b

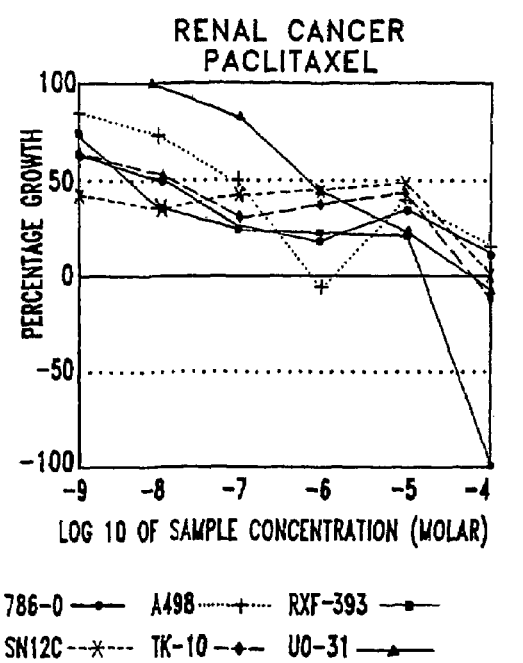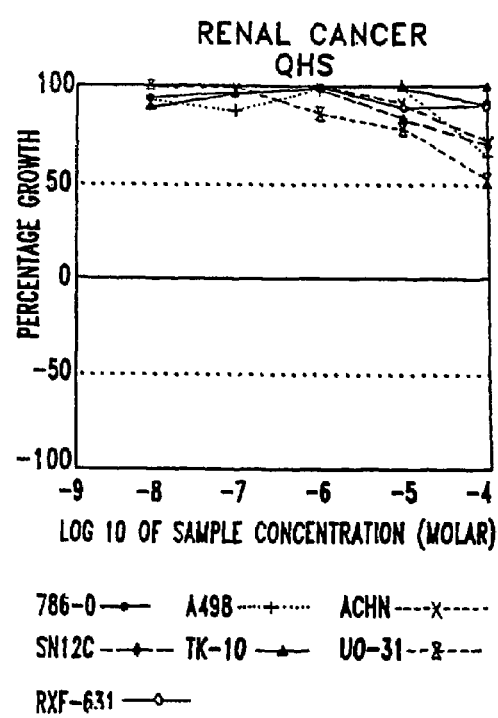
Fig. 13a
Fig. 13b

R = H, alkyl, aryl, etc.
R' = H, alkyl, aryl, etc.

ORALLY ACTIVE, ANTIMALARIAL, ANTICANCER, ARTEMISININ-DERIVED TRIOXANE DIMERS

CROSS REFERENCE TO OTHER APPLICATIONS

This application in a U.S. national filing under 35 U.S.C. § 371 of PCT/2003/030612 and claims the benefit of U.S. provisional application Nos. 60/414,786 filed Sep. 27, 2002 and 60/445,526 filed Feb. 6, 2003 all of which are incorporated herein by this reference.

CONTRACTUAL ORIGIN OF THE INVENTION

This study was supported in-part by National Institutes of Health grant AI 34885 (to G.H.P.) and grant RR-00052 and joint inventors G. H. P., I. P., A. J. M., S. S., K. B., T. L. and T. A. S., have assigned their rights to the Johns Hopkins University.

BACKGROUND OF THE INVENTION

1. Field of the Invention

The present invention relates to the formation of a novel, stable C-10 carba trioxane dimer that may easily be transformed into different trioxane dimers. Some of these dimers are 10 times more antimalarially potent in vitro than artemisinin. These anticancer dimers selectively inhibit growth in vitro of several human cancer cell lines without being cytotoxic. The present invention relates also to water-soluble carboxylic acid derivatives that are thermally stable, that are more orally efficacious antimalarials than either artelinic acid or clinically used sodium artesunate, and that have potent and selective anticancer activities. The present invention further relates to antimalarial trioxane dimers that are safer and more efficacious than sodium artesunate.

2. Description of the State of Art

Each year approximately 200-300 million people experience a malarial illness and over 1 million individuals die. In patients with severe and complicated disease, the mortality rate is between 20 and 50%.

*Plasmodium* is the genus of protozoan parasites which is responsible for all cases of human malaria and *Plasmodium falciparum* is the species of parasite that is responsible for the vast majority of fatal malaria infections. Malaria has traditionally been treated with quinolines such as chloroquine, quinine, mefloquine, and primaquine and with antifolates such as sulfadoxine-pyrimethamine. Unfortunately, most *P. falciparum* strains have now become resistant to chloroquine, and some, such as those in Southeast Asia, have also developed resistance to mefloquine and halofantrine; multidrug resistance is developing in Africa also.

The endoperoxides are a promising class of antimalarial drugs which may meet the dual challenges posed by drug-resistant parasites and the rapid progression of malarial illness. The first generation endoperoxides include natural artemisinin and several synthetic derivatives, discussed in further detail below.

*Artemisia annua L.*, also known as qinghao or sweet wormwood, is a pervasive weed that has been used for many centuries in Chinese traditional medicine as a treatment for fever and malaria. Its earliest mention, for use in hemorrhoids, occurs in the *Recipes for 52 Kinds of Diseases* found in the Mawangdui Han dynasty tomb dating from 168 B.C. Nearly five hundred years later Ge Hong wrote the *Zhou Hou Bei Ji Fang* (Handbook of Prescriptions for Emergency Treatments) in which he advised that a water extract of qinghao was effective at reducing fevers. In 1596, Li Shizhen, the famous herbalist, wrote that chills and fever of malaria can be combated by qinghao preparations. Finally, in 1972, Chinese chemists isolated from the leafy portions of the plant the substance responsible for its reputed medicinal action. This crystalline compound, called qinghaosu, also referred to as QHS or artemisinin, is a sesquiterpene lactone with an internal peroxide linkage.

Artemisinin is a member of the amorphane subgroup of cadinenes and has the following structure (I); "Art" will be used for shorthand in many of the figures.

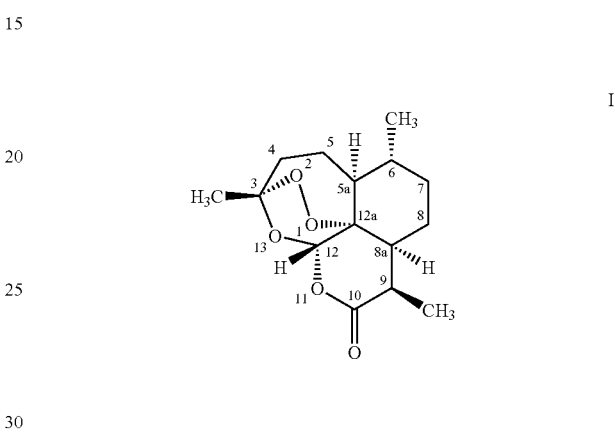

Artemisinin or QHS was the subject of a 1979 study conducted by the Qinghaosu Antimalarial Coordinating Research Group involving the treatment of 2099 cases of malaria (*P. vivax* and *P. falciparum* in a ratio of about 3:1 ) with different dosage forms of QHS, leading to the clinical cure of all patients. See, Qinghaosu Antimalarial Coordinating Research Group, *Chin. Med. J.*, 92:811 (1979). Since that time artemisinin has been used successfully in many thousand malaria patients throughout the world including those infected with both chloroquine-sensitive and chloroquine-resistant strains of *P. falciparum*. Assay of artemisinin against *P. falciparum* in vitro revealed that its potency is comparable to that of chloroquine in two Hanian strains (Z. Ye, et al., *J. Trad. Chin. Med.*, 3:95 (1983)) and of mefloquine in the Camp (chloroquine-susceptible) and Smith (chloroquine-resistant) strains, D. L. Klayman, et al., *J. Nat. Prod.*, 47:715 (1984).

Although artemisinin is effective at suppressing the parasitemias of *P. vivax* and *P. falciparum*, the problems encountered with recrudescence, and the compound's insolubility in water, led scientists to modify artemisinin chemically, a difficult task because of the chemical reactivity of the peroxide linkage which is believed to be an essential moiety for antimalarial activity.

Reduction of artemisinin in the presence of sodium borohydride results in the production of dihydroartemisinin (II-1) or DHQHS, (illustrated in structure II below), in which the lactone group is converted to a lactol (hemiacetal) function, with properties similar to artemisinin. Artemisinin in methanol is reduced with sodium borohydride to an equilibrium mixture of α- and β-isomers of dihydroartemisinin. Using dihydroartemisinin as a starting compound a large number of other derivatives, such as,

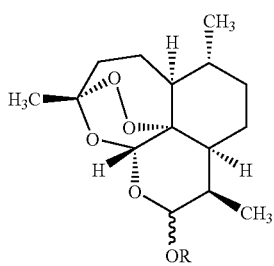

II

1 R = H
2 R = CH$_3$
3 R = CH$_2$CH$_3$
4 R = COCH$_2$CH$_2$COONa
5 R = CH$_2$C$_6$H$_4$COOH
6 R = CH$_2$C$_6$H$_4$COONa
7 R =

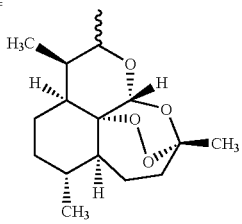

artemether (compound II-2), arteether (II-3), sodium artesunate (II-4), artelinic acid (II-5), sodium artelinate (II-6), dihydroartemisinin condensation by-product (II-7) and the olefinic compound, structure III,

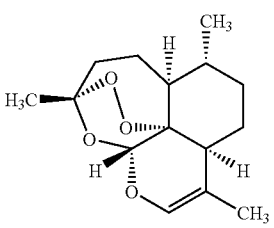

III have been produced.

Artemether (II-2) is produced by reacting β-dihydroartemisinin with boron trifluoride (BF$_3$) etherate or HCl in methanol:benzene (1:2) at room temperature. A mixture of β- and α-artemether (70:30) is obtained, from which the former is isolated by column chromatography and recrystallized from hexane or methanol, R. Haynes, *Transactions of the Royal Society of Tropical Medicine and Hygiene*, 88(1): S1/23-S1/26 (1994). For arteether (II-3), (Brossi, et al., 1988), the α-isomer is equilibrated (epimerized) to the β-isomer in ethanol:benzene mixture containing BF$_3$ etherate. Treatment of dihydroartemisinin with an unspecified dehydrating agent yields both the olefinic compound, (III), and the dihydroartemisinin condensation by-product (II-7), formed on addition of dihydroartemisinin to (III), M. Cao, et al., *Chem. Abstr.*, 100:34720k (1984). Until recently, the secondary hydroxy group in dihydroartemisinin (II-1) provided the only site in an active artemisinin-related compound that had been used for derivatization. See B. Venugopalan, "Synthesis of a Novel Ring Contracted Artemisinin Derivative," *Bioorganic & Medicinal Chemistry Letters*, 4(5):751-752 (1994).

The potency of various artemisinin-derivatives in comparison to artemisinin as a function of the concentration at which the parasitemia is 90 percent suppressed (SD$_{90}$) was reported by D. L. Klayman, "Qinghaosu (Artemisinin): An Antimalarial Drug from China," *Science* 228:1049-1055 (1985). Dr. Klayman reported that the olefinic compound III is inactive against *P. berghei*-infected mice, whereas the dihydroartemisinin condensation by-product (II-7) has an SD$_{90}$ of 10 mg/Kg in *P. berghei*-infected mice. Thus, the dihydroartemisinin ether dimer proved to be less potent than artemisinin, which has an SD$_{90}$ of 6.20 mg/Kg. Following, in order of their overall antimalarial efficacy, are the three types of derivatives of dihydroartemisinin (II-1) that have been produced: (artemisinin)<ethers (II, R=alkyl)<esters [II, R=C(=O)-alkyl or -aryl]<carbonates [II, R=C (=O)O-alkyl or -aryl].

Other rational design of structurally simpler analogs of artemisinin has led to the synthesis of various trioxanes, some of which possess excellent antimalarial activity. Posner, G. H., et al., reported the chemistry and biology of a series of new structurally simple, easily prepared, racemic 1,2,4-trioxanes (disclosed in U.S. Pat. No. 5,225,437 and incorporated herein by reference) that are tricyclic (lacking the lactone ring present in tetracyclic artemisinin I) and that are derivatives of trioxane alcohol IV

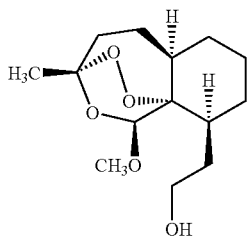

IV having the relative stereochemistry shown above. Especially attractive features of trioxane alcohol IV are the following: (1) its straightforward and easy preparation from cheap and readily available starting materials, (2) its availability on gram scale, and (3) its easy one-step conversion, using standard chemical transformations, into alcohol derivatives such as esters and ethers, without destruction of the crucial trioxane framework. See, Posner, G. H., et al., *J Med. Chem.*, 35:2459-2467 (1992), incorporated herein by reference. The complete chemical synthesis of artemisinin and a variety of other derivatives is reviewed by Sharma, R. P., et al., *Heterocycles*, 32(8):1593-1638 (1991), and is incorporated herein by reference.

Metabolic studies by Baker, et al., demonstrated that β-arteether (II-3), one of the antimalarial derivatives discussed previously, was rapidly converted by rat liver microsomes into dihydroartemisinin (II-1). See Baker, J. K., et al., *Biol. Mass. Spect.*, 20:609-628 (1991). This finding and the fact that the most effective artemisinin derivatives against malaria have been ethers or esters of (II-1) suggest that they were prodrugs for (II-1). The controlled slow formation of (II-1), however, is not desirable in view of its short half-life in plasma (less than two hours) and relatively high toxicity.

Unfortunately C-10 acetal derivatives are often unstable (i.e. easily hydrolyzed) in water. Therefore making hydrolytically stable C-10 non-acetal carba-derivatives has become a high priority internationally.

Over the past thirty years only a few drugs isolated from higher plants have yielded clinical agents, the outstanding examples being vinblastine and vincristine from the Madagascan periwinkle, *Catharanthus roseus*, etoposide, the semi-synthetic lignan, from Mayapple *Podophyllum peltatum* and the diterpenoid taxol, commonly referred to as paclitaxel, from the Pacific yew, *Taxus brevifolia*. Of these agents, paclitaxel is the most exciting, recently receiving approval by the Food and Drug Administration for the treatment of refractory ovarian cancer. Since the isolation of artemisinin, there has been a concerted effort by investigators to study other therapeutic applications of artemisinin and its derivatives.

National Institutes of Health reported that artemisinin is inactive against P388 leukemia. See NCI Report on NSC 369397 (tested on 25 Oct. 1983). Later anticancer studies that have been conducted on cell line panels consisting of 60 lines organized into nine, disease-related subpanels including leukemia, non-small-cell lung cancer, colon, CNS, melanoma, ovarian, renal, prostate and breast cancers, further confirm that artemisinin displays very little anticancer activity. A series of artemisinin-related endoperoxides were tested for cytotoxicity to Ehrlich ascites tumor (EAT) cells using the microculture tetrazolum (MTT) assay, H. J. Woerdenbag, et al., "Cytotoxicity of Artemisinin-Related Endoperoxides to Ehrlich Ascites Tumor Cells," *Journal of Natural Products*, 56(6):849-856 (1993). The MTT assay, used to test the artemisinin-related endoperoxides for cytotoxicity, is based on the metabolic reduction of soluble tetrazolium salts into insoluble colored formazan products by mitochondrial dehydrogenase activity of the tumor cells. As parameters for cytotoxicity, the $IC_{50}$ and $IC_{80}$ values, the drug concentrations causing respectively 50% and 80% growth inhibition of the tumor cells, were used. Artemisinin (I) had an $IC_{50}$ value of 29.8 µM. Derivatives of dihydroartemisinin (II-1) being developed as antimalarial drugs (artemether (II-2), arteether (III-3), sodium artesunate (II-4), artelinic acid (II-5) and sodium artelinate (II-6)), exhibited a somewhat more potent cytotoxicity. Their $IC_{50}$ values ranged from 12.2 µM to 19.9 µM. The dihydroartemisinin condensation by-product dimer (II-7), disclosed previously by M. Cao, et a., 1984, was the most potent cytotoxic agent, its $IC_{50}$ being 1.4 µM. At this drug concentration the condensation by-product (II-7) is approximately twenty-two times more cytotoxic than artemisinin and sixty times more cytotoxic than dihydroartemisinin (II-1), the parent compound.

While artemisinin and its related derivatives (II 1-6) discussed above demonstrated zero to slight antiproliferative and antitumor activity, it has been discovered that a class of artemisinin dimer compounds exhibits antiproliferative and antitumor activities that are, in vitro, equivalent to or greater than known antiproliferative and antitumor agents. See, U.S. Pat. No. 5,677,468 incorporated herein by reference. Unfortunately, while the in vitro results of these artemisinin compounds are encouraging these compounds do not appear to have significant antitumor activity on the treatment of tumor cells in mice.

There is still a need, therefore, to develop methods for the formation of hydrolytically stable C-10 non-acetal carba-derivatives and structural analogs thereof having antimalarial, and antiproliferative and antitumor activities that are equivalent to or greater than those of known antimalarial, and antiproliferative and antitumor agents, respectively.

SUMMARY OF THE INVENTION

Accordingly, this invention provides a class of artemisinin related dimers which demonstrate antimalarial and antitumor activities.

More specifically, this invention provides a class of trioxane dimers which demonstrate antimalarial and antitumor activities and that are considerably more stable toward hydrolysis than artemether and related C-10 ethers and esters.

This invention further provides artemisinin dimers to be used clinically as chemotherapeutic antimalarial and anticancer drugs.

This invention further provides artemisinin C-10-acetal derivatives for comparisson to the corresponding dimers, and to be used clinically as chemotherapeutic antimalarial drugs.

This invention further provides a C-10-carba trioxane dimer that is easily transformed in one additional step into different dimers.

This invention further provides water-soluble carboxylic acid dimers that are thermally stable, that are more orally efficacious antimalarials than either artelinic acid or clinically used sodium artesunate, and that have potent and selective anticancer activities.

Additional objects, advantages and novel features of this invention shall be set forth in part in the description and examples that follow, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

BRIEF DESCRIPTION OF THE DRAWINGS

The accompanying drawings, which are incorporated in and form a part of the specification, illustrate the preferred embodiments of the present invention, and together with the description serve to explain the principles of the invention.

In the drawings, FIGS. 7-15, the horizontal axis depicts various dilutions of the test compound, ranging from $10^{-4}$ to $10^{-9}$ molar, that were exposed to the specified cancer cell lines. The vertical axis (percentage growth) depicts the growth of the specified cancer cell line when exposed to a specific concentration of the tested compound as compared to the growth of the same cancer cell line not exposed to any compound.

In the Drawings:

Figure 1:
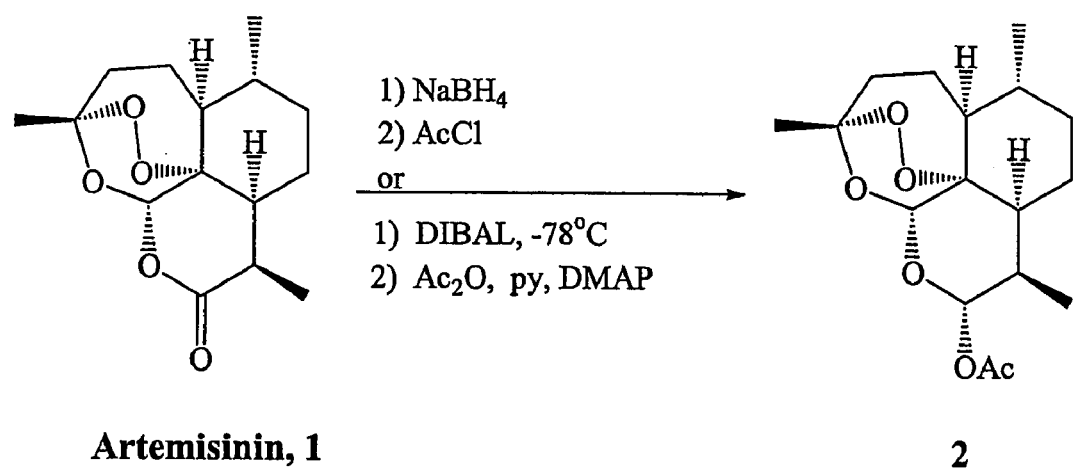

FIG. 1 schematically depicts the method of converting artemisinin I into C-10 acetate 2 of the present invention.

Figure 2:
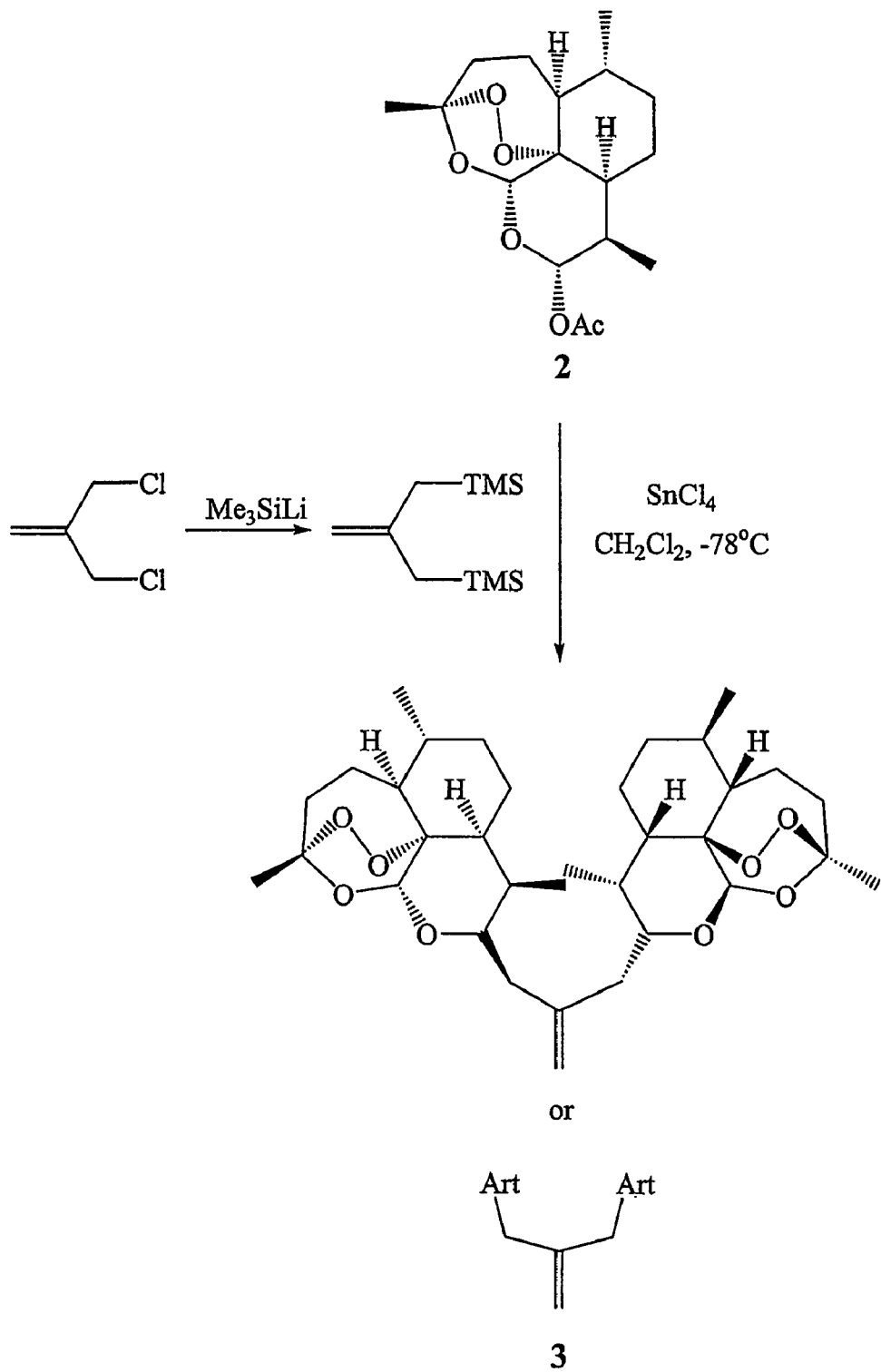

FIG. 2 schematically depicts the method of converting C-10 acetate 2 into C-10 non-acetal trioxane dimer 3 of the present invention.

Figure 3:
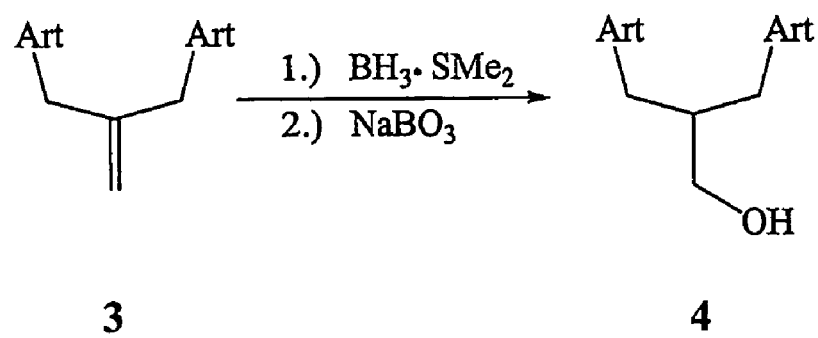

FIG. 3 schematically depicts the method of converting C-10 non-acetal trioxane dimer 3 of the present invention into bis-trioxane primary alcohol 4 of the present invention.

Figure 4:
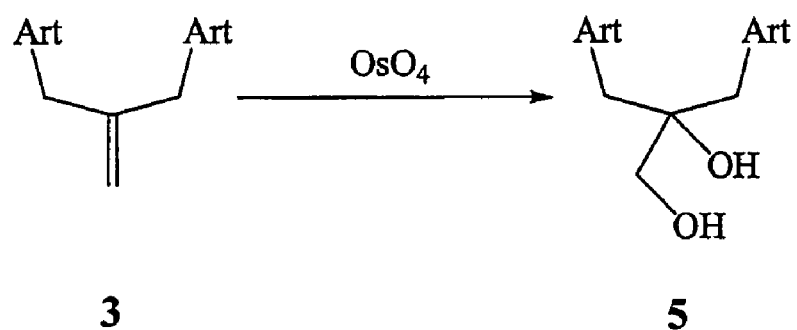

FIG. 4 schematically depicts the method of converting C-10 non-acetal trioxane dimer 3 of the present invention into bis-trioxane vicinal diol 5 of the present invention.

Figure 5:
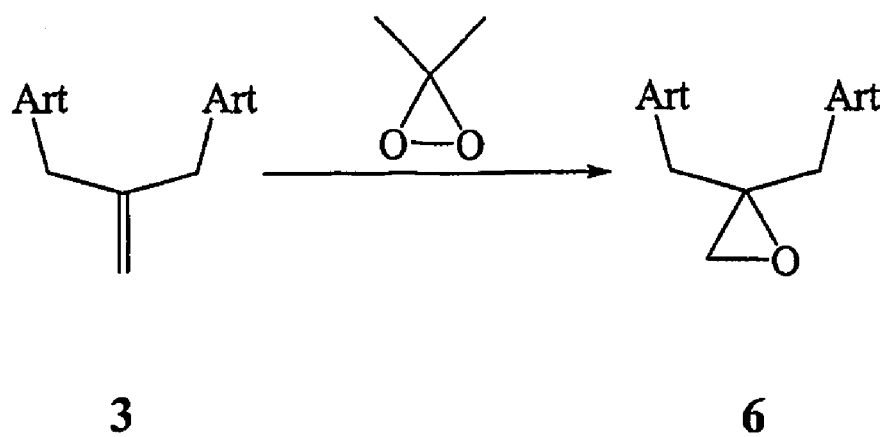

FIG. 5 schematically depicts the method of converting C-10 non-acetal trioxane dimer 3 of the present invention into bis-trioxane epoxide 6 of the present invention.

Figure 6:
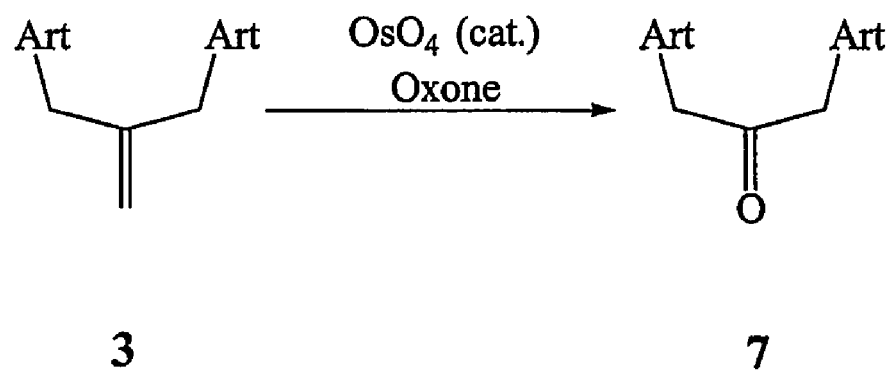

FIG. 6 schematically depicts the method of converting C-10 non-acetal trioxane dimer 3 of the present invention into bis-trioxane ketone 7 of the present invention.

Figure 7A:
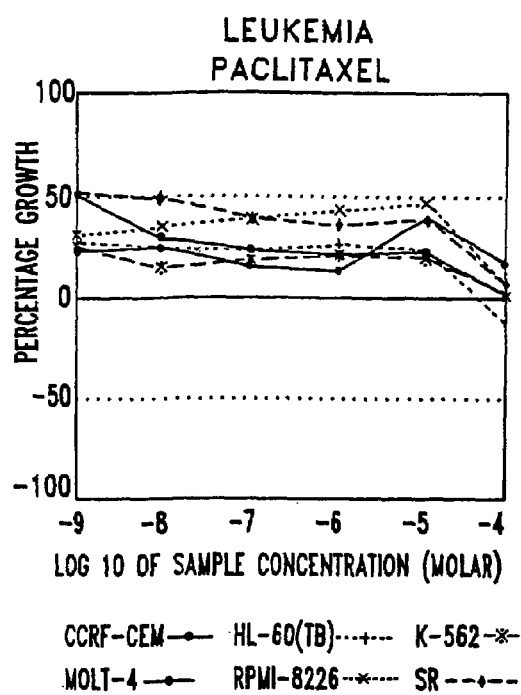

FIG. 7*a* depicts the dose response curves generated by exposing various leukemia cancer cell lines to various concentrations of paclitaxel.

Figure 7B:
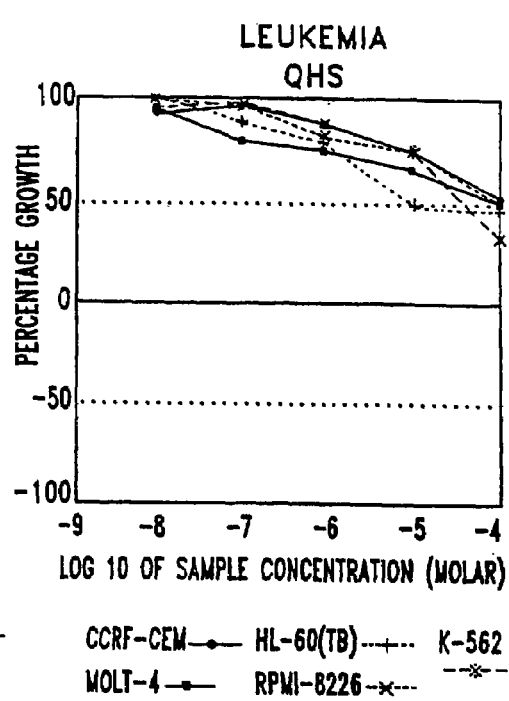

FIG. 7*b* depicts the dose response curves generated by exposing various leukemia cancer cell lines to various concentrations of artemisinin.

Figure 7C:
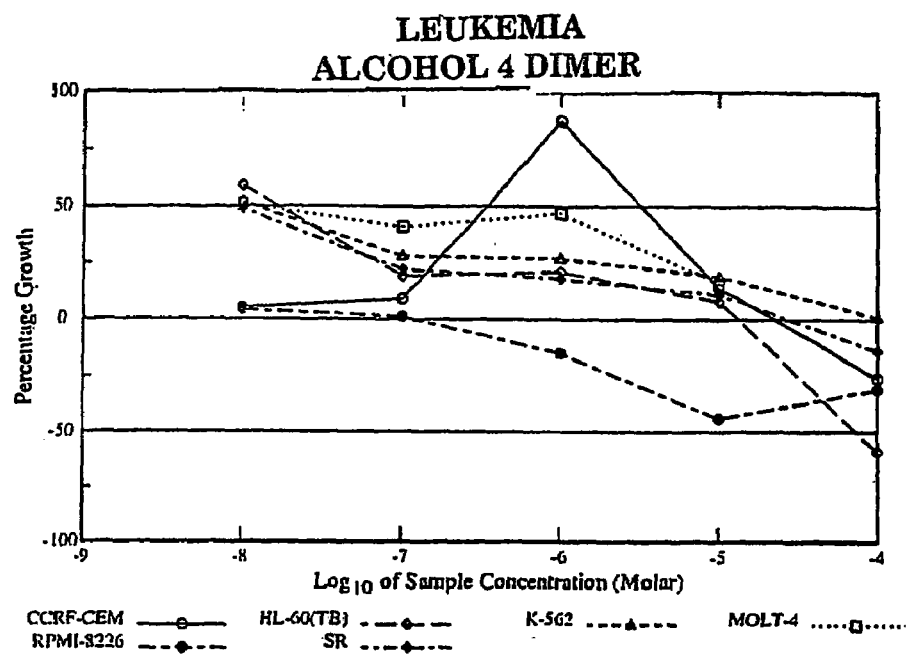

FIG. 7c depicts the dose response curves generated by exposing various leukemia cancer cell lines to various concentrations of the bis-trioxane primary alcohol 4 of the present invention.

Figure 7D:
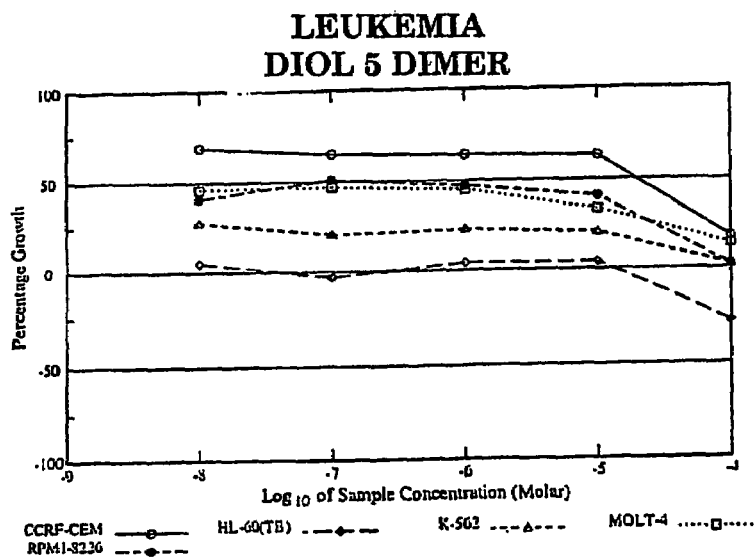

FIG. 7d depicts the dose response curves generated by exposing various leukemia cancer cell lines to various concentrations of the bis-trioxane vicinal diol 5 of the present invention.

Figure 7E:
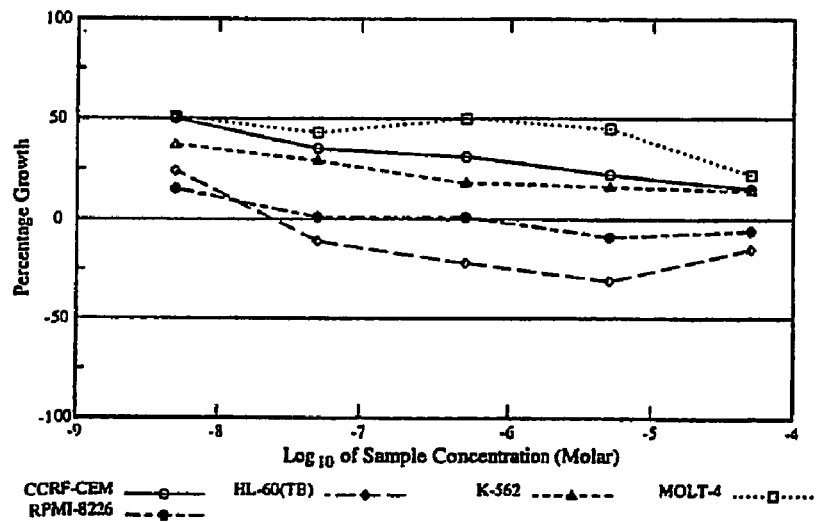

FIG. 7e depicts the dose response curves generated by exposing various leukemia cancer cell lines to various concentrations of the bis-trioxane primary succinate monoester 8a of the present invention.

Figure 7F:
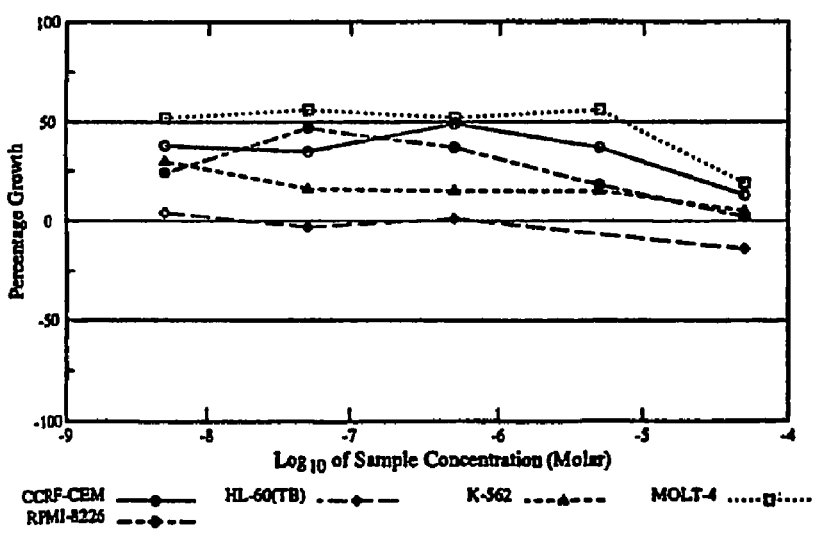

FIG. 7f depicts the dose response curves generated by exposing various leukemia cancer cell lines to various concentrations of the succinate ester 9 of the present invention.

Figure 7G:
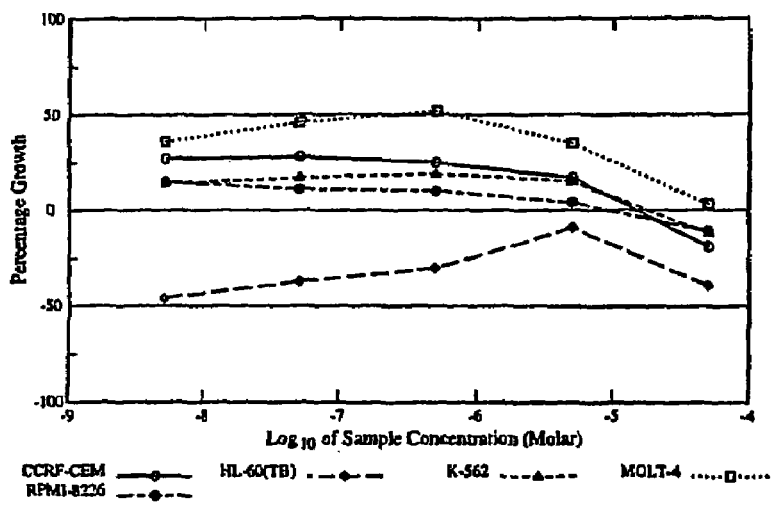

FIG. 7g depicts the dose response curves generated by exposing various leukemia cancer cell lines to various concentrations of the bis-trioxane β-hydroxysulfone benzoic acid 10c of the present invention.

Figure 7H:
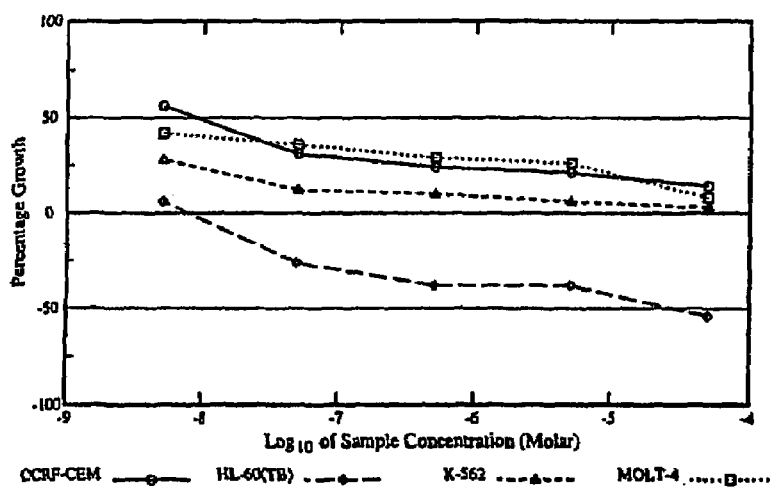

FIG. 7h depicts the dose response curves generated by exposing various leukemia cancer cell lines to various concentrations of the bis-trioxane tertiary alcohol benzoic acid 11b of the present invention.

Figure 7I:
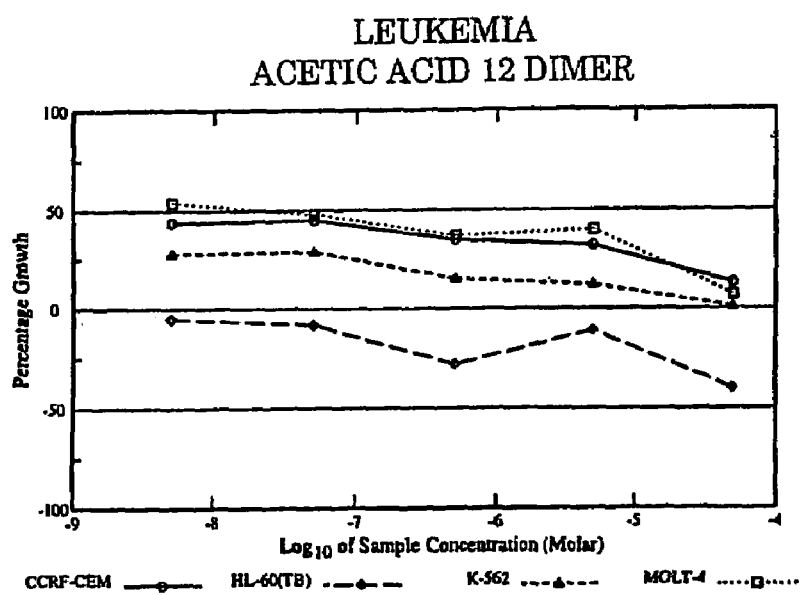

FIG. 7i depicts the dose response curves generated by exposing various leukemia cancer cell lines to various concentrations of the bis-trioxane O-acetic acid 12b of the present invention.

Figure 7J:
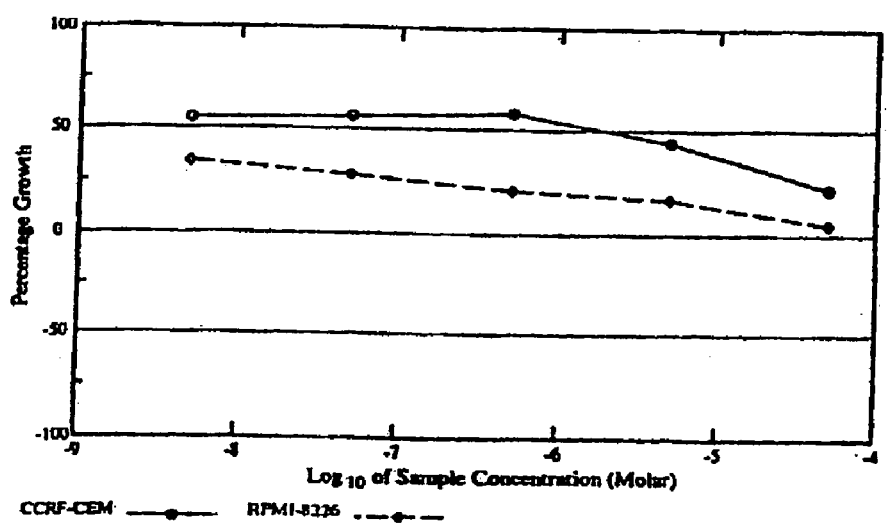

FIG. 7j depicts the dose response curves generated by exposing various leukemia cancer cell lines to various concentrations of the bis-trioxane primary alcohol isonicotinate N-oxide 13 of the present invention.

Figure 7K:
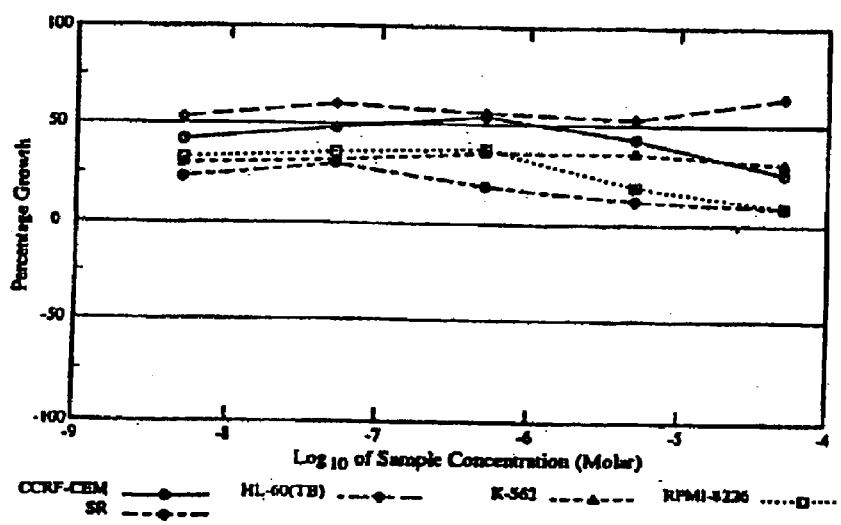

FIG. 7k depicts the dose response curves generated by exposing various leukemia cancer cell lines to various concentrations of the bis-trioxane diphenyl phosphate dimer 14 of the present invention.

FIG. 8a depicts the dose response curves generated by exposing various non-small cell lung cancer cell lines to various concentrations of paclitaxel.

FIG. 8b depicts the dose response curves generated by exposing various non-small cell lung cancer cell lines to various concentrations of the artemisinin.

Figure 8C:
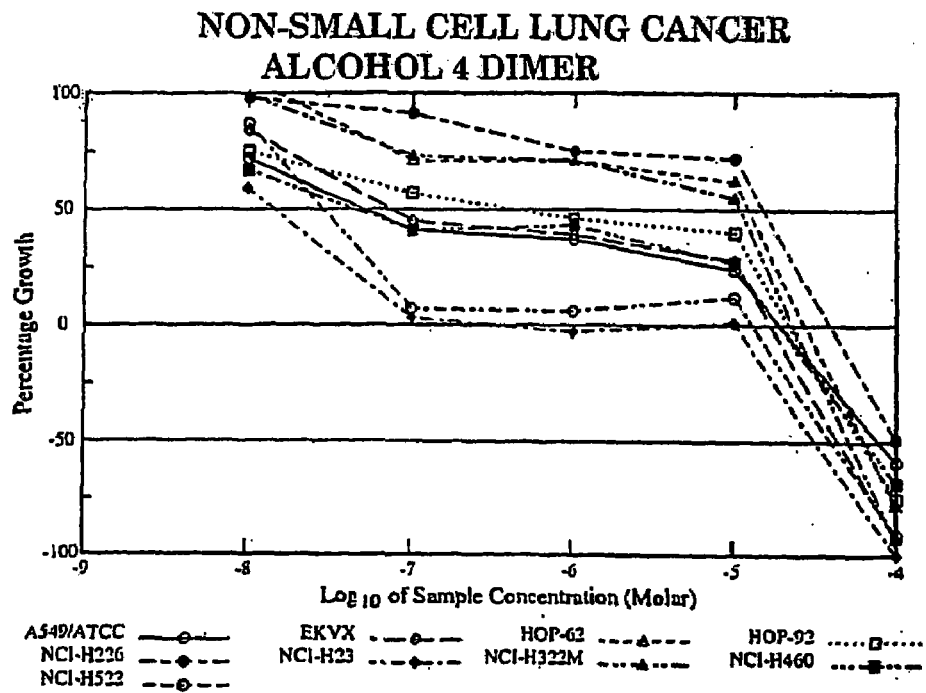

FIG. 8c depicts the dose response curves generated by exposing various non-small cell lung cancer cell lines to various concentrations of the bis-trioxane primary alcohol 4 of the present invention.

Figure 8D:
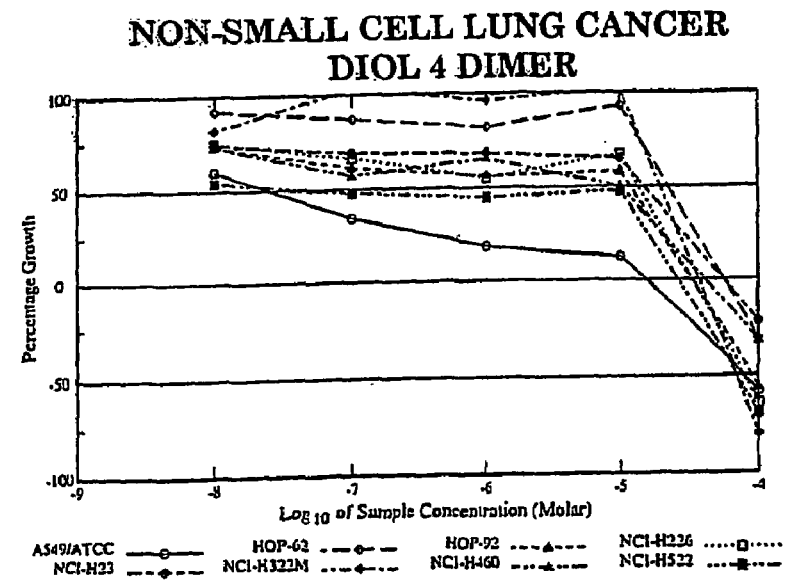

FIG. 8d depicts the dose response curves generated by exposing various non-small cell lung cancer cell lines to various concentrations of the bis-trioxane vicinal diol 5 of the present invention.

Figure 8E:
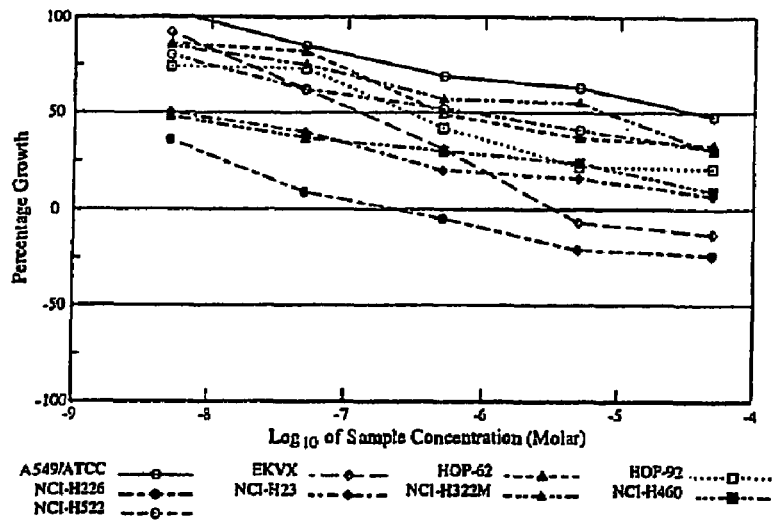

FIG. 8e depicts the dose response curves generated by exposing various non-small cell lung cancer cell lines to various concentrations of the bis-trioxane primary succinate monoester 8a of the present invention.

Figure 8F:
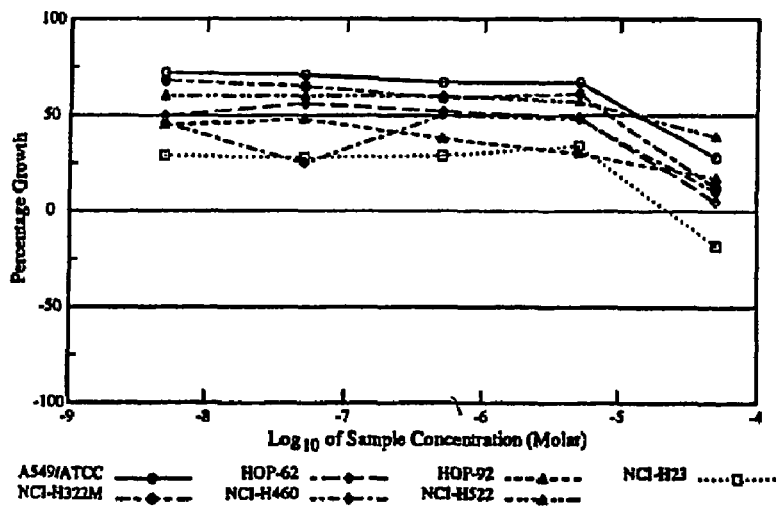

FIG. 8f depicts the dose response curves generated by exposing various non-small cell lung cancer cell lines to various concentrations of the succinate ester 9 of the present invention.

Figure 8G:
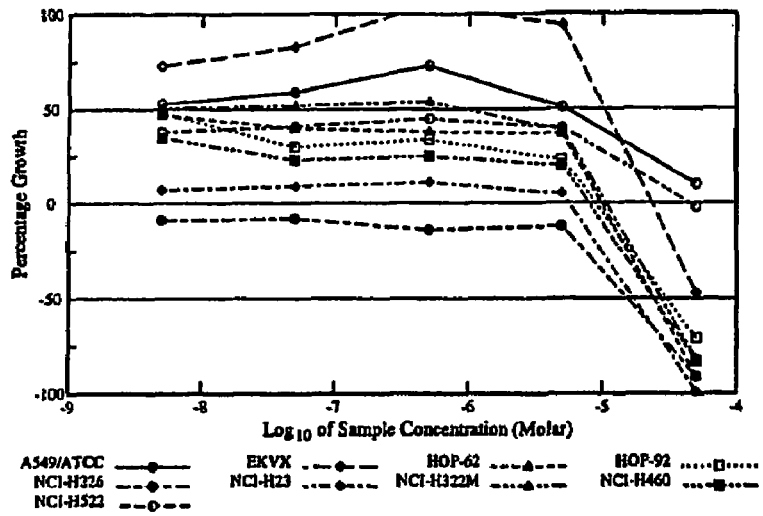

FIG. 8g depicts the dose response curves generated by exposing various non-small cell lung cancer cell lines to various concentrations of the bis-trioxane β-hydroxysulfone benzoic acid 10c of the present invention.

Figure 8H:
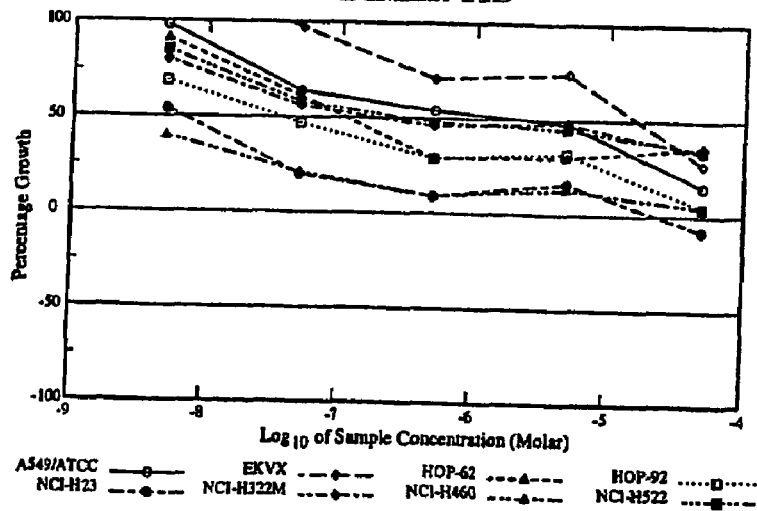

FIG. 8h depicts the dose response curves generated by exposing various non-small cell lung cancer cell lines to various concentrations of the bis-trioxane tertiary alcohol benzoic acid 11b of the present invention.

Figure 8I:
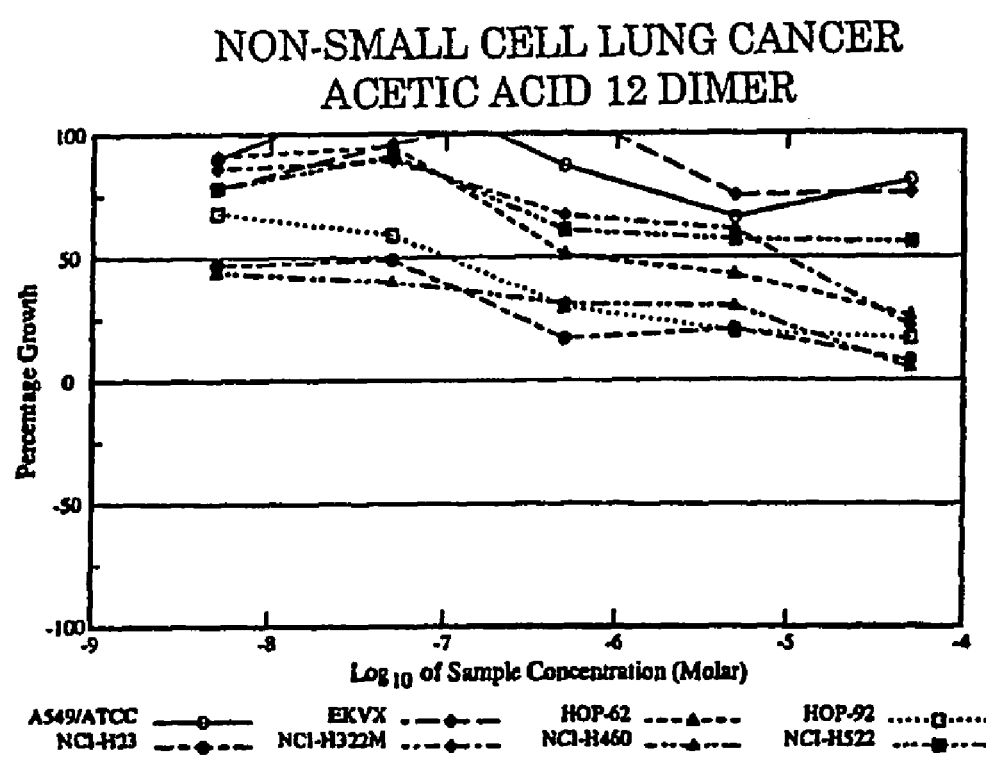

FIG. 8i depicts the dose response curves generated by exposing various non-small cell lung cancer cell lines to various concentrations of the bis-trioxane O-acetic acid 12b of the present invention.

Figure 8J:
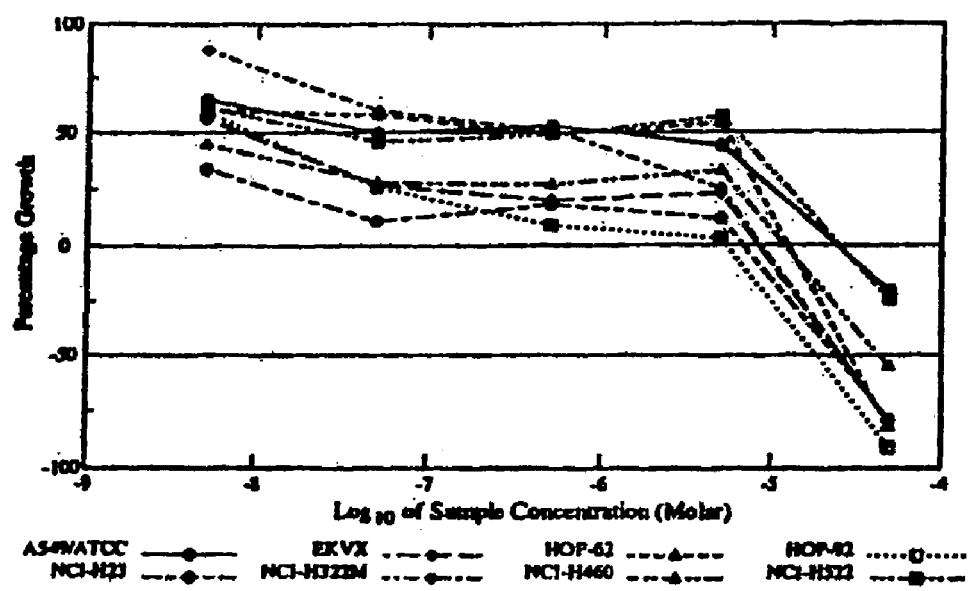

FIG. 8j depicts the dose response curves generated by exposing various non-small cell lung cancer cell lines to various concentrations of the bis-trioxane primary alcohol isonicotinate N-oxide 13 of the present invention.

Figure 8K:
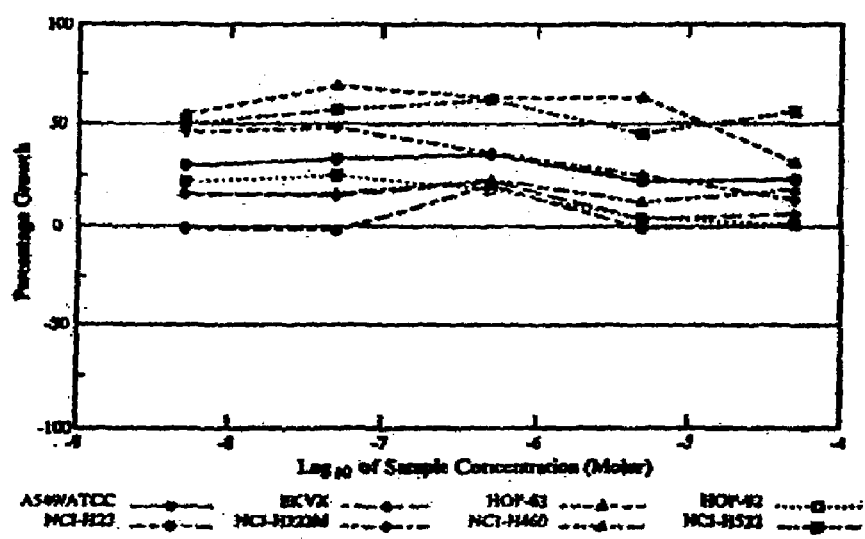

FIG. 8k depicts the dose response curves generated by exposing various non-small cell lung cancer cell lines to various concentrations of the bis-trioxane diphenyl phosphate dimer 14 of the present invention.

Figure 9A:
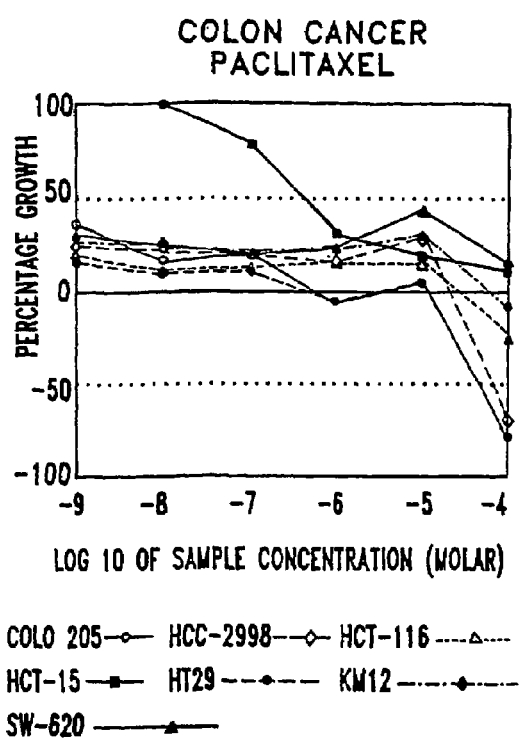

FIG. 9a depicts the dose response curves generated by exposing various colon cancer cell lines to various concentrations of paclitaxel.

Figure 9B:
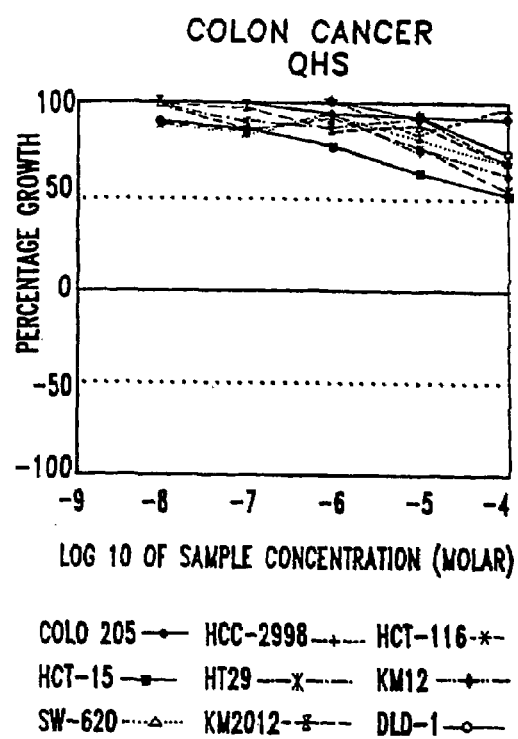

FIG. 9b depicts the dose response curves generated by exposing various colon cancer cell lines to various concentrations of artemisinin.

FIG. 9c depicts the dose response curves generated by exposing various colon cancer cell lines to various concentrations of the bis-trioxane primary alcohol 4 of the present invention.

Figure 9D:
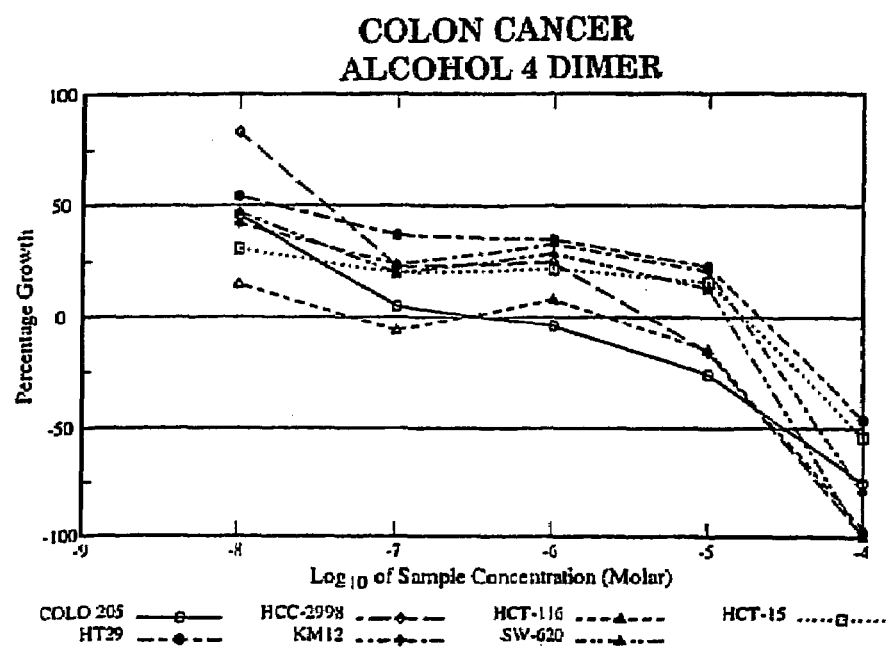
Figure 9D:
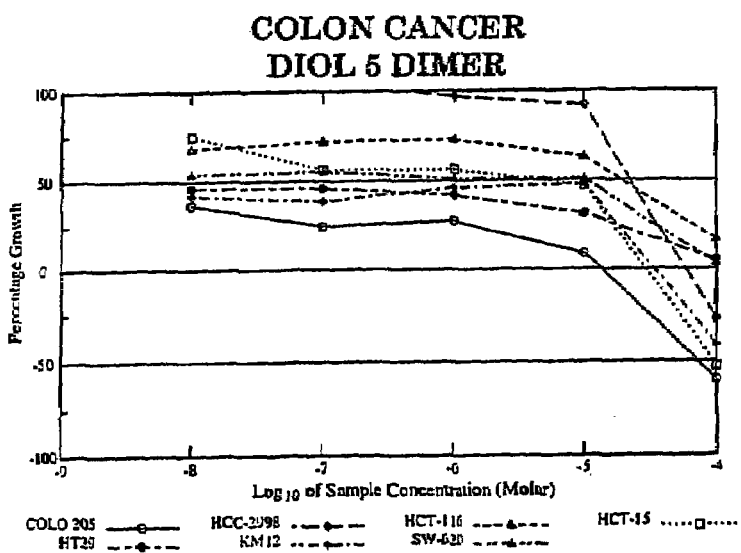

FIG. 9d depicts the dose response curves generated by exposing various colon cancer cell lines to various concentrations of the bis-trioxane vicinal diol 5 of the present invention.

Figure 9E:
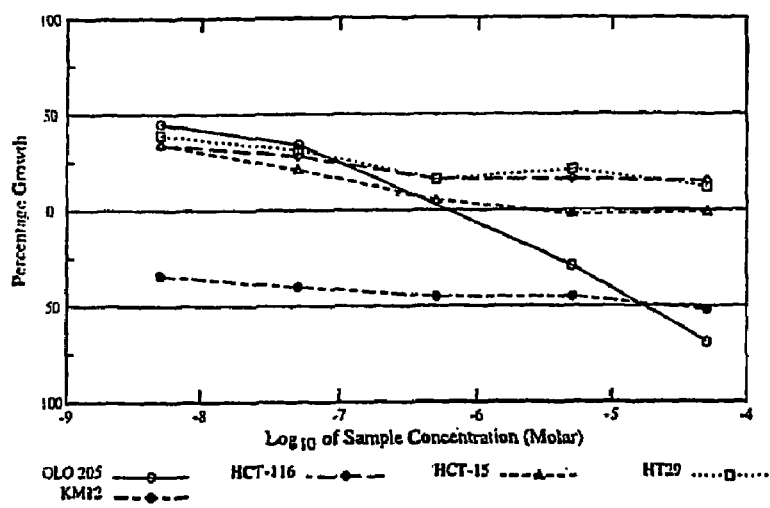

FIG. 9e depicts the dose response curves generated by exposing various colon cancer cell lines to various concentrations of the bis-trioxane primary succinate monoester 8a of the present invention.

Figure 9F:
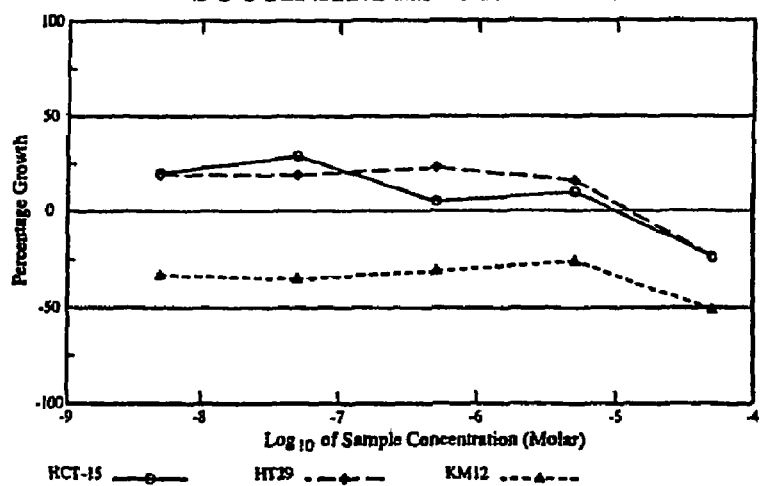

FIG. 9f depicts the dose response curves generated by exposing various colon cancer cell lines to various concentrations of the succinate ester 9 of the present invention.

Figure 9G:
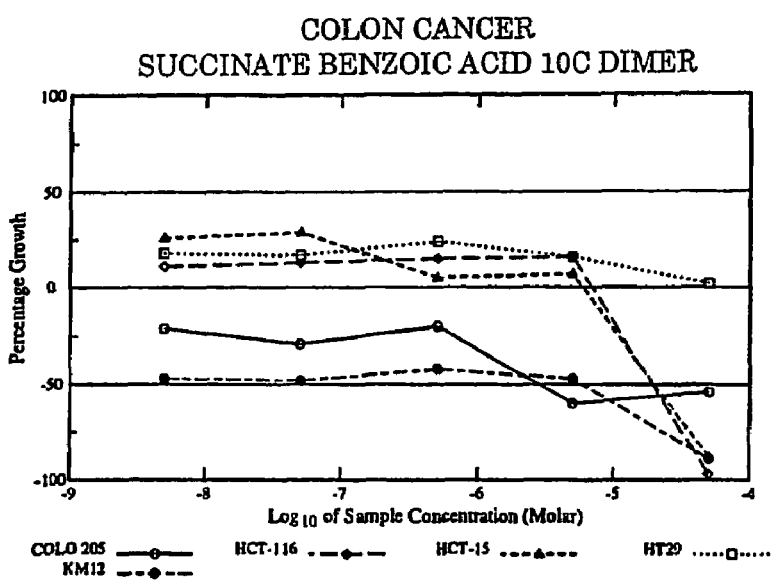

FIG. 9g depicts the dose response curves generated by exposing various colon cancer cell lines to various concentrations of the bis-trioxane β-hydroxysulfone benzoic acid 10c of the present invention.

Figure 9H:
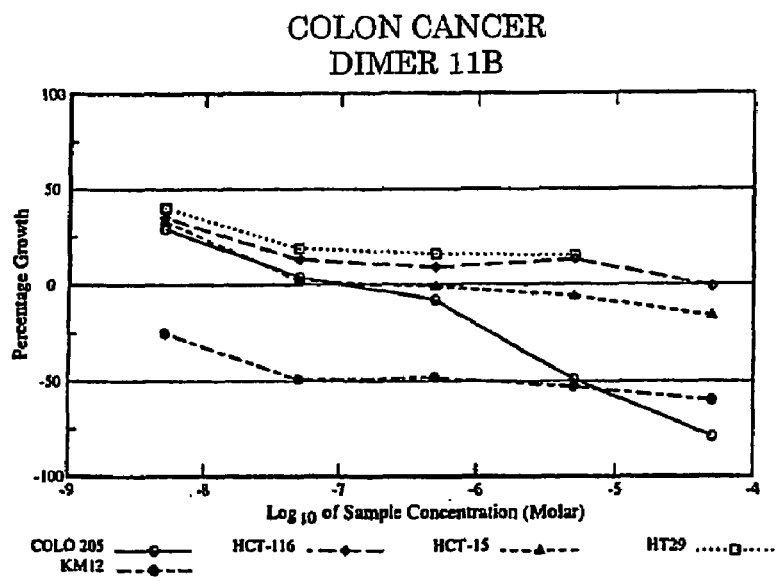

FIG. 9h depicts the dose response curves generated by exposing various colon cancer cell lines to various concentrations of the bis-trioxane tertiary alcohol benzoic acid 11b of the present invention.

Figure 9I:
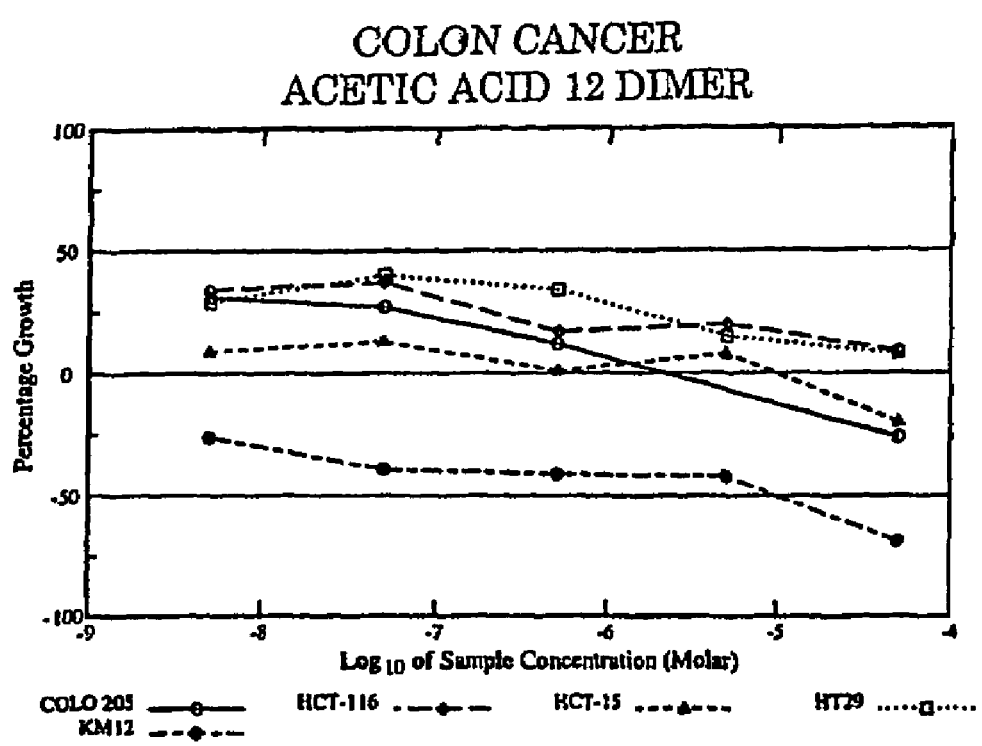

FIG. 9i depicts the dose response curves generated by exposing various colon cancer cell lines to various concentrations of the bis-trioxane O-acetic acid 12b of the present invention.

Figure 9J:
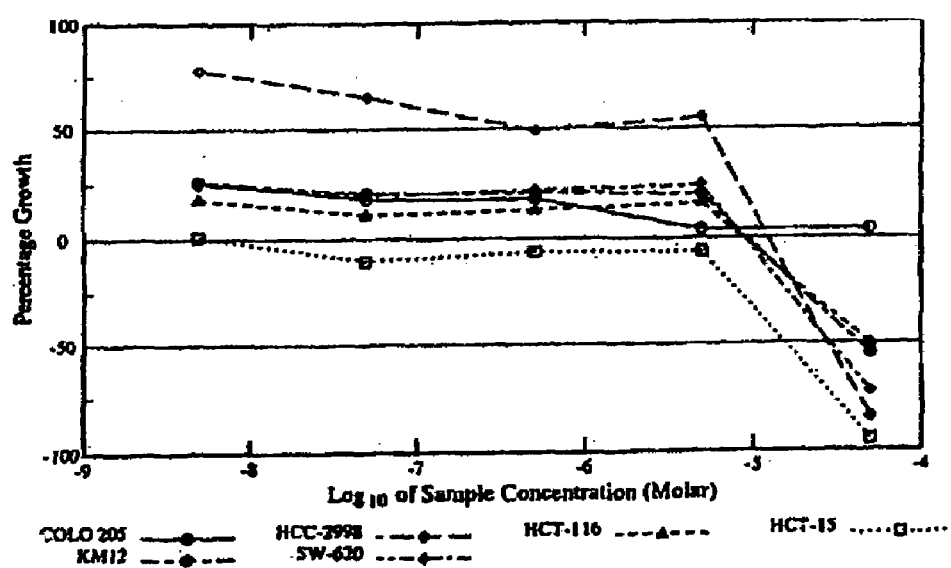

FIG. 9j depicts the dose response curves generated by exposing various colon cancer cell lines to various concentrations of the bis-trioxane primary alcohol isonicotinate N-oxide 13 of the present invention.

Figure 9K:
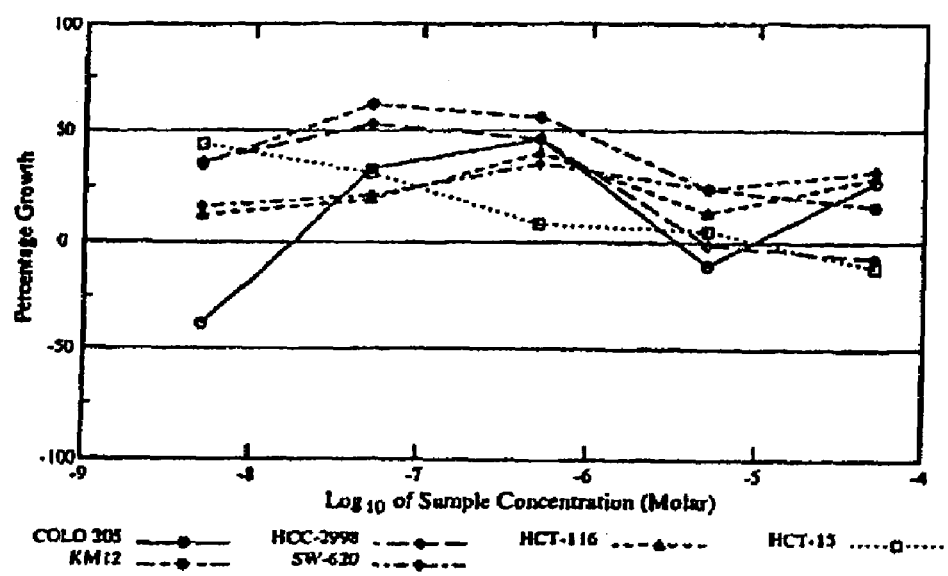

FIG. 9k depicts the dose response curves generated by exposing various colon cancer cell lines to various concentrations of the bis-trioxane diphenyl phosphate dimer 14 of the present invention.

Figure 10A:
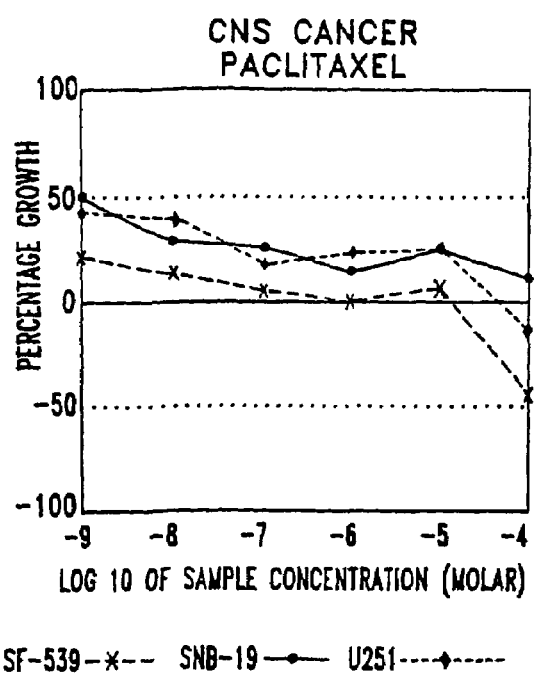

FIG. 10a depicts the dose response curves generated by exposing various CNS cancer cell lines to various concentrations of paclitaxel.

Figure 10B:
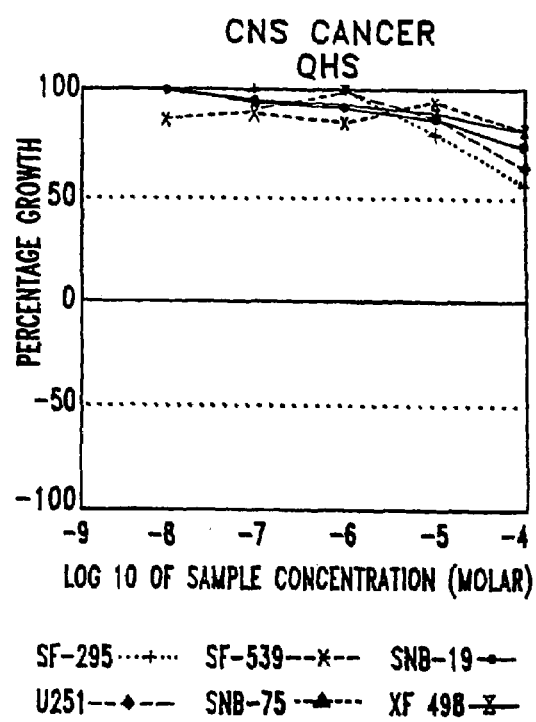

FIG. 10b depicts the dose response curves generated by exposing various CNS cancer cell lines to various concentrations of artemisinin.

Figure 10C:
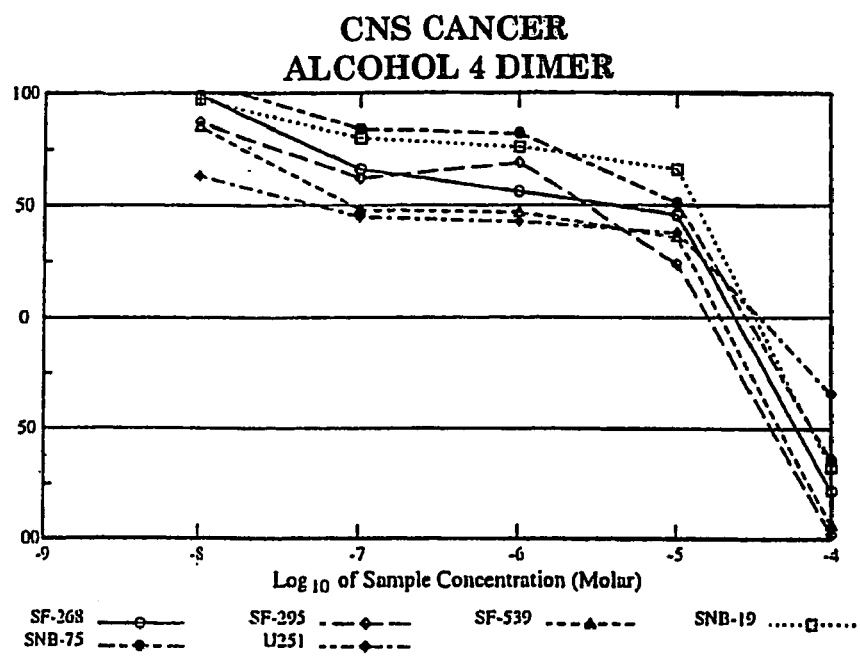

FIG. 10c depicts the dose response curves generated by exposing various CNS cancer cell lines to various concentrations of the bis-trioxane primary alcohol 4 of the present invention.

Figure 10D:
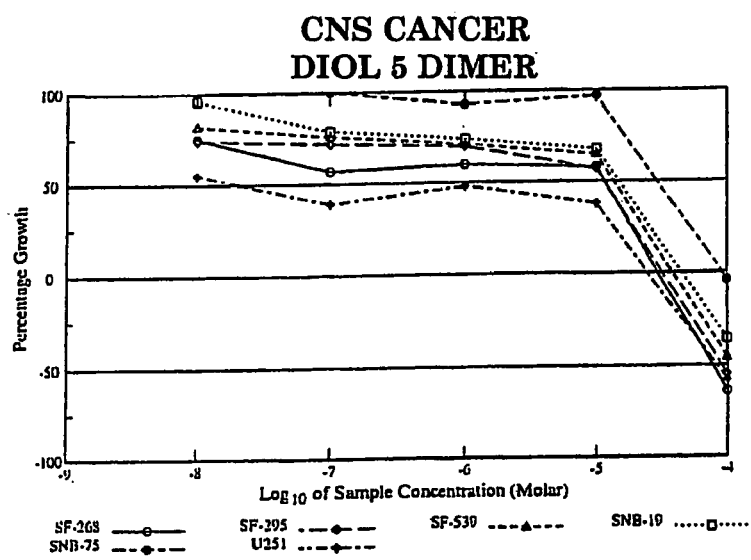

FIG. 10d depicts the dose response curves generated by exposing various CNS cancer cell lines to various concentrations of the bis-trioxane vicinal diol 5 of the present invention.

Figure 10E:
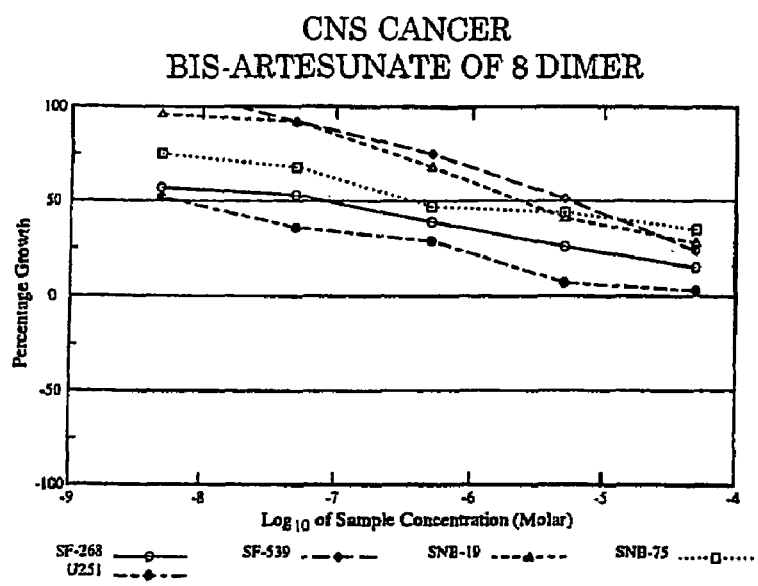

FIG. 10e depicts the dose response curves generated by exposing various CNS cancer cancer cell lines to various concentrations of the bis-trioxane primary succinate monoester 8a of the present invention.

Figure 10F:
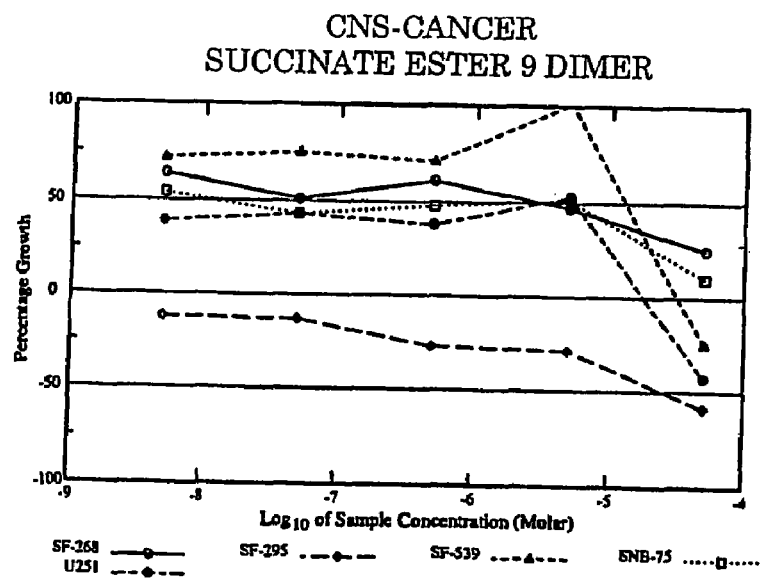

FIG. 10f depicts the dose response curves generated by exposing various CNS cancer cancer cell lines to various concentrations of the succinate ester 9 of the present invention.

Figure 10G:
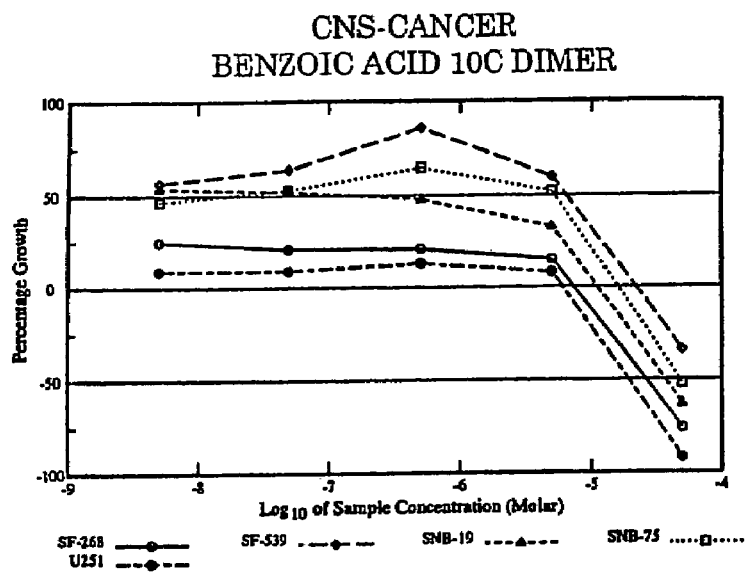

FIG. 10g depicts the dose response curves generated by exposing various CNS cancer cancer cell lines to various concentrations of the bis-trioxane β-hydroxysulfone benzoic acid 10c of the present invention.

Figure 10H:
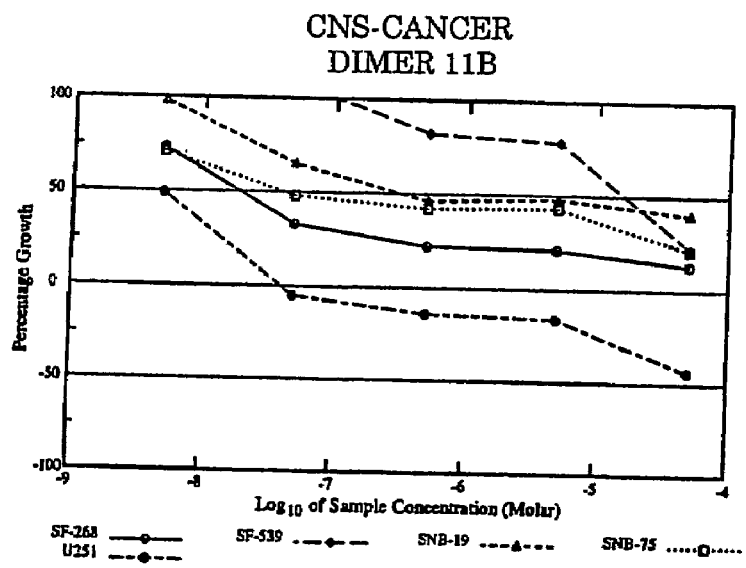

FIG. 10h depicts the dose response curves generated by exposing various CNS cancer cancer cell lines to various concentrations of the bis-trioxane tertiary alcohol benzoic acid 11b of the present invention.

Figure 10I:
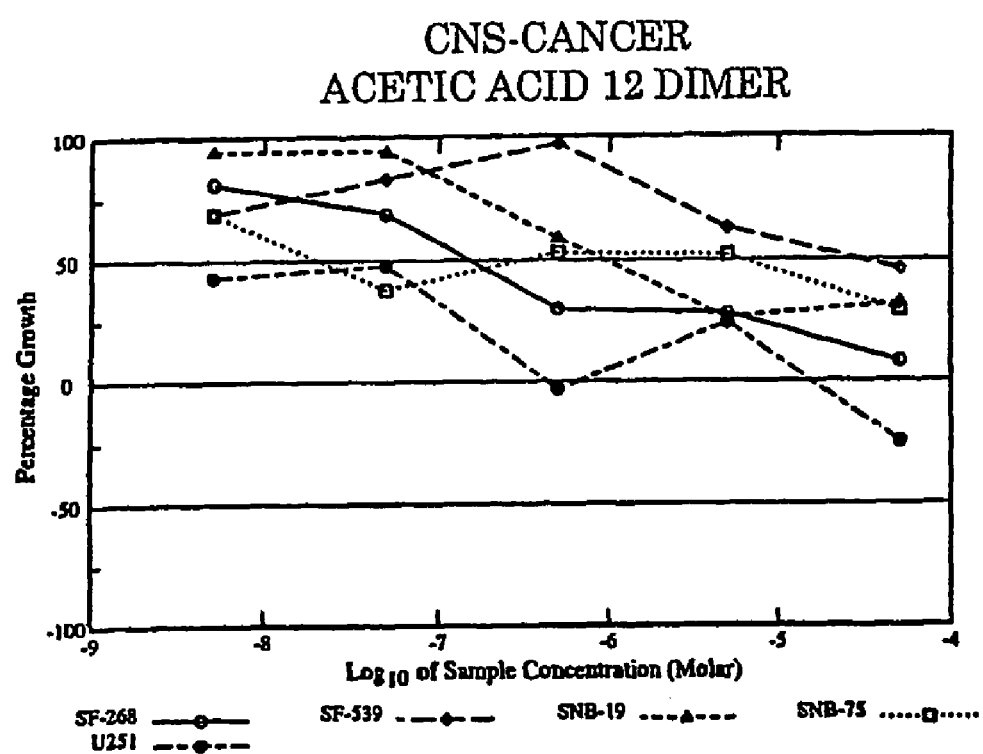

FIG. 10i depicts the dose response curves generated by exposing various CNS cancer cancer cell lines to various concentrations of the bis-trioxane O-acetic acid 12b of the present invention.

Figure 10J:
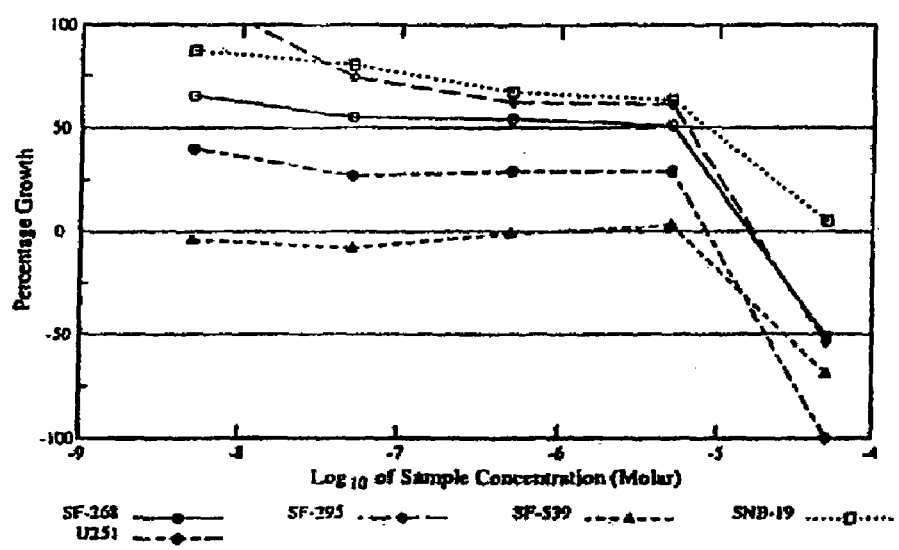

FIG. 10j depicts the dose response curves generated by exposing various CNS cancer cancer cell lines to various concentrations of the bis-trioxane primary alcohol isonicotinate N-oxide 13 of the present invention.

Figure 10K:
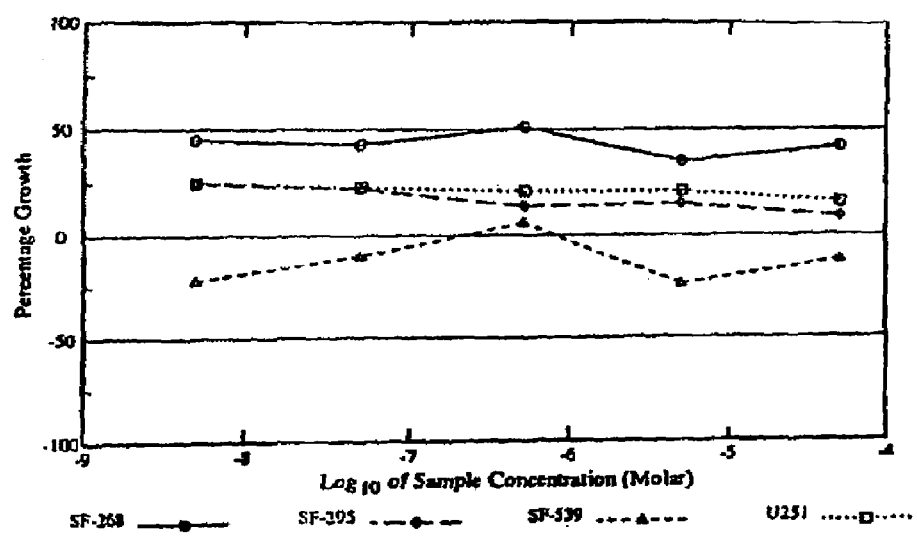

FIG. 10k depicts the dose response curves generated by exposing various CNS cancer cancer cell lines to various concentrations of the bis-trioxane diphenyl phosphate dimer 14 of the present invention.

Figure 11A:
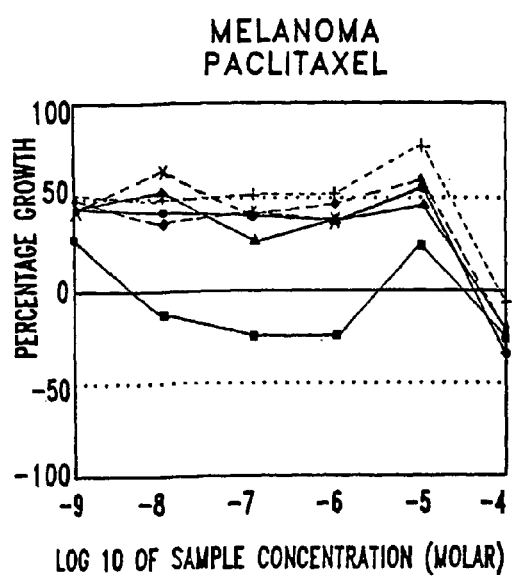

FIG. 11a depicts the dose response curves generated by exposing various melanoma cancer cell lines to various concentrations of paclitaxel.

Figure 11B:
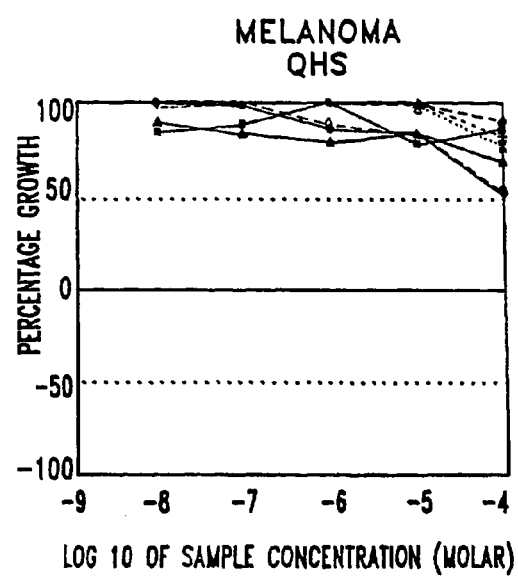

FIG. 11b depicts the dose response curves generated by exposing various melanoma cancer cell lines to various concentrations of artemisinin.

Figure 11C:
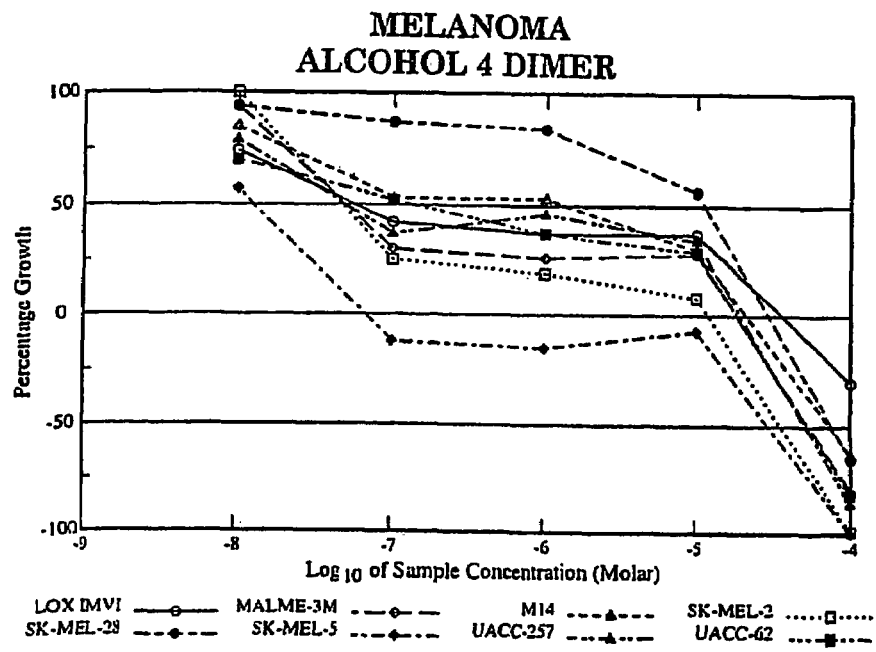

FIG. 11c depicts the dose response curves generated by exposing various melanoma cancer cell lines to various concentrations of the bis-trioxane primary alcohol 4 of the present invention.

Figure 11D:
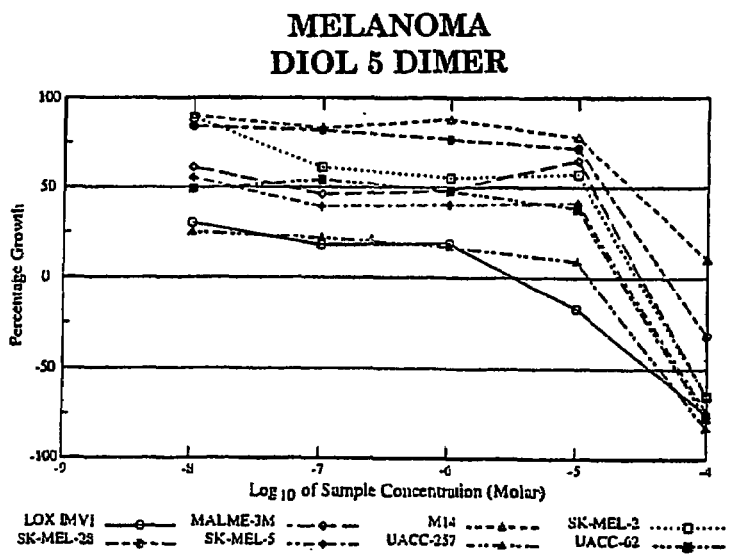

FIG. 11d depicts the dose response curves generated by exposing various melanoma cancer cell lines to various concentrations of the bis-trioxane vicinal diol 5 of the present invention.

Figure 11E:
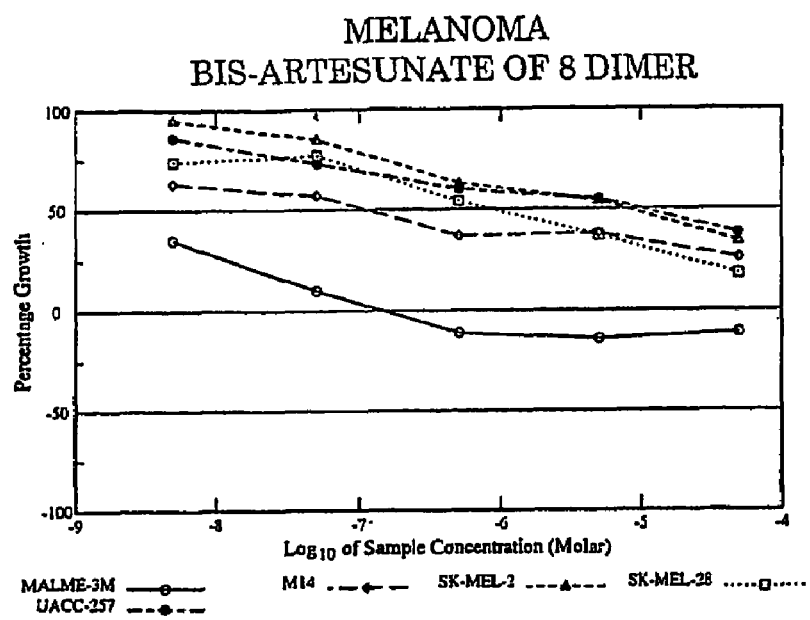

FIG. 11e depicts the dose response curves generated by exposing various melanoma cancer cell lines to various concentrations of the bis-trioxane primary succinate monoester 8a of the present invention.

Figure 11F:
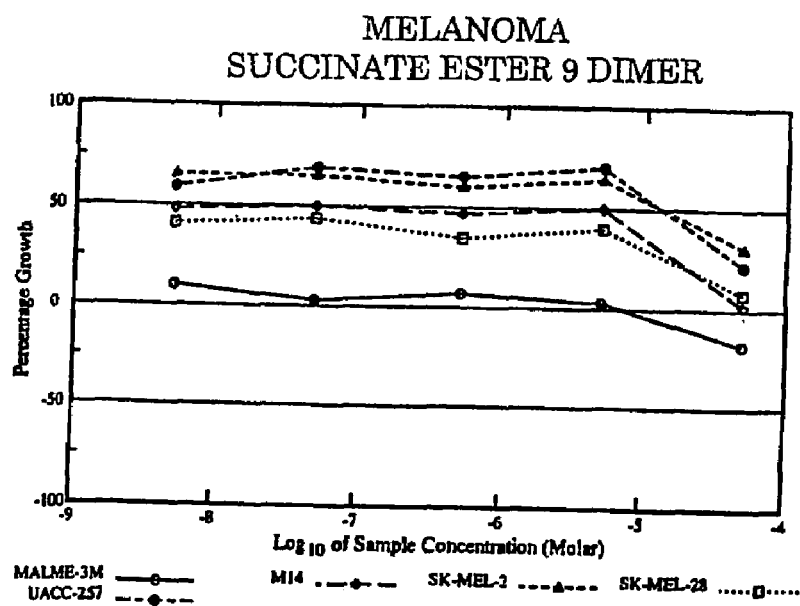

FIG. 11f depicts the dose response curves generated by exposing various melanoma cancer cell lines to various concentrations of the succinate ester 9 of the present invention.

Figure 11G:
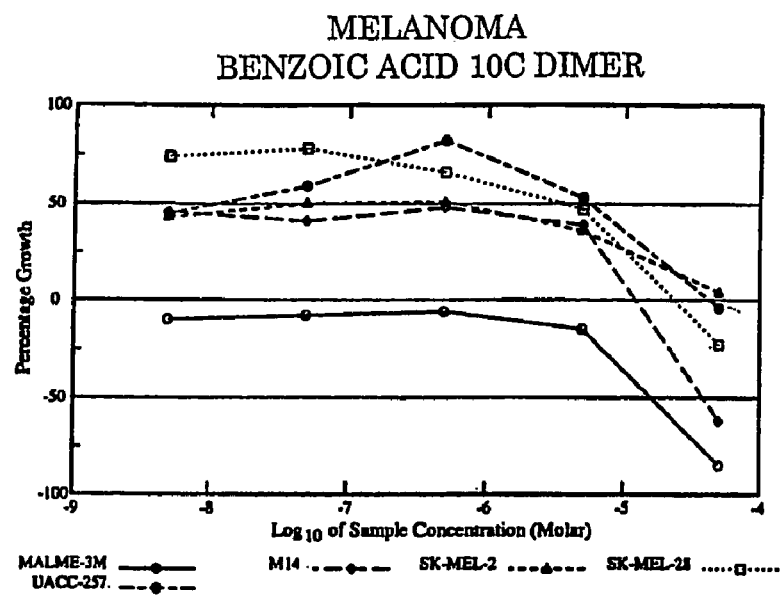

FIG. 11g depicts the dose response curves generated by exposing various melanoma cancer cell lines to various concentrations of the bis-trioxane β-hydroxysulfone benzoic acid 10c of the present invention.

Figure 11H:
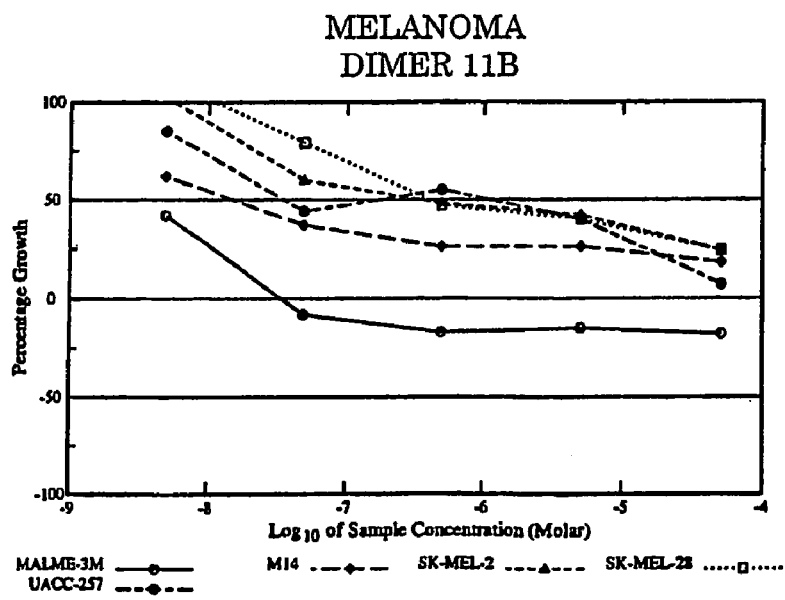

FIG. 11h depicts the dose response curves generated by exposing various melanoma cancer cell lines to various concentrations of the bis-trioxane tertiary alcohol benzoic acid 11b of the present invention.

Figure 11I:
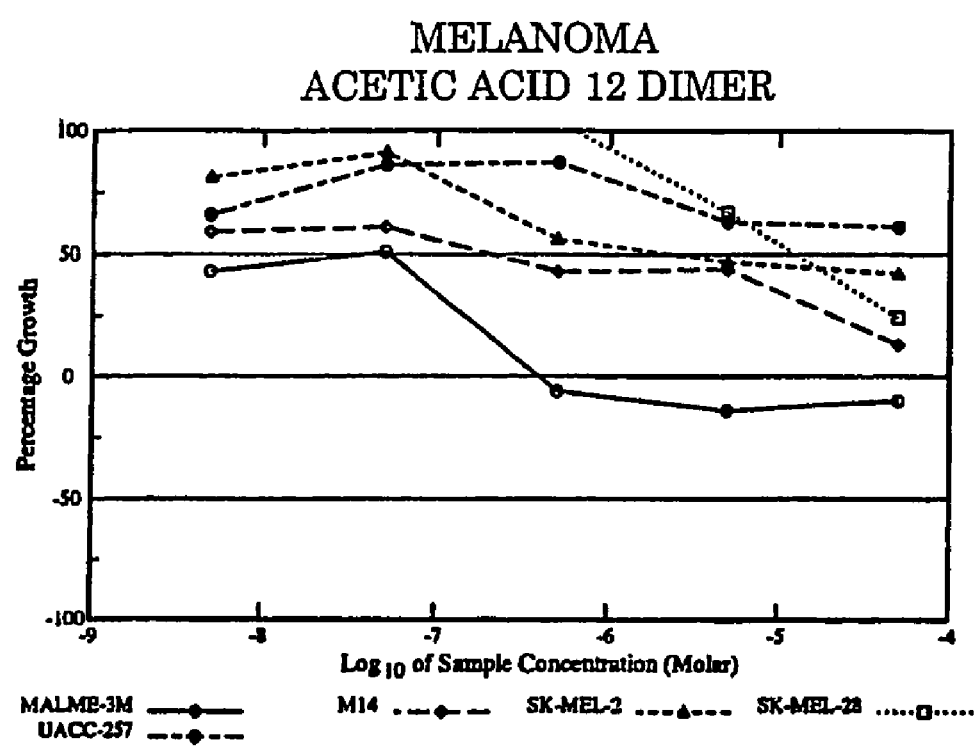

FIG. 11i depicts the dose response curves generated by exposing various melanoma cancer cell lines to various concentrations of the bis-trioxane O-acetic acid 12b of the present invention.

Figure 11J:
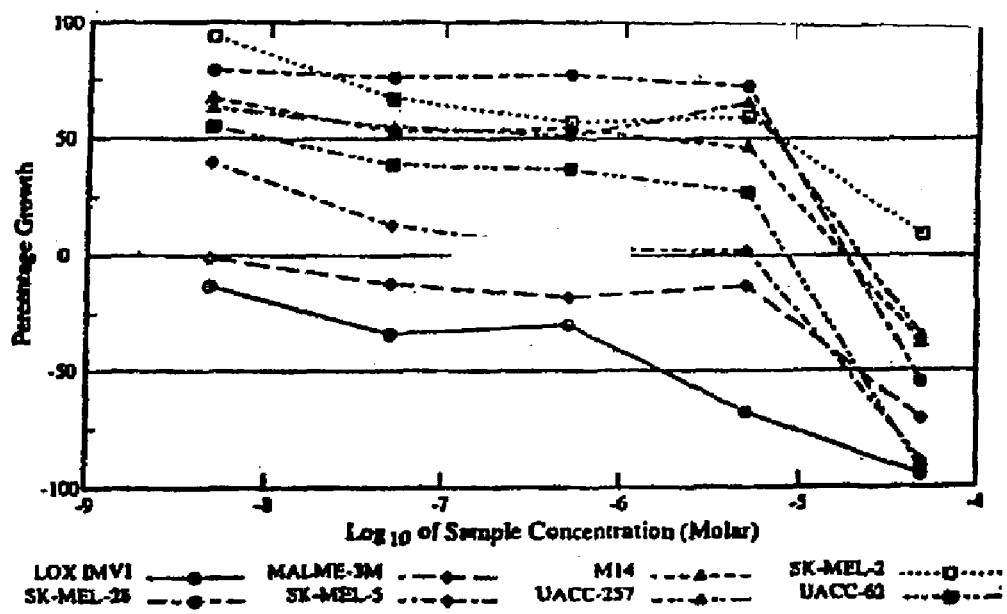

FIG. 11j depicts the dose response curves generated by exposing various melanoma cancer cell lines to various concentrations of the bis-trioxane primary alcohol isonicotinate N-oxide 13 of the present invention.

Figure 11K:
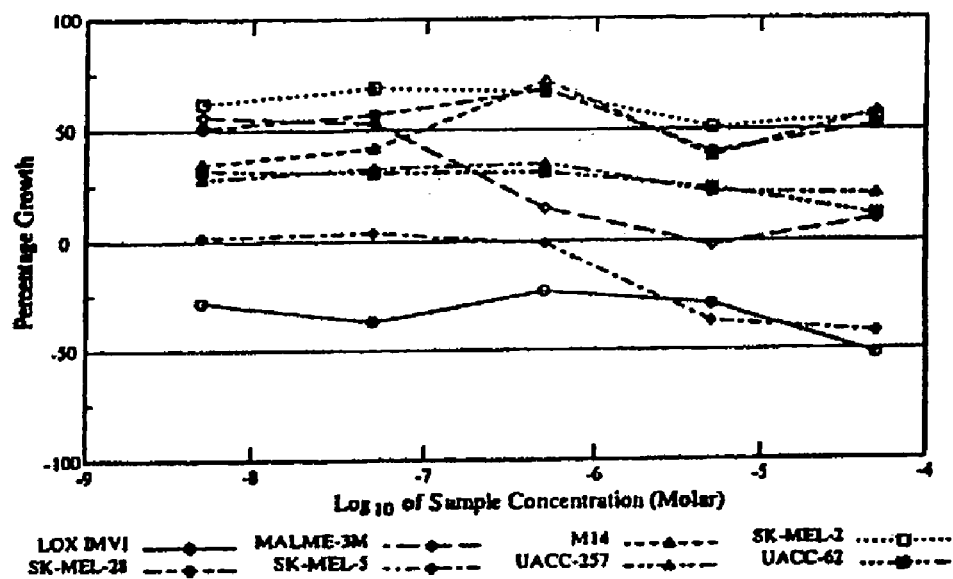

FIG. 11k depicts the dose response curves generated by exposing various melanoma cancer cell lines to various concentrations of the bis-trioxane diphenyl phosphate dimer 14 of the present invention.

FIG. 12a depicts the dose response curves generated by exposing various ovarian cancer cell lines to various concentrations of paclitaxel.

FIG. 12b depicts the dose response curves generated by exposing various ovarian cancer cell lines to various concentrations of artemisinin.

Figure 12C:
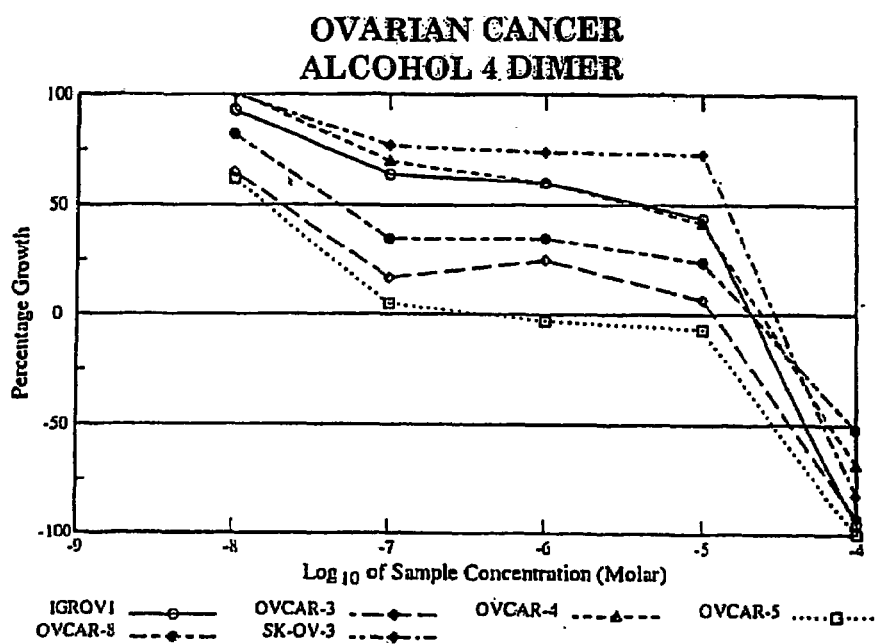

FIG. 12c depicts the dose response curves generated by exposing various ovarian cancer cell lines to various concentrations of the bis-trioxane primary alcohol 4 of the present invention.

Figure 12D:
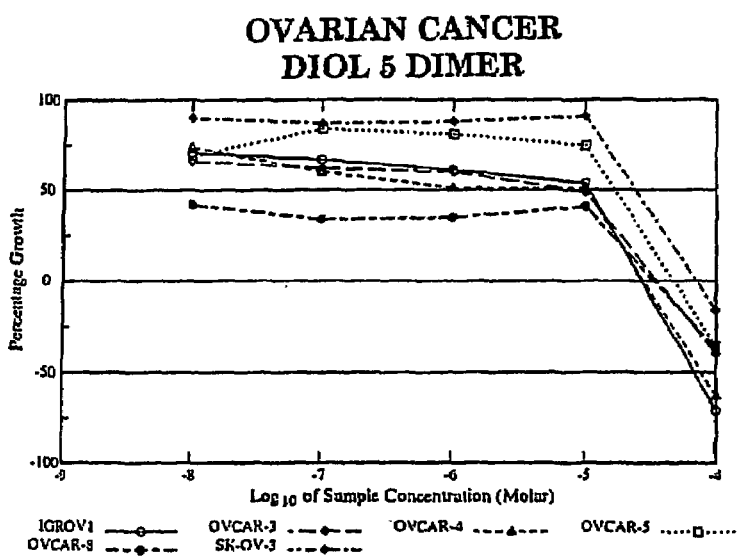

FIG. 12d depicts the dose response curves generated by exposing various ovarian cancer cell lines to various concentrations of the bis-trioxane vicinal diol 5 of the present invention.

Figure 12E:
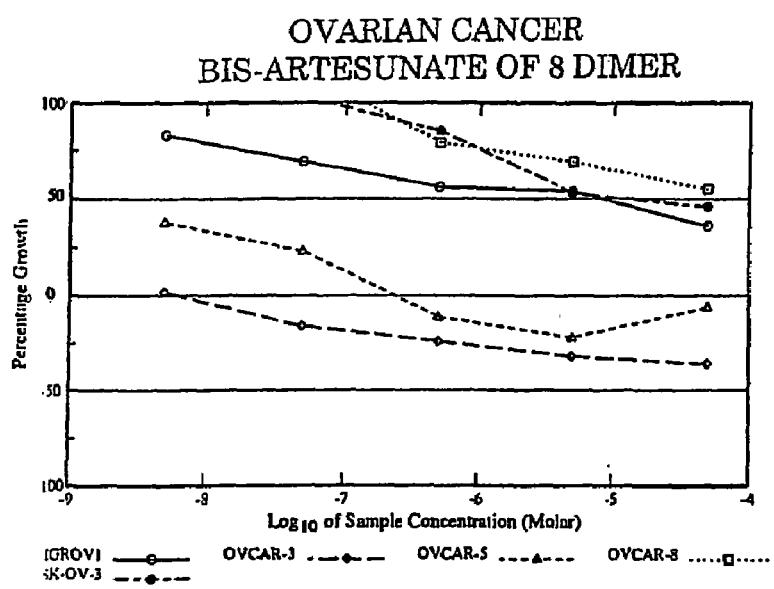

FIG. 12e depicts the dose response curves generated by exposing various ovarian cancer cell lines to various concentrations of the bis-trioxane primary succinate monoester 8a of the present invention.

Figure 12F:
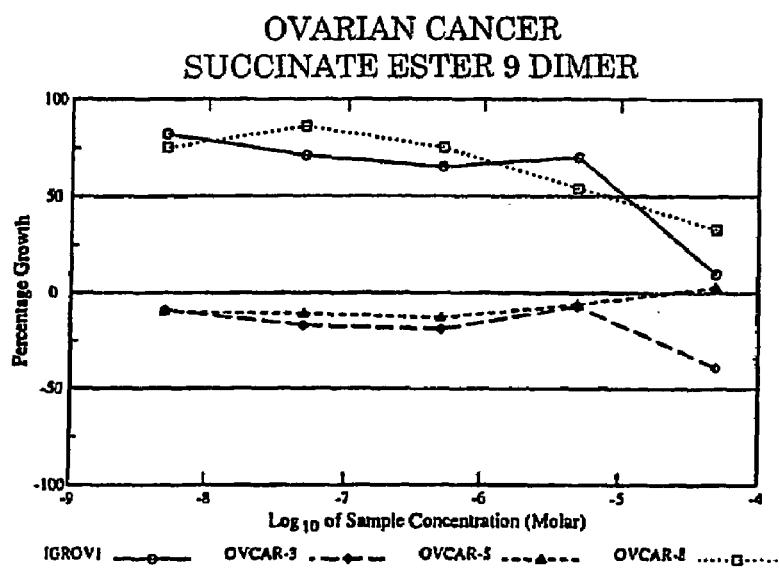

FIG. 12f depicts the dose response curves generated by exposing various ovarian cancer cell lines to various concentrations of the succinate ester 9 of the present invention.

Figure 12G:
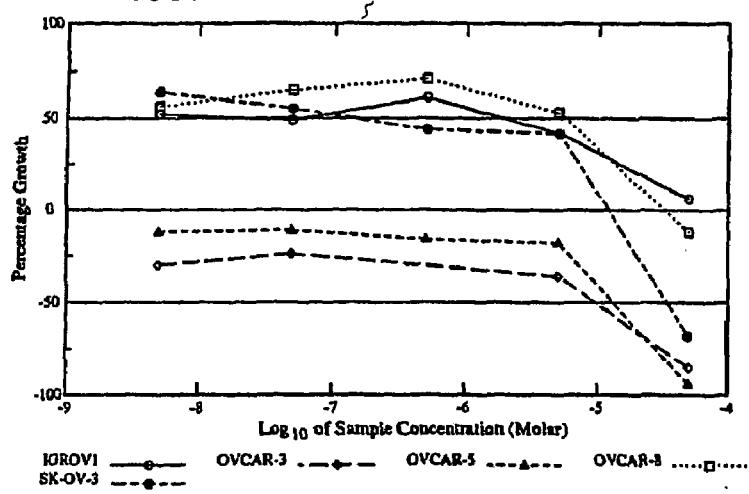

FIG. 12g depicts the dose response curves generated by exposing various ovarian cancer cell lines to various concentrations of the bis-trioxane β-hydroxysulfone benzoic acid 10c of the present invention.

Figure 12H:
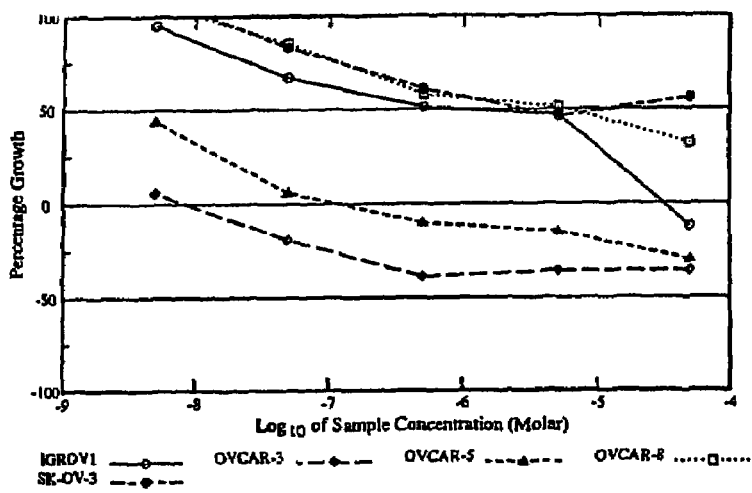

FIG. 12h depicts the dose response curves generated by exposing various ovarian cancer cell lines to various concentrations of the bis-trioxane tertiary alcohol benzoic acid 11b of the present invention.

Figure 12I:
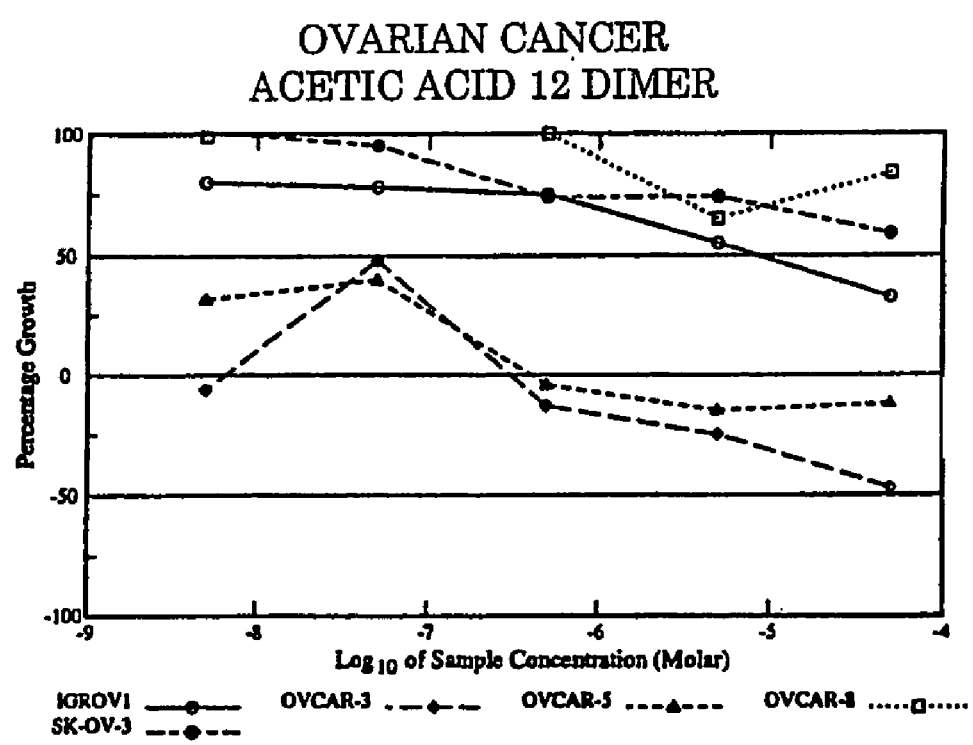

FIG. 12i depicts the dose response curves generated by exposing various ovarian cancer cell lines to various concentrations of the bis-trioxane O-acetic acid 12b of the present invention.

Figure 12J:
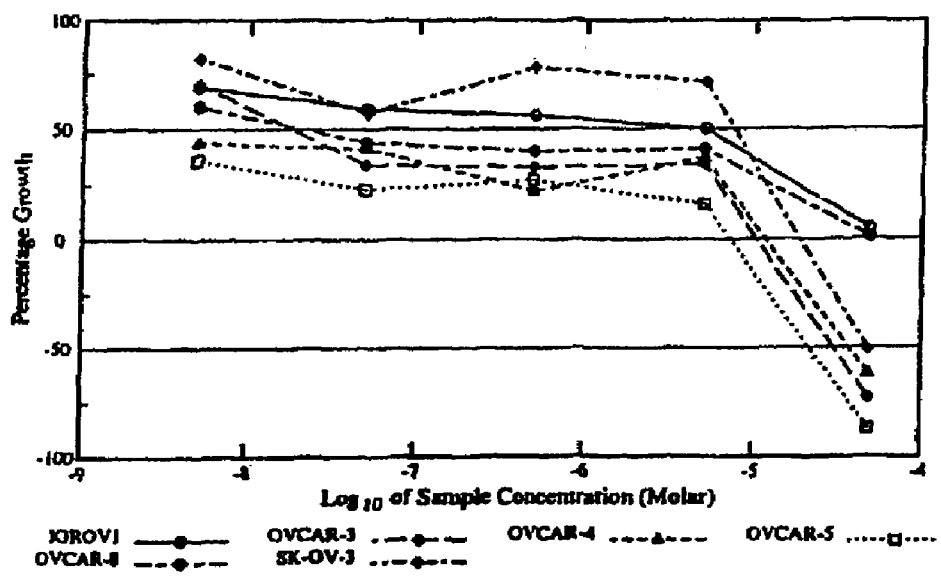

FIG. 12j depicts the dose response curves generated by exposing various ovarian cancer cell lines to various concentrations of the bis-trioxane primary alcohol isonicotinate N-oxide 13 of the present invention.

Figure 12K:
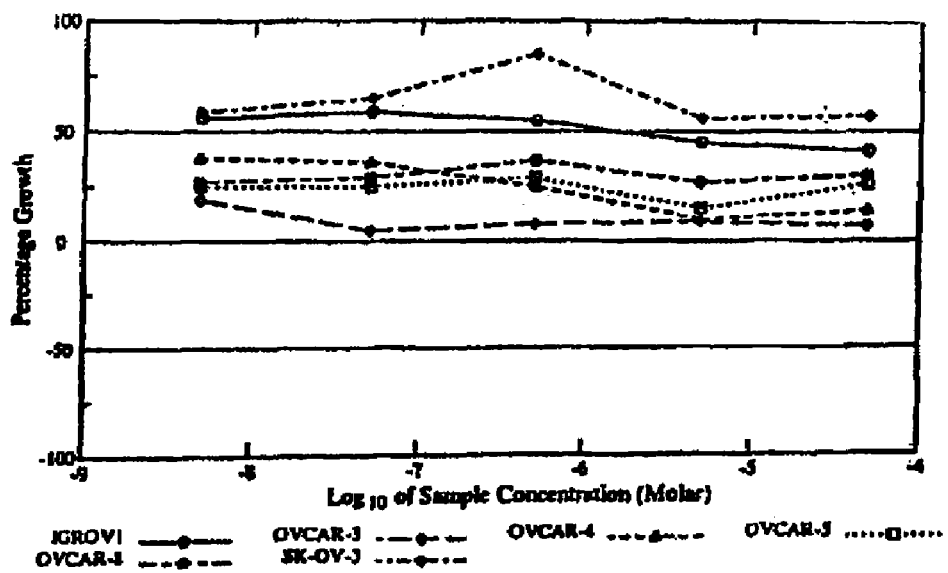

FIG. 12k depicts the dose response curves generated by exposing various ovarian cancer cell lines to various concentrations of the bis-trioxane diphenyl phosphate dimer 14 of the present invention.

FIG. 13a depicts the dose response curves generated by exposing various renal cancer cell lines to various concentrations of paclitaxel.

FIG. 13b depicts the dose response curves generated by exposing various renal cancer cell lines to various concentrations of artemisinin.

Figure 13C:
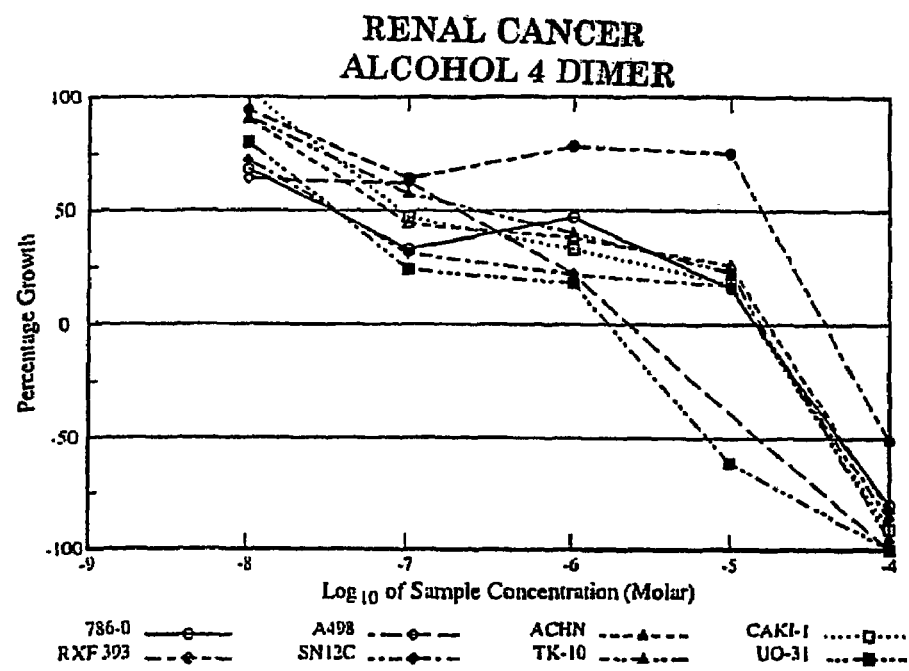

FIG. 13c depicts the dose response curves generated by exposing various renal cancer cell lines to various concentrations of the bis-trioxane primary alcohol 4 of the present invention.

Figure 13D:
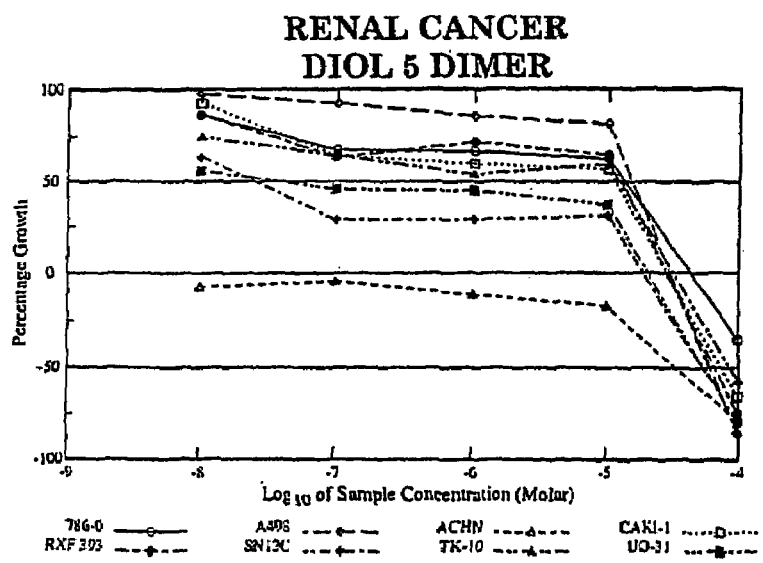

FIG. 13d depicts the dose response curves generated by exposing various renal cancer cell lines to various concentrations of the bis-trioxane vicinal diol 5 of the present invention.

Figure 13E:
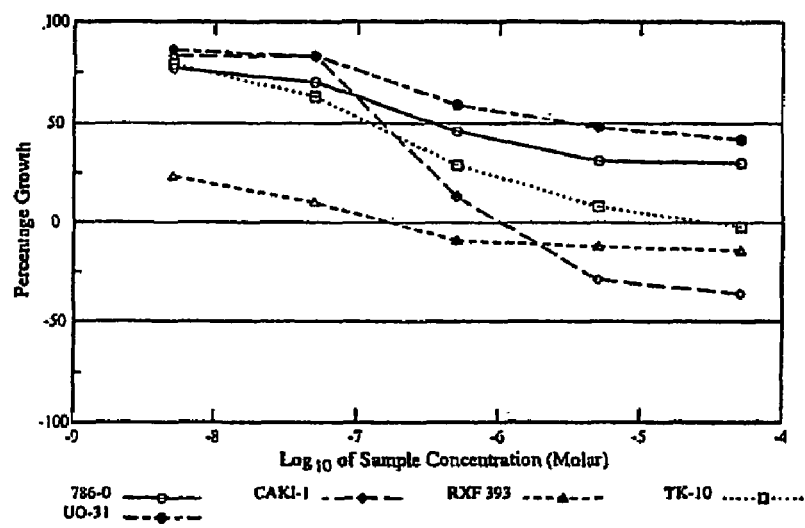

FIG. 13e depicts the dose response curves generated by exposing various renal cancer cell lines to various concentrations of the bis-trioxane primary succinate monoester 8a of the present invention.

Figure 13F:
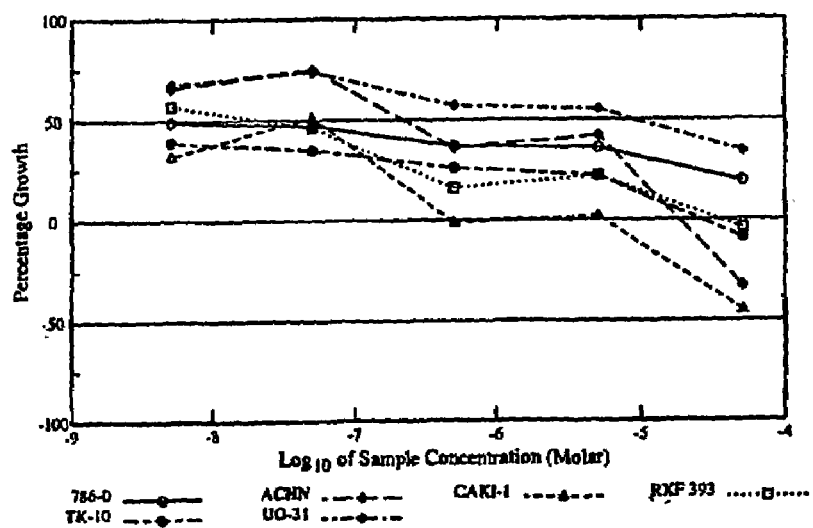

FIG. 13f depicts the dose response curves generated by exposing various I renal cancer cell lines to various concentrations of the succinate ester 9 of the present invention.

Figure 13G:
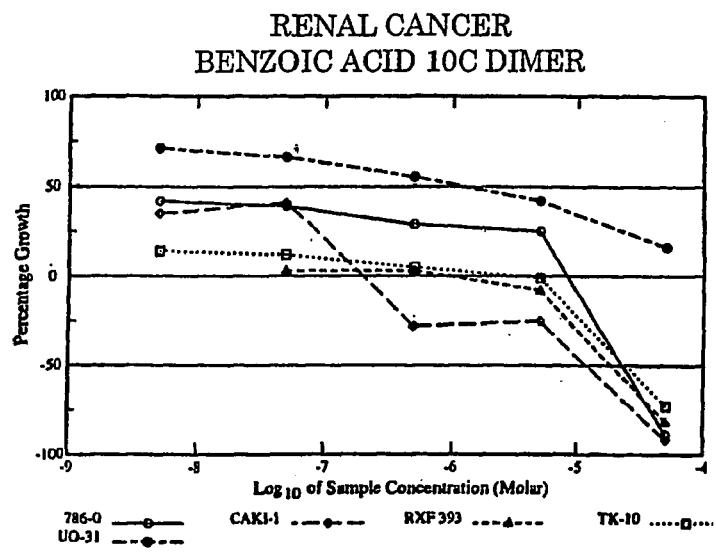

FIG. 13g depicts the dose response curves generated by exposing various renal cancer cell lines to various concentrations of the bis-trioxane β-hydroxysulfone benzoic acid 10c of the present invention.

Figure 13H:
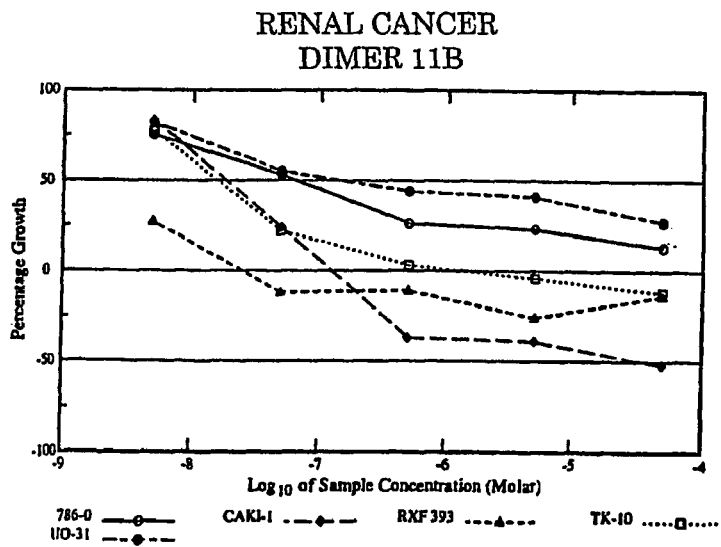

FIG. 13h depicts the dose response curves generated by exposing various renal cancer cell lines to various concentrations of the bis-trioxane tertiary alcohol benzoic acid 11b of the present invention.

Figure 13I:
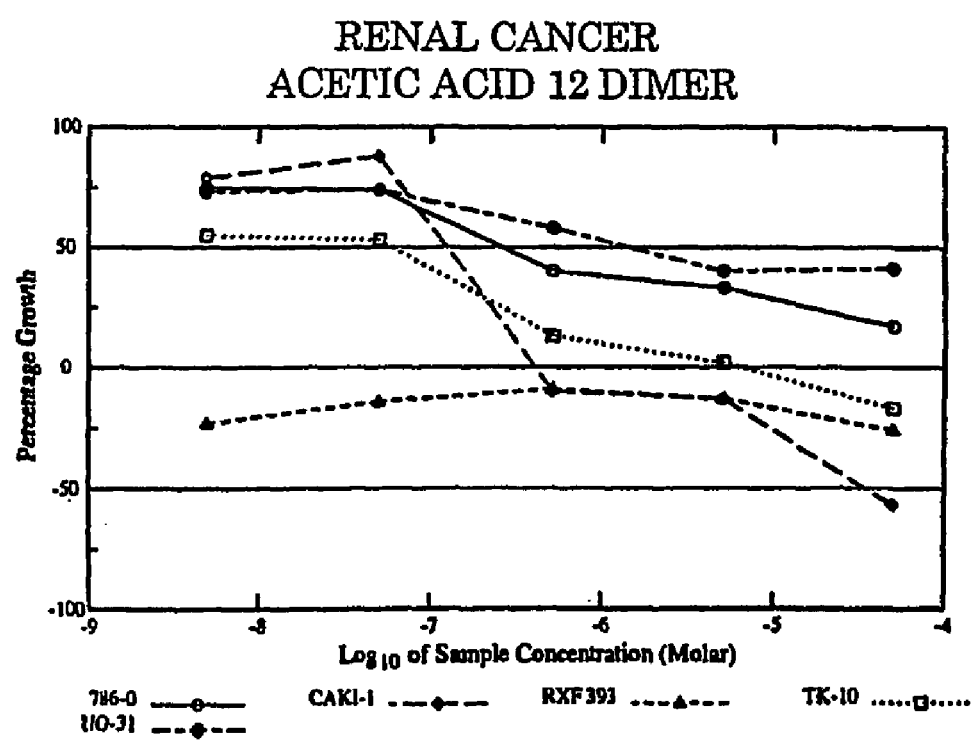

FIG. 13i depicts the dose response curves generated by exposing various renal cancer cell lines to various concentrations of the bis-trioxane O-acetic acid 12b of the present invention.

Figure 13J:
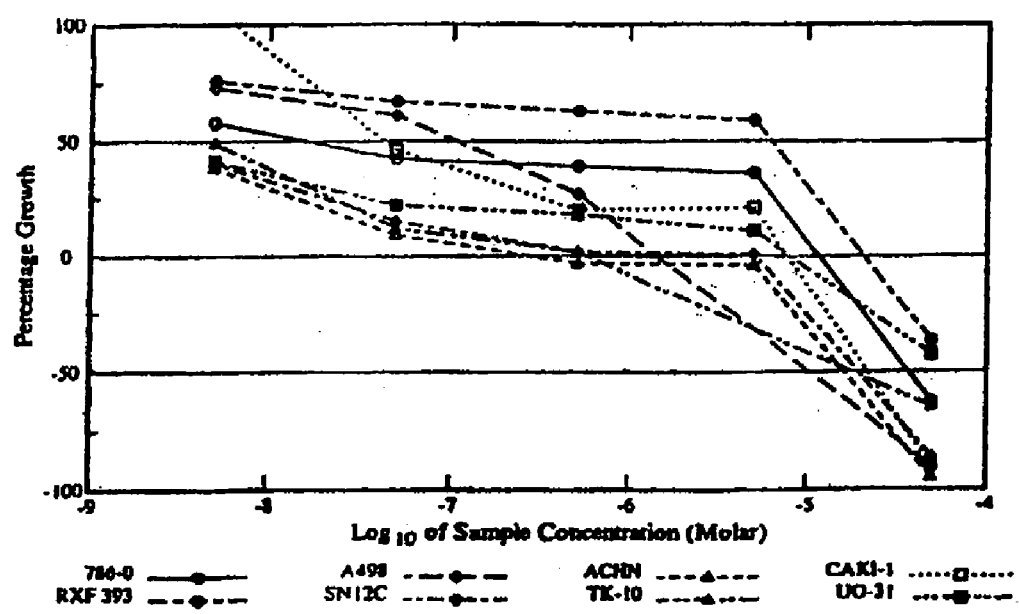

FIG. 13j depicts the dose response curves generated by exposing various renal cancer cell lines to various concentrations of the bis-trioxane primary alcohol isonicotinate N-oxide 13 of the present invention.

Figure 13K:
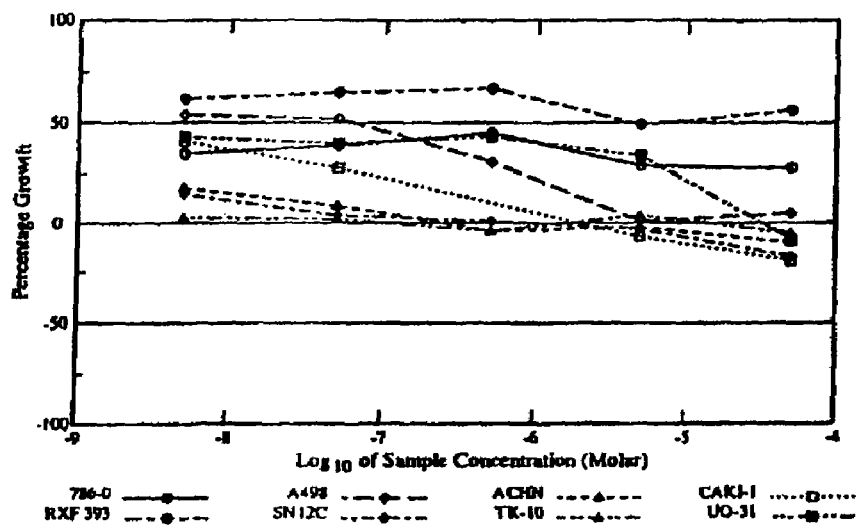

FIG. 13k depicts the dose response curves generated by exposing various renal cancer cell lines to various concentrations of the bis-trioxane diphenyl phosphate dimer 14 of the present invention.

Figure 14A:
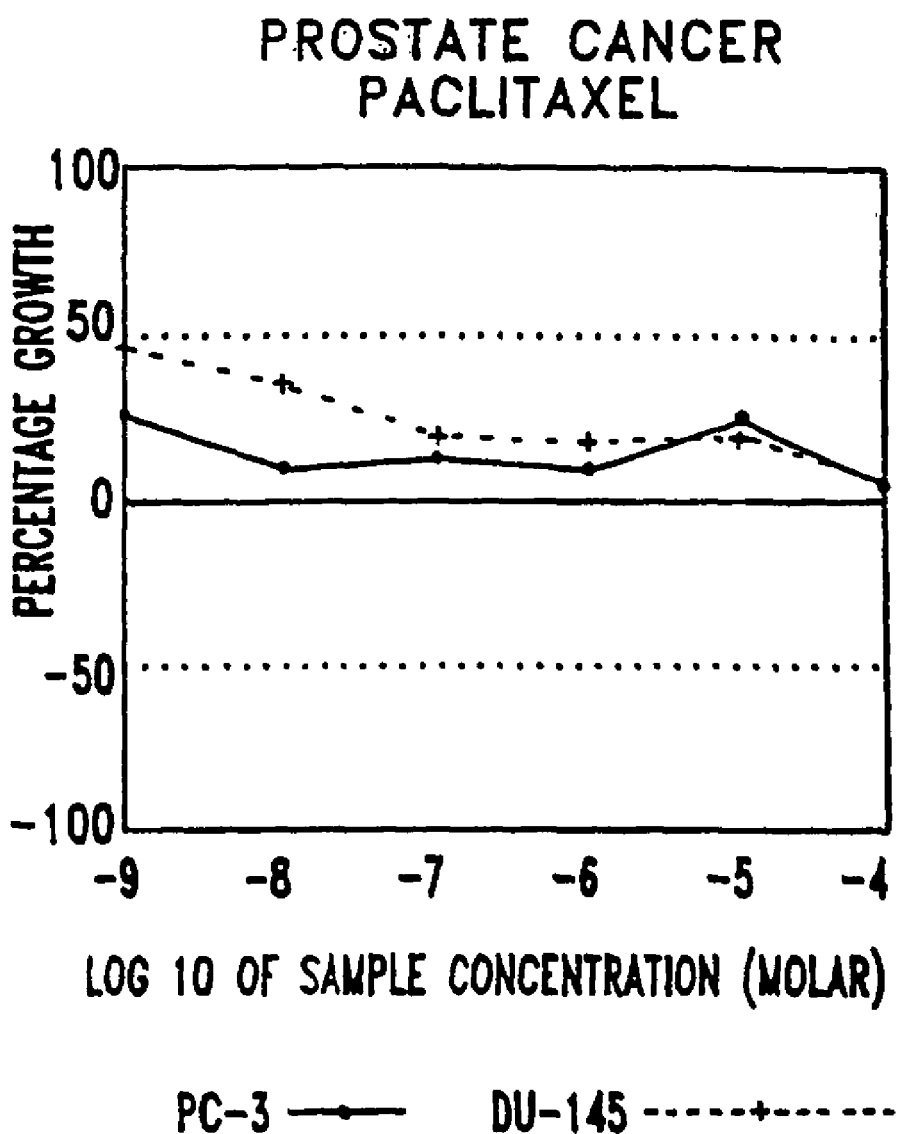

FIG. 14a depicts the dose response curves generated by exposing various prostate cancer cell lines to various concentrations of paclitaxel.

Figure 14B:
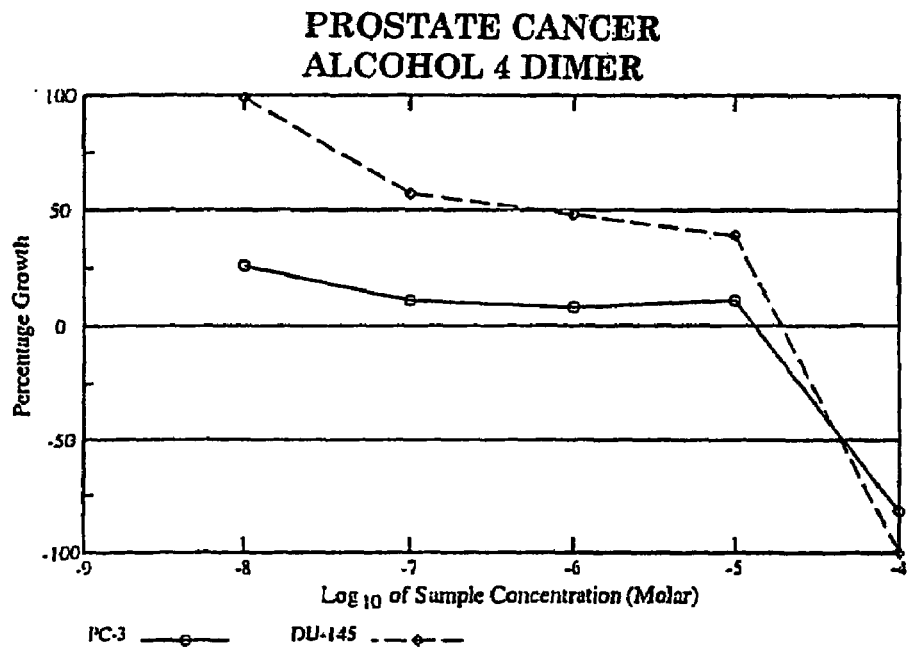

FIG. 14b depicts the dose response curves generated by exposing various prostate cancer cell lines to various concentrations of the bis-trioxane primary alcohol 4 of the present invention.

Figure 14C:
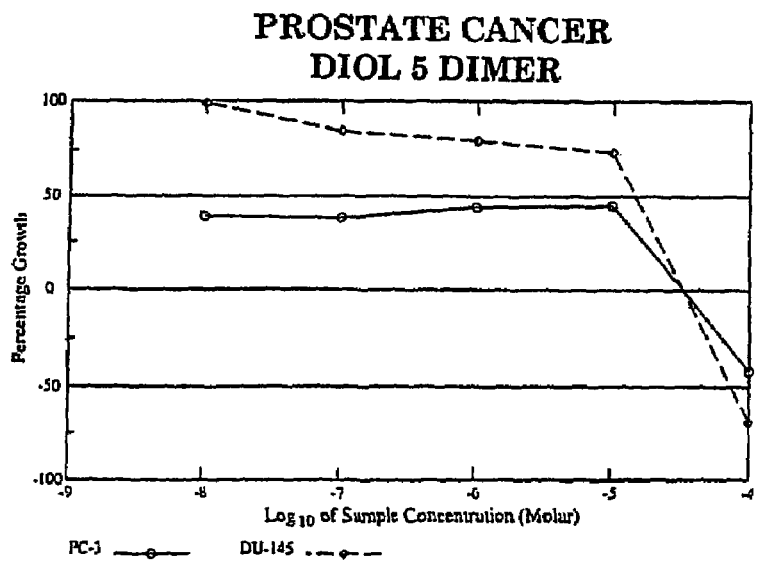

FIG. 14c depicts the dose response curves generated by exposing various prostate cancer cell lines to various concentrations of the bis-trioxane vicinal diol 5 of the present invention.

Figure 14D:
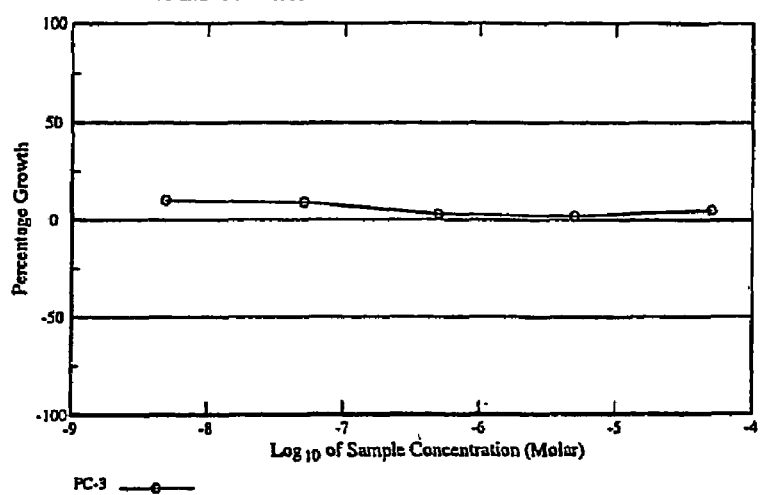

FIG. 14d depicts the dose response curves generated by exposing various prostate cancer cell lines to various concentrations of the bis-trioxane primary succinate monoester 8a of the present invention.

Figure 14E:
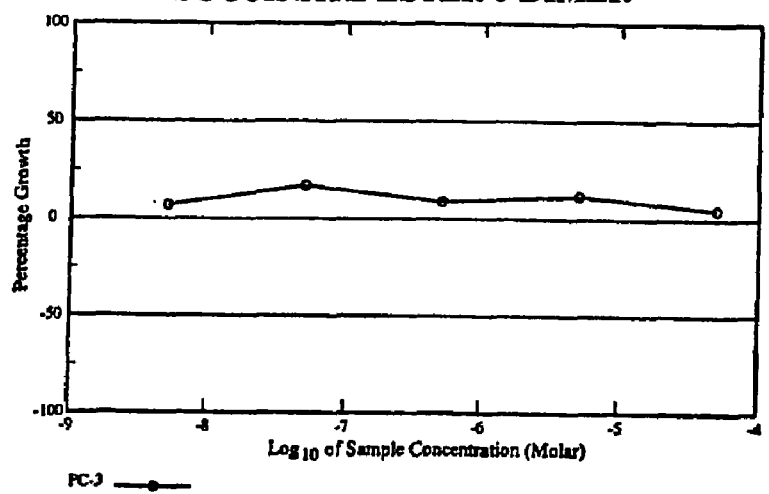

FIG. 14e depicts the dose response curves generated by exposing various prostate cancer cell lines to various concentrations of the succinate ester 9 of the present invention.

Figure 14F:
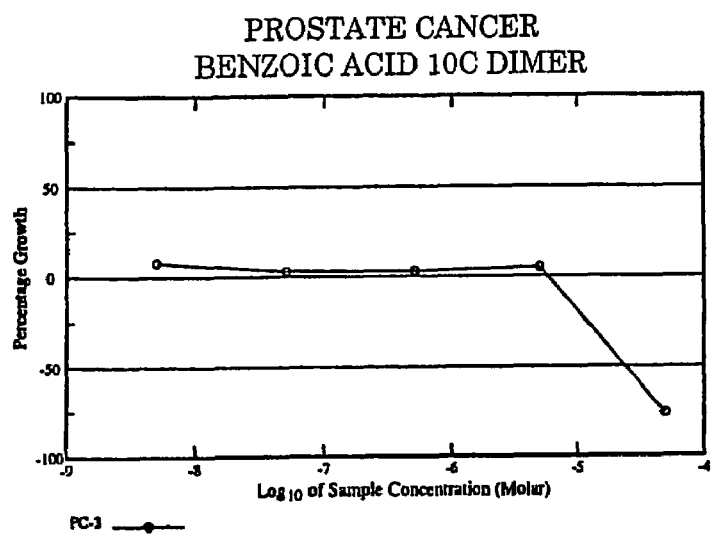

FIG. 14f depicts the dose response curves generated by exposing various prostate cancer cell lines to various concentrations of the bis-trioxane β-hydroxysulfone benzoic acid 10c of the present invention.

Figure 14G:
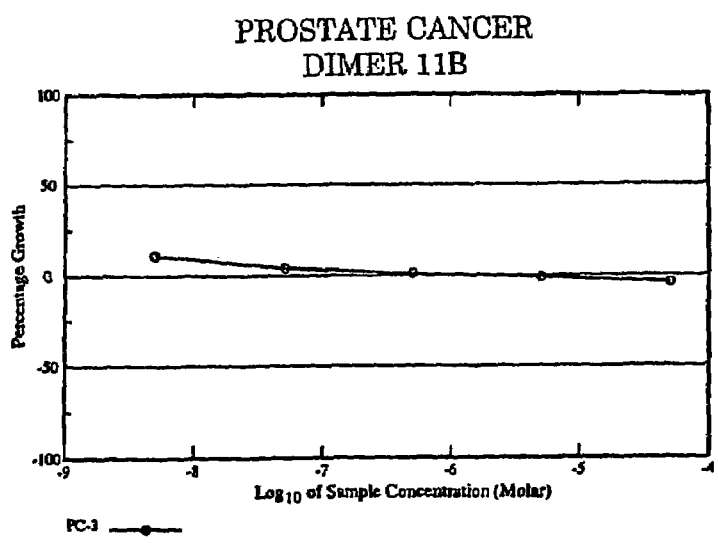

FIG. 14g depicts the dose response curves generated by exposing various prostate cancer cell lines to various concentrations of the bis-trioxane tertiary alcohol benzoic acid 11b of the present invention.

Figure 14H:
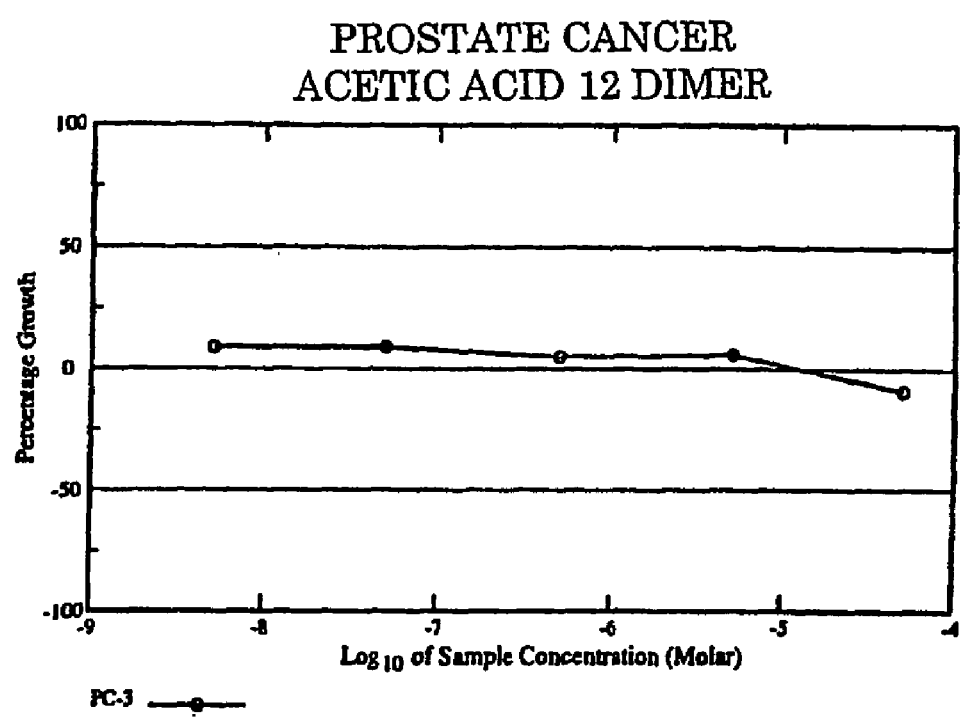

FIG. 14h depicts the dose response curves generated by exposing various prostate cancer cell lines to various concentrations of the bis-trioxane O-acetic acid 12b of the present invention.

Figure 14I:
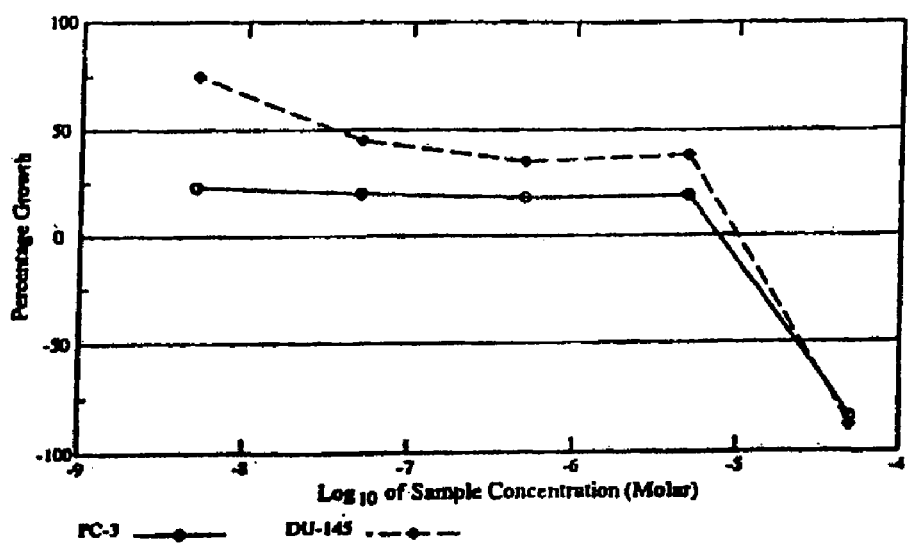

FIG. 14i depicts the dose response curves generated by exposing various prostate cancer cell lines to various concentrations of the bis-trioxane primary alcohol isonicotinate N-oxide 13 of the present invention.

Figure 14J:
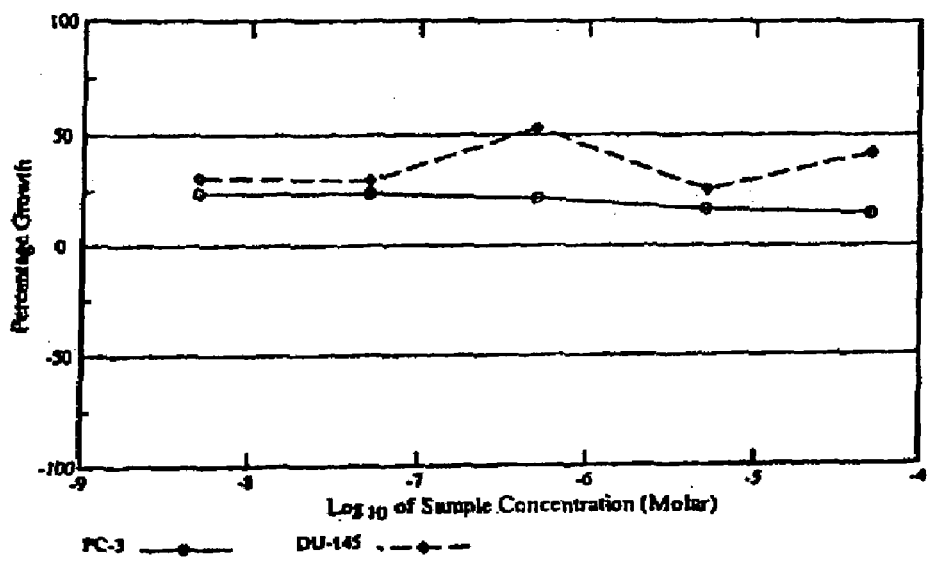

FIG. 14j depicts the dose response curves generated by exposing various prostate cancer cell lines to various concentrations of the bis-trioxane diphenyl phosphate dimer 14 of the present invention.

Figure 15A:
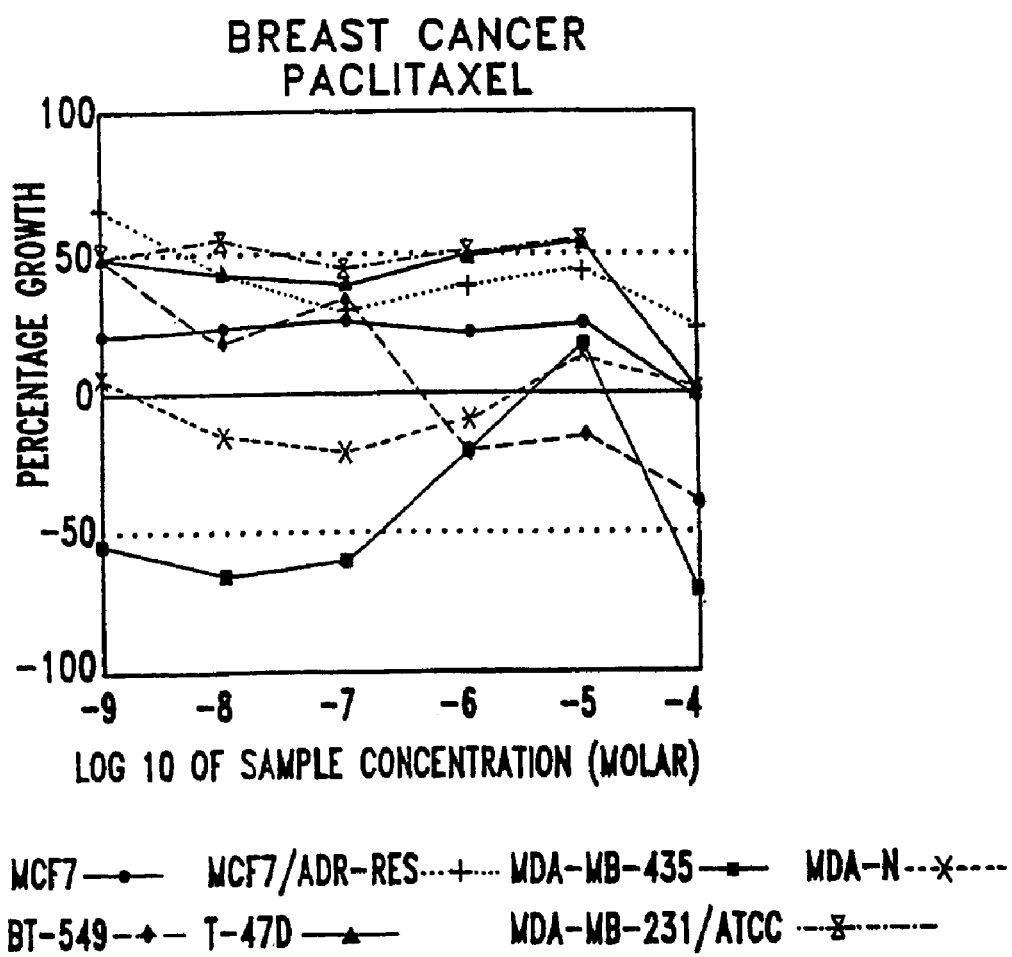

FIG. 15a depicts the dose response curves generated by exposing various breast cancer cell lines to various concentrations of paclitaxel.

Figure 15B:
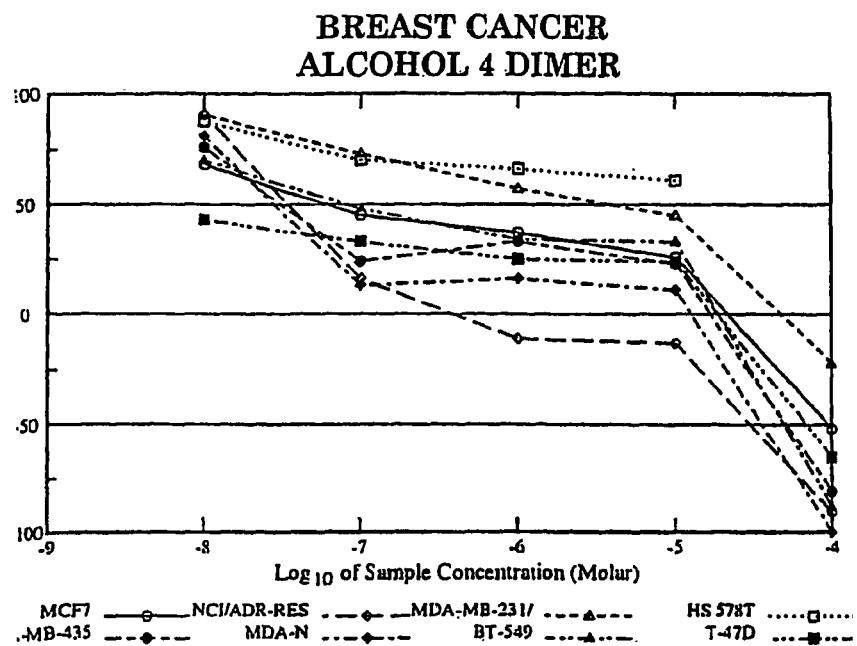

FIG. 15b depicts the dose response curves generated by exposing various breast cancer cell lines to various concentrations of the bis-trioxane primary alcohol 4 of the present invention.

Figure 15C:
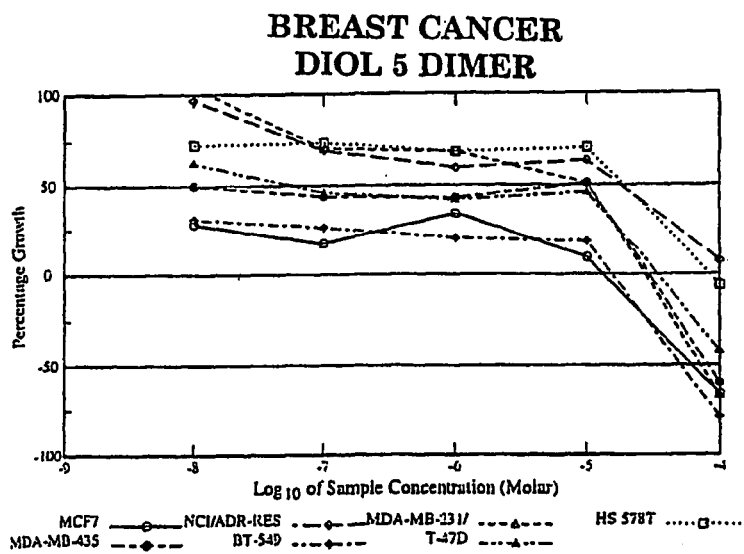

FIG. 15c depicts the dose response curves generated by exposing various breast cancer cell lines to various concentrations of the bis-trioxane vicinal diol 5 of the present invention.

Figure 15D:
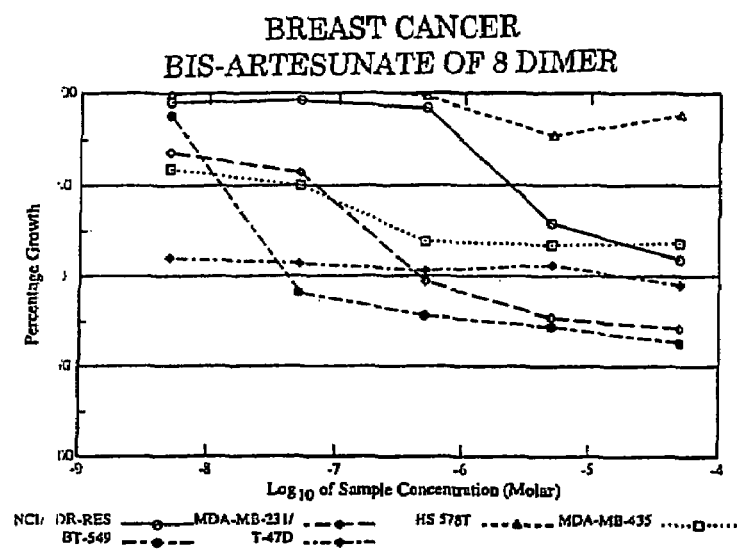

FIG. 15d depicts the dose response curves generated by exposing various breast cancer cell lines to various concentrations of the bis-trioxane primary succinate monoester 8a of the present invention.

Figure 15E:
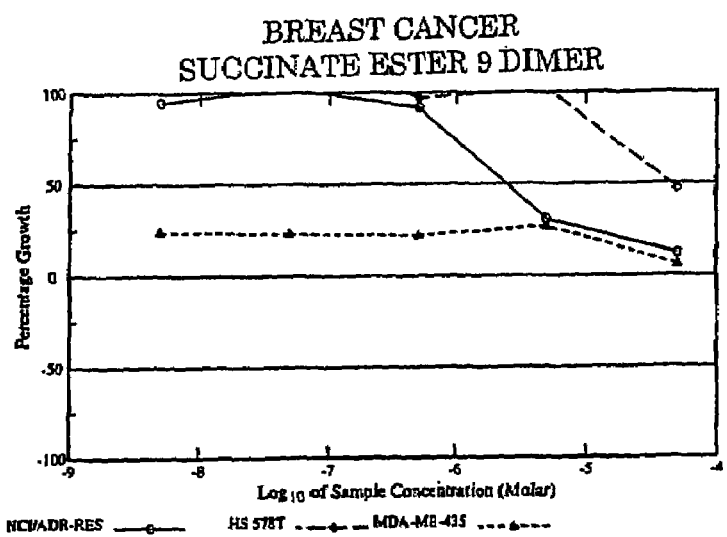

FIG. 15e depicts the dose response curves generated by exposing various breast cancer cell lines to various concentrations of the succinate ester 9 of the present invention.

Figure 15F:
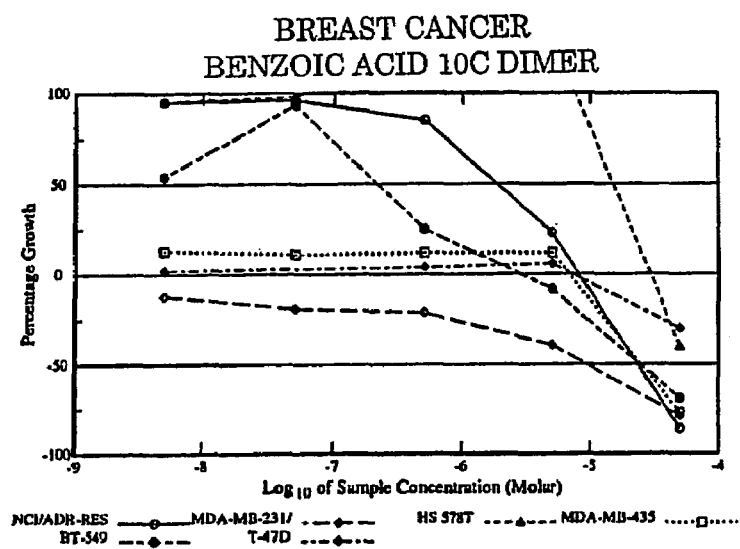

FIG. 15f depicts the dose response curves generated by exposing various breast cancer cell lines to various concentrations of the bis-trioxane β-hydroxysulfone benzoic acid 10c of the present invention.

Figure 15G:
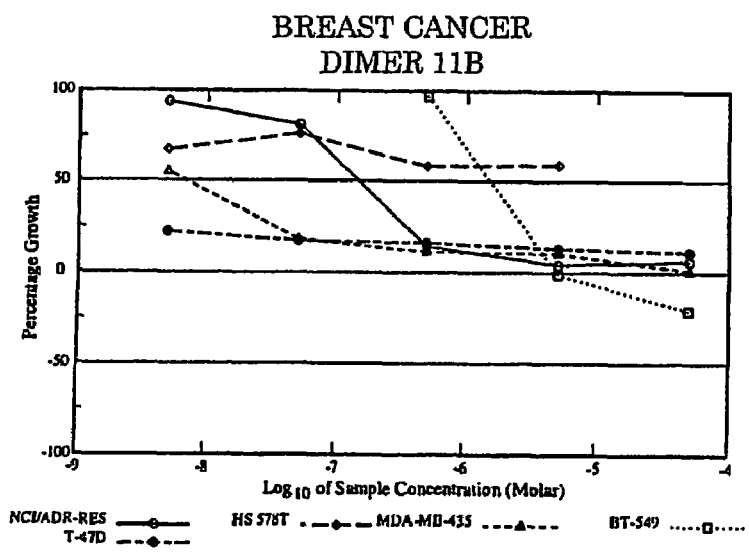

FIG. 15g depicts the dose response curves generated by exposing various breast cancer cell lines to various concentrations of the bis-trioxane tertiary alcohol benzoic acid 11b of the present invention.

Figure 15H:
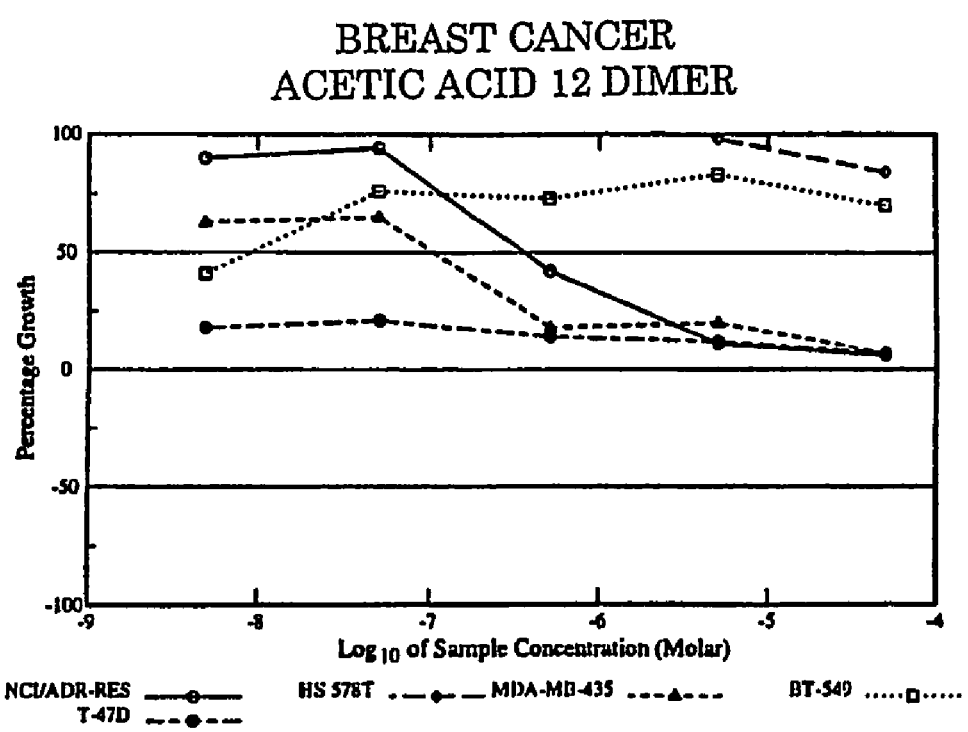

FIG. 15h depicts the dose response curves generated by exposing various breast cancer cell lines to various concentrations of the bis-trioxane O-acetic acid 12b of the present invention.

Figure 15I:
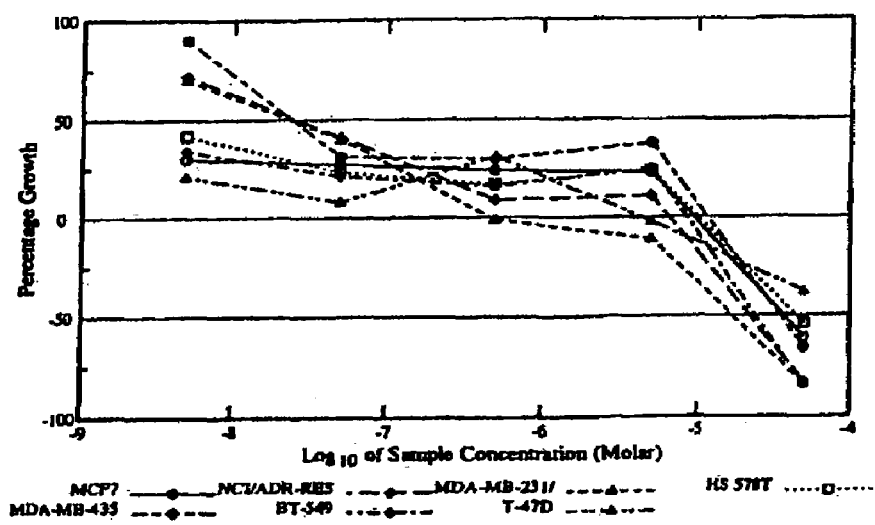

FIG. 15i depicts the dose response curves generated by exposing various breast cancer cell lines to various concentrations of the bis-trioxane primary alcohol isonicotinate N-oxide 13 of the present invention.

Figure 15J:
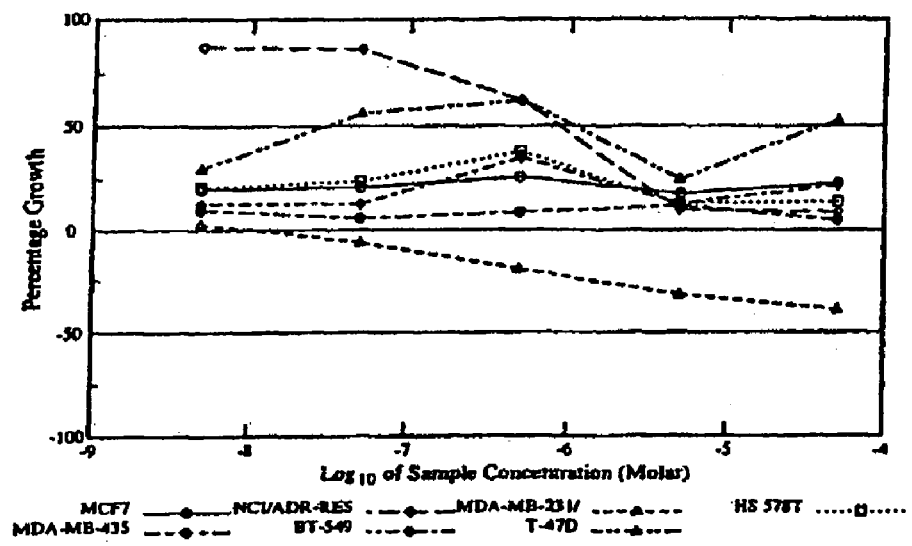

FIG. 15j depicts the dose response curves generated by exposing various breast cancer cell lines to various concentrations of the bis-trioxane diphenyl phosphate dimer 14 of the present invention.

Figure 16:
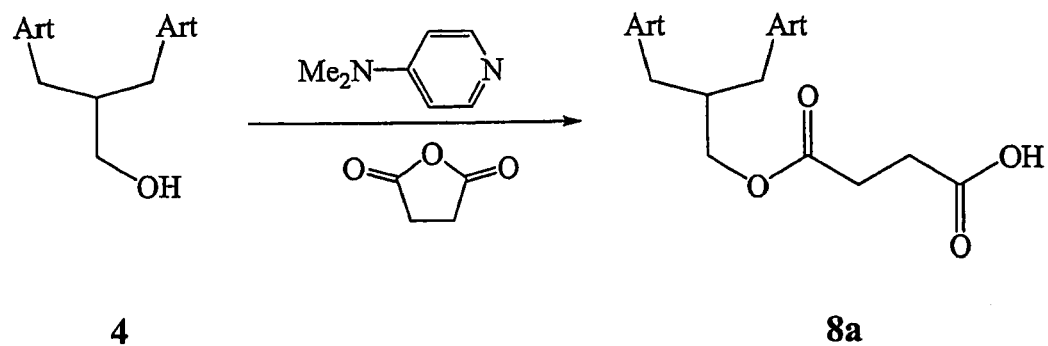

FIG. 16 schematically depicts the method of converting bis-trioxane primary alcohol 4 into bis-trioxane primary succinate monoester 8a of the present invention.

Figure 17:
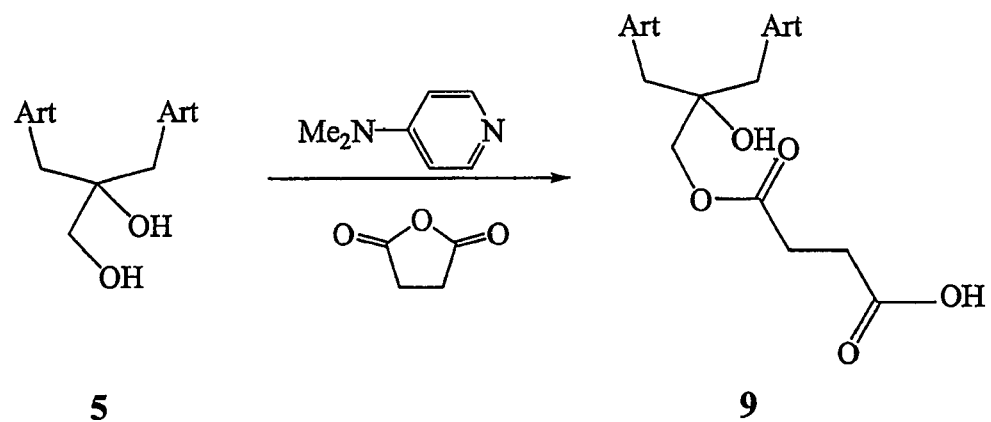

FIG. 17 schematically depicts the method of converting bis-trioxane vicinal diol 5 into the tertiary alcohol primary succinate ester 9 of the present invention.

Figure 18:
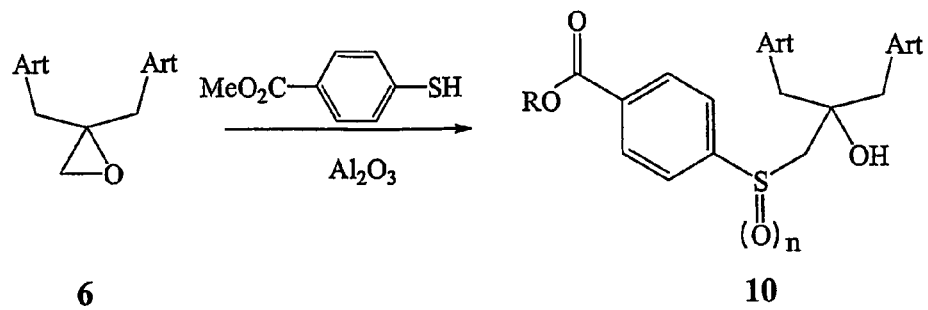
Figure 18:
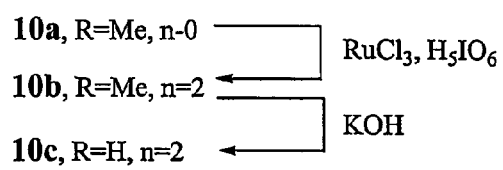

FIG. 18 schematically depicts the method of converting bis-trioxane epoxide 6 into bis-trioxane β-hydroxysulfide ester 10a, sulfide to sulfone oxidation gave bis-trioxane β-hydroxysulfone ester 10b that was saponified into bis-trioxane β-hydroxysulfone benzoic acid 10c of the present invention.

Figure 19:
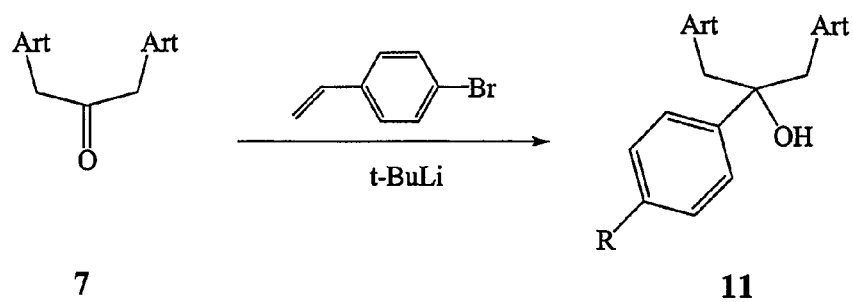
Figure 19:
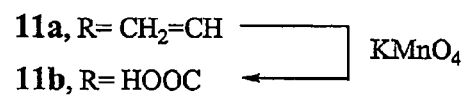

FIG. 19 schematically depicts the method of converting bis-trioxane ketone 7 into bis-trioxane styryl tertiary alcohol 11a and bis-trioxane tertiary alcohol benzoic acid 11b of the present invention.

Figure 20:
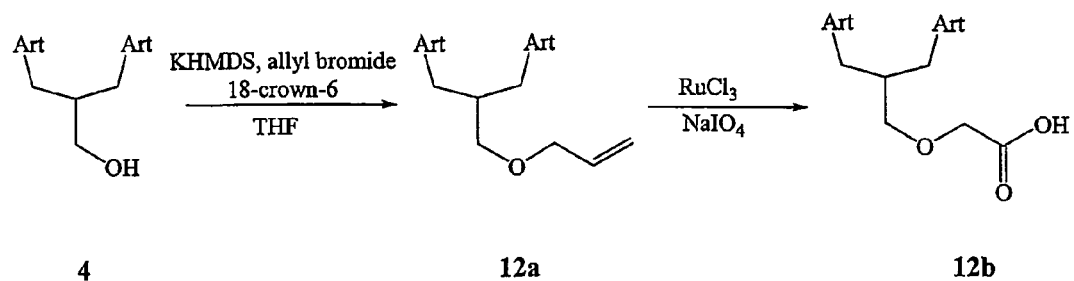

FIG. 20 schematically depicts the method of converting primary alcohol 4 to the bis-trioxane O-allyl ether 12a and bis-trioxane O-acetic acid 12b of the present invention.

Figure 21:
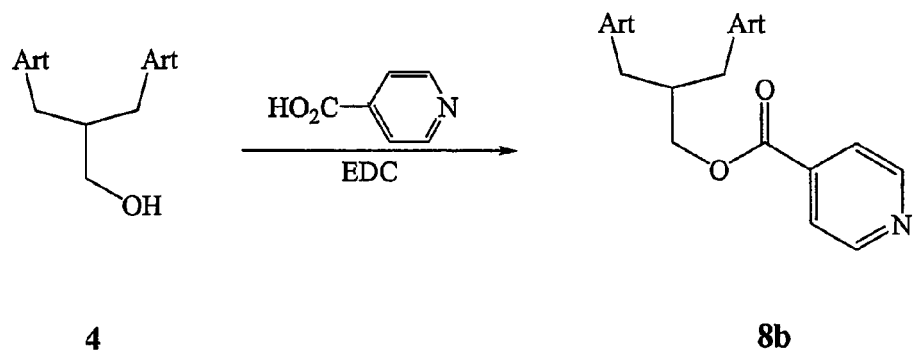

FIG. 21 schematically depicts the method of converting primary alcohol 4 to the bis-trioxane primary alcohol isonicotinate 8b of the present invention.

Figure 22:
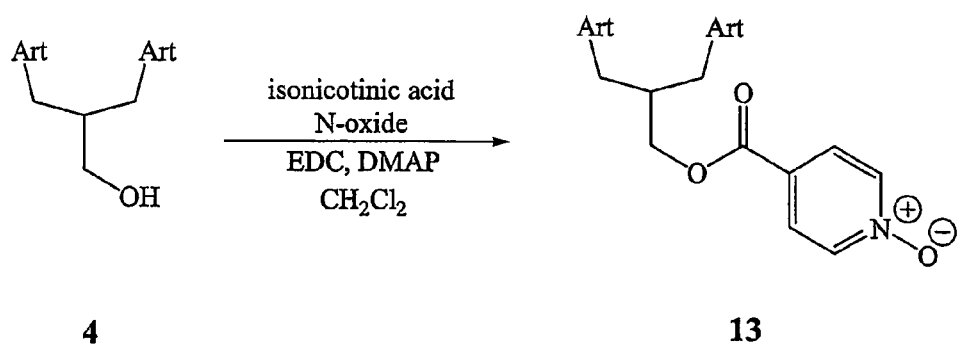

FIG. 22 schematically depicts the method of converting primary alcohol 4 to the bis-trioxane primary alcohol isonicotinate N-oxide 13 of the present invention.

Figure 23:
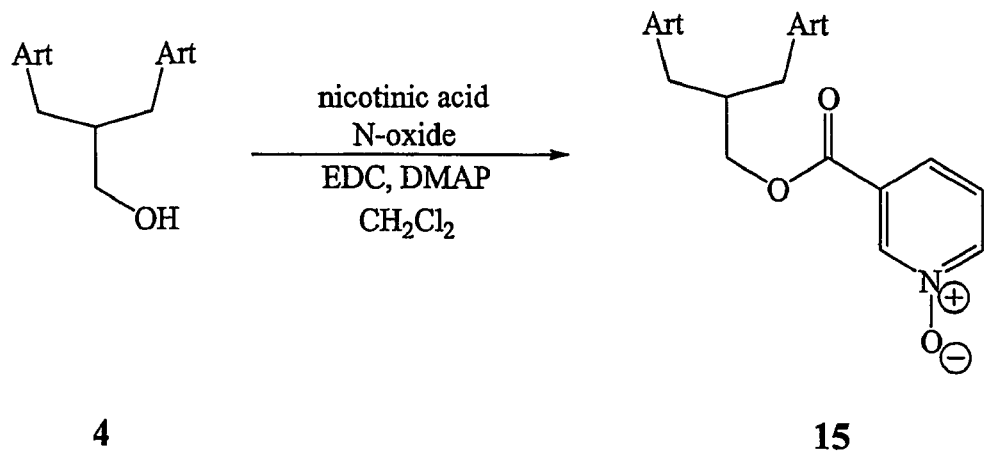

FIG. 23 schematically depicts the method of converting primary alcohol 4 to the bis-trioxane primary alcohol nicotinate N-oxide 15 of the present invention.

Figure 24:
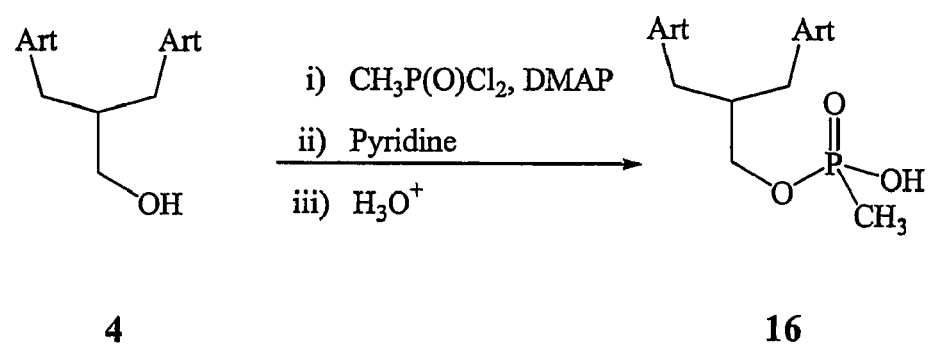

FIG. 24 schematically depicts the method of converting primary alcohol 4 to the bis-trioxane phosphonic acid monoester 16 of the present invention.

Figure 25:
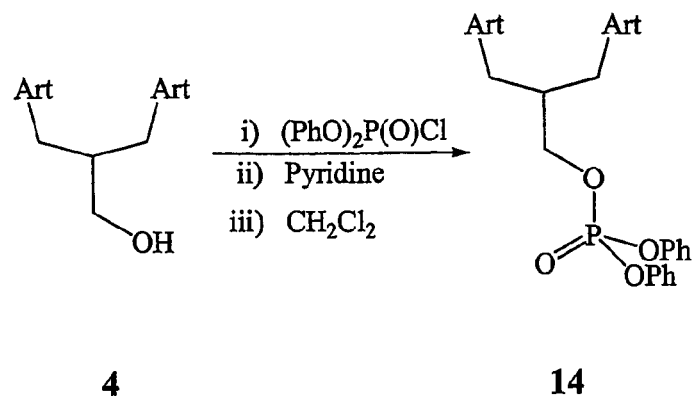

FIG. 25 schematically depicts the method of converting primary alcohol 4 to the bis-trioxane diphenyl phosphate 14 of the present invention.

Figure 26:
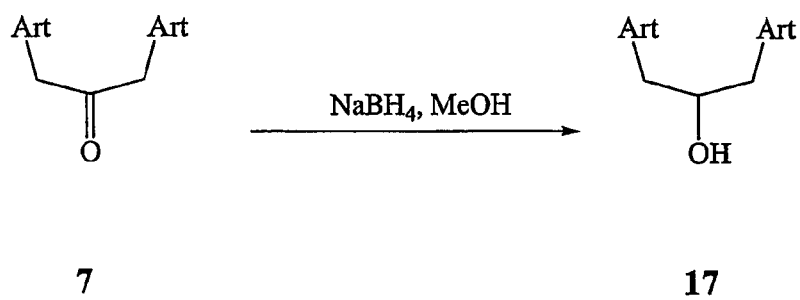

FIG. 26 schematically depicts the method of converting bis-trioxane ketone 7 to the bis-trioxane secondary alcohol 17 of the present invention.

Figure 27:
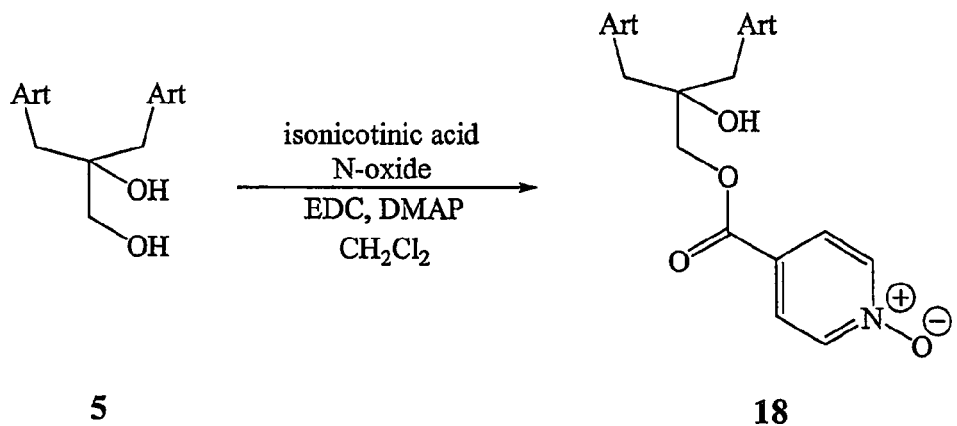

FIG. 27 schematically depicts the method of converting bis-trioxane vicinal diol 5 to the bis-trioxane vicinal diol isonicotinate N-oxide 18 of the present invention.

Figure 28:
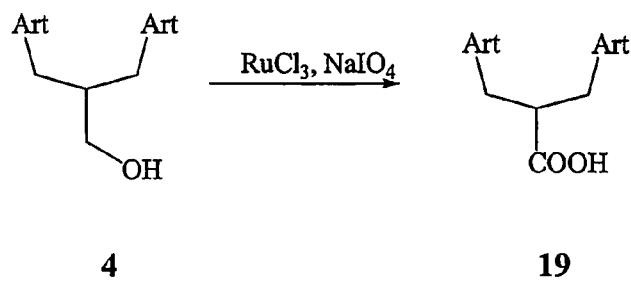

FIG. 28 schematically depicts the method of converting bis-trioxane vicinal diol 5 to the bis-trioxane isobutyric acid 19 of the present invention.

Figure 29:
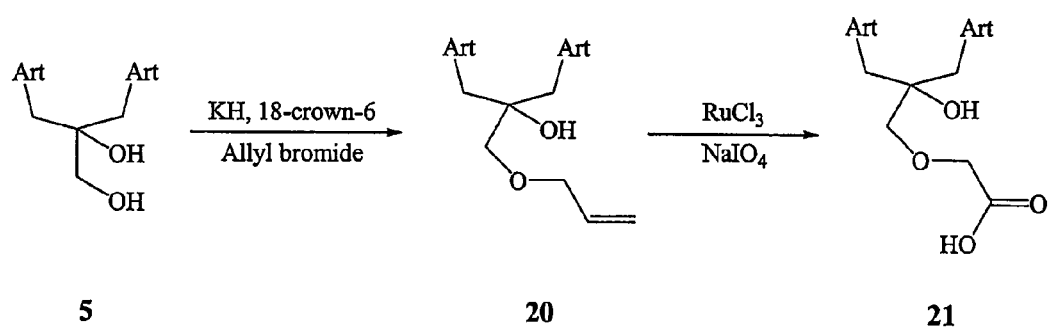

FIG. 29 schematically depicts the method of converting bis-trioxane vicinal diol 5 to the bis-trioxane β-hydroxy O-allyl ether 20 and then on to the bis-trioxane β-hydroxy O-acetic acid 21 of the present invention.

Figure 30:
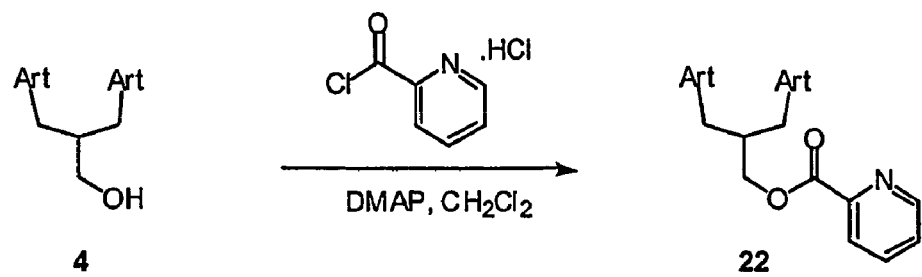

FIG. 30 schematically depicts the method of converting bis-trioxane primary alcohol 4 to the bis-trioxane primary alcohol picolinate 22 of the present invention.

Figure 31:
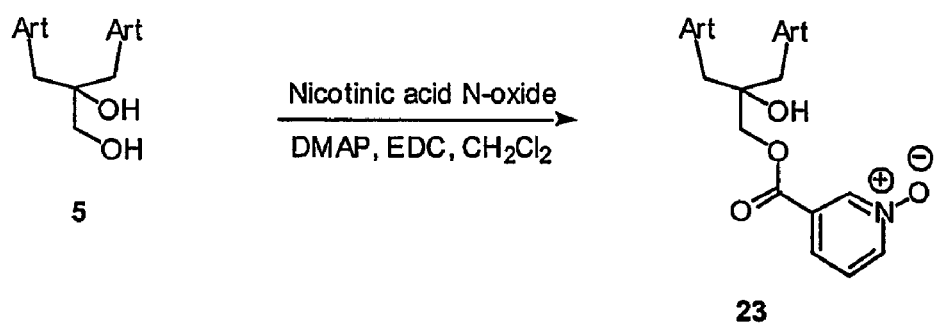

FIG. 31 schematically depicts the method of converting bis-trioxane vicinal diol 5 to the bis-trioxane vicinal diol nicotinate N-oxide 23 of the present invention.

Figure 32:
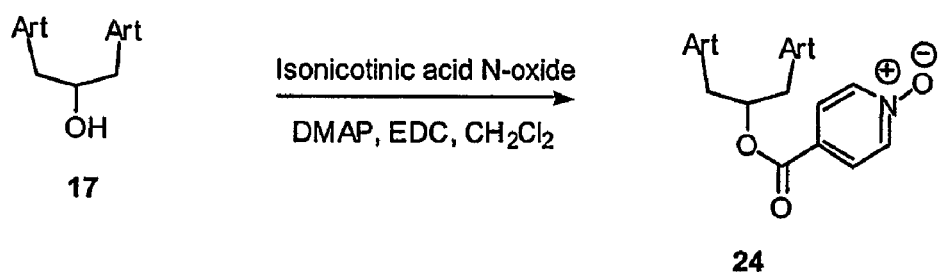

FIG. 32 schematically depicts the method of converting bis-trioxane secondary alcohol 17 to the bis-trioxane secondary alcohol isonicotinate N-oxide 24 of the present invention.

Figure 33:
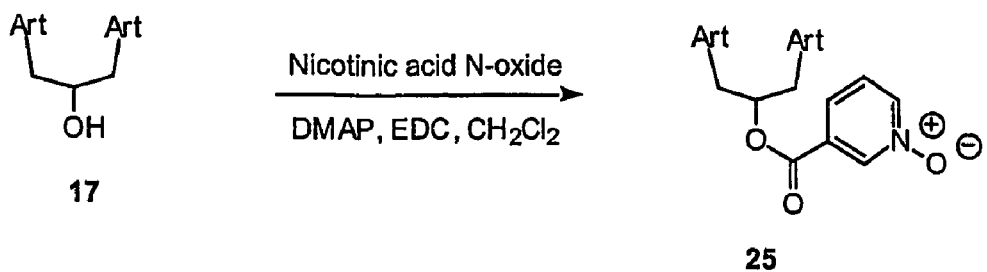

FIG. 33 schematically depicts the method of converting bis-trioxane secondary alcohol 17 to the bis-trioxane secondary alcohol nicotinate N-oxide 25 of the present invention.

Figure 34:
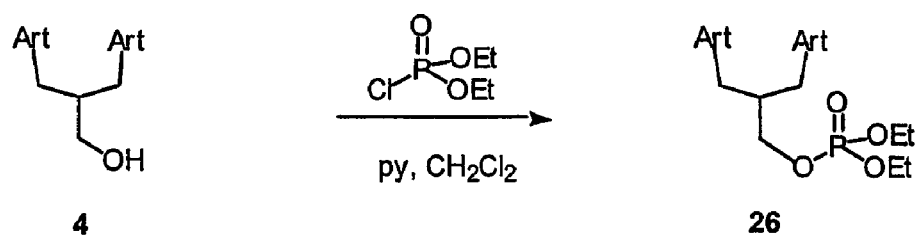

FIG. 34 schematically depicts the method of converting bis-trioxane primary alcohol 4 to the bis-trioxane primary alcohol diethyl phosphoric acid triester 26 of the present invention.

Figure 35:
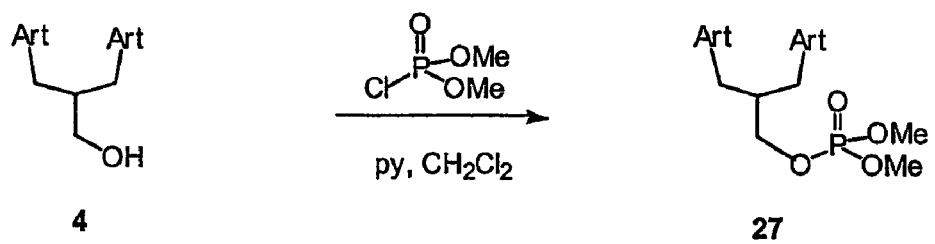

FIG. 35 schematically depicts the method of converting bis-trioxane primary alcohol 4 to the bis-trioxane primary alcohol dimethyl phosphoric acid triester 27 of the present invention.

Figure 36:
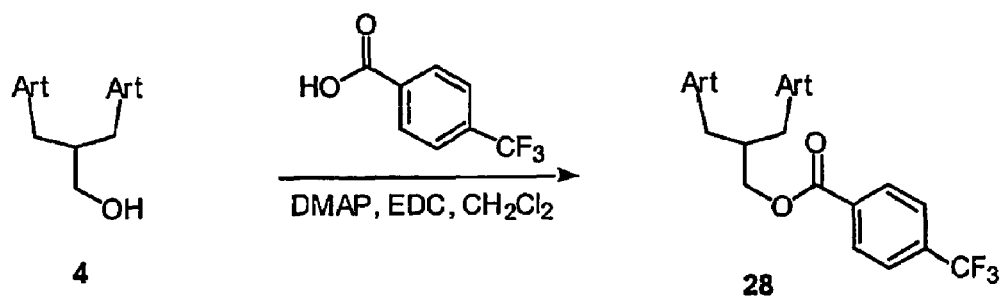

FIG. 36 schematically depicts the method of converting bis-trioxane primary alcohol 4 to the bis-trioxane primary alcohol p-trifluoromethylbenzoate 28 of the present invention.

Figure 37:
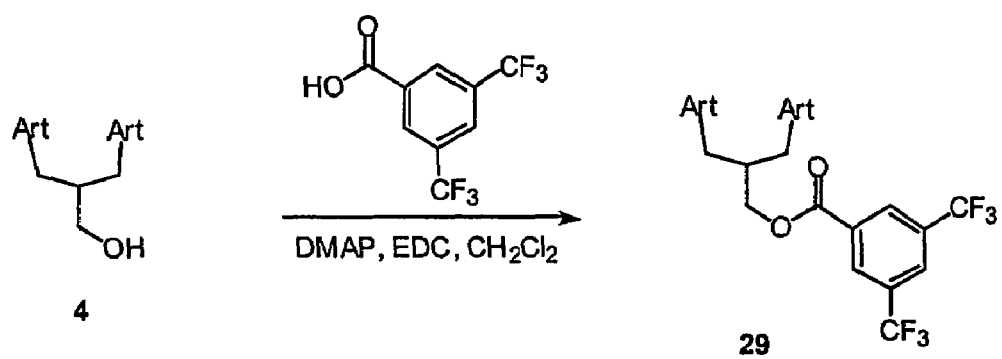

FIG. 37 schematically depicts the method of converting bis-trioxane primary alcohol 4 to the bis-trioxane primary alcohol 3,5-ditrifluoromethylbenzoate 29 of the present invention.

Figure 38:
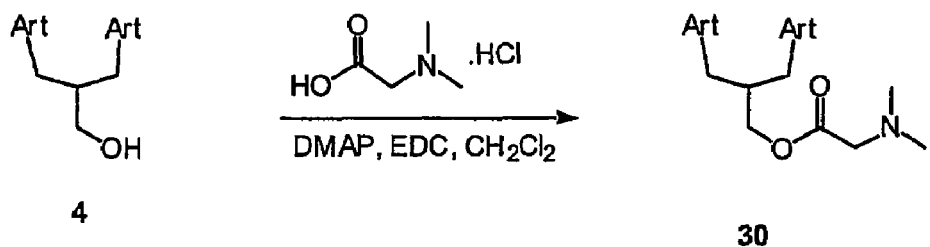

FIG. 38 schematically depicts the method of converting bis-trioxane primary alcohol 4 to the bis-trioxane primary alcohol dimethylgylcinate 30 of the present invention.

Figure 39:
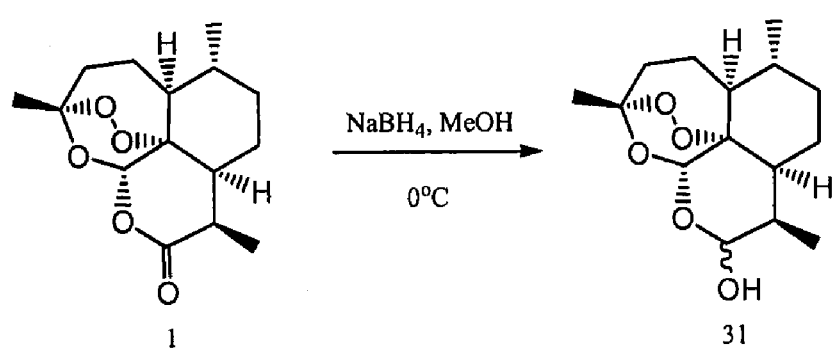

FIG. 39 schematically depicts the method of converting artemisinin 1 to the dihydroartemisinin 31 of the present invention.

Figure 40:
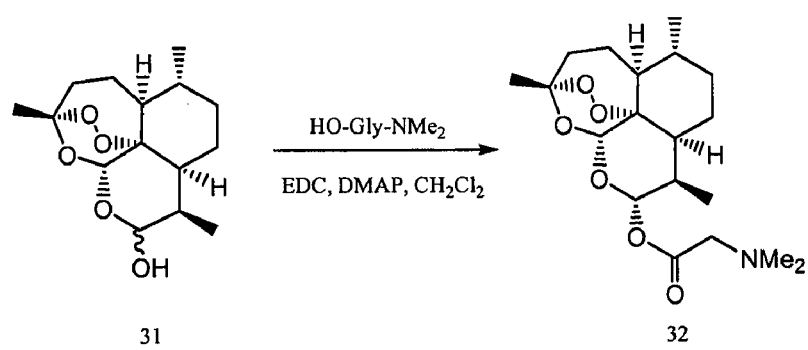

FIG. 40 schematically depicts the method of converting dihydroartemisinin 31 to the α-dihydroartemisinin dimethylglycinate 32 of the present invention.

Figure 41:
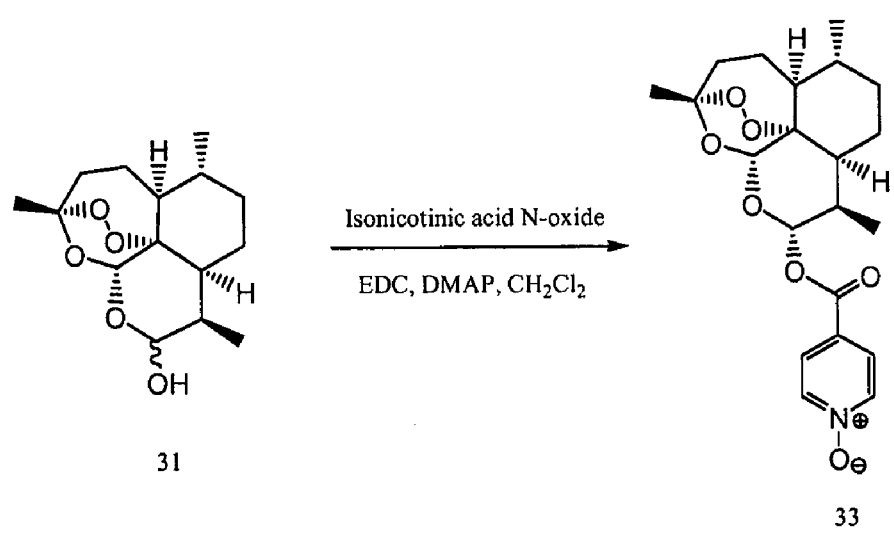
Figure 41:
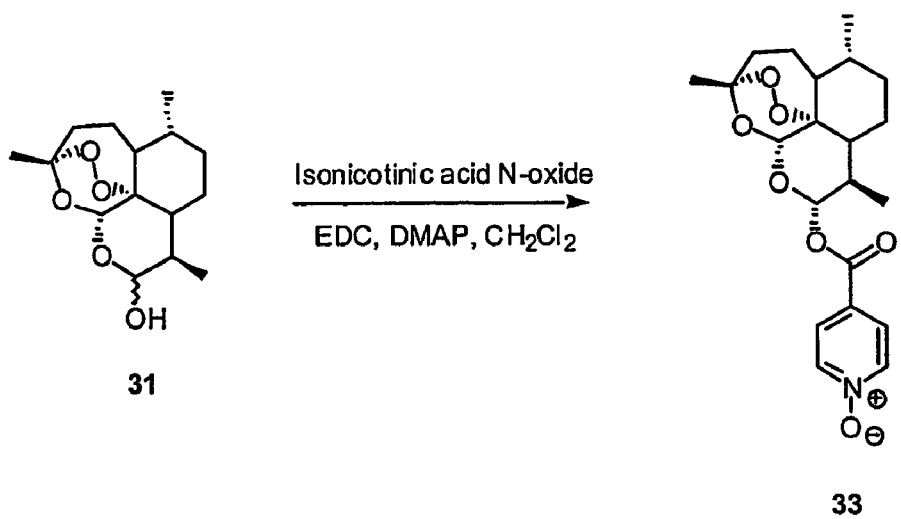

FIG. 41 schematically depicts the method of converting dihydroartemisinin 31 to the α-dihydroartemisinin isonicotinate N-oxide 33 of the present invention.

Figure 42:
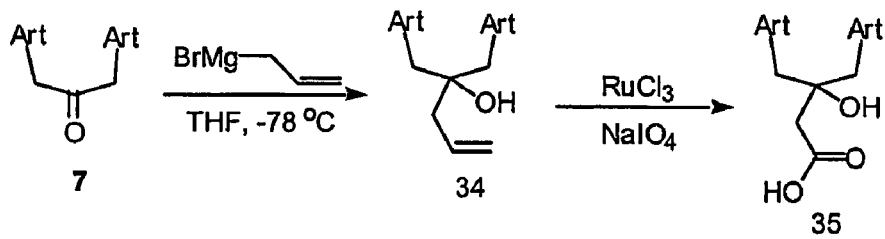

FIG. 42 schematically depicts the method of converting bis-trioxane ketone 7 to the bis-trioxane allyl tertiary alcohol 34 and the method of converting bis-trioxane allyl tertiary alcohol 34 to the bis-trioxane tertiary alcohol carboxylic acid 35 of the present invention.

Figure 43:
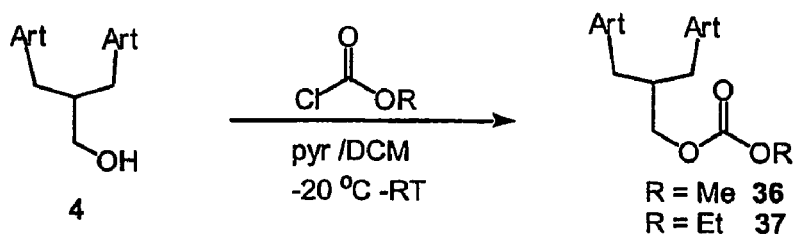

FIG. 43 schematically depicts the method of converting bis-trioxane primary alcohol 4 to the bis-trioxane primary alcohol methyl carbonate 36 and the method of converting bis-trioxane primary alcohol 4 to the bis-trioxane primary alcohol ethyl carbonate 37 of the present invention.

Figure 44:
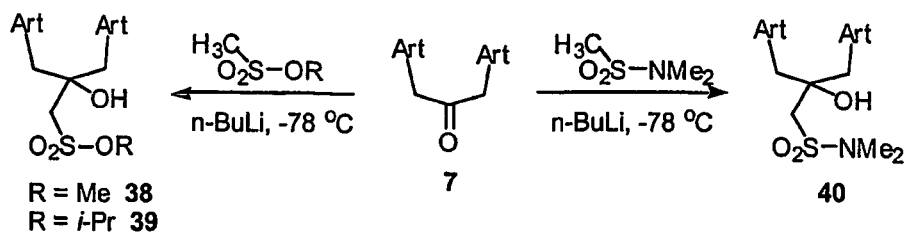

FIG. 44 schematically depicts the method of converting bis-trioxane ketone 7 to the bis-trioxane tertiary alcohol methyl sulfonate 38, the method of converting bis-trioxane ketone 7 to the bis-trioxane bis-trioxane tertiary alcohol isopropyl sulfonate 39 and the method of converting bis-trioxane ketone 7 to the bis-trioxane tertiary alcohol N,N-dimethylsulfonamide 40 of the present invention.

Figure 45:
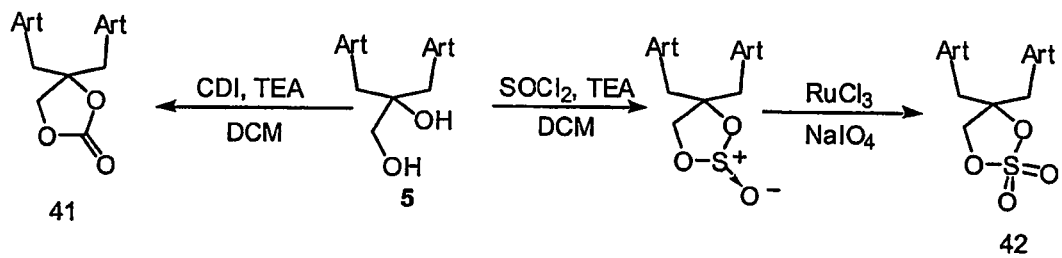

FIG. 45 schematically depicts the method of converting bis-trioxane vicinal diol 5 to the bis-trioxane vicinal diol cyclic carbonate 41 and the method of converting bis-trioxane vicinal diol 5 to the bis-trioxane vicinal diol cyclic sulfate 42 of the present invention.

Figure 46:
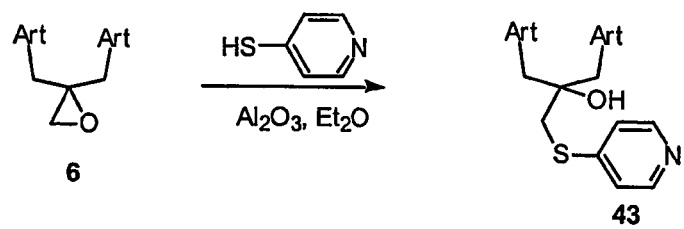

FIG. 46 schematically depicts the method of converting bis-trioxane epoxide 6 to the bis-trioxane tertiary alcohol pyridine sulfide 43 of the present invention.

Figure 47:
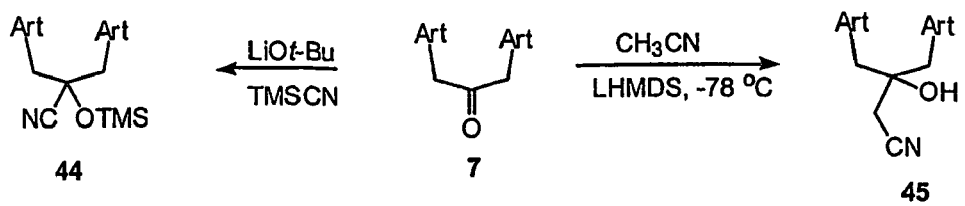

FIG. 47 schematically depicts the method of converting bis-trioxane ketone 7 to the bis-trioxane ketone O-TMS cyanohdrin 44 and the method of converting bis-trioxane ketone 7 to the bis-trioxane tertiary alcohol nitrile 45 of the present invention.

Figure 48:
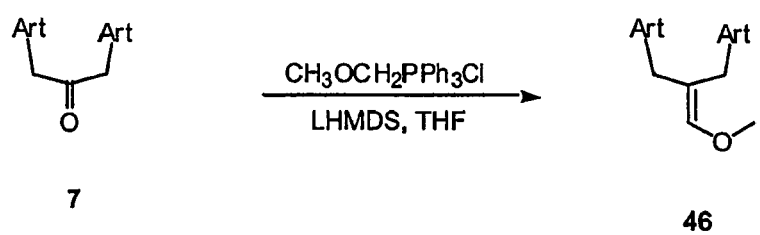

FIG. 48 schematically depicts the method of converting bis-trioxane ketone 7 to the bis-trioxane methyl enol ether 46 of the present invention.

Figure 49:
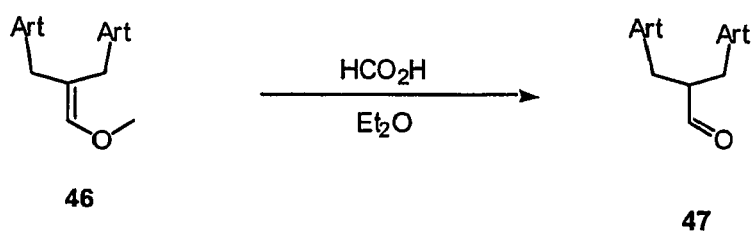

FIG. 49 schematically depicts the method of converting bis-trioxane methyl enol ether 46 to the bis-trioxane aldehyde 47 of the present invention.

Figure 50:
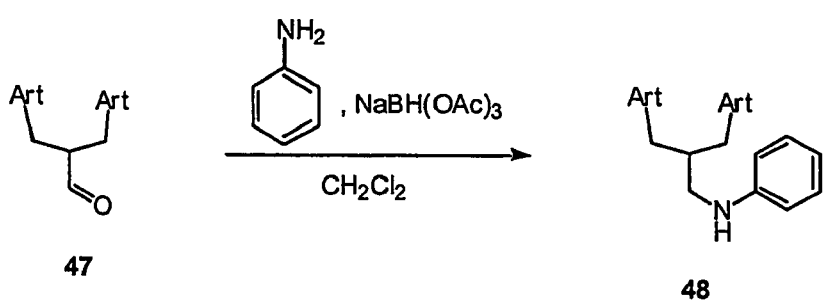

FIG. 50 schematically depicts the method of converting bis-trioxane aldehyde 47 to the bis-trioxane aniline 48 of the present invention.

Figure 51:
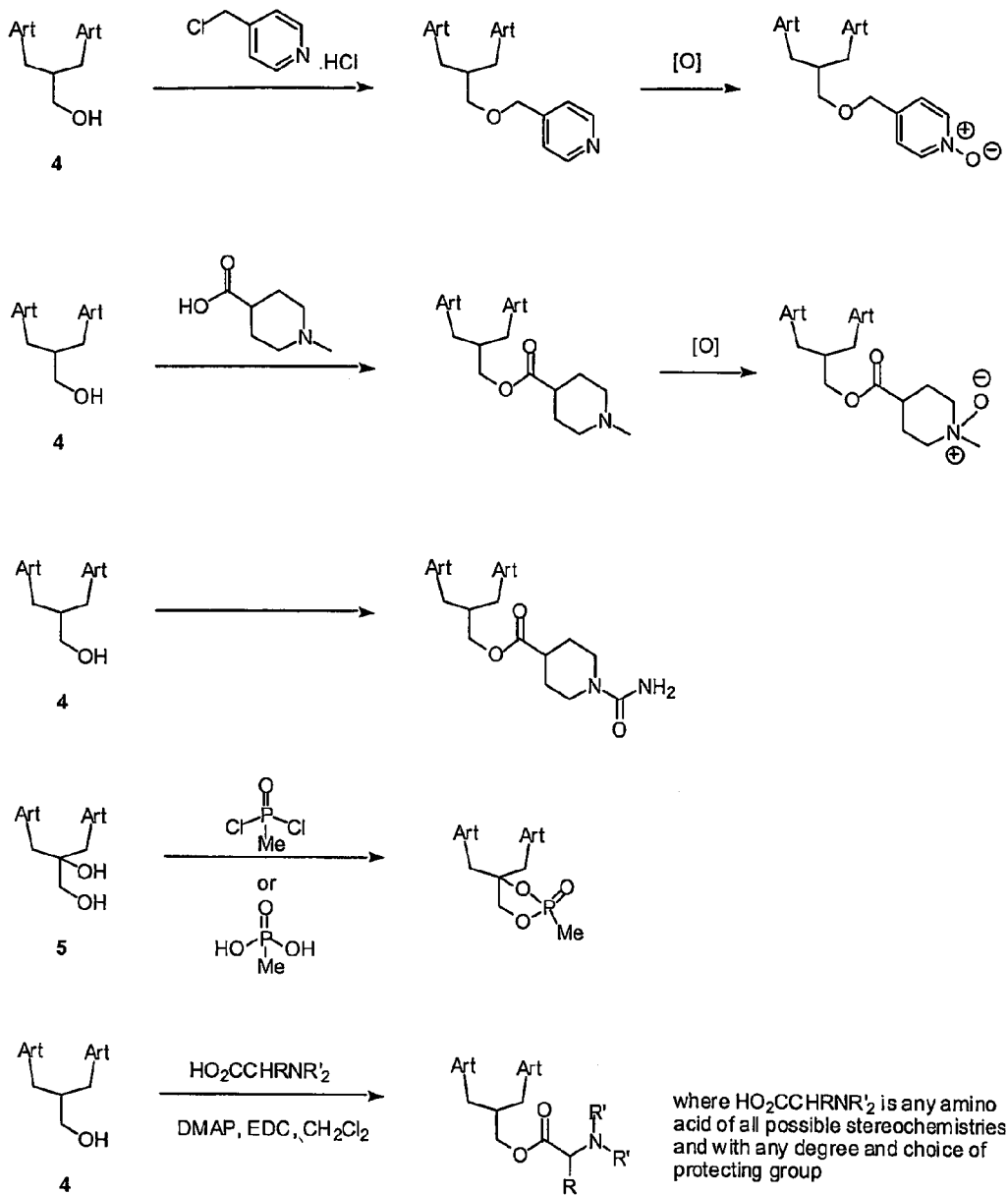

FIG. 51 schematically depicts the method of converting bis-trioxane primary alchol 4 and bis-trioxane diol 5 to a number of compounds according to the present invention. In cases where the derivatization of bis-trioxane primary alcohol 4 is shown, conversion of bis-trioxane secondary alcohol 17 and bis-trioxane diol 5 to their corresponding analogs is also in accordance with the present invention.

Figure 52:
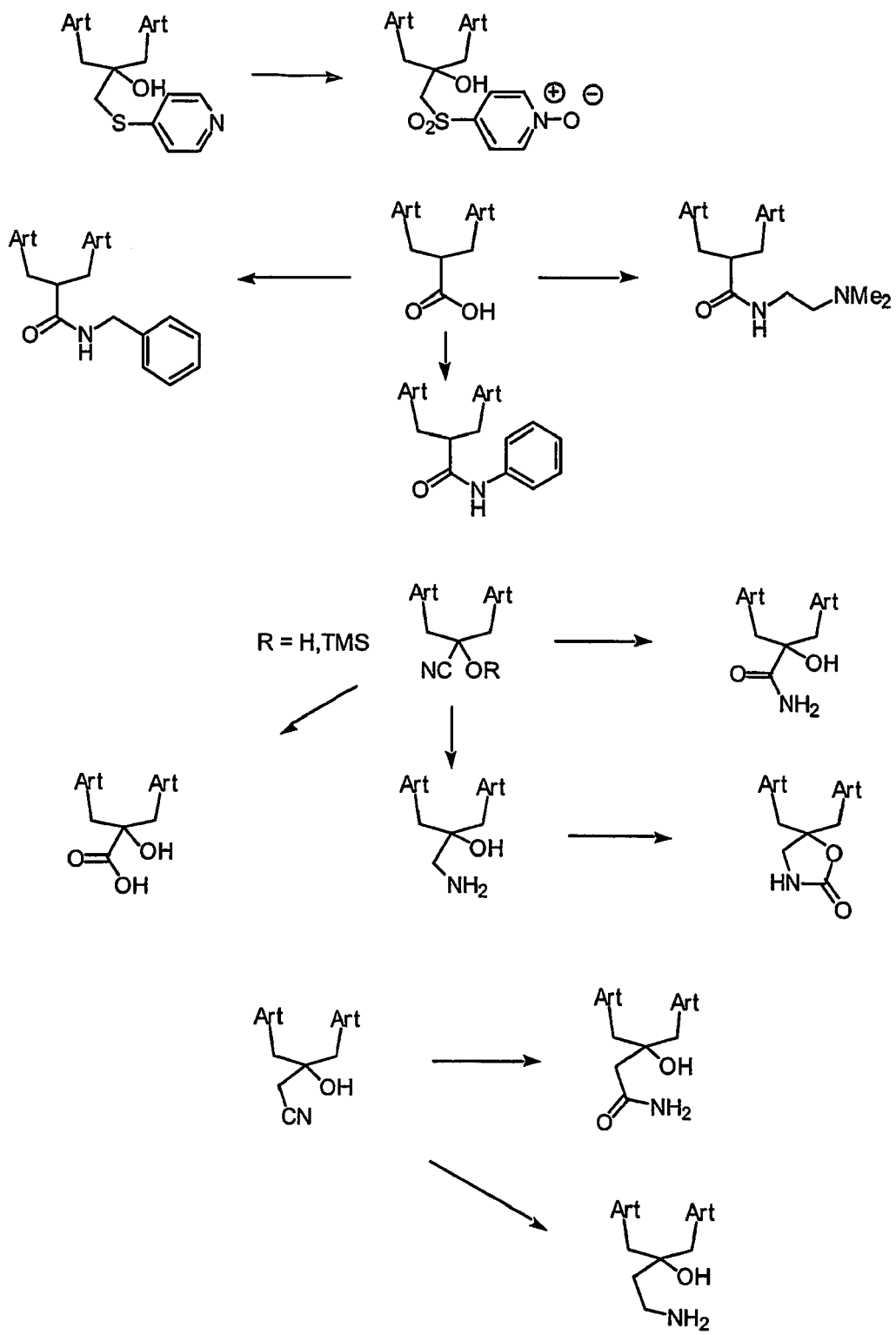

FIG. 52 schematically depicts the method of converting a number of compounds of the present invention to ten other compounds that can be synthesized according to the present invention.

Figure 53:
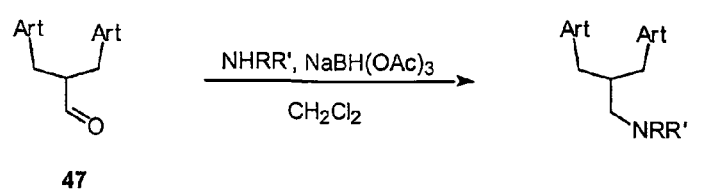

FIG. 53 schematically depicts the method of converting bis-trioxane aldehyde 47 to a range of substituted and unsubstituted amine/amide derivatives of the current invention.

Figure 54:
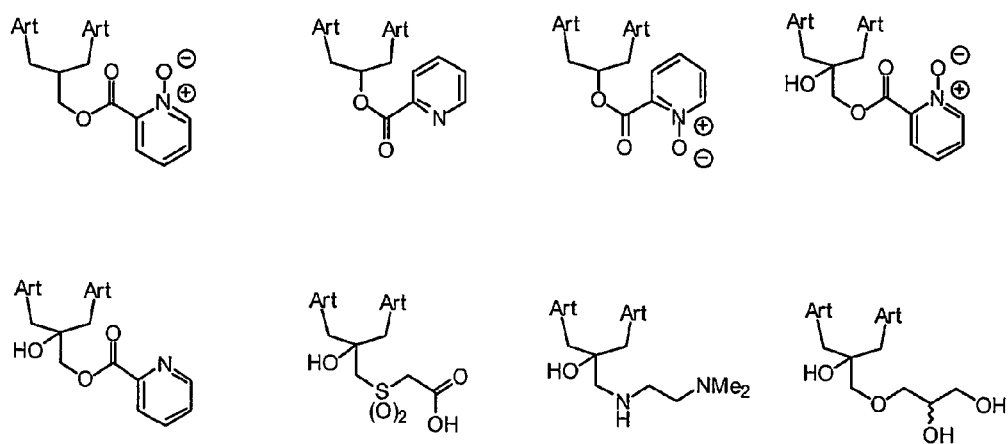

FIG. 54 represents other compounds that can be synthesized according to the present invention.

DETAILED DESCRIPTION OF THE PREFERRED EMBODIMENT

The present invention provides a direct method for converting a novel C-10-carba trioxane dimer in one step into a number of different dimers, all of which are hydrolytically stable. The resulting trioxane dimers may then be further reacted to form 3-carbon atom linked, oxygenated dimers. These C-10 non-acetal derivatives of natural trioxane artemisinin have high in vitro antimalarial and antitumor activities.

In general, the compound of the present invention includes resolved enantiomers, diastereomers, solvates and pharmaceutical acceptable salts thereof, and may be illustrated as follows:

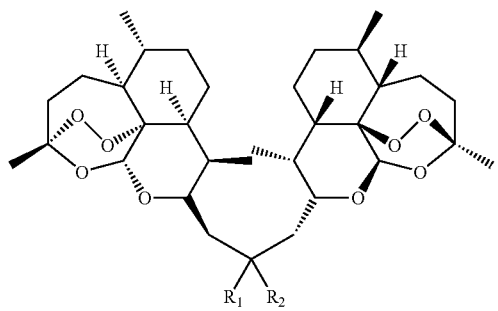

Where if $R_1$ is hydrogen or OH then $R_2$ is AX, and if $R_2$ is hydrogen or OH then $R_1$ is AX, and A may be absent or A may be any alkyl or aryl group where X is hydrogen, a phosphate group, a phosphonic acid derivative group, an alcohol group, a carboxylic acid group, an ether group, an ester group, a nitrile group, a sulfone group, a sulfide group, an amino acid derivative group, an amine group, and amide group, an aldehyde group, or an aromatic group.

The alcohol group may be represented by —$R^3$OH, where $R^3$ is a straight chained or branched alkyl group having 1 to 5 carbon atoms. The carboxylic acid group may be represented by —$R^4$COOH, where $R^4$ is at least one saturated or unsaturated alkyl group, an ester group, an ether group or a combintion thereof. When $R^4$ is an ester group, it may be represented by —$R^5$COO—, where $R^5$ is bonded to the carboxylic acid group and has 0 to 5 carbon atoms. When $R^4$ is an ether group, it may be represented by $R^6$—O—$R^7$ wherein $R^6$ and $R^7$ are, independently, an alkyl or allyl group having 0 to 5 carbon atoms. The aromatic group may be represented by Ar—$(R^8)_m$, where Ar represents a benzene ring, and m is 1 or 2, and $R^8$ may represent —CH=$CH_2$, or —COOH. The ester group may be represented by —$CR^9$, where $R^9$ is an ester of nicotinic acid, an ester of isonicotinic acid, or the ester group is represented by —CO(C=O)$R^{9a}$, where $R^{9a}$ is Ph$(CY_3)_o$, where o is 1 or 2, and Y may be, independently, H, F, Cl, Br, or 1, or where $R^{9a}$ is a substituted heterocyclohexane compound. The phosphonic acid derivative group may be represented by —CO—P$(R^{10})$OOH, where $R^{10}$ is an alkyl group having 0 to 5 carbon atoms. The phosphate group is —COP(O)$(OR^{11})_2$, where $R^{11}$ is an alkyl group having 0 to 5 carbon atoms, or a phenyl group. The nitrile group is $R^{12}$CN, where $R^{12}$ is an alkyl group having 0 to 5 carbon atoms. The sulfone group may be represented by —CS(=O)$_2R^{13}$, wherein $R^{13}$ is —N$(CH_3)_2$, —$OR^{14}$, or —Ph—$COOR^{14}$, where $R^{14}$ is H, $CH_3$, or —CH$(CH_3)_2$. The sulfide group may be represented by —$CSR^{15}$, where $R^{15}$ is pyridine or —Ph—$COOR^{16}$, where $R^{16}$ is H or $CH_3$. The amino acid derivative group is —COC(=O)CN$(R^{17})_2$, where each $R^{17}$ group is, independently, H or $CH_3$. The amine group may be represented by —CN$(R^{18})_2$, where each $R^{18}$ group is, independently, H, an alkyl group, or a phenyl group. The ether group may be represented by —C—O—$CR^{19}$, where $R^{19}$ is a substituted pyridine. The amide group is —(C=O)N$(R^{20})_2$, or —$CH_2$(C=O)N$(R^{20})_2$ where each $R^{20}$ is, independently, H or —$CH_2CH_2N(CH_3)_2$.

The compound of the present invention may also be illustrated as: formula:

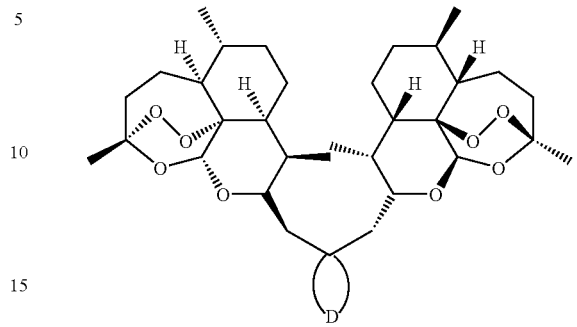

where D forms a heterocyclic ring having 3 to 5 atoms. For example, the heterocyclic ring may be a 3-membered ring and one of the atoms in the ring is oxygen. The heterocyclic ring may also be a 5-membered ring and two of the atoms in the ring are oxygen, and the ring may also be substituted with an oxygen atom and another atom in the 5-membered ring may be a sulfur or phosphorus atom. In another example, the 5-membered ring may also be substituted with 1 or 2 oxygen atoms bonded to the sulfur atom.

The compound of the present invention may further be illustrated as:

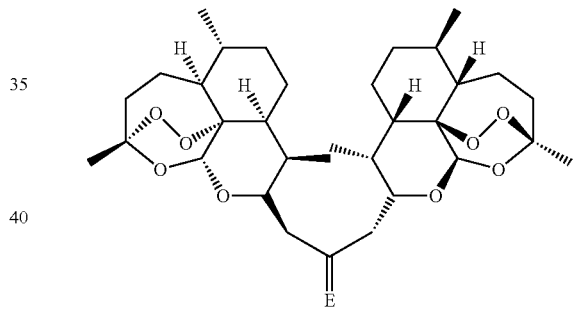

where where E is H, O, NR, $CH_2$ or S wherein R may be hydrogen, alkyl, aryl or any other substituent.

In general, the first step of the preferred process of the present invention, shown in FIG. 1, conversion of artemisinin (I) into α-dihydroartemisinin acetate (2), is accomplished by using an effective amount of a hydride nucleophile in combination with an acetylating agent which chemoselectively reacts at the C-10 position of the artemisinin skeleton without disrupting the O—O bond in this trioxane. Effective nucleophilic hydride reagents include, but are not limited to sodium borohydride, and DIBAL. The relative amounts of the various possible nucleophilic hydride reagents depends upon the concentration employed and other conditions of the reaction. Various amounts of the nucleophilic reagents can be employed, but generally it should be present in the range of 1.0 to 1.5 molar equivalents of nucleophilic hydride per molar equivalent of artemisinin for the reaction to proceed to completion. Effective acetylating agents include, but are not limited to acetyl chloride and acetic anhydride. The relative amounts of the various possible acetylating agents depends upon the concentration employed and other conditions of the reaction. Various amounts of the acetylating agents can be employed, but generally it should be present in the range of 1.0 to 1.5 molar equivalents of acetylating agent per molar equivalent of dihydroartemisinin for the reaction to proceed to completion.

The next step, shown in FIG. 2, in the production of the novel meso trioxane dimer 3 involves the substitution of the acetoxy group from the C-10 acetate 2 product to form the meso trioxane dimer 3 product. Inspiration for this bis-allylation of C-10 acetate 2 was based on the pioneering trioxane mono-allylations of Ziffer (Pu, Y. M.; Ziffer, H., Synthesis and Antimalarial Activities of 12β-Allyldeoxoartemisinin. *J. Med. Chem.* 1995, 38, 613-616) and O'Neill (O'Neill, et al., *J. Med. Chem.* 1999, 42, 5487-5493; and O'Neill, P. M., et al., *J. Chem. Soc., Perkin Trans.* 2001, 1, 2682-2689.) using allylsilane and based also on allylic bis-silane chemistry, see Rychnovsky, S. D., et. al., *Tetrahedron Lett.* 1999, 40, 41-44. The requisite allylic bis-silane is easily prepared in one step from the corresponding commercial allylic dichloride (Shown in FIG. 2); in the presence of fresh tin tetrachloride, the allylic bis-silane converts acetate 2 on gram scale into meso dimer 3, characterized by $^1$H NMR spectroscopy as done before in structurally related trioxanes. This double substitution reaction undoubtedly proceeds sequentially via initial monoallylation, producing an intermediate C-10 allylic silane that then reacts with another molecule of trioxane acetate 2 to form the product dimer 3. This new dimer 3, with an unsaturated 3-carbon atom linker between the two trioxane units, is stable in air and light at room temperature for at least six months, and its preparation on much larger industrial scale should be feasible.

In contrast to most simple peroxides that are easily cleaved by reducing agents and by reactive organometallics, the peroxide linkage in artemisinin-like trioxanes is relatively robust. Therefore, several different chemical transformations chemospecifically involving only the linker isobutylene carbon-carbon double bond in dimer 3 may be performed and are discussed in further detail below.

Borane reduction and in situ oxidation produced bis-trioxane primary alcohol 4, shown in FIG. 3. Dihydroxylation using osmium tetroxide gave bis-trioxane vicinal diol 5, shown in FIG. 4. Dimethyldioxirane formed bis-trioxane epoxide 6, shown in FIG. 5. Oxidative cleavage using catalytic osmium tetroxide and Oxone led to bis-trioxane ketone 7, shown in FIG. 6. Bis-Trioxanes 4-7 are stable even when heated neat in air for 24 h at 60° C.; $^1$H NMR spectroscopy showed less than 5% decomposition under these accelerated aging conditions.

To illustrate further the chemical inertness of the peroxide unit in these trioxane dimers, and especially to generate some water-soluble dimers that can be easily administered in vivo, each dimer 4-7 was converted into a carboxylic acid (FIGS. 16-20). Primary alcohol 4 opened succinic anhydride to form bis-artesunate 8a in high yield, see FIG. 16. Likewise, diol 5 opened succinic anhydride to produce the tertiary alcohol primary succinate ester 9, see FIG. 17. Epoxide 6 reacted chemospecifically with a benzenethiol in the presence of chromatographic alumina to give β hydroxysulfide 10a in high yield; sulfide to sulfone oxidation gave dimer benzoate ester 10b that was saponified into benzoic acid 10c, see FIG. 18. Ketone 7 underwent chemospecific addition of styryllithium to afford styryl tertiary alcohol 11a; oxidative cleavage of the styrene double bond produced benzoic acid 11b, see FIG. 19. Primary alcohol 4 was allylated and the allyl double bond was oxidatively cleaved to generate acetic acid 12b, see FIG. 20.

Each of these new carboxylic acid dimers is at least as soluble in water at pH 7.4 as is the antimalarial drug candidate artelinic acid, and tertiary alcohol primary succinate ester 9 is close to 30 times more water-soluble than artelinic acid, and phosphonic acid 16 is even more water soluble than succinate ester 9. Trioxane dimer carboxylic acids 8a-10c and 12b are stable in air even at 60° C. for 24 hours.

Primary alcohol 4 may also be transformed into a variety of other compounds as shown in FIGS. 21-25, 28, 30, 34-38 and 43. Likewise, diol 5 may be converted into a variety of compounds as shown in FIGS. 27, 29, 31 and 45. Additionally, secondary alcohol 17 may be transformed into a variety of compounds as shown in FIGS. 32 and 33. Likewise, ketone 7 may be converted into a variety of compounds as shown in FIGS. 42, 44, 47 and 48 and epoxide 6 may be reacted further as shown in FIG. 46. Finally, dimer 3 may be converted to a variety of compounds as shown in FIGS. 51, 52 and 53.

Determination of Antimalarial Activity

To determine the antimalarial effect of various dimers of the present invention, screening assays were performed against chloroquine-sensitive *P. falciparum* (NF54), according to the method described below, and their $IC_{50}$ values are included in Table 1.

Activity was determined by measuring the incorporation of [$^3$H]hypoxanthine, by the methods of DesJardins and Milhous, with the following modifications, see Desjardins, R. E.; Canfield, C. J.; Haynes, J. D.; Chulay, J. D., *Antimicrob. Agents Chemother.*, 16:710 (1979); Milhous, W. K.; Weatherly, N. F.; Bowdre, J. H.; Desjardins, R., *Antimicrob. Agents Chemother.*, 27:525 (1985). Chloroquine-sensitive *P. falciparum* (NF54 strain) were maintained in a 2.4% suspension of type O$^+$ human erythrocytes (obtained weekly from a rotating pool of screened healthy volunteers) in RPMI 1640 (Gibco BRL # 13200-076), supplemented with 25 mM N-2-hydroxyethylpiperazine-N'-2-ethanesulfonic acid (HEPES; Calbiochem #391338), 27 mM NaHCO$_3$ (Gibco BRL # 11810-025), and 10% heat-inactivated human type O$^+$ serum (Interstate Blood Bank, Inc.), under 3% O$_2$, 4% CO$_2$, and 93% N$_2$. Parasitemia was maintained at 0.05-3% and doubling time at approximately 15 hours by twice weekly change of medium and replenishment with fresh erythrocytes.

Stock solutions (approximately 2.5 mg/mL of HPLC-purified or recrystallized test compound) were prepared in dimethyl sulfoxide (DMSO; Sigma-Aldrich #27,043-1). DMSO solutions were diluted 500-fold in medium, serially diluted in 0.2% DMSO in medium (to maintain constant solvent concentration), then 100 µL aliquots were pipetted into microtiter plate wells (Costar3595). Provisional $EC_{50}$ values were obtained in a survey of seven 5-fold dilutions yielding final concentrations (in triplicate) of 0.16-2500 ng/mL. Assays were later expanded to include ten concentrations (in quadruplicate) of approximately 1.8-fold dilutions which flank the provisional $EC_{50}$. Plates included at least 8 wells of no drug controls (4 with and 4 without DMSO) and 4 wells of uninfected erythrocytes. Parasite culture (0.25% parasitemia in 2.4% hematocrit; 100 µL per well) was added and the plate was incubated for 48 hours prior to the addition of 25 µL [$^3$H]hypoxanthine (14.1 Ci/mmol, 1 mCi/mL in 70% ethanol, New England Nuclear NET-177, diluted to 25 µCi/mL with medium) and subsequent 20 hour incubation. Cells were harvested (Brandel MB-48R) onto GF-C glass filters (Brandel). The filters were washed five times with 3 mL water per sample spot, dried under a heat lamp, and counted (Beckman Model LS-6500) in scintillation cocktail (ICN Cytoscint).

Decays per minute (dpm) values were downloaded and analyzed (Power Macintosh 7200/90; Microsoft Excel 5.0), to yield the mean and standard deviation at each drug concentration. Dose-response curves were fit to the experimental data (Delta Point DeltaGraph 3.5.3) by means of the Marquardt algorithm, were solved for the drug concentration that kills 50% of parasites, and were analyzed for goodness of fit ($R^2$ value).

TABLE I

Antimalarial Activities in vitro[a]

| Trioxane | $IC_{50}$ (nM) |
|---|---|
| 3 | 24.0 |
| 4 | 0.87 |
| 5 | 0.59 |
| 6 | 2.8 |
| 7 | 0.91 |
| 8a | 2.0 |
| 8b | 1.7 |
| 9 | 3.0 |
| 10c | 2.4 |
| 11b | 2.1 |
| 12b | 3.2 |
| 13 | 0.53 |
| 14 | 10.0 |
| 15 | 0.58 |
| 16 | 320 |
| 17 | 0.66 |
| 18 | 0.34 |
| 19 | 2.4 |
| 21 | 4.4 |
| 23 | 0.40 |
| 24 | 0.42 |
| 25 | 0.31 |
| 26 | 0.74 |
| 27 | 0.48 |
| 32 | 1.1 |
| 33 | 0.81 |
| 35 | 2.0 |
| 36 | 1.7 |
| 37 | 2.8 |
| 38 | 200 |
| 40 | 0.73 |
| 41 | 0.59 |
| 42 | 19 |
| 48 | 4.8 |
| Artemisinin | 9.2 ± 1.7 |

[a]The standard deviation for each set of quadruplicates was an average of 8.6% (≦22%) of the mean. $R^2$ values for the fitted curves were ≧0.933. Artemisinin activity is mean ± standard deviation of concurrent control (n = 34).

In sharp contrast to the potency of the natural trioxane artemisinin ($IC_{50}$=7.7 nm) and of the initial olefinic dimer 3 ($IC_{50}$=24 nM), alcohol dimers 4 and 17, diol dimer 5 and ketone dimer 7 all have substantially enhanced potencies, with $IC_{50}$ values below one nM. In addition, further derivitization of these potent antimalarials has produced a number of analogs also antimalarially active in sub-nanomolar concentrations (most notably: pyridine N-oxides 13, 15, 18, 23, 24 and 25, phosphoric acid triesters 26 and 27, sulfonamide 40 and cyclic carbonate 41).

The in vivo antimalarial efficacies of water-soluble dimer carboxylic acids 8a-10c and 12b (11b not tested), as measured in mice according to a published protocol, are shown in Table II. In all cases, these water-soluble dimeric trioxanes are more efficacious than the drug candidate artelinic acid administered intravenously (IV) and than the clinically used drug sodium artesunate administered orally (PO). At an IV dose of 10 mg/kg of mouse body weight, each dimeric trioxane 8a-10c and 12b suppressed *P. berghei* NY malaria parasite growth considerably better (>80%) than did artelinic acid or sodium artesunate. Neither overt toxicity nor behavioral modification was observed due to drug administration in any of these mouse experiments.

TABLE II

Antimalarial Efficacies in vivo

| Trioxane Carboxylic Acid | Administration Route | $ED_{50}$[b] | $ED_{90}$[b] | % Parasite Supression at 10 mg/kg |
|---|---|---|---|---|
| 8a | IV | 2.2 | 6.3 | 81.0 |
|  | PO | 9.0 | 15.0 | 79.2 |
| 12b | IV | 1.0 | 3.5 | 95.7 |
|  | PO | 6.5 | 17.0 | 46.5 |
| Artelinic Acid | IV | 11.0 | 25.0 | 54.7 |
| Sodium Artesunate | PO | 10.0 | 39.0 | 52.8 |
| 9 | IV | 2.4 | 11.0 | 83.4 |
|  | PO | 4.8 | 34.0 | 55.4 |
| 10c | IV | 2.7 | 10.0 | 83.4 |
|  | PO | 7.5 | 35.0 | 46.1 |
| Artelinic Acid | IV | 5.6 | 43.0 | 42.4 |
| Sodium Artesunate | PO | 5.5 | 70.0 | 50.9 |

[b]mg/kg × 4

Determination of Antitumor Activities

Growth Inhibition. To determine the growth inhibition (GI) and cytotoxicity of dimers 4, 5, 8a, 9, 10c, 11b, 12b, 13, and 14 respectively, of the present invention, screening assays were performed by the National Cancer Institute using a 60 cell line panel; these activities are summarized in Tables III, IV and V (set out below). The screening assay is performed on 96-well microtitre plates. Relatively high initial inoculation densities are used, in order to permit measurement of "time-zero" values and to enhance the screen's ability to detect and provide some differentiation between growth inhibition and cytotoxic response parameters. The specific inoculation densities (which range from 5,000 to 40,000 cells/well) used for each cell line are those which, for the respective line, were determined to give an optical density signal for both the "time-zero" value (at 24 hours) and the "no-drug" control (at 72 hours) above the noise level and within the linear range of the end-point assay (which measures cellular protein). The inoculated microtitre plates are pre-incubated for 24 hours at 37° C. prior to drug additions. The five drug dilutions tested routinely range from $10^{-4}$ to $10^{-8}$ molar. Higher or lower concentration ranges may be selected on a non-routine basis if appropriate solubility and/or prior biological information or other screening data so dictate. Duplicate wells are prepared for all concentrations, (concentration is often denoted by placing brackets around a number); "time-zero" and "no drug" controls are also provided for each test. The minimum amount of compound required for a one-time evaluation in the routine screen can be calculated from the knowledge that each test requires a total of approximately 40 ml (0.04 liter) of cell culture medium containing the highest desired drug concentration. Thus, the amount (grams) of sample required (assuming an upper test concentration limit of $10^{-4}$ M) is: molecular weight of compound×$10^{-4}$×0.04. After a 48 hour incubation (37° C.) with the test compound, the cells are fixed in situ to the bottoms of the microtitre wells by addition of 50 μl of either 50% trichloroacetic acid (for adherent cell lines) or 80% trichloroacetic acid (for settled cell suspension lines), followed by incubation for 60 minutes at 4° C. The cellular protein in each well is assayed using a sulforhodamine B (SRB) stain procedure. Briefly, after discarding the supernatants, the microtitre plates are washed 5 times with deionized water and air-dried. One hundred microliters of SRB solution (0.4% w/v in 1% acetic acid) is added to each microtitre well and incubated for 10 minutes at room temperature. Unbound SRB is removed by washing 5 times with 1% acetic acid. The plates are air-dried, the bound stain is solubilized with Tris buffer, and the optical densities read at 515 nm. SRB is a bright pink anionic dye which, in dilute acetic acid, binds electrostatically to the basic amino acids of TCA-fixed cells. Cryopreserved master stocks of all the lines are maintained, and cultures used for screening are replaced from the master stock after no more than twenty passages in the screening laboratory. The cell line panel consists of 60 lines, organized into nine, disease-related subpanels including leukemia, non-small-cell lung cancer, colon, CNS, melanoma, ovarian, renal, prostate and breast cancers.

The response parameters $GI_{50}$ and $LC_{50}$ are interpolated values representing the concentrations at which the percentage growth (PG) is +50 and −50, respectively:

$GI_{50}$ is the concentration for which the PG=+50. At this value the increase from time $t_{zero}$, in the number or mass of cells in the test well is only 50% as much as the corresponding increase in the control well during this period of the experiment, see Table III. A drug effect of this intensity is interpreted as primary growth inhibition.

TGI is the concentration for which PG=0. At this value the number or mass of cells in the well at the end of the experiment equals the number or mass of cells in the well at time $t_{zero}$, see Table IV. A drug effect of this intensity is regarded as cytostasis.

$LC_{50}$ is the concentration for which the PG=−50. At this value, the number or mass of cells in the test well at the end of the experiment is half that at time $t_{zero}$, see Table V. This is interpreted as cytotoxicity.

TABLE III

| | | \multicolumn{9}{c|}{$Log_{10}GI_{50}$} | |
|---|---|---|---|---|---|---|---|---|---|---|---|
| Panel/Cell Line | Artemisinin | \multicolumn{9}{c|}{Trioxane Dimers} | Paclitaxel |
| | | 4 | 5 | 8a | 9 | 10c | 11b | 12b | 13 | 14 | |
| Leukemia | | | | | | | | | | | |
| CCRF-CEM | — | — | −4.71 | <−8.30 | <−8.30 | <−8.30 | −8.07 | <−8.30 | 5.73 | >−4.30 | −11.61 |
| HL-60(TB) | −4.26 | −7.78 | <−8.00 | <−8.30 | <−8.30 | <−8.30 | <−8.30 | <−8.30 | | <−8.30 | −11.57 |
| K-562 | −4.33 | −7.91 | <−8.00 | <−8.30 | −8.30 | <−8.30 | <−8.30 | <−8.30 | | <−8.30 | −10.83 |
| MOLT-4 | −4.73 | −7.92 | <−8.00 | −8.18 | −5.15 | — | <−8.30 | −7.66 | | — | −11.07 |
| RPMI-8226 | >−4.00 | <−8.00 | — | <−8.30 | <−8.30 | <−8.30 | — | — | <−8.30 | <−8.30 | <−13.00 |
| SR | >−4.00 | <−8.00 | — | — | — | — | — | — | — | — | 8.34 |
| Non-Small Cell Lung Cancer | | | | | | | | | | | |
| A549/ATCC | −4.17 | −7.29 | −7.59 | −4.42 | −4.86 | −5.28 | −5.69 | >−4.30 | −5.98 | <−8.30 | — |
| EKVX | >−4.00 | −7.12 | — | −6.90 | — | −4.99 | −4.79 | >−4.30 | −8.19 | <−8.30 | — |
| HOP-62 | >−4.00 | −4.92 | −4.66 | −6.34 | −5.69 | <−8.30 | −6.96 | −6.23 | — | −4.90 | −9.67 |
| HOP-92 | >−4.00 | −6.37 | −4.93 | −6.56 | <−8.30 | <−8.30 | −7.43 | −7.00 | −8.04 | <−8.30 | — |
| NCI-H226 | >−4.00 | −4.82 | −4.87 | <−8.30 | — | <−8.30 | — | — | — | — | — |
| NCI-H23 | >−4.00 | −7.84 | −4.83 | <−8.30 | <−8.30 | <−8.30 | −8.19 | <−8.30 | <−8.30 | <−8.30 | — |
| NCI-H322M | — | −4.97 | −4.71 | −5.11 | −5.07 | −6.03 | −6.72 | −5.03 | −6.26 | <−8.30 | −10.12 |
| NCI-H460 | >−4.00 | −7.35 | −5.02 | <−8.30 | <−8.30 | <−8.30 | <−8.30 | <−8.30 | <−8.30 | <−8.30 | −12.16 |
| NCI-H522 | — | −7.53 | −7.33 | −6.16 | −4.91 | <−8.30 | −6.54 | >−4.30 | — | — | <−13.00 |
| Colon Cancer | | | | | | | | | | | |
| COLO 205 | >−4.00 | <−8.00 | <−8.00 | <−8.30 | — | <−8.30 | <−8.30 | <−8.30 | <−8.30 | <−8.30 | −11.07 |
| HCC-2998 | >−4.00 | −7.45 | −4.65 | — | — | — | — | — | — | — | −12.34 |
| HCT-116 | −4.18 | <−8.00 | −4.72 | <−8.30 | <−8.30 | <−8.30 | <−8.30 | <−8.30 | <−8.30 | <−8.30 | <−13.00 |
| HCT-15 | >−4.00 | <−8.00 | −5.28 | <−8.30 | <−8.30 | <−8.30 | <−8.30 | <−8.30 | <−8.30 | <−8.30 | −6.37 |
| HT29 | >−4.00 | −7.75 | <−8.00 | <−8.30 | <−8.30 | <−8.30 | <−8.30 | <−8.30 | — | — | <−13.00 |
| KM12 | >−4.00 | <−8.00 | <−8.00 | <−8.30 | <−8.30 | <−8.30 | <−8.30 | <−8.30 | <−8.30 | — | −11.43 |
| SW-620 | >−4.00 | <−8.00 | −4.97 | — | — | — | — | — | <−8.30 | <−8.30 | −11.60 |
| CNS Cancer | | | | | | | | | | | |
| SF-268 | — | −5.40 | −4.94 | −7.11 | −5.48 | <−8.30 | −7.72 | −6.82 | −5.29 | — | — |
| SF-295 | — | −5.59 | −4.94 | — | <−8.30 | — | — | — | −5.21 | <−8.30 | — |
| SF-539 | — | −7.05 | −4.86 | −5.27 | −4.90 | −5.19 | −4.80 | −4.53 | <−8.30 | <−8.30 | −11.09 |
| SNB-19 | >−4.00 | −4.88 | −4.82 | −5.62 | — | −6.72 | −6.53 | −6.03 | −5.08 | — | −8.98 |
| SNB-75 | >−4.00 | −4.99 | −4.53 | −6.47 | — | — | −7.40 | — | — | — | — |
| U251 | >−4.00 | −7.27 | −7.68 | −8.20 | — | <−8.30 | <−8.30 | <−8.30 | <−8.30 | <−8.30 | −11.29 |
| Melanoma | | | | | | | | | | | |
| LOX IMVI | — | −7.26 | <−8.00 | — | — | — | — | — | <−8.30 | <−8.30 | −11.80 |
| MALME-3M | — | −7.31 | — | <−8.30 | <−8.30 | <−8.30 | <−8.30 | — | <−8.30 | −7.22 | — |
| M14 | — | −5.87 | −4.59 | −6.94 | — | <−8.30 | −7.81 | −6.68 | −5.81 | — | −11.73 |
| SK-MEL-2 | — | −7.33 | −4.94 | −5.12 | −4.88 | — | −6.43 | −5.62 | −5.12 | >−4.30 | −9.53 |
| SK-MEL-28 | >−4.00 | −4.95 | −4.79 | −6.09 | <−8.30 | −5.45 | −6.40 | −4.92 | −5.13 | — | — |
| SK-MEL-5 | >−4.10 | −7.90 | −7.69 | — | — | — | — | — | <−8.30 | <−8.30 | — |
| UACC-257 | >−4.00 | −7.31 | <−8.00 | −5.02 | −4.89 | — | — | >−4.30 | −5.15 | <−8.30 | −10.30 |
| UACC-62 | >−4.00 | −6.86 | — | — | — | — | — | — | −8.00 | <−8.30 | −10.46 |

TABLE III-continued

| | | \multicolumn{10}{c}{Log$_{10}$GI$_{50}$} | |
| Panel/Cell Line | Artem- isinin | \multicolumn{10}{c}{Trioxane Dimers} | Pacli- taxel |
|---|---|---|---|---|---|---|---|---|---|---|---|
| | | 4 | 5 | 8a | 9 | 10c | 11b | 12b | 13 | 14 | |
| Ovarian Cancer | | | | | | | | | | | |
| IGROVI | −4.31 | −5.36 | −4.97 | −5.07 | −4.97 | — | −5.98 | −5.06 | −5.36 | −5.81 | −8.61 |
| OVCAR-3 | — | −7.68 | −5.09 | <−8.30 | <−8.30 | <−8.30 | <−8.30 | <−8.30 | −7.75 | <−8.30 | −10.40 |
| OVCAR-4 | — | −5.44 | −4.99 | — | — | — | — | — | <−8.30 | <−8.30 | −5.00 |
| OVCAR-5 | >−4.00 | −7.79 | −4.78 | <−8.30 | <−8.30 | <−8.30 | <−8.30 | <−8.30 | <−8.30 | <−8.30 | −9.38 |
| OVCAR-8 | >−4.00 | −7.33 | <−8.00 | >−4.30 | −5.12 | −5.25 | −5.26 | >−4.30 | −7.69 | <−8.30 | −10.75 |
| SK-OV-3 | — | −4.85 | −4.62 | −4.89 | — | −6.82 | — | >−4.30 | −5.13 | >−4.30 | — |
| Leukemia | | | | | | | | | | | |
| CCRF-CEM | — | — | −4.71 | <−8.30 | <−8.30 | <−8.30 | −8.07 | <−8.30 | 5.73 | >−4.30 | −11.61 |
| HL-60(TB) | −4.26 | −7.78 | <−8.00 | <−8.30 | <−8.30 | <−8.30 | <−8.30 | <−8.30 | | <−8.30 | −11.57 |
| K-562 | −4.33 | −7.91 | <−8.00 | <−8.30 | −8.30 | <−8.30 | <−8.30 | <−8.30 | | <−8.30 | −10.83 |
| MOLT-4 | −4.73 | −7.92 | <−8.00 | −8.18 | −5.15 | — | <−8.30 | −7.66 | | — | −11.07 |
| RPMI-8226 | >−4.00 | <−8.00 | — | <−8.30 | <−8.30 | <−8.30 | — | — | <−8.30 | <−8.30 | <−13.00 |
| SR | >−4.00 | <−8.00 | — | — | — | — | — | — | — | — | 8.34 |
| Non-Small Cell Lung Cancer | | | | | | | | | | | |
| A549/ATCC | −4.17 | −7.29 | −7.59 | −4.42 | −4.86 | −5.28 | −5.69 | >−4.30 | −5.98 | <−8.30 | — |
| EKVX | >−4.00 | −7.12 | — | −6.90 | — | −4.99 | −4.79 | >−4.30 | −8.19 | <−8.30 | — |
| HOP-62 | >−4.00 | −4.92 | −4.66 | −6.34 | −5.69 | <−8.30 | −6.96 | −6.23 | — | −4.90 | −9.67 |
| HOP-92 | >−4.00 | −6.37 | −4.93 | −6.56 | <−8.30 | <−8.30 | −7.43 | −7.00 | −8.04 | <−8.30 | — |
| NCI-H226 | >−4.00 | −4.82 | −4.87 | <−8.30 | — | <−8.30 | — | — | — | — | — |
| NCI-H23 | >−4.00 | −7.84 | −4.83 | <−8.30 | <−8.30 | <−8.30 | −8.19 | <−8.30 | <−8.30 | <−8.30 | — |
| NCI-H322M | — | −4.97 | −4.71 | −5.11 | −5.07 | −6.03 | −6.72 | −5.03 | −6.26 | <−8.30 | −10.12 |
| NCI-H460 | >−4.00 | −7.35 | −5.02 | <−8.30 | <−8.30 | <−8.30 | <−8.30 | <−8.30 | <−8.30 | <−8.30 | −12.16 |
| NCI-H522 | — | −7.53 | −7.33 | −6.16 | −4.91 | <−8.30 | −6.54 | >−4.30 | — | — | <−13.00 |
| Renal Cancer | | | | | | | | | | | |
| 786-0 | >−4.00 | −7.48 | −4.87 | −6.45 | <−8.30 | <−8.30 | −7.17 | −6.59 | −7.81 | <−8.30 | −8.01 |
| A498 | >−4.00 | −6.69 | −4.81 | — | — | — | — | — | −6.97 | −7.20 | −7.14 |
| ACHN | >−4.00 | −7.12 | <−8.00 | — | −6.67 | — | — | — | <−8.30 | <−8.30 | — |
| CAKI-1 | — | −7.05 | −4.94 | −6.84 | — | <−8.30 | −7.74 | −6.91 | −7.36 | <−8.30 | — |
| RXF 393 | −4.08 | −4.80 | −4.89 | <−8.30 | −7.67 | <−8.30 | <−8.30 | <−8.30 | −5.20 | — | −8.32 |
| SN12C | −4.21 | −7.46 | −7.60 | — | — | — | — | — | <−8.30 | <−8.30 | −9.53 |
| TK-10 | >−4.00 | −6.60 | −4.91 | −6.92 | <−8.30 | <−8.30 | −7.81 | −7.22 | <−8.30 | <−8.30 | −7.89 |
| UO-31 | −4.06 | −7.46 | −7.38 | −5.46 | −5.05 | −5.91 | −6.78 | −5.84 | <−8.30 | <−8.30 | −6.09 |
| Prostate Cancer | | | | | | | | | | | |
| PC-3 | −4.17 | <−8.00 | <−8.00 | <−8.30 | <−8.30 | <−8.30 | <−8.30 | <−8.30 | <−8.30 | <−8.30 | −10.85 |
| DU-145 | — | −6.24 | −4.83 | — | — | — | — | — | −7.48 | — | −9.38 |
| Breast Cancer | | | | | | | | | | | |
| MCF7 | >−4.00 | −7.22 | <−8.00 | <−8.30 | <−8.30 | <−8.30 | <−8.30 | −7.37 | <−8.30 | <−8.30 | −11.69 |
| NCI/ADR-RES | — | −7.45 | −4.75 | −5.64 | −5.61 | −5.73 | −6.84 | −6.45 | −7.60 | −6.07 | −8.48 |
| MDA-MB231/ATCC | −4.20 | −5.40 | −4.99 | −7.19 | — | <−8.30 | — | — | −7.64 | <−8.30 | −8.54 |
| HS 578T | >−4.00 | −4.82 | −4.72 | >−4.30 | −4.36 | −4.82 | −5.15 | >−4.30 | <−8.30 | <−8.30 | — |
| MDA-MB-435 | — | −7.50 | — | — | <−8.30 | <−8.30 | −8.16 | −6.97 | −7.62 | <−8.30 | <−13.00 |
| MDA-N | >−4.00 | −7.54 | — | −7.29 | — | — | — | — | — | — | <−13.00 |
| BT-549 | −4.06 | −7.11 | <−8.00 | −7.91 | — | −6.67 | −5.82 | — | <−8.30 | <−8.30 | −9.31 |
| T-47D | — | <8.00 | −7.23 | <−8.30 | — | <−8.30 | <−8.30 | <−8.30 | <−8.30 | — | −9.81 |
| MG MID | — | −6.87 | −5.97 | −7.01 | −7.02 | −7.57 | −7.37 | −6.73 | −7.38 | −7.79 | — |
| Delta | −4.07 | 1.13 | 2.03 | 1.29 | 1.28 | −0.73 | 0.93 | 1.57 | 0.92 | −.51 | −10.15 |
| Range | 0.73 | 3.20 | 3.47 | 4.00 | 3.94 | 3.48 | 3.52 | 4.00 | 3.22 | 4.00 | 8.00 |

TABLE IV

| Panel/Cell Line | Artemisinin | Trioxane Dimers | | | | | | | | | Paclitaxel |
|---|---|---|---|---|---|---|---|---|---|---|---|
| | | 4 | 5 | 8a | 9 | 10c | 11b | 12b | 13 | 14 | |
| Leukemia | | | | | | | | | | | |
| CCRF-CEM | — | −4.66 | >−4.00 | >−4.30 | >−4.30 | −4.84 | >−4.30 | >−4.30 | >−4.30 | >−4.30 | >−4.00 |
| HL-60(TB) | >−4.00 | −4.88 | — | −7.61 | — | <−8.30 | −8.11 | <−8.30 | — | >−4.30 | −4.53 |
| K-562 | >−4.00 | >−4.00 | >−4.00 | >−4.30 | >−4.30 | −4.75 | >−4.30 | >−4.30 | — | >−4.30 | >−4.00 |
| MOLT-4 | >−4.00 | >−4.00 | >−4.00 | >−4.30 | >−4.30 | >−4.30 | >−4.30 | >−4.30 | — | — | >−4.00 |
| RPMI-8226 | >−4.00 | −6.91 | >−4.00 | −6.19 | >−4.30 | −5.03 | — | — | >−4.30 | >−4.30 | >−4.00 |
| SR | >−4.00 | −4.58 | — | — | — | — | — | — | — | >−4.30 | >−4.00 |
| Non-Small Cell Lung Cancer | | | | | | | | | | | |
| A549/ATCC | >−4.00 | −4.71 | −4.82 | >−4.30 | >−4.30 | >−4.30 | >−4.30 | >−4.30 | −4.61 | >−4.30 | — |
| EKVX | >−4.00 | −4.77 | — | −5.47 | — | −4.63 | >−4.30 | >−4.30 | −5.08 | >−4.30 | — |
| HOP-62 | >−4.00 | −4.56 | −4.26 | >−4.30 | >−4.30 | −5.01 | >−4.30 | >−4.30 | −4.91 | >−4.30 | −4.80 |
| HOP-92 | >−4.00 | −4.65 | −4.49 | >−4.30 | >−4.30 | −5.05 | >−4.30 | >−4.30 | −5.27 | >−4.30 | — |
| NCI-H226 | >−4.00 | −4.40 | −4.49 | −6.67 | — | <−8.30 | — | — | — | — | — |
| NCI-H23 | >−4.00 | — | −4.26 | >−4.30 | −4.65 | −5.25 | −4.63 | >−4.30 | −5.17 | — | — |
| NCI-H322M | — | −4.63 | −4.44 | >−4.30 | >−4.30 | −4.98 | >−4.30 | >−4.30 | −5.06 | >−4.30 | −4.46 |
| NCI-H460 | >−4.00 | −4.71 | −4.40 | >−4.30 | >−4.30 | −5.11 | >−4.30 | >−4.30 | −4.92 | >−4.30 | −4.92 |
| NCI-H522 | — | −4.88 | −4.59 | >−4.30 | >−4.30 | −4.34 | >−4.30 | >−4.30 | −4.60 | >−4.30 | −11.20 |
| Colon Cancer | | | | | | | | | | | |
| COLO 205 | >−4.00 | −6.43 | −4.87 | −6.29 | — | <−8.30 | −6.99 | −5.28 | >−4.30 | — | — |
| HCC-2998 | >−4.00 | −5.39 | −4.23 | — | — | — | — | — | −4.91 | −5.33 | −4.77 |
| HCT-116 | >−4.00 | — | >−4.00 | >−4.30 | >−4.30 | −5.16 | −4.40 | >−4.30 | −5.06 | >−4.30 | −4.82 |
| HCT-15 | >−4.00 | −4.78 | −4.53 | −5.61 | −5.01 | −5.23 | −6.70 | −5.00 | −8.19 | −4.96 | >−4.00 |
| HT29 | >−4.00 | −4.67 | >−4.00 | >−4.30 | 4.91 | >−4.30 | >−4.30 | >−4.30 | — | — | — |
| KM12 | >−4.00 | −4.79 | −4.47 | <−8.30 | <−8.30 | <−8.30 | <−8.30 | <−8.30 | −5.04 | >−4.30 | −4.36 |
| SW-620 | >−4.00 | −4.89 | >−4.00 | — | — | — | — | — | −5.05 | >−4.30 | >−4.00 |
| CNS Cancer | | | | | | | | | | | |
| SF-268 | — | −4.63 | −4.53 | >−4.30 | >−4.30 | −5.14 | >−4.30 | >−4.30 | −4.80 | >−4.30 | — |
| SF-295 | — | −4.80 | −4.49 | — | <−8.30 | — | — | — | −4.77 | >−4.30 | — |
| SF-539 | — | −4.72 | −4.41 | >−4.30 | −4.50 | −4.66 | >−4.30 | >−4.30 | — | — | — |
| SNB-19 | >−4.00 | −4.50 | −4.34 | >−4.30 | — | −4.96 | >−4.30 | >−4.30 | >−4.30 | — | >−4.00 |
| SNB-75 | >−4.00 | −4.55 | −4.04 | >−4.30 | >−4.30 | −4.80 | >−4.30 | >−4.30 | — | — | — |
| U251 | >−4.00 | −4.47 | −4.61 | >−4.30 | −4.75 | −5.22 | −7.39 | >−4.3 | −5.08 | >−4.30 | −4.32 |
| Melanoma | | | | | | | | | | | |
| LOX IMVI | — | −4.45 | −5.47 | — | — | — | — | — | <−8.30 | <−8.30 | −4.65 |
| MALME-3M | −4.06 | −4.74 | −4.50 | −6.82 | −5.14 | <−8.30 | −7.46 | −6.40 | <−8.30 | — | −4.46 |
| M-14 | >−4.00 | −4.68 | >−4.00 | >−4.30 | >−4.30 | −4.91 | >−4.30 | >−4.30 | −4.75 | >−4.30 | −4.62 |
| SK-MEL-2 | >−4.00 | −4.92 | −4.53 | >−4.30 | >−4.30 | >−4.30 | >−4.30 | >−4.30 | >−4.30 | >−4.30 | — |
| SK-MEL-28 | >−4.00 | −4.54 | −4.31 | >−4.30 | >−4.30 | −4.63 | >−4.30 | >−4.30 | −4.73 | >−4.30 | — |
| SK-MEL-5 | >−4.00 | −7.18 | −4.64 | — | — | — | — | — | −5.28 | −6.49 | — |
| UACC-257 | >−4.00 | −4.71 | −4.90 | >−4.30 | >−4.30 | −4.38 | >−4.30 | >4.30 | −4.65 | >−4.30 | −4.52 |
| UACC-62 | >−4.00 | −4.74 | −4.67 | — | — | — | — | — | −5.07 | >−4.30 | −4.71 |
| Ovarian Cancer | | | | | | | | | | | |
| IGROVI | >−4.00 | −4.68 | −4.57 | >−4.30 | >−4.30 | >−4.30 | −4.50 | >−4.30 | >−4.30 | >−4.30 | −4.19 |
| OVCAR-3 | — | −4.92 | −4.45 | −8.21 | <−8.30 | <−8.30 | −8.07 | — | −4.98 | >−4.30 | −4.55 |
| OVCAR-4 | — | −4.62 | −4.55 | — | — | — | — | — | −4.93 | >−4.30 | −4.19 |
| OVCAR-5 | >−4.00 | −6.42 | −4.33 | −6.62 | — | <−8.30 | −6.95 | −6.39 | −5.14 | >−4.30 | −4.92 |
| OVCAR-8 | >−4.00 | −4.69 | −4.47 | >−4.30 | >−4.30 | −4.48 | >−4.30 | >−4.30 | >4.30 | >−4.30 | — |
| SK-OV-3 | — | −4.53 | −4.15 | >−4.30 | — | −4.92 | >−4.30 | >−4.30 | −4.72 | >−4.30 | — |
| Renal Cancer | | | | | | | | | | | |
| 786-0 | >−4.00 | −4.83 | −4.36 | >−4.30 | >4.30 | −5.08 | >−4.30 | >−4.30 | −4.94 | >−4.30 | >−4.00 |
| A498 | >−4.00 | −5.00 | −4.51 | — | — | — | — | — | −5.31 | >−4.30 | — |
| ACHN | >−4.00 | −4.76 | <−8.00 | — | −4.74 | — | — | — | −6.57 | −6.61 | −4.90 |
| CAKI-1 | — | −4.84 | −4.54 | >−5.99 | — | −6.71 | −6.91 | −6.40 | −5.11 | −6.30 | −4.04 |
| RXF 393 | >−4.00 | −4.41 | −4.53 | −6.77 | −4.45 | −5.99 | −7.60 | <−8.30 | −4.69 | >−4.30 | >−4.00 |
| SN12C | >−4.00 | −4.84 | −4.72 | — | — | — | — | — | −5.29 | −6.02 | −4.29 |
| TK-10 | >−4.00 | −4.81 | −4.49 | −4.52 | −4.60 | −5.40 | −5.86 | −5.22 | −5.34 | — | — |
| UO-31 | >−4.00 | −5.77 | −4.68 | >−4.30 | >−4.30 | >−4.30 | >−4.30 | >−4.30 | −5.10 | −4.49 | — |

TABLE IV-continued

| Panel/Cell Line | Artem- isinin | Trioxane Dimers $\log_{10}TGI_{50}$ | | | | | | | | | Pacli- taxel |
|---|---|---|---|---|---|---|---|---|---|---|---|
| | | 4 | 5 | 8a | 9 | 10c | 11b | 12b | 13 | 14 | |
| Prostate Cancer | | | | | | | | | | | |
| PC-3 | −4.00 | −4.89 | −4.49 | >−4.30 | >−4.30 | −5.23 | −5.75 | −4.92 | −5.11 | >−4.30 | >−4.00 |
| DU-145 | — | −4.72 | −4.48 | — | — | — | — | — | −5.00 | >−4.30 | >−4.00 |
| Breast Cancer | | | | | | | | | | | |
| MCF7 | >−4.00 | −4.67 | −4.88 | >−4.30 | >−4.30 | −5.13 | >−4.30 | >−4.30 | −5.03 | >−4.30 | −4.05 |
| NCI/ADR-RES | — | −6.41 | >4.00 | >−4.30 | >−4.30 | −5.09 | >−4.30 | >−4.30 | −5.18 | >−4.30 | >−4.00 |
| MDA-MB231/ATCC | >−4.00 | −4.33 | −4.57 | −6.35 | — | <−8.30 | — | — | −6.32 | −7.94 | −4.84 |
| HS 578T | >−4.00 | >−4.00 | −4.08 | >−4.30 | >−4.30 | −4.53 | >−4.31 | >−4.30 | −5.00 | >−4.30 | — |
| MDA-MB-435 | — | −4.78 | −4.54 | >−4.30 | >−4.30 | −5.17 | >−4.30 | >−4.30 | −4.94 | >−4.30 | — |
| MDA-N | >−4.00 | −4.90 | — | — | — | — | — | — | — | — | — |
| BT-549 | >−4.00 | −4.73 | −4.81 | −7.39 | — | −5.54 | −5.32 | >−4.30 | −5.07 | >−4.30 | −6.32 |
| T-47D | >−4.00 | −4.73 | −4.48 | −4.77 | — | — | >−4.30 | >−4.30 | −5.36 | >−4.30 | −4.05 |
| MG MID | — | −4.87 | −4.50 | −5.04 | −4.72 | −5.51 | −5.12 | −4.81 | −5.15 | −4.66 | |
| Delta | −4.00 | 2.31 | 3.50 | 3.26 | 3.58 | 2.79 | 3.18 | 3.49 | 3.15 | 3.64 | −4.54 |
| Range | 0.06 | 3.18 | 4.00 | 4.00 | 4.00 | 4.00 | 4.00 | 4.00 | 4.00 | 4.00 | 7.20 |

TABLE V

| Panel/Cell Line | Artem- isinin | Trioxane Dimers $\log_{10}LC_{50}$ | | | | | | | | | Pacli- taxel |
|---|---|---|---|---|---|---|---|---|---|---|---|
| | | 4 | 5 | 8a | 9 | 10c | 11b | 12b | 13 | 14 | |
| Leukemia | | | | | | | | | | | |
| CCRF-CEM | — | >−4.00 | >−4.00 | >−4.30 | >−4.30 | >−4.30 | >−4.30 | >−4.30 | >−4.30 | >−4.30 | >−4.00 |
| HL-60(TB) | >−4.00 | −4.13 | >−4.00 | >−4.30 | >−4.30 | >−4.30 | −4.55 | >−4.30 | — | >−4.30 | >−4.53 |
| K-562 | >−4.00 | >−4.00 | >−4.00 | >−4.30 | >−4.30 | >−4.30 | >−4.30 | >−4.30 | — | >−4.30 | >−4.00 |
| MOLT-4 | >−4.00 | >−4.00 | >−4.00 | >−4.30 | >−4.30 | >−4.30 | >−4.30 | >−4.30 | — | — | >−4.00 |
| RPMI-8226 | >−4.00 | >−4.00 | >−4.00 | >−4.30 | >−4.30 | >−4.30 | — | — | >−4.30 | — | >−4.00 |
| SR | >−4.00 | >−4.00 | — | — | — | — | — | — | — | >−4.30 | >−4.00 |
| Non-Small Cell Lung Cancer | | | | | | | | | | | |
| A549/ATCC | >−4.00 | −4.11 | −4.11 | >−4.30 | >−4.30 | >−4.30 | >−4.30 | >−4.30 | >−4.30 | >−4.30 | — |
| EKVX | >−4.00 | −4.36 | — | >−4.30 | — | >−4.30 | >−4.30 | >−4.30 | −4.59 | >−4.30 | — |
| HOP-62 | >−4.00 | −4.20 | >−4.00 | >−4.30 | >−4.30 | −4.62 | >−4.30 | >−4.30 | −4.54 | >−4.30 | −4.10 |
| HOP-92 | >−4.00 | −4.22 | −4.05 | >−4.30 | >−4.30 | −4.52 | >−4.30 | >−4.30 | −4.74 | >−4.30 | — |
| NCI-H226 | >−4.00 | >−4.00 | −4.11 | >−4.30 | — | −4.82 | — | — | — | — | — |
| NCI-H23 | >−4.00 | −4.49 | >−4.00 | >−4.30 | >−4.30 | −4.77 | >−4.30 | >−4.30 | −4.62 | >−4.30 | — |
| NCI-H322M | — | −4.29 | −4.16 | >−4.30 | >−4.30 | −4.57 | >−4.30 | >−4.30 | −4.59 | >−4.30 | >−4.00 |
| NCI-H460 | >−4.00 | −4.19 | >−4.00 | >−4.30 | >−4.30 | −4.62 | >−4.30 | >−4.30 | −4.36 | >−4.30 | >−4.00 |
| NCI-H-522 | — | −4.40 | −4.17 | >−4.30 | >−4.30 | >−4.30 | >−4.30 | <−4.30 | >−4.30 | >−4.30 | >−4.00 |
| Colon Cancer | | | | | | | | | | | |
| COLO 205 | >−4.00 | −4.50 | −4.15 | 4.78 | — | −5.55 | −5.28 | >−4.30 | >−4.30 | >−4.30 | >−4.41 |
| HCC-2998 | >−4.00 | −4.59 | >−4.00 | — | — | — | — | — | −4.55 | >−4.30 | −4.26 |
| HCT-116 | >−4.00 | −4.57 | >−4.00 | >−4.30 | >−4.30 | −4.72 | >−4.30 | >−4.30 | >−4.30 | >−4.30 | >−4.00 |
| HCT-15 | >−4.00 | −4.06 | −4.03 | >−4.30 | >−4.30 | −4.70 | >−4.30 | >−4.30 | −4.81 | >−4.30 | >−4.00 |
| HT29 | >−4.00 | >−4.00 | >−4.00 | >−4.30 | >−4.30 | >−4.30 | >−4.30 | >−4.30 | — | — | −4.39 |
| KM12 | >−4.00 | −4.29 | >−4.00 | −4.60 | −4.36 | −5.23 | −5.95 | −5.02 | −4.37 | >−4.30 | >−4.00 |
| SW-620 | >−4.00 | −4.44 | >−4.00 | — | — | — | — | — | −4.53 | >−4.30 | >−4.00 |
| CNS Cancer | | | | | | | | | | | |
| SF-268 | — | −4.23 | −4.12 | >−4.30 | >−4.30 | −4.59 | >−4.30 | <−4.30 | −4.31 | >−4.30 | — |
| SF-295 | — | −4.39 | −4.04 | — | −4.60 | — | — | — | −4.33 | >−4.30 | — |
| SF-539 | — | −4.34 | >−4.00 | >−4.30 | >−4.30 | >−4.30 | >−4.30 | >−4.30 | −4.56 | >−4.30 | >−4.00 |
| SNB-19 | >−4.00 | −4.13 | >−4.00 | >−4.30 | — | −4.44 | >−4.30 | >−4.30 | >−4.30 | — | >−4.00 |
| SNB-75 | >−4.00 | −4.12 | >−4.00 | >−4.30 | >−4.30 | −4.32 | >−4.30 | >−4.30 | — | — | — |
| U251 | >−4.00 | >−4.00 | −4.08 | >−4.30 | >−4.30 | −4.72 | >−4.30 | — | −4.69 | >−4.30 | −4.15 |

TABLE V-continued

| Panel/Cell Line | Artem-isinin | Trioxane Dimers | | | | | | | | | Pacli-taxel |
| --- | --- | --- | --- | --- | --- | --- | --- | --- | --- | --- | --- |
| | | 4 | 5 | 8a | 9 | 10c | 11b | 12b | 13 | 14 | |
| Melanoma | | | | | | | | | | | |
| LOX IMVI | — | >−4.00 | −4.44 | — | — | — | — | — | −5.78 | −4.39 | >−4.15 |
| MALME-3M | >−4.00 | −4.28 | −4.11 | >−4.30 | >−4.30 | −4.80 | >−4.30 | >−4.30 | −4.66 | >−4.30 | −4.11 |
| M14 | >−4.00 | −4.14 | >−4.00 | >−4.30 | >−4.30 | −4.42 | >−4.30 | >−4.30 | >−4.30 | >−4.30 | −4.13 |
| SK-MEL2 | >−4.00 | −4.46 | −4.12 | >−4.30 | >−4.30 | >−4.30 | >−4.30 | >−4.30 | >−4.30 | >−4.30 | >−4.00 |
| SK-MEL-28 | >−4.00 | −4.12 | >−4.00 | >−4.30 | >−4.30 | >−4.30 | >−4.30 | >−4.30 | −4.34 | >−4.30 | — |
| SK-MEL-5 | >4.00 | −4.53 | −4.21 | — | — | — | — | — | −4.73 | >−4.30 | — |
| UACC-257 | >−4.00 | −4.30 | −4.36 | >−4.30 | >−4.30 | >−4.30 | >−4.30 | >−4.30 | >−4.30 | >−4.30 | −4.03 |
| UACC-62 | >−4.00 | −4.29 | −4.24 | — | — | — | — | — | −4.66 | >−4.30 | −4.19 |
| Ovarian Cancer | | | | | | | | | | | |
| IGROVI | >−4.00 | −4.32 | −4.17 | >−4.30 | >−4.30 | >−4.30 | >−4.30 | >−4.30 | >−4.30 | >−4.30 | >−4.00 |
| OVCAR-3 | — | −4.42 | >−4.00 | >−4.30 | >−4.30 | −5.01 | >−4.30 | >−4.30 | −4.51 | >−4.30 | >−4.00 |
| OVCAR-4 | — | −4.16 | −4.12 | — | — | — | — | — | −4.42 | >−4.30 | >−4.00 |
| OVCAR-5 | >−4.00 | −4.54 | >−4.00 | >−4.30 | >−4.30 | −4.88 | >−4.30 | >−4.30 | −4.66 | >−4.30 | >−4.00 |
| OVCAR-8 | >−4.00 | −4.03 | >−4.00 | >−4.30 | >−4.30 | >−4.30 | >−4.30 | >−4.30 | >−4.30 | >−4.30 | >−4.00 |
| SK-OV-3 | — | −4.21 | >−4.00 | >−4.30 | — | −4.47 | >−4.30 | >−4.30 | −4.31 | >−4.30 | — |
| Renal Cancer | | | | | | | | | | | |
| 786-0 | >−4.00 | −4.31 | >−4.00 | >−4.30 | >−4.30 | −4.64 | >−4.30 | >−4.30 | −4.43 | >−4.30 | >−4.00 |
| A498 | >−4.00 | −4.50 | −4.21 | — | — | — | — | — | −4.74 | >−4.30 | −4.13 |
| ACHN | >−4.00 | −4.30 | 4.47 | — | >−4.30 | — | — | — | −4.79 | >−4.30 | −4.45 |
| CAKI-1 | — | −4.38 | −4.13 | >−4.30 | >−4.30 | −4.93 | −4.44 | −4.47 | −4.66 | >−4.30 | >−4.00 |
| RXF 393 | >−4.00 | −4.01 | −4.18 | >−4.30 | >−4.30 | −4.73 | >−4.30 | >−4.30 | >−4.30 | >−4.30 | >−4.00 |
| SN12C | >−4.00 | −4.35 | −4.26 | — | — | — | — | — | −4.72 | >−4.30 | >−4.00 |
| TK-10 | >−4.00 | −4.38 | −4.06 | >−4.30 | >−4.30 | −4.62 | >−4.30 | >−4.30 | −4.53 | >−4.30 | — |
| UO-31 | >−4.00 | −5.14 | −4.26 | >−4.30 | >−4.30 | >−4.30 | >−4.30 | >−4.30 | >−4.30 | >−4.30 | — |
| Prostate Cancer | | | | | | | | | | | |
| PC-3 | >−4.00 | −4.34 | >−4.00 | >−4.30 | >−4.30 | −4.62 | >−4.30 | >−4.30 | −4.63 | >−4.30 | >−4.00 |
| DU-145 | — | −4.36 | −4.13 | — | — | — | — | — | −4.6- | >−4.30 | >−4.00 |
| Breast Cancer | | | | | | | | | | | |
| MCF7 | >−4.00 | −4.03 | −4.22 | >−4.30 | >−4.30 | >−4.30 | >−4.30 | >−4.30 | −4.44 | >−4.30 | >−4.00 |
| NCI/ADR-RES | — | −4.52 | >−4.00 | >−4.30 | >−4.30 | −4.63 | >−4.30 | >−4.30 | −4.65 | >−4.30 | >−4.00 |
| MDA-MB231/ATCC | >−4.00 | >−4.00 | −4.15 | >−4.30 | — | −5.02 | — | — | −4.77 | >−4.30 | −4.29 |
| HS 578T | >−4.00 | >−4.00 | >−4.00 | >−4.30 | >−4.30 | >−4.30 | >−4.30 | >−4.30 | −4.35 | >−4.30 | — |
| MDA-MB-435 | — | −4.30 | −4.09 | >−4.30 | >−4.30 | −4.60 | >−4.30 | >−4.30 | −4.46 | >−4.30 | — |
| MDA-N | >−4.00 | −4.45 | — | — | — | — | — | — | — | — | — |
| BT-549 | >−4.00 | −4.31 | −4.30 | >−4.30 | — | −4.61 | >−4.30 | >−4.30 | −4.61 | >−4.30 | >−4.00 |
| T-47D | >−4.00 | −4.17 | >−4.00 | >−4.30 | — | >−4.30 | >−4.30 | >−4.30 | >−4.30 | >−4.30 | >−4.00 |
| MG MID | — | −4.26 | −4.09 | −4.32 | −4.31 | −4.55 | −4.37 | −4.32 | −4.51 | −4.30 | — |
| Delta | −4.00 | 0.88 | 0.37 | 0.46 | 0.29 | 1.00 | 1.58 | 0.70 | 1.27 | 0.08 | −4.06 |
| Range | 0.00 | 1.14 | 0.47 | 0.48 | 0.30 | 1.25 | 1.65 | 0.72 | 1.49 | 0.09 | .045 |

The data indicate that alcohol and diol dimers 4 and 5 are selectively and strongly inhibitory to leukemia cell line RPM 1-8226, to melanoma cell line SK-MEL-5, and to renal cancer cell line ACHN. The epoxide dimer 6 and the ketone dimer 7 are less inhibitory. The data further indicate that the carboxylic acid derivatives 8a, 9, 10c, 11b, and 12b are also selectively and strong inhibitory to colon cancer KM12, ovarian cancer OVCAR 3, and to breast cancer MDA-MB-435. The data lastly indicate that the acetic acid derivative 12b is highly selective and especially inhibitory.

The dimers 4, 5, 8a, 9, 10c, 11b and 12b of the present invention in most instances are as potent and in some instances more potent than paclitaxel. The data in Tables III, IV and V are graphically represented in FIGS. 7a, 7b, 7c, 7d, 7e, 7f, 7g, 7h, 7i, 7j and 7k through FIGS. 15j. Dose response curves, shown in the above mentioned Figures, are obtained by exposing various cancer cell lines to compounds having a known concentration ($[\log_{10}M]$), as discussed in detail above, and then plotting the percentage growth of each cell line for each concentration. The drug concentration limits that are tested are between $10^{-4}$ or −4.00M and $10^{-9}$ or −9.00M. The −4.00M value being the high concentration and the −9.00M value being the low concentration. Percentage growth is determined by dividing the number or mass of cells in the test well by the number or mass of cells in a control well. Referring to the leukemia cell line MOLT-4 in FIGS. 7a, 7b, 7c, 7d, 7e, 7f, 7g, 7h, 7i, 7j and 7k the first comparison that is made between artemisinin, paclitaxel, and the dimers 4, 5, 8a, 9, 10c, 11b, and 12b of the present invention are the drug concentrations which are necessary to inhibit growth, graphically represented in FIGS. 7a, 7b, 7c, 7d, 7e, 7f, 7g, 7h, 7i, 7j and 7k as the concentration necessary to achieve the percentage growth value of +50. As discussed previously, the five drug dilutions routinely tested range from $10^{-4}$ to $10^{-9}$ molar.

Therefore, concentrations less than or greater than $10^{-9}$ and $10^{-4}$ molar, respectively, that are required to achieve a desired result are not determined. Referring now to FIG. 7a, some concentration of paclitaxel that is less than $10^{-8}$M is necessary to achieve primary growth inhibition; in fact the lower concentrations have been determined for this drug and the concentration at which primary growth inhibition occurs using paclitaxel is at $10^{-11}$ molar. FIG. 7b indicates that some concentration of artemisinin that is greater than $10^{-4}$ molar is necessary to achieve primary growth inhibition. Referring to the alcohol and diol trioxane dimers 4 and 5, dose response curves in FIGS. 7c and 7d, respectively, the leukemia cell line MOLT-4 displays primary growth inhibition at drug concentrations that are less than $10^{-7}$ and less than $10^{-8}$ molar, respectively. Referring to the carboxylic acid derivatives 8a, 9, 10c, 11b and 12b, dose response curves in FIGS. 7e, 7f, 7g, 7h and 7i, respectively, the leukemia cell line MOLT-4 displays primary growth inhibition at drug concentrations that are less than $10^{-8}$, $10^{-5}$, $10^{-8}$ and $10^{-7}$ molar respectively. The drug concentration at which artemisinin is considered cytostatic, i.e., percentage growth is equal to 0, is at a concentration greater than $10^{-4}$ molar. The dimers 4, 5, 8a, 9, 10c, 11b, and 12b reach cytostasis at some concentration greater than $10^{-4}$ M, while the paclitaxel concentration necessary to achieve cytostasis is also some value greater than $10^{-4}$ M. Cytotoxicity, i.e., the concentration for which the percentage growth is equal to –50, occurs at a concentration greater than $10^{-4}$ M for paclitaxel, artemisinin, for both alcohol and diol trioxane dimers 4 and 5, and for carboxylic acid dimers 8a, 9, 10c, 11 and 12b, respectively.

The potency of the dimers 4, 5, 8a, 9, 10c, 11b, and 12b, respectively, of the present invention as compared to artemisinin and paclitaxel varies from cell line to cell line. The mean values for each drug are presented at the end Tables III, IV and V and the dimers 4, 5, 8a, 9, 10c, 11b, and 12b of the present invention are more potent than artemisinin and equivalent to and in many instances higher in potency than paclitaxel.

The dihydroartemisinin dimer disclosed by M. Cao, et al., and tested by D. L. Klayman and H. J. Woerdenbag, discussed previously, was approximately twenty-two times more potent at causing 50% growth inhibition in one cancer cell line than artemisinin. With respect to the drug concentrations causing 50% growth inhibition, the dimers 4, 5, 8a, 9, 10c, 11b, and 12b were at least 100 times more potent than artemisinin. When interpreting the mean values, it is important to take into consideration that drug concentrations less than $10^{-9}$M and greater then 10M were not collected, and this factor is reflected in the range.

For a further comparison on the effects of the trioxane dimers of the present invention on various cancer cell lines versus the effects of artemisinin and paclitaxel on the same cell lines see FIGS. 8a, b, c, d, e, f, g, h, i, j and k for non-small cell lung cancer cell lines, FIGS. 9a, b, c, d, e, f, g, h, i, j and k for colon cancer cell lines, FIGS. 10a, b, c, d, e, f, g, h, I, j and k for CNS cancer cell lines, FIGS. 11a, b, c, d, e, f, g, h, i, j and k for melanoma cancer cell lines, FIGS. 12a, b, c, d, e, f, g, h, i, j and k for ovarian cancer cell lines, FIGS. 13a, b, c, d, e, f, g, h, i, j and k for renal cancer cell lines, FIGS. 14a, b, c, d, e, f, g, h, i, and j for prostate cancer cell lines and FIGS. 15a, b, c, d, e, f, g, h, i, and j for breast cancer cell lines.

Acute Toxicity Study of Three Anti-Malarial Compounds in Male CD-1 Mice

The purpose of this study was to determine the relative toxicity of four structurally similar anti-malarial compounds (13, 16, 19, and sodium artesunate) following a single intraperitoneal (ip) injection. This study was not performed in compliance with the U.S. FDA "Good Laboratory Practice for Nonclinical Laboratory Studies" (GLP) as described in 21 CFR Part 58; however, documentation of all procedures and quality control checking of data was performed as for GLP studies.

Materials and Methods

A. Test Article and Dose Preparation

Compounds 13, 16, 19 and sodium artesunate (Mepha Ltd., Lot No. 1), were provided by NIAID via McKesson BioServices HBOC (Rockville, Md.). Each compound was dissolved in DMSO (Mallinkrodt Lot No. V18H15) to achieve a concentration of 200 mg/ml, and then 3 parts sesame oil (Spectrum Lot No. M10656) was added to make a working concentration of 50 mg/ml for dose administration. Stability, strength, and uniformity of the test articles in the dose formulations were not determined for this study.

B. Test System

Forty-two CD1 male mice purchased from Charles River Laboratories (Wilmington, Mass.) were used in the study. Mice were quarantined for 3 days prior to initiation of the study. General procedures for animal care and housing were in accordance with the National Research Council (NRC) *Guide for the Care and Use of Laboratory Animals* (1996) and the animal welfare standards incorporated in 9 CFR Part 3, 1991. Mice were approximately 6 weeks old and weighed 25.2-31.2 g at study initiation. They were individually housed under a 12 hr light-dark cycle, with a temperature range of 68-72° F. and 33-67% humidity. Purina Certified Rodent Chow #5002 and purified tap water were available ad libitum.

C. Experimental Design and Data Collection

Mice were weighed and randomized into treatment groups on the day prior to the first dose administration. Due to limitations in the amount of available test materials, fewer mice in 1000 mg/kg groups were treated than specified in the protocol. The numbers of animals intended to be used and actually used with each compound at each dose level are shown in the table below; the only differences are in the high-dose groups.

Mice were administered either compounds 13, 16,19 or sodium artesunate once ip at does levels at 125, 250, 500, or 1000 mg/kg. Control animals were administered a vehicle solution (25% DMSO and 75% sesame oil) at a volume of 20 ml/kg. Surviving animals were sacrificed on Day 8 and blood was collected for clinical pathology evaluations.

Clinical signs were observed daily, including evaluation of the injection site 1 to 2 hr. after treatment on Day 1 and once daily on Days 2-8. Mortality and morbidity were checked twice daily on weekdays and once daily on the weekend, see Table VI. Animals were weighed daily and prior to necropsy.

TABLE VI

| | Mortality Data | | | |
|---|---|---|---|---|
| | 750 mg/kg | 500 mg/kg | 250 mg/kg | 125 mg/kg |
| Control | No death (12.5 and 18.75 ml/kg) | | | |
| Na Artesunate | — | 3/3 dead | 1/3 dead | No death |
| 13 | 2/3 dead | 3/3 dead | No death | No death |
| 16 | 3/3 dead | 3/3 dead | No death | No death |
| 19 | 3/3 dead | 1/3 dead | No death | No death |

TABLE VII

Efficacy Study Blood Schizontocidal Activity

| Compound | Route: IV | | Route: PO | |
| --- | --- | --- | --- | --- |
| | $ED_{50}$ | $ED_{90}$ | $ED_{50}$ | $ED_{90}$ |
| Na Artesunate | 5.0 | 40.0 | 6.0 | 60.0 |
| | (2.9-7.5) | (23.0-60.0) | (4.0-10.0) | (40.0-100.0) |
| 13 | 0.55 | 2.0 | 4.0 | 9.0 |
| | (0.1-0.8) | (0.8-3.2) | (2.0-7.0) | (4.3-17.0) |
| 16 | 60.0 | 1000.0 | | |
| 12b | 5.2 | 10.0 | 6.0 | 19.0 |
| | (4.9-6.0) | (6.9-15.0) | (2.7-13.0) | (8.0-39.0) |
| 19 | 1.7 | 4.5 | 5.5 | 18.0 |
| | (1.1-4.9) | (3.0-11.0) | (2.9-13.0) | (8.0-38.0) |

In conclusion, new C-10 non-acetal trioxane dimer 3, easily prepared on gram scale and thermally stable, can be used to make a diverse series of 3-carbon atom linked, oxygenated dimers 4-7 without destroying the critical pharmacophore peroxide bond. Each of the new trioxane dimers 4, 5, and 7 is 10 times more antimalarially potent in vitro than the natural trioxane artemisinin (I), and alcohol and diol dimers 4 and 5 are strongly inhibitory but not cytotoxic toward several human cancer cell lines. Moreover, water-soluble trioxane dimers 8a-10c and 12b are orally active new antimalarials that are more efficacious than artelinic acid and than sodium artesunate in mice. These semi-synthetic new chemical entities 4 and 5 and especially 8a-10c and 12b, therefore, deserve further preclinical evaluation as potential drug candidates for chemotherapy of malaria and cancer. Dimers 13 and 19 are more efficacious (when administered both orally and i.v.) and less toxic (when administered intraperitoneally to mice as a single dose) than clinically-used sodium artesunate, thereby giving them a better antimalarial therapeutic index than sodium artesunate.

The invention is further illustrated by the following non-limited examples. All scientific and technical terms have the meanings as understood by one with ordinary skill in the art. The specific examples which follow illustrate the synthesis of representative compounds of the instant invention and are not to be construed as limiting the invention in sphere or scope. The methods may be adapted to variation in order to produce compounds embraced by this invention but not specifically disclosed. Further, variations of the methods to produce the same compounds in somewhat different fashion will be evident to one skilled in the art. The synthetic descriptions and specific examples that follow are only intended for the purposes of illustration, and are not to be construed as limiting in any manner to make compounds of the present invention by other methods.

EXAMPLES

Unless otherwise noted, reactions were run in oven-dried glassware under an atmosphere of argon. Diethyl ether (ether) and tetrahydrofuran (THF) were distilled from sodium benzophenone ketyl prior to use. Methylene chloride ($CH_2Cl_2$) was distilled from calcium hydride prior to use. All other compounds were purchased from Aldrich Chemical Company and used without further purification. Analytical thin-layer chromatography (TLC) was conducted with Silica Gel 60 F254 plates (250 micrometer thickness, Merck). Column chromatography was performed using flash silica gel (particle size 400-230 mesh). Yields are not optimized. Purity of final products was judged to be >95% based on their chromatographic homogeneity. High performance liquid chromatography (HPLC) was carried out with a Rainin HPLX system equipped with two 25 mL/min preparative pump heads using a Rainin Dynamax 10 mm×250 mm (semi-preparative) column packed with 60 Å silica gel (8 μm pore size) as bare silica. Melting points were measured using a Mel-Temp metal-block apparatus and are uncorrected. Nuclear magnetic resonance (NMR) spectra were obtained on a Varian XL-400 spectrometer, operating at 400 MHz for $^1H$, 162 MHz for $^{31}P$ 100 MHz for $^{13}C$. $^1H$ and $^{13}C$ chemical shifts are reported in parts per million (ppm) downfield from tetramethylsilane, $^{31}P$ chemical shifts are measured using 85% phosphoric acid as an external reference. Splitting patterns are described as singlet(s), doublet(d), triplet(t), quartet(q), quintet (qt), sextet (st), multiplet (m) and broad (br). Infrared (IR) spectra were obtained using a Perkin-Elmer 1600 FT-IR spectrometer. Resonances are reported in wavenumbers ($cm^{-1}$). Low and high resolution mass spectra (LRMS and HRMS) were obtained with electronic or chemical ionization (EI or CI) either (1) at Johns Hopkins University on a VG Instruments 70-S Spectrometer run at 70 eV for EI and run with ammonia ($NH_3$), butane ($C4H_{10}$) or methane ($CH_4$) as carrier gas for CI or (2) at Ohio State University with a 3-Tesla Finnigan FTMS-2000 Fourier Transform mass spectrometer. Samples were sprayed from a commercial Analytica electrospray ionization source, and then focused into the FTMS cell using a home-built set of ion optics. For ESI analysis, most compounds were sprayed from a micromolar concentration of the analyte in various solvent mixtures, such as tetrahydrofuran/$CH_3OH$, with added NaCl. This process generated the sodiated molecular ion (usually as the singly-charged species), denoted as $(M+Na)^+$. But in some cases, acetic acid or trifluoroacetic acid was used to generate the protonated molecular ion (M+H)+ instead. Electron impact (EI) ionization was performed with a Kratos MS-25, using 70 eV ionization conditions. Combustion analyses were conducted by Atlantic Microlab (Norcross, Ga.). Various methods of purifying the products of the present invention are known and understood by those skilled in the art and the purification methods presented in the Examples is solely listed by way of example and is not intended to limit the invention.

Example 1

Synthesis of bis-trioxane O-allyl ether 12a and bis-trioxane O-acetic acid 12b

Synthesis of bis-trioxane O-allyl ether 12a.

To a solution of bis-trioxane primary alcohol 4 (200 mg, 0.33 mmol) in anhydrous tetrahydrofuran (20 mL) at −78° C. was added KHMDS (0.5 M sol. in toluene, 2 mL, 1 mmol) in a dropwise manner. The reaction was stirred at −78° C. for 30 mins, at which time allyl bromide (0.4 mL, 1 mmol) and 18-crown-6 (catalytic) were added. The reaction was then stirred at −78° C. for a further 1 hour, at which time TLC analysis showed complete consumption of starting material. The reaction was quenched with water (5 mL) and organics were extracted with methylene chloride (3×20 mL), dried ($MgSO_4$) and concentrated in vacuo. Column chromatography on silica eluting with 10-12% ethyl acetate/hexanes isolated bis-trioxane O-allyl ether 12a as a viscous oil (204 mg, 96%). $^1H$ NMR (400 MHz, $CDCl_3$) δ 5.98-5.88 (m, 1H), 5.32 (s, 2H), 5.28-5.23 (m, 1H), 5.14-5.10 (m, 1H), 4.34-4.28 (m, 1H), 4.24-4.17 (m, 1H), 4.04-3.90 (m, 2H), 3.61-3.54 (m, 2H), 2.76-2.60 (m, 2H), 2.38-3.26 (m, 2H), 2.10-1.20 (m), 0.99-0.81 (m, 14H); $^{13}C$ NMR (100 MHz, $CDCl_3$) δ 135.4, 116.1, 103.1, 102.9, 88.9, 88.4, 81.1, 74.7, 72.7, 71.7, 71.5, 52.4, 52.2, 44.6, 44.4, 37.3, 36.5, 35.6, 34.5, 34.4, 30.5, 30.4, 29.9, 29.6, 26.1, 26.0, 24.9, 24.6, 24.5, 20.2, 20.1, 13.3, 13.0.

Synthesis of bis-trioxane O-acetic acid 12.

To a solution of bis-trioxane O-allyl ether 12a (115 mg, 0.178 mmol) in ethyl acetate (3.0 mL), acetonitrile (3.0 mL) and water (1.0 mL) was added ruthenium (III) chloride hydrate (7.4 mg, 0.036 mmol) and sodium periodate (266 mg, 1.25 mmol) (on addition of ruthenium chloride the solution turned black). The reaction was stirred at room temperature for 30 mins (the color of the solution turned to pale orange) before the reaction mixture was poured into a mixture of ethyl acetate (30 mL) and saturated aqueous $NH_4Cl$ solution (20 mL). Organics were extracted with ethyl acetate (2×30 mL), filtered through a pad of celite, dried ($MgSO_4$) and concentrated in vacuo. Flash column chromatography (1% acetic acid in 40% ethyl acetate/hexane) isolated bis-trioxane O-acetic acid 12b as a white solid (52.0 mg, 0.078 mmol, 44%). Mp=86-90° C.; $^1$H NMR (400 MHz, $CDCl_3$) δ 5.33 (s, 2H), 4.46-4.39 (m, 1H), 4.38-4.33 (m, 1H), 4.15 (d, 1H, J=16.4), 4.03 (d, 1H, J=16.4), 3.86 (dd, 1H, J=8.8, J=5.2), 3.57 (dd, 1H, J=8.8, J=4.4), 2.71-2.52 (m, 2H), 2.37-2.29 (m, 2H), 2.08-1.18 (m, 30H, including two singlets at 1.39 and 1.38), 0.98-0.85 (m, 2H), 0.94 (apparent doublet, 6H, J=6.0), 0.86 (d, 3H, J=7.2), 0.85 (d, 3H, J=7.2); $^{13}$C NMR (100 MHz, $CDCl_3$) δ 171.7, 103.4, 103.1, 89.4, 89.2, 81.1, 81.0, 74.3, 73.6, 71.5, 69.1, 52.2, 52.1, 44.3, 44.1, 37.5, 36.5, 36.0, 34.4, 30.7, 30.7, 30.6, 26.0, 25.9, 24.8, 24.7, 20.2, 20.1, 12.9, 12.8; IR (film, cm$^{-1}$) 3506 (br), 2939, 2875, 1759, 1739, 1451, 1377, 1279, 1251, 1206, 1187, 1125, 1052, 1011, 929, 910, 826, 731; HRMS(ES) m/z calcd for $C_{36}H_{56}O_{11}Na$ (M+Na) 687.3715, found 687.3695.

Example 2

Synthesis of α-dihydroartemisinin acetate 2

To a solution of artemisinin 1 (565 mg, 2.00 mmol) in anhydrous methylene chloride (15.0 mL) at −78° C. was added DIBAL (1.0 M in toluene, 2.4 mL, 2.4 mmol) in a dropwise manner. The reaction was stirred at −78° C. for one hour, at which time TLC analysis confirmed complete consumption of starting material. Pyridine (0.50 mL, 6.18 mmol), 4-(dimethylamino)-pyridine (292 mg, 2.4 mmol) and finally acetic anhydride (0.760 mL, 8.05 mmol) were addded and the reaction was stirred vigorously at −78° C. for 3 hours before being allowed to warm to room temperature and stir overnight. The reaction was then quenched with saturated $NH_4Cl$ solution (20 mL) and organics were extracted with methylene chloride (3×20 mL), washed with brine, dried ($MgSO_4$) and concentrated in vacuo. Flash column chromatography on silica eluting with 14% ethyl acetate/hexanes isolated α-dihydroartemisinin acetate 2 as a white solid (600 mg, 1.84 mmol, 92%) with the following characteristic peaks: $^1$H NMR (400 MHz, $CDCl_3$) δ 5.78 (d, 1H, J=9.6), 5.44 (s, 1H), 2.60-2.51 (m, 1H), 2.41-2.33 (m, 1H), 2.12 (s, 3H), 1.43 (s, 3H), 0.96 (d, 3H, J=6.0), 0.84 (d, 3H, J=7.2).

Example 3

Synthesis of trioxane isobutene dimer 3

A solution of dihydroartemisinin acetate 2 (DHA acetate) (872 mg, 2.67 mmol) and the allylic bis-silane linker (267 mg, 1.34 mmol) in methylene chloride (50 mL) was cooled to −78° C. Tin tetrachloride (1M solution in $CH_2Cl_2$, 2.67 ml, 2.67 mmol) was further diluted with $CH_2Cl_2$ (3 mL) and was added to the reaction mixture dropwise using a syringe pump at the rate of 6 ml/hour. The reaction was stirred at −78° C. for a further 45 minutes at which time TLC analysis confirmed complete consumption of starting material. Saturated ammonium chloride solution (10 mL) was then added and the reaction was allowed to warm to room temperature naturally. Organics were extracted with methylene chloride (3×20 mL), dried ($Na_2SO_4$) and concentrated in vacuo. Gradient column chromatography on silica eluting with 5%, 7%, 8% and finally 10% ethyl acetate/hexanes isolated trioxane isobutene dimer 3 as a white solid (564 mg, 0.96 mmol, 71%). Mp=132-133° C.; $^1$H NMR (400 MHz, $CDCl_3$) δ 5.41 (s, 2H), 4.87 (s, 2H), 4.30 (ddd, 2H, J=10.4, J=5.6, J=4.0), 2.75-2.67 (m, 2H), 2.61-2.54 (m, 2H), 2.37-2.23 (m, 4H), 2.04-1.98 (m, 2H), 1.91-1.84 (m, 2H), 1.81-1.75 (m, 2H), 1.67-1.56 (m, 4H), 1.52-1.32 (m, 6H), 1.39 (s, 6H), 1.23-1.20 (m, 2H), 0.94 (d, 6H, J=6.0), 0.90 (d, 6H, J=7.6), 0.98-0.86 (m, 2H); $^{13}$C NMR (100 MHz, $CDCl_3$) δ 147.4, 113.1, 103.1, 88.6, 81.2, 75.5, 52.4, 44.5, 37.1, 36.7, 35.2, 34.5, 30.6, 26.2, 24.7, 24.6, 20.2, 13.3; IR (film, cm$^{-1}$) 3060, 2938, 2875, 1641, 1451, 1375, 1121, 1092, 1054, 1007, 878, 732; HRMS(ES) m/z calcd for $C_{34}H_{52}O_8Na$ (M+Na) 611.3560, found 611.3555; Anal ($C_{34}H_{52}O_8$) C, H.

Example 4

Synthesis of bis-trioxane primary alcohol 4

A solution of trioxane isobutene dimer 3 (0.89 g, 1.51 mmol) in anhydrous tetrahydrofuran (25 mL) was cooled to 0° C. Borane-dimethyl sulfide complex ($BH_3$·DMS) (2.0 M solution in diethyl ether, 0.9 mL, 1.80 mmol) was carefully added and the reaction was allowed to warm to room temperature and stir for 3 hours. At this time TLC analysis confirmed that no starting material remained. A suspension of sodium perborate·4$H_2O$ ($NaBO_3$·4$H_2O$) (1.17 g, 7.60 mmol) in water (12 mL) was slowly added and the resulting suspension was allowed to stir for 17 hours. Water (10 mL) and methylene chloride (50 mL) were added and organics were extracted with methylene chloride (3×20 mL), dried ($Na_2SO_4$) and concentrated in vacuo to give a white solid. Gradient column chromatography on silica eluting with 20%, 30% and finally 40% ethyl acetate/petroleum ether isolated bis-trioxane primary alcohol 4 as a white solid (0.85 g, 1.40 mmol, 93%). $^1$H NMR ($CDCl_3$, 400 MHz) δ 6 35 (s, 1H), 5.34 (s, 1H), 4.47-4.40 (m, 1H), 4.33 (qt, 1H, J=6.0), 3.83-3.75 (m, 1H), 3.67-3.60 (m, 1H), 3.17 (dd, 1H, J=7.6, J=6.1), 2.64 (qt, 1H, J=6.9), 2.59 (qt, 1H, J=6.9), 2.32 (t, br, 2H, J=14.1), 2.06-1.97 (m, 3H), 1.95-1.87 (m, 2H), 1.86-1.74 (m, 2H), 1.70-1.55 (m, 8H), 1.50-1.30 (m, 14H, including singlet at 1.40), 0.99-0.90 (m, 2H), 0.95 (d, 6H, J=5.8), 0.87 (apparent t, 6H, J=6.9); $^{13}$C NMR ($CDCl_3$, 100 MHz) δ 103.12, 102.97, 89.47, 89.22, 81.11 (2), 73.86, 71.27, 65.12, 52.20, 52.07, 44.18, 44.01, 37.68, 37.46, 37.43, 36.52, 36.51, 34.40, 34.37, 31.26, 30.74 (2), 30.65, 25.95, 25.89, 24.83 (2), 24.73, 24.70, 20.15, 20.10, 12.89, 12.61; HRMS (El, m/z) for $C_{34}H_{54}O_9Na$ requires 629.3660, found 629.3697; IR (film, cm$^{-1}$) 3490; Mp. 81-82° C.; Anal ($C_{34}H_{56}O_{10}$) C, H.

Example 5

Synthesis of bis-trioxane vicinal diol 5

To a solution of trioxane isobutene dimer 3 (21.0 mg, 0.036 mmol) and 4-methylmorpholine N-oxide (5.0 mg, 0.043 mmol) in acetone (2.0 mL) was added osmium tetroxide (25 mg/2 mL aqueous solution, 0.016 mL, catalytic) and the reaction was stirred vigorously at room temperature for 24 hrs. The reaction mixture was then quenched with saturated aqueous NaHSO$_3$ solution (2.0 mL) and stirred for an additional 30 mins (during which time the reaction turned a pale orange color). The reaction mixture was poured into a mixture of diethyl ether (20 mL) and saturated aqueous NH$_4$Cl solution (20 mL) and organics were extracted with ethyl acetate (2×30 mL), washed with brine, dried (MgSO$_4$) and concentrated in vacuo. Flash column chromatography on silica eluting with 50% ethyl acetate/hexanes) isolated bis-trioxane vicinal diol 5 as a white solid (20.3 mg, 0.033 mmol, 92%). Mp=159-160° C.; $^1$H NMR (400 MHz, CDCl$_3$) δ 5.36 (s, 1H), 5.35 (s, 1H), 4.74-4.70 (m, 1H), 4.56-4.51 (m, 1H), 4.09 (s, 1H), 3.71-3.62 (m, 2H), 3.12 (t, 1H, J=7.2), 2.64-2.52 (m, 2H), 2.36-2.26 (m, 2H), 2.04-1.99 (m, 2H), 1.96-1.63 (m, 12H), 1.46-1.20 (m, 14H, including two singlets at 1.40 and 1.39), 0.96 (d, 3H, J=6.0), 0.95 (d, 3H, J=6.0), 0.89 (d, 3H, J=7.6), 0.88 (d, 3H, J=7.6), 0.98-0.86 (m, 2H); $^{13}$C NMR (100 MHz, CDCl$_3$) δ 103.0, 102.9, 89.7, 89.5, 81.1, 81.0, 74.7, 70.6, 70.5, 68.4, 52.0, 43.8, 43.7, 37.8, 37.5, 36.5, 34.9, 34.3, 31.0, 30.9, 25.9, 25.9, 24.9, 24.8, 24.8, 20.1, 12.5, 12.4; IR (film, cm$^{-1}$) 3499, 2951, 2876, 1453, 1378, 1207, 1108, 1054, 1009, 912, 878, 844, 732; HRMS(ES) m/z calcd for C$_{34}$H$_{54}$O$_{10}$Na (M+Na) 645.3609, found 645.3559.

Example 6

Synthesis of bis-trioxane epoxide 6

To a solution of trioxane isobutene dimer 3 (34.1 mg, 0.058 mmol) in anhydrous methylene chloride (10.0 mL) at −78° C. was rapidly added dimethyl dioxirane (DMDO) (0.08 M solution in acetone, 3.8 mL, 0.29 mmol). The reaction was stirred at −78° C. for 30 minutes before being allowed to warm to room temperature. The reaction was then concentrated in vacuo, giving a yellow oil. Flash column chromatography on silica eluting with 20% theyl acetate/hexanes isolated bis-trioxane epoxide 6 as a white solid (28.1 mg, 0.047 mmol, 80%). Mp=147-148° C.; $^1$H NMR (400 MHz, CDCl$_3$) δ 5.48 (s, H), 5.43 (s, H), 4.45 (dd, 1H, J=10.0, J=6.0), 4.22 (dd, 1H, J=10.0, J=6.0), 2.82-2.72 (m, 2H), 2.68-2.62 (m, 3H), 2.43-2.33 (m, 3H), 2.02-1.97 (m, 2H), 1.88-1.82 (m, 2H), 1.75-1.70 (m, 2H), 1.62-1.58 (m, 2H), 1.54-1.26 (m, 11H), 1.39 (s, 6H), 0.98-0.88 (m, 3H), 0.93 (d, 6H, J=6.4), 0.92 (d, 6H, J=6.4), 0.80 (d, 6H, J=7.6); $^{13}$C NMR (100 MHz, CDCl$_3$) δ 103.43, 103.40, 87.94, 87.93, 81.10, 81.07, 75.44, 74.37, 60.43, 54.46, 52.54, 52.50, 44.58, 36.91, 36.70, 34.40, 33.50, 33.01, 30.40, 30.36, 26.18, 24.45, 24.35, 24.32, 20.22, 20.19, 13.69, 13.51; IR (film, cm$^{-1}$) 2939, 2875, 1452, 1376, 1280, 1208, 1188, 1123, 1091, 1057, 1006, 941, 878, 754; HRMS (ES) m/z calcd for C$_{34}$H$_{52}$O$_9$Na (M+Na) 627.3509, found 627.3478.

Example 7

Synthesis of bis-trioxane ketone 7

To a solution of trioxane isobutene dimer 3 (30 mg, 0.051 mmol) in anhydrous N,N-dimethylformamide (25 μL) was added OsO$_4$ (2.5% weight % in t-BuOH, 0.1 mol %). The reaction mixture was stirred for 5 minutes before Oxone® (63 mg, 0.2 mmol) was added in one portion. The reaction was then stirred for a further 2 hours, at which time TLC analysis confirmed full consumption of starting material. The reaction was quenched with saturated Na$_2$SO$_3$ solution (10 mL) and water (10 mL) and stirred for 1 hour before organics were extracted with methylene chloride (3×20 mL), dried (Na$_2$SO$_4$) and concentrated in vacuo. Flash column chromatography on silica eluting with 25% ethyl acetate/hexanes) isolated bis-trioxane ketone 7 as a white solid (21 mg, 0.035 mmol, 70%). Mp=120-121° C.; $^1$H NMR (400 MHz, CDCl$_3$) δ 5.34 (s, 2H), 4.75 (m, 2H), 2.90 (m, 2H), 2.75 (m, 2H), 2.59 (dd, 2H, J=16, J=4), 2.33 (dt, 2H, J=16, J=9), 2.04-1.96 (m, 2H), 1.94 (m, 2H), 1.79 (m, 2H), 1.68-1.57 (m, 6H), 1.48-1.22 (m, 14H), 0.99 (d, 6H, J=6.4), 0.88 (d, 6H, J=7.2); $^{13}$C NMR (100 MHz, CDCl$_3$) δ 196.8, 103.8, 89.3, 71.6, 52.5, 44.5, 44.3, 37.7, 36.8, 34.7, 30.3, 26.3, 25.0, 24.8, 20.4, 13.8; IR (film, cm$^{-1}$) 1722; HRMS(ES) m/z calcd for C$_{33}$H$_{50}$O$_9$Na (M+Na) 613.3347, found 613.3303.

Example 8

Synthesis of bis-trioxane primary succinate monoester 8a

To a solution of bis-trioxane primary alcohol 4 (50 mg, 0.082 mmol) and succinic anhydride (24 mg, 0.24 mmol) in methylene chloride (10 mL) at 0° C. was added 4-(dimethylamino)-pyridine (10 mg, 0.082 mmol). The reaction was allowed to warm to room temperature and was then stirred for 12 hours, at which TLC analysis showed complete consumption of starting material. Organics were extracted with ethyl acetate (3×30 mL), washed with brine (10 mL), dried (MgSO$_4$) and concentrated in vacuo. Flash column chromatography on silica eluting with 50% ethyl acetate/hexanes to isolated bis-trioxane primary succinate monoester 8a as a white solid (40 mg, 0.068 mmol, 84%). $^1$H NMR (400 MHz, CDCl$_3$) δ 5.39 (s, 1H), 5.31 (s, 1H), 4.39-4.32 (m, 2H), 4.28-4.18 (m, 3H), 2.74-2.54 (m, 6H), 2.38-2.24 (m, 2H), 2.22-2.12 (m, 1H), 2.06-1.96 (m, 2H), 1.95-1.85 (m, 2H), 1.84-1.60 (m, 11H), 1.48-1.20 (m, 16H), 1.00-0.80 (m, 12H); $^{13}$C NMR (100 MHz, CDCl$_3$) δ 175.4, 172.0, 102.9, 103.6, 89.4, 88.5, 81.1, 74.1, 71.1, 67.1, 52.4, 52.1, 44.6, 44.1, 37.4, 37.3, 36.6, 36.5, 34.4, 34.3, 30.5, 30.4, 30.0, 29.7, 29.4, 29.0, 26.0, 25.9, 24.7, 20.3, 20.1, 13.3, 12.7; HRMS(ES) m/z calcd for C$_{38}$H$_{58}$O$_{12}$Na (M+Na) 729.3820, found 729.3795.

Example 9

Synthesis of bis-trioxane primary alcohol isonicotinate 8b

To a stirring suspension of bis-trioxane primary alcohol 4 (30.4 mg, 0.050 mmol) and isonicotinic acid (20.1 mg, 0.163 mmol) in anhydrous methylene chloride (1 mL) was added 4-(dimethylamino)-pyridine (23.5 mg, 0.192 mmol) and 1-(3-(dimethylamino)propyl)-3-ethylcarbodiimide (EDC) hydrochloride (39.2 mg, 0.204 mmol). A further 1.5 mL of anhydrous methylene chloride was added to wash down the flask walls and the reaction was stirred at room temperature for 3 hours, at which time TLC analysis showed full consumption of starting material. Water (5 mL), saturated NaHCO$_3$ solution (5 mL) and methylene chloride (5 mL) were added and organics were extracted with methylene chloride (3×20 mL), dried (Na$_2$SO$_4$) and concentrated in vacuo to give a white solid. Gradient column chromatography on silica (crude was dry-loaded) eluting firstly with 25% ethyl acetate/petroleum ether and then 30% ethyl acetate/petroleum ether isolated bis-trioxane primary alcohol isonicotinate 8b as a white solid (32.6 mg, 0.046 mmol, 91%). Mp=74-78° C.; [α]$_D^{24.5}$ 77.8 (CHCl$_3$, c=0.06); $^1$H NMR (400 MHz, CDCl$_3$) δ 8.78 (s, br, 2H), 7.86 (s, br, 2H), 5.33 (s, 1H), 5.29 (s, 1H), 4.55 (s, 1H), 4.54 (s, 1H), 4.51-4.44 (m, 1H), 4.37-4.30 (m, 1H), 2.70 (st, 1H, J=7.0), 2.59 (st, 1H, J=7.0), 2.45-2.36 (m, br, 1H), 2.31 (td, 2H, J=14.0, J=3.7), 2.05-1.96 (m, 2H), 1.95-1.73 (m, 6H), 1.69-1.50 (m, 6H), 1.41-1.15 (m, 14H, including two singlets at 1.40 and 1.39), 0.98-0.92 (m, 2H), 0.96 (d, 3H, J=5.9), 0.94 (d, 3H, J=5.9), 0.88 (d, 3H, J=7.4), 0.87 (d, 3H, J=7.4); $^{13}$C NMR (100 MHz, CDCl$_3$) δ 164.99, 150.49 (2), 137.93, 122.91 (2), 103.16, 102.87, 89.52, 88.83, 81.12, 81.11, 73.23, 70.83, 68.10, 52.30, 52.07, 44.32, 44.06, 37.50, 37.47, 36.64, 36.54, 34.42, 34.39, 33.95, 30.61, 30.58, 30.49, 30.15, 26.02, 26.01, 24.97, 24.89, 24.76, 24.67, 20.17, 20.10, 13.08, 12.72; IR (film, cm$^{-1}$) 2942, 1866, 1726, 1452, 1407, 1372, 1321, 1276, 1210, 1123, 1106, 1057, 1046, 1006, 931, 876, 756, 707; HRMS (El, m/z) calcd for C$_{40}$H$_{57}$NO$_{10}$Na (M+Na) 734.3875, found 734.3855; Anal (C$_{40}$H$_{57}$NO$_{10}$) C, H.

Example 10

Synthesis of tertiary alcohol primary succinate ester 9

To a solution of bis-trioxane vicinal diol 5 (52.9 mg, 0.085 mmol) in anhydrous methylene chloride (3.0 mL) was added succinic anhydride (25.5 mg, 0.255 mmol) and 4-(dimethylamino)-pyridine (10.4 mg, 0.085 mmol). The reaction was stirred for 24 hours at room temperature, at which time TLC analysis confirmed full consumption of starting material. The reaction mixture was then poured into a mixture of methylene chloride (30 mL) and saturated NH$_4$Cl solution (30 mL). Organics were extracted with methylene chloride (3×20 mL), washed with brine, dried (MgSO$_4$) and concentrated in vacuo. Flash column chromatography on silica eluting with 2-propanol/methylene chloride/ethyl acetate (1:3:18) isolated tertiary alcohol primary succinate ester 9 as a white solid (52.0 mg, 0.071 mmol, 85%). Mp=95-97° C.; $^1$H NMR (400 MHz, CDCl$_3$) δ 5.38 (s, 1H), 5.34 (s, 1H), 4.61-4.52 (m, 2H), 4.29 (Abq, 2H, J$_{AB}$=18.8, Δv$_{AB}$=11.6), 2.72-2.66 (m, 4H), 2.58-2.50 (m, 2H), 2.36-2.24 (m, 2H), 2.04-1.58 (m, 13H), 1.46-1.18 (m, 11 H), 1.40 (s, 3H), 1.39 (s, 3H), 0.95 (d, 6H, J=6.0), 0.88 (d, 3H, J =7.6), 0.87 (d, 3H, J=7.6), 0.98-0.86 (m, 2H); $^{13}$C NMR (100 MHz, CDCl$_3$) 6176.4, 171.7, 103.2, 102.9, 89.6, 89.0, 81.1, 81.0, 73.3, 70.6, 70.3, 68.6, 52.1, 51.9, 44.1, 43.7, 37.5, 36.6, 36.5, 36.3, 35.1, 34.4, 34.3, 30.8, 30.7, 29.2, 29.1, 25.9, 25.8, 24.8, 24.7, 20.2, 20.1, 12.8, 12.5; IR (film, cm$^{-1}$) 3502, 2950, 2872, 1737, 1713, 1453, 1378, 1208, 1168, 1106, 1054, 1009, 942, 878, 844, 735; HRMS(ES) m/z calcd for C$_{38}$H$_{58}$O$_{13}$Na (M+Na) 745.3769, found 745.3726; [α]$^{p23.5}$ 56.6 (CHCl$_3$, c=0.16); Anal (C$_{38}$H$_{58}$O$_{13}$) C, H.

Example 11

Synthesis of bis-trioxane β-hydroxysulfide ester 10a

To a solution of bis-trioxane epoxide 6 (80.0 mg, 0.132 mmol) in anhydrous diethyl ether (10.0 mL) was added methyl 4-mercaptobenzoate (44.4 mg, 0.264 mmol) and neutral aluminum oxide (1.0 g, type W 200 super I, Woelm Pharma, Germany). The resulting slurry was stirred at room temperature for 3 hours, at which time TLC analysis confirmed full consumption of starting material. The reaction mixture was then filtered through a pad of celite and the remaining solid was washed with ethyl acetate (2×30 mL) before concentration of the organics in vacuo. Flash column chromatography on silica eluting with 25% ethyl acetate/hexanes isolated bis-trioxane p-hydroxysulfide ester 10a as a sticky solid (81.2 mg, 0.105 mmol, 80%). $^1$H NMR (400 MHz, CDCl$_3$) δ 7.67 (ABq, 4H, J$_{AB}$=8.4, Δv$_{AB}$=154.4), 5.36 (s, 1H), 5.35 (s, 1H), 4.69 (dd, 1H, J=10.4, J=6.0), 4.69 (dd, 1H, J=10.0, J=6.0), 3.88 (s, 3H), 3.52 (ABq, 2H, J$_{AB}$=12.4, Δv$_{AB}$=44.4), 2.65-2.55 (m, 1H), 2.52-2.42 (m, 1H), 2.34-2.24 (m, 2H), 2.08-1.58 (m, 12H), 1.46-1.18 (m, 10H), 1.36 (s, 3H), 1.31 (s, 3H), 0.94 (d, 3H, J=6.0), 0.85 (d, 3H, J=6.8), 0.84 (d, 3H, J=7.2), 0.98-0.86 (m, 2H). $^{13}$C NMR (100 MHz, CDCl$_3$) δ166.9, 145.0, 129.6, 127.7, 126.4, 102.9, 102.8, 89.7, 89.3, 81.1, 81.0, 74.9, 70.8, 70.5, 52.1, 51.9, 43.9, 43.6, 42.4, 38.3, 37.4, 36.5, 36.4, 36.1, 34.4, 34.3, 30.8, 30.7, 26.0, 25.9, 24.8, 24.7, 20.1, 20.0, 12.7, 12.4; IR (film, cm$^{-1}$) 3498, 2951, 2876, 1721, 1594, 1430, 1377, 1276, 1182, 1110, 1054, 1008, 942, 880, 845, 762, 736.

Example 12

Synthesis of bis-trioxane P-hydroxysulfone ester 10b

To a solution of bis-trioxane β-hydroxysulfide ester 10a (40.0 mg, 0.052 mmol) in tetrachloromethane (1.5 mL), acetonitrile (1.5 mL) and H$_2$O (2.3 mL) was added ruthenium (III) chloride hydrate (catalytic) and periodic acid (23.7 mg, 0.104 mmol, 2.0) (on addition of ruthenium chloride the solution turned black). On stirring for 30 minutes at room temperature, diethyl ether (30 mL) was added and the reaction was stirred for a further 10 minutes. The reaction mixture was then dried (MgSO$_4$), filtered through a pad of celite and the remaining solid was washed with ethyl acetate (30 mL). The organics were then concentrated in vacuo and flash column chromatography on silica eluting with 30% ethyl acetate/hexanes isolated bis-trioxane β-hydroxysulfone ester 10b as a white solid (32.0 mg, 0.040 mmol, 76%). Mp=115-117° C.; $^1$H NMR (400 MHz, CDCl$_3$) δ 8.21 (ABq, 4H, J$_{AB}$=8.4, Δv$_{AB}$=73.6), 5.70 (s, 1H), 5.36 (s, 1H), 5.19 (dd, 1H, J=10.8, J=6.0), 4.88 (s, 1H), 4.58 (dd, 1H, J=9.6, J=6.4), 3.95 (s, 3H), 3.81 (ABq, 2H, J$_{AB}$=13.6, Δv$_{AB}$=278.4), 2.90-2.82 (m, 1H), 2.70-2.56 (m, 1H), 2.43-2.30 (m, 2H), 2.20-1.20 (m, 16H), 1.54 (s, 3H), 1.24 (s, 3H), 0.96 (d, 6H, J =6.0), 0.93 (d, 3H, J=8.0), 0.88 (d, 3H, J=7.6), 0.98-0.86 (m, 2H); $^{13}$C NMR (100 MHz, CDCl$_3$) δ 165.8, 145.3, 134.3, 129.9, 128.5, 103.6, 102.8, 90.1, 88.5, 81.2, 73.6, 71.6, 71.1, 60.1, 52.6, 52.5, 51.8, 45.0, 43.3, 39.5, 37.5, 37.3, 36.5, 34.5, 34.3, 30.5, 30.4, 26.4, 26.0, 25.0, 24.8, 24.6, 24.3, 20.3, 20.0, 13.7, 11.9; IR (film, cm$^{-1}$) 3458, 2951, 2875, 1731, 1435, 1377, 1320, 1280, 1153, 1105, 1051, 1015, 911, 880, 733; HRMS(ES) mlzcalcd for C$_{42}$H$_{60}$O$_{13}$SNa (M+Na) 827.3646, found 827.3661.

Example 13

Synthesis of bis-trioxane β-hydroxysulfone benzoic acid 10c

A solution of bis-trioxane β-hydroxysulfone ester 10b (19.7 mg, 0.024 mmol) in 2.5% KOH/MeOH (1.0 mL) was stirred vigorously at room temperature for three hours, at which time TLC analysis confirmed complete consumption of starting material. The solution was then evaporated to dryness in vacuo, before the addition of water (10 mL). This solution was acidified with acetic acid until pH=4.0 was attained and organics were then extracted with ethyl acetate (2×30 mL), dried (MgSO$_4$) and concentrated in vacuo. Flash column chromatography on silica eluting with 2-propanol/methylene chloride/ethyl acetate (1:3:18) isolated bis-trioxane β-hydroxysulfone benzoic acid 10c as a white solid (14.7 mg, 0.019 mmol, 79%). Mp=143-145° C.; [α]$_D^{23.9}$ 105.2 (CHCl$_3$, c=0.07); $^1$H NMR (400 MHz, CDCl$_3$) δ 8.21 (ABq, 4H, J$_{AB}$=8.4, Δv$_{AB}$=76.4), 5.71 (s, 1H), 5.38 (s, 1H), 5.19 (dd, 1H, J=10.8, J=6.4), 4.63 (dd, 1H, J=9.2, J=6.0 Hz), 3.82

(ABq, 2H, $J_{AB}$=13.6, $\Delta v_{AB}$=266.4 Hz), 2.85-2.82 (m, 1H), 2.70-2.56 (m, 2H), 2.43-2.30 (m, 2H), 2.20-1.20 (m, 22H, including two singlets at 1.56 and 1.25), 0.96 (d, 6H, J=6.0), 0.93 (d, 3H, J=8.0), 0.88 (d, 3H, J=7.6), 0.98-0.86 (m, 2H); $^{13}$C NMR (100 MHz, CDCl$_3$) δ 168.0, 145.7, 133.5, 130.4, 128.5, 103.8, 102.9, 90.1, 88.7, 81.3, 73.7, 71.8, 71.2, 60.2, 52.6, 51.9, 44.9, 43.3, 39.4, 37.5, 37.4, 37.3, 36.5, 34.5, 34.3, 30.6, 30.5, 26.1, 25.9, 25.0, 24.8, 24.5, 24.4, 20.2, 20.0, 13.6, 11.9; IR (film, cm$^{-1}$) 3459, 2939, 2875, 1723, 1432, 1403, 1378, 1319, 1300, 1228, 1154, 1099, 1051, 1015, 911, 877, 732, 616; HRMS(ES) m/z calcd for $C_{41}H_{58}O_{13}SNa$ (M+Na) 813.3490, found 813.3500; Anal ($C_{41}H_{58}O_{13}$) C, H.

Example 14

Synthesis of bis-trioxane styryl tertiary alcohol 11a

A solution of styryllithium was prepared by adding t-BuLi (1.7 M in hexanes, 1.2 ml, 2.04 mmol) to a solution of 4-bromostyrene (0.13 mL, 1 mmol) in anhydrous diethyl ether (5 mL). The resulting deep red solution was stirred for 30 minutes to ensure complete formation of styryllithium. To a solution of bis-trioxane ketone 7 (30 mg, 0.051 mmol) in anhydrous tetrahydrofuran was added the solution of styryllithium (0.35 ml, ~0.07 mmol) at −78° C. and the reaction was stirred for 30 minutes, at which time TLC analysis confirmed full consumption of starting material. Saturated ammonium chloride solution (5 mL) was added and organics were extracted with methylene chloride (3×20 mL), dried (MgSO$_4$) and concentrated in vacuo. Gradient column chromatography on silica eluting with 10 and then 15% ethyl acetate/petroleum ether isolated bis-trioxane styryl tertiary alcohol 11a as a viscous oil (26 mg, 0.037 mmol, 74%). $^1$H NMR (400 MHz, CDCl$_3$) δ 7.45 (d, J=8.4, 2H), 7.35 (d, J=8.4, 2H), 6.68 (dd, J=10.9, J=17.6, 1 H), 5.70 (d, J=17.6, 1 H), 5.35 (s, 2H), 5.2 (d, J=10.9, 2H), 4.50-4.40 (m, 1H), 4.25-4.12 (m, 1H), 2.78-2.42 (m, 4H), 2.38-1.60 (m, 14H), 1.48-1.20 (m, 14H), 1.00-0.80 (m, 14H).

Example 15

Synthesis of bis-trioxane tertiary alcohol benzoic acid 11b

To a solution of bis-trioxane styryl tertiary alcohol 11a (20 mg, 0.028 mmol) in acetone (3 mL) was added KMnO$_4$ (large excess) as a solid. The reaction was stirred at room temperature for 6 hours, at which time TLC analysis confirmed full consumption of starting material. 2-propanol was added to quench any excess KMnO$_4$ and the reaction mixture was concentrated in vacuo. Ethyl acetate (10 mL) and water (10 mL) were added and organics were extracted with ethyl acetate (3×10 mL), dried (MgSO$_4$) and concentrated in vacuo. Flash column chromatography on silica eluting with 90% ethyl acetate/petroleum ether isolated bis-trioxane tertiary alcohol benzoic acid 11b as a white solid (19 mg, 0.014 mmol, 50%). $^1$H NMR (400 MHz, CDCl$_3$) δ 7.80 (d, 2H, J=8.4), 7.39 (d, 2H, J=8.4), 5.36 (s, 2H), 4.40-4.32 (m, 1H), 4.12-4.06 (m,1H), 2.80-2.42 (m, 4H), 2.40-2.10 (m, 3H), 2.10-1.60 (m, 15H), 1.48-1.20 (m, 14H), 1.00-0.80 (m, 14H); $^{13}$C NMR (100 MHz, CDCl$_3$) δ 167.4, 132.5, 130.6, 130.0, 127.7, 104.7, 104.6, 90.5, 89.9, 82.3, 82.1, 78.4, 74.1, 73.6, 54.1, 53.8, 46.4, 45.9, 43.4, 39.8, 38.6, 38.5, 37.8, 37.7, 35.9, 35.8, 32.1, 31.9, 26.4, 26.1, 26.0, 25.9, 25.8, 25.7, 20.8, 20.7, 13.9, 13.6; HRMS(ES) m/z calcd for $C_{40}H_{56}O_{11}Na$ (M+Na) 735.3715, found 735.3717.

Example 16

Synthesis of bis-trioxane primary alcohol isonicotinate N-oxide 13

To a stirring suspension of bis-trioxane primary alcohol 4 (0.14 g, 0.24 mmol) and commercially available (Aldrich) isonicotinic acid N-oxide (0.11 g, 0.76 mmol) in anhydrous methylene chloride (10 mL) was added 4-(dimethylamino)-pyridine (0.11 g, 0.93 mmol) and 1-(3-(dimethylamino)propyl)-3-ethylcarbodiimide hydrochloride (0.17 g, 0.90 mmol). A further 5 mL of anhydrous methylene chloride was added to wash down the flask walls and the reaction was stirred at room temperature for 4 hours, at which time TLC analysis showed full consumption of starting material. Water (5 mL), 3M HCl solution (10 mL) and methylene chloride (5 mL) were added and organics were extracted with methylene chloride (3×30 mL), dried (Na$_2$SO$_4$) and concentrated in vacuo to give a colorless oil (0.23 g). Gradient column chromatography on silica (crude was dry-loaded) eluting firstly with 70% ethyl acetate/petroleum ether and then with 80% ethyl acetate/petroleum ether isolated bis-trioxane primary alcohol isonicotinate N-oxide 13 as a white solid (0.17 g, 0.23 mmol, 98%). $^1$H NMR (CDCl$_3$, 400 MHz) δ 8.22 (d, 2H, J=7.3), 7.89 (d, 2H, J =7.3), 5.32 (s, 1H), 5.29 (s, 1H), 4.52 (s, 1H), 4.51 (s, 1H), 4.51-4.54 (m, 1H), 4.39-4.32 (m, 1H), 2.67 (st, 1H, J=7.0), 2.57 (st, 1H, J=7.0), 2.42-2.26 (m, 3H), 2.07-1.97 (m, 2H), 1.97-1.85 (m, 2H), 1.84-1.74 (m, 4H), 1.70 -1.47 (m, 6H), 1.41-1.19 (m, 14H, including two singlets at 1.40 and 1.39), 1.00-0.91 (m, 2H), 0.96 (d, 3H, J=5.6), 0.95 (d, 3H, J=5.6), 0.88 (d, 3H, J=6.9), 0.86 (d, 3H, J=6.9); $^{13}$C NMR (CDCl$_3$, 100 MHz) δ 163.27, 139.35 (2), 127.26, 126.39 (2), 103.10, 102.80, 89.64, 89.01, 81.12, 81.09, 72.99, 70.52, 68.37, 52.22, 52.01, 44.21, 43.97, 37.56, 37.49, 36.63, 36.53, 34.40, 34.36, 33.98, 30.95, 30.58, 30.52, 29.68, 26.03, 25.98. 24.92, 24.88, 24.77, 24.75, 20.16, 20.07, 12.96, 12.62; HRMS (El, m/z) for $C_{40}H_{57}NO_{11}Na$ requires 750.3824, found 750.3845; IR (film, cm$^{-1}$) 2931, 2871, 1719, 1609, 1448, 1373, 1261, 1156, 1108, 1049, 1037, 1008, 925, 732; Mp. 114-122° C.; $[\alpha]_D^{231}$ 51.7 (CHCl$_3$, c=0.67); Anal ($C_{40}H_{59}NO_{12}$) C, H, N.

Example 17

Synthesis of bis-trioxane diphenyl phosphate 14

To a stirring solution of bis-trioxane primary alcohol 4 (8.0 mg, 0.013 mmol) in anhydrous methylene chloride (0.5 mL) was added diphenyl chlorophosphate (10 μL, 0.048 mmol) and pyridine (20 μL, 0.247 mmol). A further 1 mL of anhydrous methylene chloride was used to wash down the inside walls of the flask and the reaction was stirred at room temperature. TLC analysis after 18 hours showed a substantial amount of starting material still present. A second portion of diphenyl chlorophosphate (50 μL, 0.241 mmol) and 4-(dimethylamino)-pyridine (15.0 mg, 0.123 mmol) were added and the reaction stirred at room temperature for a further 2 hours. At this time, TLC analysis confirmed that no starting material remained. Water (10 mL), 3M HCl (2 mL) and methylene chloride (10 mL) were added and organics were extracted with methylene chloride (3×15 mL), dried (Na$_2$SO$_4$) and concentrated in vacuo to give a yellow oil. Gradient column chromatography on silica (crude was dry-loaded) eluting firstly with 20% and then 25% ethyl acetate/petroleum ether isolated bis-trioxane diphenyl phosphate 14 as a cloudy white oil (10.3 mg, 0.012 mmol, 93%). $^1$H NMR (CDCl$_3$, 400 MHz) δ 7.33 (t, 4H, J=7.7), 7.28-7.22 (m, 4H), 7.17 (t, 2H, J=7.7), 5.30 (s, 1H), 5.29 (s, 1H), 4.58-4.51 (m, 1H), 4.50-4.37 (m, 2H), 4.25 (dd, 1H, J=10.1, 2.05-1.97 (m, 2H), 1.95-1.79 (m, 4H), 1.79-1.33 (m, 16H, including two singlets at 1.40 and 1.37), 1.32-1.17 (m, 6H), 0.98-0.78 (m, 14H); $^{13}$C NMR (CDCl$_3$, 100 MHz) δ 150.68 (d, 2, J=7.2), 129.67 (4), 125.11 (2), 120.17 (d, 2, J=3.9), 120.12 (d, 2, J=3.9), 103.19, 102.78, 89.45, 88.73, 81.14, 81.10, 73.80, 71.92 (d, J=7.0), 70.80, 52.39, 52.11, 44.47, 44.09, 37.40, 37.28, 36.64, 36.58, 35.33 (d, J=7.7), 34.46, 34.42, 30.49, 30.42, 30.15, 29.38, 26.11, 26.05, 24.86, 24.79, 24.74, 24.61, 20.19, 20.09, 13.17, 12.61; $^{31}$P NMR (162 MHz) δ −11.77; HRMS (El, m/z) for C$_{46}$H$_{63}$O$_{12}$PNa requires 861.3949, found 861.3879; IR (film, cm$^{-1}$) 2919, 2861, 1589, 1485, 1455, 1376, 1290, 1220, 1190, 1108, 1008, 944, 767, 686; [α]$_D^{24.1}$ 67.6 (CHCl$_3$, c=0.26).

Example 18

Synthesis of bis-trioxane primary alcohol nicotinate N-oxide 15

To a stirring suspension of bis-trixane primary alcohol 4 (19.7 mg, 0.033 mmol) and nicotinic acid N-oxide (13.1 mg, 0.094 mmol) in anhydrous methylene chloride (1 mL) was added 4-(dimethylamino)-pyridine (14.1 mg, 0.115 mmol) and 1-(3-(dimethylamino)propyl)-3-ethylcarbodiimide hydrochloride (21.4 mg, 0.112 mmol). A further 1 mL of anhydrous methylene chloride was added to wash down the flask walls and the reaction was stirred at room temperature for 2 hours 30 minutes, at which time TLC analysis showed full consumption of starting material. Water (5 mL), 3M HCl solution (5 mL) and methylene chloride (5 mL) were added and organics were extracted with methylene chloride (3×20 mL), dried (Na$_2$SO$_4$) and concentrated in vacuo to give a white cloudy oil (33.2 mg). Gradient column chromatography on silica (crude was dry-loaded) eluting firstly with ethyl acetate and then with 3% methanol/ethyl acetate isolated bis-trioxane primary alcohol nicotinate N-oxide 15 as a glassy solid. Treatment with hexanes (2×10 mL) (followed by drying overnight under high vacuum) gave a white solid (23.6 mg, 0.032 mmol, 99%). $^1$H NMR (CDCl$_3$, 400 MHz) δ 8.76 (s, br, 1H), 8.33 (d, 1H, J=6.3), 7.87 (d, 1H, J=7.9), 7.36 (t, br, 1H, J=7.1), 5.31 (s, 1H), 5.27 (s, 1H), 4.61-4.51 (m, 2H), 4.46 (dd, 1H, J=10.0, J=6.2), 4.35 (dd, 1H, J=10.0, J=6.2), 2.65 (q, 1H, J=6.8), 2.55 (q, 1H, J=6.8), 2.40-2.24 (m, 3H), 2.06-1.71 (m, 8H), 1.70-1.47 (m, 6H), 1.42-1.18 (m, 14H, including two singlets at 1.40 and 1.38), 0.99-0.89 (m, 8H), 0.86 (apparent triplet, 6H, J=7.0); $^{13}$C NMR (CDCl$_3$, 100 MHz) δ 162.65, 142.15, 140.12, 130.57, 126.41, 125.68, 103.01, 102.77, 89.63, 89.02, 81.12, 81.10, 73.00, 70.36, 68.34, 52.18, 51.98, 44.16, 43.93, 37.47, 37.45, 36.62, 36.51, 34.36, 34.33, 33.95, 30.96, 30.59, 30.56, 30.30, 25.99, 25.96, 24.90, 24.86, 24.75, 24.66, 20.16, 20.07, 12.92, 12.60; HRMS (El, m/z) for C$_{40}$H$_{57}$NO$_{11}$Na requires 750.3824, found 750.3858; IR (film, cm$^{-1}$) 2931, 2870, 1727, 1435, 1375, 1296, 1223, 1106, 1043, 1008, 879, 749; Mp. 104-108° C. (morphological change observed beginning at −80° C.); [α]$_D^{24.4}$ 49.7 (CHCl$_3$, c=0.205); Anal (C$_{40}$H$_{57}$NO$_{11}$+0.5 H$_2$O) C, H, N.

Example 19

Synthesis of bis-trioxane phosphonic acid monoester 16

To a solution of methylphosphonic dichloride (32.2 mg, 0.242 mmol) in anhydrous methylene chloride (1 mL) was added 4-(dimethylamino)-pyridine (5.2 mg, 0.043 mmol). The mixture was stirred at room temperature for five minutes before addition of bis-trioxane primary alcohol 4 (25.7 mg, 0.042 mmol) in anhydrous methylene chloride (1.25 mL) by canula. On stirring at room temperature for 1 hour 45 minutes, TLC analysis showed a large amount of starting material remaining and so a second portion of 4-(dimethylamino)-pyridine (5.2 mg, 0.043 mmol) was added. Continued stirring for a further 2 hours followed by TLC analysis showed that starting material still remained. A third portion of 4-(dimethylamino)-pyridine (10.0 mg, 0.082 mmol) was added and the reaction was stirred at room temperature. After 15 hours, TLC analysis confirmed full consumption of starting material and pyridine (0.2 mL, 2.47 mmol) was added and the mixture stirred vigorously for 1 hour before careful addition of 3M HCl (3 mL, ~9 mmol) and continued stirring for a further 1 hour. Methylene chloride (5 mL) and water (5 mL) were added and organics were extracted with methylene chloride (3×10 mL), dried (Na$_2$SO$_4$) and concentrated in vacuo to give a white cloudy oil (34.7 mg). Gradient column chromatography on silica (crude was dry-loaded) eluting with 10% then 30% methanol/ethyl acetate isolated bis-trioxane phosphonic acid monoester 16 as a glassy solid. Treatment with hexanes (2×10 mL) and then acetonitrile (3×10 mL) (followed by drying overnight under high vacuum) gave a white solid (22.9 mg, 0.033 mmol, 79%). $^1$H NMR (CD$_3$OD, 400 MHz) δ 5.39 (s, br, 2H), 4.30 (dd, 1H, J=10.4, J=6.1), 4.20 (dd, 1H, J=10.4, J=6.1), 3.99-3.87 (m, 2H), 2.70-2.54 (m, 2H), 2.29 (t, br, 2H, J=13.9), 2.10-1.99 (m, 3H), 1.97-1.87 (m, 3H), 1.86-1.75 (m, 3H), 1.68 (d, br, 2H, J=13.2), 1.61-1.33 (m, 16H, including singlet at 1.35), 1.30-1.17 (m, 5H, including doublet (J=16.6) at 1.27), 1.02-0.94 (m, 2H), 0.97 (d, br, 6H, J=6.1), 0.90 (dd, 6H, J=7.5, J=2.8); $^{13}$C NMR (CD$_3$OD, 100 MHz) δ 104.75, 104.53, 90.54, 90.22, 82.52, 82.49, 75.60, 74.84, 67.77 (d, J=5.4), 54.14, 54.00, 46.28, 46.08, 38.62, 38.60, 37.81, 37.77, 37.52 (d, J=7.6), 35.91, 35.87, 32.12, 32.10, 31.48 (2), 26.46 (2), 26.14, 26.08, 26.01, 25.99, 20.81, 20.74, 13.90, 13.66, 12.56 (d, J=139.1); $^3$P NMR (CD$_3$OD, 162 MHz) δ 22.07; HRMS (El, m/z) for C$_{35}$H$_{56}$O$_{11}$PNa$_2$ requires 729.3350, found 729.3370; IR (film, cm$^{-1}$) 2940, 2862, 1449, 1372, 1196, 1188, 1090, 1037, 1008, 937, 896, 878, 826, 732; Mp. 142-147° C.; [α]$_D^{23.4}$ 8.9 (CHCl$_3$, c=3.09).

Example 20

Synthesis of bis-trioxane secondary alcohol 17

Bis-trioxane ketone 7 (10 mg, 0.016 mmol) was dissolved in MeOH (1 mL) and the solution was cooled to 0° C. To this cooled solution was added NaBH$_4$ (4.2 mg, 0.112 mmol, 7.7 eq.) in 4 portions. The reaction mixture was then stirred for 1 hour and quenched with dropwise addition of 1% AcOH—MeOH until neutral pH was attained. The reaction mixture was then concentrated in vacuo and the crude product charged onto a silica column. Column chromatography gave bis-trioxane secondary alcohol 17 as a white solid (8 mg, 84%). $^1$H NMR (400 MHz, CDCl$_3$) δ 5.37 (s, 1H), 5.31 (s, 1H), 4.54-4.40 (m, 2H), 4.10-3.99 (bm,1H), 3.75 (s,1H), 2.76-2.60 (m, 2H), 2.38-2.24 (m, 2H), 2.08-1.20 (m, 28H), 0.96-0.84 (m, 14H); $^{13}$CNMR (100 MHz, CDCl$_3$) δ 133.9, 133.7, 128.8, 128.6, 128.5, 103.3, 89.0, 88.9, 81.1, 76.2, 72.4, 71.3, 52.2, 52.4, 52.3, 44.5, 44.2, 37.6, 37.5, 36.6, 36.5, 36.3, 36.2, 34.6, 34.5, 30.6, 30.4, 26,2, 26.1, 24.9, 24.8, 24.7, 20.3, 13.2, 13.1; HRMS (El, m/z) for C$_{33}$H$_{52}$O$_9$Na$^+$ required 615.3503, found 615.3466.

Example 21

Synthesis of bis-trioxane vicinal diol isonicotinate N-oxide 18

To a stirring suspension of bis-trioxane vicinal diol 5 (19.4 mg, 0.031 mmol) and commercially available (Aldrich) isonicotinic acid N-oxide (14.5 mg, 0.104 mmol) in anhydrous methylene chloride (1 mL) was added 4-(dimethylamino)-pyridine (14.5 mg, 0.119 mmol) and 1-(3-(dimethylamino) propyl)-3-ethylcarbodiimide hydrochloride (23.0 mg, 0.120 mmol). A further 1 mL of anhydrous methylene chloride was added to wash down the flask walls and the reaction was stirred at room temperature for 1 hour 30 minutes, at which time TLC analysis showed full consumption of starting material. Water (5 mL), 3M HCl solution (5 mL) and methylene chloride (5 mL) were added and organics were extracted with methylene chloride (3×20 mL), dried ($Na_2SO_4$) and concentrated in vacuo to give a colorless oil. Gradient column chromatography on silica (crude was dry-loaded) eluting firstly with 100% ethyl acetate and then with 3% methanol/ethyl acetate isolated bis-trioxane vicinal diol isonicotinate N-oxide 18 as a colorless oil. Treatment with methylene chloride (2×10 mL) and then hexanes (2×10 mL) (followed by drying overnight under high vacuum) gave a white solid (22.7 mg, 0.031 mmol, 99%). $^1$H NMR (400 MHz, $CDCl_3$) δ 8.21 (d, 2H, J =7.3), 7.92 (d, 2H, J=7.3), 5.33 (s, 1H), 5.31 (s, 1H), 4.75 (dd, 1H, J=10.3, J=6.2), 4.65-4.51 (m, 3H), 4.34 (s, br, 1H), 2.58 (qt, 1H, J=7.0), 2.56 (qt, 1H, J=7.0), 2.30 (t, br, 2H, J=13.3), 2.08-1.85 (m, 7H), 1.83-1.60 (m, 7H), 1.42-1.17 (m, 14H, including two singlets at 1.40 and 1.37), 0.99-0.93 (m, 8H), 0.89 (apparent triplet, br, 6H, J=7.7); $^{13}$C NMR (100 MHz, $CDCl_3$) δ 163.04, 139.27 (2), 127.39, 126.45 (2),102.86, 102.84, 89.74, 89.41, 81.02 (2), 73.62, 70.04, 69.85, 51.91, 51.83, 43.64, 43.52, 37.58, 37.55, 36.75, 36.53, 36.46, 35.38 (2), 34.27, 34.25, 30.86, 30.82, 25.92, 25.87, 24.85 (2), 24.77 (2), 20.08, 20.02, 12.50, 12.39; HRMS (EI, m/z) for $C_{40}H_{57}NO_{12}Na^+$ requires 766.3773, found 766.3770; IR (film, cm$^{-1}$) 3483, 2931, 2861, 1719, 1608, 1443,1377, 1257, 1165, 1102, 1008, 908, 732; Mp. 114-118° C.

Example 22

Synthesis of bis-trioxane isobutyric acid 19

To a solution of bis-trioxane primary alcohol 4 (132 mg, 0.218 mmol) in ethyl acetate (4 mL), acetonitrile (4.0 mL) and H20 (1.3 mL) was added ruthenium (III) chloride hydrate (4.5 mg, 0.022 mmol) and sodium periodate (326 mg, 1.53 mmol, 7.0) (on addition of ruthenium chloride the solution turned black). After stirring for 30 mins at room temperature (the color of solution turned to pale orange), the reaction mixture was poured into a mixture of ethyl acetate (30 mL) and saturated aqueous $NH_4Cl$ solution (30 mL). Organics were extracted with ethyl acetate (2×30 mL), dried ($MgSO_4$), filtered through a pad of celite and concentrated in vacuo. Flash column chromatography on silica eluting with 1% acetic acid in 30% ethyl acetate/hexane isolated bis-trioxane isobutyric acid 19 as a white solid (126 mg, 0.204 mmol, 94%). Mp=105-110° C. Further purification by medium pressure liquid chromatography (MPLC: LiChroprep Si60 (40-63□m)-EM Science) with the same solvent system (1% acetic acid in 30% ethyl acetate/hexane) removed unknown impurities and gave a white solid (118 mg, 0.190 mmol, 87%); Mp=110-113° C.; $^1$H NMR (400 MHz, $CDCl_3$) δ 5.30 (s,1H), 5.29 (s, 1H), 4.30-4.20 (m, 2H), 2.92-2.84 (m, 1H), 2.75-2.55 (m, 2H), 2.35-2.23 (m, 2H), 2.15-1.95 (m, 3H), 1.94-1.50 (m,11H), 1.46-1.20 (m, 15H, including two singlets at 1.39 and 1.38), 0.94 (d, 6H, J=6.0), 0.86 (d, 6H, J=7.6), 0.98-0.86 (m, 2H); $^{13}$C NMR (100 MHz, $CDCl_3$) δ 179.9, 103.3, 103.1, 89.0, 88.6, 81.1, 81.0, 74.3, 72.8, 52.3, 52.2, 44.4, 44.2, 41.8, 37.4, 37.3, 36.5, 36.5, 34.4, 31.5, 31.4, 30.3, 30.2, 25.9, 25.8, 24.7, 24.6, 20.2, 20.1, 13.1, 12.7; IR (film, cm$^{-1}$) 3500 (br), 2940, 2875, 1705, 1450, 1377, 1279, 1187, 1094, 1053, 1011, 941, 877, 826, 734; HRMS(ES) m/z calcd for $C_{34}H_{52}O_{10}Na$ (M+Na) 643.3457, found 643.3470.

Example 23

Synthesis of bis-trioxane P-hydroxy O-allyl ether 20

To a suspension of KH (~35% in mineral oil, 16 mg (~5.6 mg actual), 0.14 mmol) in anhydrous diethyl ether (1.0 mL) at 0° C. was added a solution of bis-trioxane vicinal diol 5 (28.9 mg, 0.046 mmol) in diethyl ether (0.7 mL). The reaction was stirred for 30 mins (to ensure complete formation of the alkoxide) before addition of allyl bromide (0.012 mL, 0.14 mmol) and 18-crown-6 (2.4 mg, 0.009 mmol). The reaction was then allowed to warm to room temperature and was stirred until TLC analysis showed no starting material remaining. The reaction mixture was poured into a mixture of diethyl ether (20 mL) and saturated aqueous $NH_4Cl$ solution (20 mL) and organics were extracted with diethyl ether (3×10 mL), washed with brine, dried ($MgSO_4$) and concentrated in vacuo. Flash column chromatography on silica eluting with 20% ethyl acetate/hexanes isolated bis-trioxane P-hydroxy O-allyl ether 20 as a sticky solid (22.3 mg, 0.034 mmol, 74%); $^1$H NMR (400 MHz, CDCl3) 6 5.98-5.88 (m, 1H), 5.32 (s, 2H), 5.25 (ddd, 1H, J=17.2, J=3.6, J=1.6), 5.12 (apparent doublet, br,$_1$ H, J=10.4), 4.33-4.28 (m, 1H), 4.23-4.17 (m, 1H), 4.02-3.90 (m, 2H), 3.60-3.53 (m, 2H), 2.75-2.60 (m, 2H), 2.35-2.25 (m, 2H), 2.10-1.18 (m, 28H, including two singlets at 1.40 and 1.39); 0.94 (d, 6H, J=6.0), 0.86 (d, 3H, J=7.6), 0.84 (d, 3H, J=7.6), 0.98-0.86 (m, 2H); $^{13}$C NMR (100 MHz, $CDCl_3$) δ 135.6, 116.4, 103.1, 103.0, 89.2, 88.6, 81.1, 81.0, 73.9, 73.8, 72.1, 71.5, 71.3, 52.4, 52.2, 44.5, 44.1, 37.4, 36.6, 35.8, 35.0, 34.5, 34.4, 30.7, 30.7, 26.1, 26.0, 24.8, 24.7, 20.2, 20.1, 13.2, 12.9; IR (film, cm$^{-1}$) 3506, 2953, 2925, 2874, 1452, 1376,1222, 1190, 1127, 1093, 1053, 1011, 942, 878, 843, 731; HRMS(ES) m/z calcd for $C_{37}H_{58}NaO_{10}$ (M+Na) 685.3922, found 685.3915.

Example 24

Synthesis of bis-trioxane P-hydroxy O-acetic acid 21

To a solution of bis-trioxane β-hydroxy O-allyl ether 20 (40.3 mg, 0.061 mmol) in ethyl acetate (1.2 mL), acetonitrile (1.2 mL) and water (0.4 mL) was added ruthenium (III) chloride hydrate (catalytic) and sodium periodate (65.0 mg, 0.304 mmol) (on addition of ruthenium chloride the solution turned black). The reaction was stirred at room temperature for 30 mins (the color of solution turned to pale orange), at which time TLC analysis confirmed complete consumption of starting material. The reaction mixture was poured into a mixture of ethyl acetate (20 mL) and saturated aqueous $NH_4Cl$ solution (20 mL) and organics were extracted with ethyl acetate (2×20 mL), dried ($MgSO_4$), filtered through a pad of celite and concentrated in vacuo. Flash column chromatography on silica eluting with 1% acetic acid in 4% methanol/methylene chloride isolated bis-trioxane p-hydroxy O-acetic acid 21 as a white solid (5.3 mg, 0.008 mmol, 13%). Mp=85-89° C.; $^1$H NMR (400 MHz, $CDCl_3$) δ 5.35 (s, 1H), 5.34 (s, 1H), 4.82-4.76 (m, 1H), 4.52-4.46 (m, 1H), 4.25 (d, 1H, J=17.0), 4.09 (d, 1H, J=17.0), 3.80 (d, 1H, J=9.4), 3.67 (d, 1H, J=9.4), 1.40 (s, 3H), 1.38 (s, 3H), 0.94 (d, 6H, J=6.0), 0.86 (d, 3H, J=7.6), 0.84 (d, 3H, J=7.6), 0.98-0.86 (m, 2H); HRMS(ES) m/z calcd for $C_{36}H_{56}NaO_{12}$(M+Na) 703.3664, found 703.3681.

Example 25

Synthesis of bis-trioxane primary alcohol picolinate 22

To a solution of bis-trioxane primary alcohol 4 (29.9 mg, 0.049 mmol) in anhydrous methylene chloride (0.5 mL) was added picolinyl chloride hydrochloride (22.1 mg, 0.124 mmol) and 4-(dimethylamino)-pyridine (34.2 mg, 0.280 mmol). A further portion of anhydrous methylene chloride (1 mL) was added to wash down the flask walls and the reaction was stirred at room temperature for 18 hours, at which time TLC analysis confirmed full consumption of starting material. Water (5 mL), saturated $NaHCO_3$ solution (5 mL) and methylene chloride (5 mL) were added and organics were extracted with methylene chloride (3×20 mL), dried ($Na_2SO_4$) and concentrated in vacuo to give an off-white solid. Gradient column chromatography on silica (crude was dry-loaded) eluting with 30%, 40% and then 50% ethyl acetate/petroleum ether isolated bis-trioxane primary alcohol picolinate 22 as a colorless oil. Treatment with methylene chloride (2×10 mL) and then hexanes (2×10 mL) (followed by drying overnight under high vacuum) gave a white bubbly oil (33.1 mg, 0.047 mmol, 94%). $^1$H NMR ($CDCl_3$, 400 MHz) δ 8.74 (s, br, 1H, J=4.8), 8.12 (d,1H, J=7.8), 7.83 (dt,1H, J=7.8, J=1.7), 7.46 (dd,1H, J=7.8, J=4.8), 5.35 (s,1H), 5.33 (s, 1H), 4.62-4.54 (m, 2H), 4.44 (dd, 1H, J=10.6, J=6.0), 4.29 (dd, 1H, J=10.6, J=6.0), 2.71 (st, 1H, J=6.9), 2.61 (st, 1H, J=6.9), 2.49-2.38 (m, br, 1H), 2.29 (dt, 2H, J=13.9, J=3.7), 2.02-1.71 (m, 7H), 1.69-1.52 (m, 6H), 1.43-1.17 (m, 15H, including two singlets at 1.39 and 1.37), 1.00-0.81 (m, 14H); $^{13}$C NMR ($CDCl_3$, 100 MHz) δ 164.85, 149.59, 148.55, 136.93, 126.54, 125.03, 103.13, 102.90, 89.24, 88.58, 81.14, 81.10, 73.59, 71.46, 68.25, 52.39, 52.16, 44.49, 44.21, 37.33, 37.26, 36.61, 36.54, 34.47, 34.43, 34.16, 30.57, 30.46, 29.93, 29.63, 26.08, 26.04, 24.91, 24.83, 24.69, 24.60, 20.20, 20.11, 13.24, 12.87; HRMS (El, m/z) for $C_{40}H_{57}NO_{10}Na$ requires 734.3875, found 734.3897; IR (film, cm$^{-1}$) 2941, 2874, 1717, 1458, 1437, 1376, 1303, 1245, 1128, 1104, 1044, 1006, 931, 876, 743; $[\alpha]_D^{23.9}$ 64.5 ($CHCl_3$, c=0.270).

Example 26

Synthesis of bis-trioxane vicinal diol nicotinate N-oxide 23

To a stirring suspension of bis-trioxane vicinal diol 5 (26.0 mg, 0.042 mmol) and commercially available (Aldrich) nicotinic acid N-oxide (19.9 mg, 0.143 mmol) in anhydrous methylene chloride (2 mL) was added 4-(dimethylamino)-pyridine (19.8 mg, 0.162 mmol) and 1-(3-(dimethylamino)propyl)-3-ethylcarbodiimide hydrochloride (32.0 mg, 0.167 mmol). A further 1 mL of anhydrous methylene chloride was added to wash down the flask walls and the reaction was stirred at room temperature for 3 hours, at which time TLC analysis showed full consumption of starting material. Water (5 mL), 3M HCl solution (5 mL) and methylene chloride (5 mL) were added and organics were extracted with methylene chloride (3×20 mL), dried ($Na_2SO_4$) and concentrated in vacuo to give a white solid. The crude material was pre-absorbed on silica and gradient column chromatography on silica eluting with 100% ethyl acetate, 5% methanol/ethyl acetate and then 10% methanol/ethyl acetate isolated bis-trioxane vicinal diol nicotinate N-oxide 23 as a colorless oil. Treatment with methylene chloride (2×10 mL) and then hexanes (2×10 mL) (followed by drying overnight under high vacuum) gave a white solid (29.1 mg, 0.039 mmol, 94%). $^1$H NMR ($CDCl_3$, 400 MHz) δ 8.80 (s, br, 1H), 8.33 (d, 1H, J=6.5), 7.89 (d, 1H, J=7.9 ), 7.35 (dd, 1h, J=6.5, J=7.9), 5.32 (s, 1H), 5.28 (s, 1H), 4.74 (dd, J=6.2, J=10.4), 4.67-4.57 (m, 2H), 4.50 (d, 1H, J=11.2), 4.32 (s, br, 1H), 2.58 (st, 1H, J=7.0), 2.52 (st, 1H, J=7.0), 2.34-2.23 (m, 2H), 2.06-1.61 (m, 14H), 1.43-1.18 (m, 14H, including two singlets at 1.40 and 1.36), 1.00-0.83 (m, 14H, including doublet at 0.94 (J=5.4) and apparent triplet at 0.88 (J=7.4)); $^{13}$C NMR ($CDCl_3$, 100 MHz) δ 162.38, 142.07, 140.18, 130.63, 126.53, 126.60, 102.82, 102.78, 89.79, 89.27, 81.02 (2), 73.32, 69.88, 69.82, 69.79, 51.92, 51.79, 43.65, 43.42, 37.48 (2), 36.87, 36.52, 36.43, 35.24, 34.25, 34.21, 30.85, 30.79, 25.87, 25.82, 24.83, 24.81, 24.72, 24.69, 20.08, 20.00, 12.51, 12.31; HRMS (El, m/z) for $C_{40}H_{57}NO_{12}Na$ requires 766.3773, found 766.3817; IR (film, cm$^{-1}$) 2938, 2875, 1732, 1435, 1376, 1298, 1226, 1108, 1054, 1013, 941, 842, 754, 733; Mp. 116-118° C. (morphological change observed beginning at 102° C.); $[\alpha]^{p245}$ 33.5 ($CHCl_3$, c=0.10); Anal ($C_{40}H_{57}NO_{12}$) C, H, N.

Example 27

Synthesis of bis-trioxane secondary alcohol isonicotinate N-oxide 24

To a stirring suspension of bis-trioxane secondary alcohol 17 (21.6 mg, 0.036 mmol) and commercially available (Aldrich) isonicotinic acid N-oxide (16.2 mg, 0.116 mmol) in anhydrous methylene chloride (1 mL) was added 4-(dimethylamino)-pyridine (16.8 mg, 0.138 mmol) and 1-(3-(dimethylamino)propyl)-3-ethylcarbodiimide hydrochloride (25.9 mg, 0.135 mmol). A further 1 mL of anhydrous methylene chloride was added to wash down the flask walls and the reaction was stirred at room temperature for 3 hours, at which time TLC analysis showed full consumption of starting material. Water (5 mL), 3M HCl solution (5 mL) and methylene chloride (5 mL) were added and organics were extracted with methylene chloride (3×20 mL), dried ($Na_2SO_4$) and concentrated in vacuo to give a colorless oil (29.5 mg). Gradient column chromatography on silica (crude was dry-loaded) eluting firstly with 80% ethyl acetate/petroleum ether and then with 100% ethyl acetate isolated bis-trioxane secondary alcohol isonicotinate N-oxide 24 as a colorless oil. Treatment with methylene chloride (2×10 mL) and then hexanes (2×10 mL) (followed by drying overnight under high vacuum) gave a white solid (24.4 mg, 0.034 mmol, 94%). $^1$H NMR ($CDCl_3$, 400 MHz) δ 8.18 (d, 2H, J=6.9), 7.92 (d, 2H, J=6.9), 5.48-5.39 (m, 1H), 5.35 (s, 1H), 5.31 (s, 1H), 4.46-4.37 (m, 2H), 2.65 (st, 2H, J=6.9), 2.35-2.22 (m, 2H), 2.16-1.54 (m, 13H), 1.49-1.17 (m, 15H, including two singlets at 1.31 and 1.26), 1.00-0.80 (m, 14H, including apparent triplet at 0.95 (J=5.6) and two doublets at 0.88 (J=7.5) and 0.83 (J=7.5)); $^{13}$C NMR ($CDCl_3$, 100 MHz) δ 162.93, 139.17 (2), 127.70, 126.61 (2), 103.06, 102.99, 88.95, 88.86, 81.06 (2), 74.27, 71.73, 71.11, 52.23, 52.10, 44.21, 44.08, 37.39, 37.30, 36.51, 35.45, 34.38, 34.34, 32.72, 32.69, 30.39 (2), 25.93, 25.83, 24.72, 24.64, 24.62 (2), 20.14, 20.11, 12.99, 12.97; HRMS (El, m/z) for $C_{39}H_{55}NO_{11}Na$ requires 736.3667, found 736.3678; IR (film, cm$^{-1}$) 2937, 2873, 1717, 1611, 1445, 1376, 1265, 1163, 1094, 1054, 1011; Mp. 114-118° C. (morphological change

Example 28

Synthesis of bis-trioxane secondary alcohol nicotinate N-oxide 25

To a stirring suspension of bis-trioxane secondary alcohol 17 (30.7 mg, 0.052 mmol) and commercially available (Aldrich) nicotinic acid N-oxide (21.5 mg, 0.155 mmol) in anhydrous methylene chloride (1 mL) was added 4-(dimethylamino)-pyridine (22.0 mg, 0.180 mmol) and 1-(3-(dimethylamino)propyl)-3-ethylcarbodiimide hydrochloride (34.5 mg, 0.180 mmol). A further 1 mL of anhydrous methylene chloride was added to wash down the flask walls and the reaction was stirred at room temperature for 3 hours, at which time TLC analysis showed full consumption of starting material. Water (5 mL), 3M HCl solution (5 mL) and methylene chloride (5 mL) were added and organics were extracted with methylene chloride (3×20 mL), dried ($Na_2SO_4$) and concentrated in vacuo to give a colorless oil. Gradient column chromatography on silica (crude was dry-loaded) eluting firstly with 100% ethyl acetate and then with 5% methanol/ethyl acetate isolated bis-trioxane secondary alcohol nicotinate N-oxide 25 as a colorless oil. Treatment with methylene chloride (2×10 mL) and then hexanes (2×10 mL) (followed by drying overnight under high vacuum) gave a white solid (37.5 mg, 0.052 mmol, 100%). $^1$H NMR ($CDCl_3$, 400 MHz) δ 8.78 (s, 1H), 8.29 (d, 1H, J=6.5), 7.88 (d, 1H, J=8.0), 7.31 (dd, 1H, J=8.0, J=6.5), 5.52-5.42 (m, 1H), 5.32 (s, 1H), 5.30 (s, 1H), 4.45-4.34 (m, 2H), 2.64 (st, 2H, J=6.9), 2.34-2.21 (m, 2H), 2.16-1.53 (m, 13H), 1.49-1.15 (m, 15H, including two singlets at 1.28 and 1.27), 1.00-0.80 (m, 14H, including four doublets at 0.94 (J=6.1), 0.93 (J=6.1), 0.87 (J=7.5) and 0.83 (J=7.5); $^{13}$C NMR ($CDCl_3$, 100 MHz) δ 162.38, 141.93, 140.47, 130.87, 126.66, 125.45, 103.07, 102.98, 88.99, 88.77, 81.03, 81.01, 74.60, 71.93, 70.87, 52.25, 52.09, 44.22, 44.03, 37.35, 37.30, 36.52, 36.43, 34.38, 34.34, 32.93, 32.88, 30.36 (2), 25.85, 25.77, 24.73, 24.66, 24.63, 24.58, 20.13, 20.10, 13.01, 12.88; HRMS (EI, m/z) for $C_{39}H_{55}NO_{11}Na$ requires 736.3667, found 736.3715; IR (film, $cm^{-1}$) 2951, 2874, 1726, 1432, 1377, 1299, 1225, 1114, 1094, 1056, 1013, 950, 876, 822, 753; Mp. 106-110° C. (morphological change observed beginning at 98° C.); $[α]_D^{24.3}$ 63.1 ($CHCl_3$, c=0.225); Anal ($C_{39}H_{55}NO_{11}$+0.5 $H_2O$) C, H, N.

Example 29

Synthesis of bis-trioxane primary alcohol diethyl phosphoric acid triester 26

To a stirring solution of bis-trioxane primary alcohol 4 (26.1 mg, 0.043 mmol) in anhydrous methylene chloride (2.5 mL) was added diethylchlorophosphate (0.12 mL, 0.860 mmol) and anhydrous pyridine (0.07 mL, 0.860 mmol). On stirring at room temperature for 3 hrs, TLC analysis showed full consumption of starting material. Water (2 mL), 3M HCl (3 mL) and methylene chloride (3 mL) were added and organics were extracted with methylene chloride (3×15 mL), dried ($Na_2SO_4$) and concentrated in vacuo to give a yellow oil. Gradient column chromatography on silica eluting with 40% and then 50% ethyl acetate/petroleum ether isolated bis-trioxane primary alcohol diethyl phosphoric acid triester 26 as a colorless oil (28.1 mg, 0.038 mmol, 88%). $^1$H NMR (400 MHz, $CDCl_3$) δ 5.30 (s, 1H), 5.27 (s, 1H), 4.40-4.35 (m, 1H), 4.24-4.06 (m, 7H), 2.68 (st, 1H, J=7.6), 2.54 (st, 1H, J=6.8), 2.34-1.92 (m, 6H), 1.91-1.14 (m, 31H, including a singlet at 1.38, a singlet at 1.37, and a doublet of triplets at 1.31 (J=6.8, 0.8)), 1.02-0.68 (m, 14H, including doublets at 0.93 (J=6.0), 0.84 (J=7.6) and 0.83 (J=7.6); $^{13}$C NMR (100 MHz, $CDCl_3$) δ 103.16, 102.74, 89.35, 89.64, 81.12, 81.08, 74.00, 71.03, 69.72 (d, J=5.8), 63.54 (d, J=6.0), 63.52 (d, J=6.0), 52.40, 52.10, 44.50, 44.10, 37.36, 37.33, 36.61, 36.54, 35.36 (d, J=7.5), 34.46, 34.40, 30.51, 30.43, 30.10, 26.05, 25.99, 24.81, 24.74, 24.70, 24.62, 20.19, 20.07, 16.14 (2, d, J=6.8), 13.20, 12.67; $^{31}$P NMR (162 MHz, $CDCl_3$) δ 0.058; HRMS (EI, m/z) for $C_{38}H_{63}O_{12}PNa$ requires 765.3949, found 765.3981; IR (film, $cm^{-1}$) 2941 (m), 2880(w), 1454(w), 1373(w), 1271 (m), 1103(m), 1037 (s), 1011 (s), 878 (w), 843 (w), 665 (w); $[α]_D^{236}$ 13.4 ($CHCl_3$, c=0.30).

Example 30

Synthesis of bis-trioxane primary alcohol dimethyl phosphoric acid triester 27

To a stirring solution of bis-trioxane primary alcohol 4 (21.0 mg, 0.035 mmol) in anhydrous methylene chloride (2.0 mL) was added dimethylchlorophosphate (0.07 mL, 0.70 mmol) and anhydrous pyridine (0.06 mL, 0.70 mmol). On stirring at room temperature for 3 hrs, TLC analysis showed full consumption of starting material. Water (2 mL), 3M HCl (3 mL) and methylene chloride (3 mL) were added and organics were extracted with methylene chloride (3×15 mL), dried ($Na_2SO_4$) and concentrated in vacuo to give a yellow oil. Gradient column chromatography on silica eluting with 40% and then 50% ethyl acetate/petroleum ether isolated bis-trioxane primary alcohol dimethyl phosphoric acid triester 27 as a colorless oil (13.6 mg, 0.020 mmol, 55%). $^1$H NMR (400 MHz, $CDCl_3$) 5.32 (s, 1H), 5.29 (s, 1H), 4.45-4.35 (m, 1H), 4.28-4.17 (m, 3H), 3.78 (d, 3H, J=10.8), 3.77 (d, 3H, J=11.2), 2.69 (st, 1H, J=7.6), 2.55 (st, 1H, J=6.4), 2.34-2.25 (m, 2H), 2.17 (s, br, 1H), 2.02-1.18 (m, 28H, including singlet at 1.37), 1.02-0.80 (m, 14H, including doublets at 0.95 (J=6.0), 0.86 (J=7.6) and 0.85 (J=7.2)); $^{13}$C NMR (100 MHz, $CDCl_3$) δ 103.17, 102.77, 89.52, 88.77, 81.16, 81.14, 73.97, 70.72, 69.91 (d, J=5.8), 54.20 (2, d, J=6.1), 52.41, 52.10, 44.50, 44.09, 37.43, 37.38, 36.66, 36.58, 35.36 (d, J=7.9), 34.48, 34.40, 30.57, 30.50, 30.21, 29.57, 26.05, 25.98, 24.85, 24.78, 24.74, 24.67, 20.23, 20.09, 13.20, 12.64; $^{31}$P NMR (162 MHz, $CDCl_3$) δ 2.10; HRMS (EI, m/z) for $C_{36}H_{59}O_{12}PNa$ requires 737.3636, found 737.3646; IR (film, $cm^{-1}$) 2955 (m), 2882 (w), 1722 (w), 1452 (w), 1380 (w), 1281 (w), 1189 (w), 1109 (m), 1037 (s), 1004 (s), 879 (w), 846 (w); $[α]D^{23.7}$ 71.0 ($CHCl_3$, c=0.25).

Example 31

Synthesis of bis-trioxane primary alcohol p-trifluoromethylbenzoate 28

To a stirring solution of bis-trioxane primary alcohol 4 (47.1 mg, 0.078 mmol) and α,α,α-trifluoro-p-toluic acid (46.0 mg, 0.242 mmol) in anhydrous methylene chloride (1 mL) was added 4-(dimethylamino)-pyridine (33.5 mg, 0.274 mmol) and 1-(3-(dimethylamino)propyl)-3-ethylcarbodiimide hydrochloride (52.8 mg, 0.275 mmol). A further 2 mL of anhydrous methylene chloride was added to wash down the flask walls and the reaction was stirred at room temperature for 3 hours, at which time TLC analysis showed full consumption of starting material. Water (5 mL), 3M HCl solution (5 mL) and methylene chloride (5 mL) were added and organics were extracted with methylene chloride (3×20 mL), dried (Na$_2$SO$_4$) and concentrated in vacuo to give a white solid (101.5 mg). Gradient column chromatography on silica (crude was dry-loaded) eluting with 10% and then 20% ethyl acetate/petroleum ether isolated bis-trioxane primary alcohol p-trifluoromethylbenzoate 28 as a colorless oil (43.7 mg, 0.056 mmol, 72%). $^1$H NMR (CDCl$_3$, 400 MHz) δ 8.16 (d, 2H, J=7.9), 7.70 (d, 2H, J=7.9), 5.32 (s, 1H), 5.27 (s, 1H), 4.60-4.42 (m, 3H), 4.37-4.29 (m, 1H), 2.70 (st, 1H, J=7.0), 2.59 (st, 1H, J=7.0), 2.47-2.36 (m, 1H), 2.30 (td, 2H, J=14.0, J=3.5), 2.06-1.72 (m, 8H), 1.69-1.49 (m, 6H), 1.43-1.13 (m, 14H, including two singlets at 1.40 and 1.39), 0.98-0.84 (m, 14H, including two doublets at 0.95 and 0.91 (J=5.8) and two doublets at 0.87 and 0.86 (J=7.7)); $^{13}$C NMR (CDCl$_3$, 100 MHz) δ 165.22, 134.15 (d, J=34.5), 133.99, 129.89 (2), 125.29 (2, d, J=3.7), 123.64 (d, J=271.6), 103.14, 102.85, 89.46, 88.76, 81.09, 81.07, 73.23, 70.98, 67.87, 52.30, 52.08, 44.34, 44.09, 37.43 (2), 36.63, 36.53, 34.41, 34.39, 33.93, 30.56, 30.45, 30.09 (2), 26.05, 25.99, 24.95, 24.87, 24.73, 24.61, 20.08, 20.06, 14.09, 12.73; HRMS (EI, m/z) for C$_{42}$H$_{57}$F$_3$O$_{10}$Na requires 801.3796, found 801.3847; IR (film, cm$^{-1}$) 2941, 2878, 1725, 1375, 1323, 1275, 1167, 1133, 1098, 1058, 1014, 661; $[\alpha]_D^{243}$ 58.2 (CHCl$_3$, c=0.265).

Example 32

Synthesis of bis-trioxane primary alcohol 3,5-ditrifluoromethyl benzoate 29

To a stirring solution of bis-trioxane primary alcohol 4 (48.9 mg, 0.081 mmol) and 3,5-bis(trifluoromethyl)benzoic acid (65.5 mg, 0.254 mmol) in anhydrous methylene chloride (2 mL) was added 4-(dimethylamino)-pyridine (36.0 mg, 0.295 mmol) and 1-(3-(dimethylamino)propyl)-3-ethylcarbodiimide hydrochloride (55.1 mg, 0.287 mmol). A further 1 mL of anhydrous methylene chloride was added to wash down the flask walls and the reaction was stirred at room temperature for 15 hours, at which time TLC analysis showed full consumption of starting material. Water (5 mL), 3M HCl solution (5 mL) and methylene chloride (5 mL) were added and organics were extracted with methylene chloride (3×20 mL), dried (Na$_2$SO$_4$) and concentrated in vacuo to give a bubbly white solid. Gradient column chromatography on silica (crude was dry-loaded) eluting with 5%, 10% and then 20% ethyl acetate/petroleum ether isolated bis-trioxane primary alcohol 3,5-ditrifluoromethylbenzoate 29 as a colorless oil (64.7 mg, 0.076 mmol, 95%). $^1$H NMR (CDCl$_3$, 400 MHz) δ 8.47 (s, 2H), 8.05 (s, 1H), 5.30 (s, 1H), 5.23 (s, 1H), 4.64-4.56 (m, 2H), 4.47 (dd, 1H, J=10.1, J=6.2), 4.32 (dd, 1H, J=10.1, J=6.2), 2.69 (st, 1H, J=6.9), 2.59 (st, 1H, J=6.9), 2.45-2.35 (m, 1H), 2.35-2.24 (m, 2H), 2.05-1.51 (m, 14H), 1.42-1.13 (m, 14H, including two singlets at 1.40 and 1.37), 0.98-0.85 (m, 14H, including two doublets at 0.94 and 0.91 (J=5.5) and a broad doublet at 0.87 (J=7.3)); $^{13}$C NMR (CDCl$_3$, 100 MHz) δ 163.79, 133.08, 131.98 (2, d, J=34.0), 129.57 (2, d, J=3.0), 125.94, 122.89 (2, d, J=275.2), 103.12, 102.86, 89.45, 88.77, 81.08, 81.04, 73.31, 70.82, 68.30, 52.24, 52.04, 44.31, 44.03, 37.46 (2), 36.58, 36.47, 34.35 (2), 34.22, 30.57, 30.48, 30.21, 29.98, 25.95, 25.96, 24.92, 24.86, 24.69, 24.53, 20.06, 20.04, 13.04, 12.65; HRMS (EI, m/z) for C$_{43}$H$_{56}$F$_6$O$_{10}$Na requires 869.3670, found 869.3680; $[\alpha]_d^{23.4}$ 46.8 (CHCl$_3$, c=0.305).

Example 33

Synthesis of bis-trioxane primary alchohol dimethylglycinate 30

To a solution of bis-trioxane primary alcohol 4 (29.2 mg, 0.048 mmol) and N,N-dimethylglycine hydrochloride (22.1 mg, 0.158 mmol) in anhydrous methylene chloride (1 mL) was added 4-(dimethylamino)-pyridine (22.8 mg, 0.187 mmol) and 1-(3-(dimethylamino)propyl)-3-ethylcarbodiimide hydrochloride (36.2 mg, 0.189 mmol). A further 1 mL of anhydrous methylene chloride was added to wash down the flask walls and the reaction was stirred at room temperature for 15 hours, at which time TLC analysis showed full consumption of starting material. Water (5 mL), saturated sodium bicarbonate solution (5 mL) and methylene chloride (5 mL) were added and organics were extracted with methylene chloride (3×20 mL), dried (Na$_2$SO$_4$) and concentrated in vacuo to give an off-white solid. Gradient column chromatography on silica eluting with 60%, 70% and then 80% ethyl acetate/petroleum ether isolated bis-trioxane primary alcohol dimethylgylcinate 30 as a colorless oil. Treatment with methylene chloride (2×10 mL) and then hexanes (2×10 mL) (followed by drying overnight under high vacuum) gave a white oily solid (23.4 mg, 0.034 mmol, 70%). $^1$H NMR (CDCl$_3$, 400 MHz) δ 5.30 (s, br, 1H), 5.29 (s, br, 1H), 4.41-4.22 (m, 4H), 3.28 (s, 2H), 2.68 (st, 1H, J=6.8), 2.57 (st, 1H, J=6.8), 2.44 (s, 6H), 2.37-2.15 (m, 3H), 2.06-1.96 (m, 2H), 1.95-1.85 (m, 2H), 1.83-1.54 (m, 7H), 1.53-1.19 (m, 17H, including singlet at 1.39), 1.00-0.81 (m, 14H, including two doublets at 0.96 and 0.95 (J=5.8) and apparent triplet at 0.85 (J=6.9)); $^{13}$C NMR (CDCl$_3$, 100 MHz) δ 169.83, 103.18, 102.87, 89.42, 88.80, 81.13, 81.10, 73.47, 71.11, 66.97, 59.52, 52.35, 52.10, 44.72 (2), 44.41, 44.11, 37.45, 37.42, 34.45, 34.40, 34.01, 30.55, 30.48, 29.97 (2), 26.08, 25.99, 24.82 (2), 24.74, 24.70, 20.20, 20.10, 13.12, 12.73; HRMS (EI, m/z) for C$_{38}$H$_{61}$NO$_{10}$Na requires 714.4188, found 714.4236; IR (film, cm$^{-1}$) 2944, 2873, 1738, 1452, 1373, 1195, 1105, 1048, 1005, 933, 877; $[\alpha]_D^{23.8}$ 71.3 (CHCl$_3$, c=0.29).

Example 34

Synthesis of dihydroartemisinin 31

To a solution of artemisinin 1 (0.44 g, 1.55 mmol) in methanol (30 mL) at 0° C. was added sodium borohydride (0.47 g, 12.3 mmol) in 4 portions, each at 15 minutes intervals. After addition of the last portion, stirring was continued for 1 hour, at which time TLC analysis confirmed no starting material remained. Concentrated acetic acid was added dropwise until a pH of ~5 was achieved and the resulting mixture was then concentrated in vacuo to give a white solid. Water (30 mL) and methylene chloride (30 mL) were added and organics were extracted with methylene chloride (3×30 mL). The combined organic extracts were washed with saturated sodium bicarbonate solution (20 mL), dried (Na$_2$SO$_4$) and concentrated in vacuo to give a white solid (0.46 g). Gradient column chromatography on silica (crude was dry-loaded) eluting with 40% then 50% diethyl ether/petroleum ether isolated dihydroartemisinin 31 as a white solid (0.38 g, 1.33 mmol, 86%, isolated as a 1.0:0.9 mixture of β:α-dihydroartemisinin). $^1$H NMR (CDCl$_3$, 400 MHz) δ 5.61 (s, 1H), 5.40 (s, 0.9H), 5.31 (d, 1H, J=3.4), 4.76 (d, 0.9H, J=9.2) [only characetistic peaks listed].

Example 35

Synthesis of α-dihydroartemisinin dimethylglycinate 32

To a solution of dihydroartemisinin 31 (25.1 mg, 0.088 mmol) and N,N-dimethylglycine hydrochloride (32.9 mg, 0.236 mmol) in anhydrous methylene chloride (2 mL) was added 4-(dimethylamino)-pyridine (36.5 mg, 0.299 mmol) and 1-(3-(dimethylamino)propyl)-3-ethylcarbodiimide hydrochloride (55.8 mg, 0.291 mmol). A further 0.5 mL of anhydrous methylene chloride was added to wash down the flask walls and the reaction was stirred at room temperature for 3 hours, at which time TLC analysis showed full consumption of starting material. Water (5 mL), saturated sodium bicarbonate solution (5 mL) and methylene chloride (5 mL) were added and organics were extracted with methylene chloride (3×20 mL), dried ($Na_2SO_4$) and concentrated in vacuo to give an off-white solid (81.5 mg). Flash column chromatography on silica (crude was dry-loaded) eluting with 100% ethyl acetate isolated α-dihydroartemisinin dimethylglycinate 32 as a colorless oil (31.5 mg, 0.085 mmol, 97%). $^1$H NMR ($CDCl_3$, 400 MHz) δ 5.85 (d, 1H, J=9.9), 5.43 (s, 1H), 3.26 (AB, 2H, J=26.5, J=17.2), 2.61-2.50 (m, 1H), 2.36 (s, 6H), 2.41-2.32 (m, 1H), 2.02 (d, br,1H, J=14.4), 1.93-1.84 (m, 1H), 1.81-1.68 (m, 2H), 1.62 (dt, 1H, J=13.8, J=4.4), 1.50-1.39 (m, 4H, including singlet at 1.42), 1.38-1.22 (m, 3H), 1.07-0.95 (m, 1H), 0.95 (d, 3H, J=5.9), 0.84 (d, 3H, J=7.1); $^{13}$C NMR ($CDCl_3$, 100 MHz) δ 169.38, 104.42, 91.86, 91.48, 80.05, 59.95, 51.51, 45.20, 45.17 (2), 37.23, 36.16, 34.03, 31.80, 25.89, 24.53, 21.96, 20.18, 12.08; HRMS (El, m/z) for $C_{19}H_{31}NO_6Na$ requires 392.2044, found 392.2021; IR (film, $cm^{-1}$) 2931, 2861, 2766, 1758, 1452, 1376, 1278, 1226, 1190, 1149, 1130, 1098, 1035, 1014, 926, 874, 846.

Example 36

Synthesis of α-dihydroartemisinin isonicotinate N-oxide 33

To a stirring suspension of dihydroartemisinin 31 (33.6 mg, 0.12 mmol) and isonicotinic acid N-oxide (51.7 mg, 0.37 mmol) in anhydrous methylene chloride (1 mL) was added 4-(dimethylamino)-pyridine (52.0 mg, 0.43 mmol) and 1-(3-(dimethylamino)propyl)-3-ethylcarbodiimide hydrochloride (81.7 mg, 0.43 mmol). A further 1 mL of anhydrous methylene chloride was added to wash down the flask walls and the reaction was stirred at room temperature for 4 hours, at which time TLC analysis showed full consumption of starting material. Water (5 mL), 3M HCl solution (5 mL) and methylene chloride (5 mL) were added and organics were extracted with methylene chloride (3×20 mL), dried ($Na_2SO_4$) and concentrated in vacuo to give a yellow tinged colorless oil (76.7 mg). Gradient column chromatography on silica (crude was dry-loaded) eluting with 60%, 80%, 90% and then 95% ethyl acetate/petroleum ether isolated a-dihydroartemisinin isonicotinate N-oxide 33 as a colorless oil. Treatment with methylene chloride (2×10 mL) and then hexanes (2×10 mL) (followed by drying overnight under high vacuum) gave a white solid (42.2 mg, 0.10 mmol, 88%). $^1$H NMR ($CDCl_3$, 400 MHz) δ 8.22 (d, 2H, J=7.3), 7.95 (d, 2H, J=7.3), 5.95 (d, 1H, J=9.9), 5.51 (s, 1H), 2.78-2.67 (m, 1H), 2.38 (dt, 1H, J=13.5, J=3.9), 2.08-2.00 (m, 1H), 1.95-1.64 (m, 4H), 1.55-1.22 (m, 7H, including singlet at 1.41), 1.09-0.84 (m, 7H, including doublet at 0.97 (J=5.9) and doublet at 0.91 (J=7.1); $^{13}$C NMR ($CDCl_3$, 100 MHz) δ 162.11, 139.42 (2), 126.77 (2), 125.82, 104.50, 93.33, 91.60, 80.00, 51.47, 45.15, 37.21, 36.11, 33.96, 31.77, 25.83, 24.48, 21.94, 20.15, 12.16; HRMS (El, m/z) for $C_{21}H_{27}NO_7Na$ requires 428.1680, found 428.1674; IR (film, $cm^{-1}$) 2925, 2872, 2359, 2343, 1733, 1612, 1486, 1444, 1262, 1165, 1132, 1091, 1053, 1036, 1016, 872, 855, 827, 768; Mp. 118-122° C. (morphological change observed beginning at 90° C.); $[\alpha]_D^{24.7}$ 4.67 ($CHCl_3$, c=0.465); Anal ($C_{21}H_{27}NO_7$) C, H, N.

Example 37

Synthesis of bis-trioxane allyl tertiary alcohol 34

A solution of bis-trioxane ketone 7 (20.0 mg, 0.034 mmol) in anhydrous tetrahydrofuran (1.5 mL) was cooled to −78° C. before addition of allyl magnesium bromide (1.0 M solution in diethyl ether, 0.140 mL, 0.140 mmol). After stirring for one hour, TLC analysis confirmed that no starting material remained. The reaction was quenched with 1.0 mL distilled water. The reaction mixture was poured into a mixture of brine (20 mL) and diethyl ether (30 mL) and the organic layer was separated, dried ($Na_2SO_4$) and concentrated in vacuo to give a yellow oil. Gradient column chromatography on silica eluting with 15 to 20% ethyl acetate/hexanes isolated bis-trioxane allyl tertiary alcohol 34 as a foamy solid (20.6 mg, 0.033 mmol, 96%). $^1$H NMR ($CDCl_3$, 400 MHz) δ 5.95-5.87 (m, 1H), 5.36 (s, 1H), 5.33 (s, 1H), 5.15 (apparent d, 1H, J=17.6), 5.09 (dd, 1H, J=10.4, J=2.4), 4.80-4.63 (m, 1H), 4.60-4.54 (m, 1H), 2.70-2.41 (m, 4H), 2.34-2.27 (m, 2H), 1.40 (s, 1H), 1.39 (s, 3H), 0.95 (apparent d, 6H, J=5.6), 0.87 (apparent t, 6H, J=8.4); HRMS (ES, m/z) calcd for $C_{36}H_{56}O_9Na$ (M+Na) 655.3817, found 655.3771.

Example 38

Synthesis of bis-trioxane tertiary alcohol carboxylic acid 35

To a solution of bis-trioxane allyl tertiary alcohol 34 (20.6 mg, 0.033 mmol) in ethyl acetate (0.6 mL), acetonitrile (0.6 mL) and $H_2O$ (0.2 mL) was added ruthenium(III) chloride hydrate (1.3 mg, 0.007 mmol) and sodium periodate (27.8 mg, 0.13 mmol) (on addition of ruthenium chloride the solution turned black). After stirring for 30 mins at room temperature (during which time the color of the solution changed to pale orange), the reaction mixture was poured into a mixture of ethyl acetate (30 mL) and saturated aqueous $NH_4Cl$ solution (30 mL). Organics were extracted with ethyl acetate (2×30 mL), dried ($MgSO_4$), filtered through a pad of celite and concentrated in vacuo. Flash column chromatography on silica eluting with 1% acetic acid in 35% ethyl acetate/hexane isolated bis-trioxane tertiary alcohol carboxylic acid 35 as a white solid (16.7 mg, 0.026 mmol, 79%). Mp=108-110° C.; $^1$H NMR (400 MHz, $CDCl_3$) δ 5.35 (s, 1H), 5.34 (s, 1H), 4.75-4.68 (m, 1H), 4.65-4.59 (m, 1H), 2.90 (ABq, 2H, $J_{AB}$=15.6, $\Delta v_{AB}$=39.6), 2.61-2.48 (m, 2H), 2.36-2.25 (m, 2H), 2.05-1.60 (m, 15H), 1.46-1.20 (m, 15H, including two siglets at 1.40 and 1.38), 0.98-0.82 (m, 2H), 0.96 (apparent doublet, 6H, J=5.2), 0.87 (apparent triplet, 6H, J=7.2); $^{13}$C NMR (100 MHz, $CDCl_3$) δ 103.01, 102.81, 89.87, 89.59, 81.11, 81.04, 74.26, 70.65, 70.03, 51.91, 44.13, 43.57, 38.91, 37.48, 37.43, 36.54, 36.47, 34.28, 30.91, 30.76, 25.92, 24.88, 24.75, 20.06, 12.38, 12.20; HRMS(ES) m/z calcd for $C_{35}H_{54}O_{11}Na$ (M+Na) 673.3558, found 673.3510.

Example 39

Synthesis of bis-trioxane primary alcohol methyl carbonate 36

To a solution of bis-trioxane primary alcohol 4 (26.5 mg, 0.044 mmol) in anhydrous pyridine (1.5 mL) at −20° C. was added methyl chloroformate (0.017 mL, 0.022 mmol). The reaction was allowed to warm to room temperature and was stirred overnight before being quenched with distilled water (1.0 mL). The reaction mixture was then poured into a mixture of methylene chloride (20 mL) and saturated aqueous NH$_4$Cl solution (20 mL). Organics were extracted with methylene chloride (3×20 mL), dried (MgSO$_4$) and concentrated in vacuo. Flash column chromatography on silica eluting with 20% ethyl acetate/hexanes isolated bis-trioxane primary alcohol methyl carbonate 36 as a sticky solid (6.4 mg, 0.010 mmol, 22%). $[\alpha]_D^{23.2}$ 64.2 (CHCl$_3$, c=0.17); $^1$H NMR (400 MHz, CDCl$_3$) δ 5.30 (apparent s, 2H), 4.41-4.36 (m, 1H), 4.33 (apparent doublet, 2H, J=4.8), 4.28-4.23 (m, 1H), 2.72-2.55 (m, 2H), 2.38-2.15 (m, 3H), 2.04-1.96 (m, 2H), 1.95-1.81 (m, 2H), 1.80-1.18 (m, 27H, including three singlets at 1.58, 1.40, 1.39), 0.97-0.80 (m, 2H), 0.95 (apparent d, 6H, J=6.0), 0.86 (d, 3H, J=7.6), 0.84 (d, 3H, J=7.2); $^{13}$C NMR (100 MHz, CDCl$_3$) δ 155.79, 103.13, 102.83, 89.47, 88.86, 81.16, 81.15, 77.20, 73.60, 71.02, 70.05, 54.56, 52.38, 52.11, 44.45, 44.14, 37.42, 37.40, 36.67, 36.61, 34.48, 34.43, 34.22, 30.54, 30.49, 29.76, 26.09, 26.00, 24.83, 24.76, 24.70, 20.22, 20.11, 13.13, 12.69; IR (film, cm$^{-1}$) 2952, 2876, 1748, 1443, 1377, 1270, 1105, 1039, 1008, 928, 732; HRMS(ES) m/z calcd for C$_{36}$H$_{56}$O$_{11}$Na (M+Na) 687.3715, found 687.3728.

Example 40

Synthesis of bis-trioxane primary alcohol ethyl cabonate 37

To a solution of bis-trioxane primary alcohol 4 (15.5 mg, 0.026 mmol) in anhydrous pyridine (1.5 mL) at 0° C. was added ethyl chloroformate (large excess, ~10.0 equiv). The reaction was allowed to warm to room temperature and was stirred overnight, before being quenched with distilled water (1.0 mL). The reaction mixture was then poured into a mixture of methylene chloride (20 mL) and saturated aqueous NH$_4$Cl solution (20 mL). Organics were extracted with methylene chloride (3×20 mL), dried (MgSO$_4$) and concentrated in vacuo. Flash column chromatography on silica eluting with 20% ethyl acetate/hexane isolated bis-trioxane primary alcohol ethyl carbonate 37 as a sticky solid (8.5 mg, 0.013 mmol, 49%). $[\alpha]_D^{23.7}$ 75.9 (CHCl$_3$, c=0.23); $^1$H NMR (400 MHz, CDCl$_3$) δ 5.30 (apparent s, 2H), 4.41-4.35 (m, 1H), 4.32 (apparent d, 2H, J=4.8), 4.28-4.22 (m, 1H), 4.17 (q, 2H, J=6.8), 2.73-2.55 (m, 2H), 2.38-2.15 (m, 3H), 2.04-1.96 (m, 2H), 1.96-1.18 (m, 29H, including a singlet at 1.39 and a triplet at 1.30 (J=7.2)), 0.97-0.80 (m, 2H), 0.95 (apparent d, 6H, J=5.6), 0.85 (apparent t, 6H, J=7.2); $^{13}$C NMR (100 MHz, CDCl$_3$) δ 155.23, 163.13, 102.84, 89.43, 88.80, 81.15, 81.13, 73.72, 71.13, 69.80, 63.67, 52.39, 52.13, 44.48, 44.16, 37.42, 37.39, 36.67, 36.61, 34.50, 34.44, 34.26, 30.53, 30.42, 29.73, 26.10, 26.09, 24.83, 24.76, 24.70, 20.21, 20.12, 14.31, 13.17, 12.71; IR (film, cm$^{-1}$) 2939, 2872, 1744, 1453, 1377, 1260, 1105, 1038, 1008, 928, 880, 792; HRMS(ES) m/z calcd for C$_{37}$H$_{58}$O$_{11}$Na (M+Na) 701.3873, found 701.3919.

Example 41

Synthesis of bis-trioxane tertiary alcohol methyl sulfonate 38

To a solution of methyl methanesulfonate (0.027 mL, 0.32 mmol) in anhydrous tetrahydrofuran (1.5 mL) at −78° C. was added n-butyl lithium (1.3 M sol. in hexanes, 0.26 mL, 0.35 mmol). The reaction was stirred at −78° C. for 30 mins before slow addition of a solution of bis-trioxane ketone 7 (37.6 mg, 0.064 mmol) in anhydrous tetrahydrofuran (0.8 mL). After stirring for 30 min., the reaction was quenched with distilled water (1.0 mL) and the reaction mixture was poured into a mixture of diethyl ether (20 mL) and saturated aqueous NH$_4$Cl solution (20 mL). The organic layer was then separated, dried (MgSO$_4$) and concentrated in vacuo. Flash column chromatography on nsilica eluting with 30% ethyl acetate/hexanes isolated bis-trioxane tertiary alcohol methyl sulfonate 38 as a white solid (42.0 mg, 0.060 mmol, 94%). Mp=87-90° C.; $^1$H NMR (400 MHz, CDCl$_3$) δ 5.44 (s, 1H), 5.36 (s, 1H), 4.85-4.79 (m, 1H), 4.71-4.65 (m, 2H), 3.81 (ABq, 2H, J$_{AB}$=14.4, Δv$_{AB}$=142.4), 3.96 (s, 3H), 2.76-2.67 (m, 1H), 2.59-2.91 (m, 1H), 2.38-2.15 (m, 3H), 2.06-1.82 (m, 6H), 1.81-1.19 (m, 21H, including two singlets at 1.40 and 1.37), 0.97-0.80 (m, 2H), 0.96 (d, 3H, J=5.6), 0.95 (d, 3H, J=6.0), 0.89 (d, 3H, J=7.2), 0.88 (d, 3H, J=7.2 Hz); $^{13}$C NMR (100 MHz, CDCl$_3$) δ 103.17, 102.81, 89.97, 88.96, 81.12, 72.84, 70.74, 70.28, 56.60, 55.69, 52.25, 51.84, 44.27, 43.37, 39.02, 37.48, 37.39, 36.62, 36.49, 34.27, 30.74, 30.56, 25.96, 25.92, 24.91, 24.77, 24.54, 20.15, 20.12, 13.04, 12.00; IR (film, cm$^{-1}$) 3469, 2951, 2875, 1451, 1377, 1356, 1175, 1099, 1053, 1007, 911, 879, 731; HRMS(ES) m/z calcd for C$_{35}$H$_{56}$O$_{12}$SNa (M+Na) 723.3385, found 723.3397.

Example 42

Synthesis of bis-trioxane tertiary alcohol isopropyl sulfonate 39

To a solution of isopropyl methanesulfonate (0.009 mL, 0.066 mmol) in anhydrous tetrahydrofuran (1.0 mL) at −78° C. was added n-butyl lithium (1.3 M sol. in hexanes, 0.055 mL, 0.073 mmol). The reaction was stirred at −78° C. for 30 mins before slow addition of a solution of bis-trioxane ketone 7 (7.8 mg, 0.013 mmol) in anhydrous tetrahydrofuran (0.4 mL). After stirring for a further 30 mins, the reaction was quenched with distilled water (1.0 mL) and the reaction mixture was poured into a mixture of diethyl ether (20 mL) and saturated aqueous NH$_4$Cl solution (20 mL). The organic layer was then separated, dried (MgSO$_4$) and concentrated in vacuo. Flash column chromatography on silica eluting with 20% ethyl acetate/hexanes to afford bis-trioxane tertiary alcohol isopropyl sulfonate 39 as a sticky solid (5.8 mg, 0.008 mmol, 60%). $^1$H NMR (400 MHz, CDCl$_3$) δ 5.46 (s, 1H), 5.36 (s, 1H), 5.11 (st, 1H, J=6.4), 4.88-4.84 (m, 1H), 4.67-4.63 (m, 2H), 3.78 (ABq, 2H, J$_{AB}$=14.0, Δv$_{AB}$=146.8), 1.43 (s, 3H), 1.41 (s, 3H), 0.96 (d, 3H, J=6.0), 0.94 (d, 3H, J=6.0), 0.88(d, 3H, J=7.2), 0.87 (d, 3H, J=7.2); HRMS(ES) m/z calcd for C$_{37}$H$_{60}$O$_{12}$SNa (M+Na) 751.3698, found 751.3749.

Example 43

Synthesis of bis-trioxane tertiary alcohol N,N-dimethylsulfonamide 40

To a solution of N,N-dimethyl methanesulfonamide (10.8 mg, 0.088 mmol) in anhydrous tetrahydrofuran (1.5 mL) at −78° C. was added n-butyl lithium (1.3 M sol. in hexanes, 0.072 mL, 0.097 mmol). The reaction was stirred at −78° C. for 30 mins before slow addition of a solution of bis-trioxane ketone 7 (10.4 mg, 0.018 mmol) in anhydrous tetrahydrofuran (0.5 mL). After stirring for a further 30 mins, the reaction was quenched with distilled water (1.0 mL) and the reaction mixture was poured into a mixture of diethyl ether (20 mL) and saturated aqueous $NH_4Cl$ solution (20 mL). The organic layer was then separated, dried ($MgSO_4$) and concentrated in vacuo. Gradient column chromatography on silica eluting with 25% and then 30% ethyl acetate/hexanes isolated bis-trioxane tertiary alcohol N,N-dimethylsulfonamide 40 as a white solid (7.9 mg, 0.011 mmol, 63%). Mp=107-110° C.; $[\alpha]_D^{24.5}$ 74.7 ($CHCl_3$, c=0.25); $^1$H NMR (400 MHz, $CDCl_3$) δ 5.50 (s, 1H), 5.37 (s, 1H), 5.01-4.95 (m, 1H), 4.63-4.59 (s, 1H), 4.61 (m, 1H), 3.56 (ABq, 2H, $J_{AB}$=13.6, $\Delta v_{AB}$=207.2), 2.90 (s, 6H), 2.86-2.78 (m, 1H), 2.66-2.57 (m, 1H), 2.44-2.27 (m, 3H), 2.08-1.88 (m, 4H), 1.87-1.19 (m, 23H, including two singlets at 1.39 and 1.34), 0.97-0.80 (m, 2H), 0.95 (d, 3H, J=8.0), 0.94 (d, 3H, J=8.4 Hz), 0.88 (apparent triplet, 6H, J = 7.2); $^{13}$C NMR (100 MHz, $CDCl_3$) δ 103.38, 102.82, 89.87, 88.33, 81.27, 81.22, 72.80, 71.50, 71.10, 52.51, 51.93, 51.13, 44.86, 43.42, 39.22, 37.85, 37.50, 37.30, 37.00, 36.48, 34.51, 34.32, 30.58, 30.51, 26.04, 25.99, 24.98, 24.77, 24.60, 24.36, 20.24, 20.05, 13.61, 11.94; IR (film, $cm^{-1}$) 3470, 2938, 2875, 1453, 1377, 1330, 1197, 1151, 1099, 1052, 1009, 955, 878, 734, 709; HRMS(ES) m/z calcd for $C_{36}H_{59}NO_{11}SNa$ (M+Na) 736.3701, found 736.3660.

Example 44

Synthesis of bis-trioxane vicinal diol cyclic carbonate 41

To a solution of bis-trioxane vicinal diol 5 (5.8 mg, 0.009 mmol) in methylene chloride (1.0 mL) was added 1,1'-carbonyl diimidazole (4.5 mg, 0.028 mmol) and 4-(dimethylamino)-pyridine (3.4 mg, 0.028 mmol). The mixture was then stirred at room temperature overnight. The reaction was poured into a mixture of methylene chloride (20 mL) and saturated aqueous $NH_4Cl$ solution (20 mL) and the organic layer was separated. The organics were then washed with brine, dried ($MgSO_4$) and concentrated in vacuo. Flash column chromatography on silica eluting with 25% ethyl acetate/hexanes isolated bis-trioxane vicinal diol cyclic carbonate 41 as a white solid (5.8 mg, 0.009 mmol, 96%). $^1$H NMR (400 MHz, $CDCl_3$) δ 5.31 (s, 1H), 5.30 (s, 1H), 4.84 (d, 1H, J=8.8), 4.67 (dd, 1H, J=6.4, 1.6), 4.62 (dd, 1H, J=6.4, J=1.6), 4.45 (d, 1H, J=8.8), 2.65-2.48 (m, 2H), 2.35-2.25 (m, 2H), 2.38-1.58 (m, 14H), 1.46-1.18 (m, 20H, including two singlets at 1.40 and 1.37), 0.95 (d, 6H, J=5.6), 0.88 (d, 3H, J=7.6), 0.86 (d, 3H, J=7.6), 0.98-0.86 (m, 2H); $^{13}$C NMR (100 MHz, $CDCl_3$) δ 154.9, 102.8, 102.8, 89.9, 89.6, 85.4, 81.0, 80.8, 72.2, 68.9, 68.0, 51.8, 51.8, 43.7, 43.5, 39.0, 37.5, 37.4, 36.7, 36.6, 35.6, 34.3, 34.2, 30.8, 30.7, 25.9, 25.7, 24.8, 24.7, 20.0, 12.4, 12.3; HRMS(ES) m/z calcd for $C_{35}H_{52}O_{11}Na$ (M+Na) 671.3407, found 671.3412.

Example 45

Synthesis of bis-trioxane vicinal diol cyclic sulfate 42

To a solution of bis-trioxane vicinal diol 5 (18.0 mg, 0.029 mmol) in anhydrous methylene chloride (2.0 mL) at 0° C. was added thionyl chloride (0.021 mL, 0.29 mmol) and triethylamine (0.064 mL, 0.46 mmol) (on addition of triethylamine the solution turned light yellow). The reaction was stirred for one hour, at which time TLC analysis showed complete consumption of starting material. The reaction was quenched with distilled water (1.0 mL) and was poured into a mixture of methylene chloride (20 mL) and saturated aqueous $NH_4Cl$ solution (20 mL). The organic layer was then separated, dried ($MgSO_4$) and concentrated in vacuo to give a yellow oil. A 10 mL round-bottomed flask was charged with the crude material, followed by the addition of ethyl acetate (0.7 mL), and then acetonitrile (0.7 mL) and water (0.3 mL). Ruthenium (III) chloride hydrate (1.2 mg, 0.006 mmol, 0.2 equiv—based on 5) and sodium periodate (24.8 mg, 0.116 mmol, 4.0 equiv—based on 5) were added (on addition of ruthenium chloride the solution turned black). After stirring for 30 mins at room temperature (the color of the solution changed to pale orange), the reaction mixture was poured into a mixture of ethyl acetate (30 mL) and saturated aqueous $NH_4Cl$ solution (30 mL). The aqueous layer was extracted with ethyl acetate (2×30 mL), and the combined organics were dried ($MgSO_4$), filtered through a pad of celite and concentrated in vacuo. Gradient column chromatography on silica eluting with 10%, 15% and then 20% ethyl acetate/hexanes isolated bis-trioxane vicinal diol cyclic sulfate 42 as a white solid (17.1 mg, 0.026 mmol, 86%). Mp=107-110° C.; $^1$H NMR (400 MHz, $CDCl_3$) δ 5.37 (s, 1H), 5.30 (s, 1H), 4.84 (ABq, 2H, $J_{AB}$=9.6, $\Delta v_{AB}$=58.4), 4.61-4.55 (m, 2H), 2.75-2.66 (m, 1H), 2.60-2.48 (m, 2H), 2.36-2.20 (m, 4H), 2.07-1.85 (m, 6H), 1.82-1.56 (m, 8H), 1.42 (s, 3H), 1.37(s, 3H), 0.97-0.80 (m, 2H), 0.96 (apparent triplet, 6H, J =6.0), 0.89 (d, 3H, J=7.6), 0.88 (d, 3H, J=7.2); $^{13}$C NMR (100 MHz, $CDCl_3$) δ 103.20, 102.68, 95.49, 89.83, 89.28, 81.16, 80.86, 77.32, 68.95, 68.87, 52.19, 51.76, 44.15, 43.30, 37.53, 37.30, 36.62, 36.54, 34.57, 34.45, 34.19, 30.75, 30.23, 29.69, 25.98, 25.86, 24.83, 24.76, 20.15, 19.99, 12.92, 12.05; IR (film, $cm^{-1}$) 2941, 2876, 1455, 1380, 1209, 1114, 1093, 1009, 978, 828, 731; HRMS(ES) m/z calcd for $C_{34}H_{52}O_{12}SNa$ (M+Na) 707.3072, found 707.3087.

Example 46

Synthesis of bis-trioxane tertiary alcohol pyridine sulfide 43

A 10 mL round-bottomed flask was charged with bis-trioxane epoxide 6 (8.2 mg, 0.013 mmol), 4-mercaptopyridine (15 mg, 0.13 mmol) and neutral aluminum oxide (1.0 g, type W 200 super I, Woelm Pharma, Germany). Anhydrous diethyl ether (0.9 mL) and methylene chloride (0.6 mL) were then added to make a slurry and the reaction was stirred at room temperature overnight. The reaction mixture was then filtered through a pad of celite and the solid was washed with ethyl acetate (2×30 mL) before concentration of the organics in vacuo. Flash column chromatography on silica eluting with 45% ethyl acetate/hexanes isolated bis-trioxane tertiary alcohol pyridine sulfide 43 as a sticky solid (3.0 mg, 0.04 mmol, 31%). $^1$H NMR (400 MHz, $CDCl_3$) δ 8.36-8.32 (m, 2H), 7.31-7.25 (m, 2H), 5.36 (s, 1H), 5.35 (s, 1H), 4.75-4.71 (m, 1H), 4.57-4.53 (m, 1H), 4.37 (s, 1H), 3.51 (ABq, 2H, $J_{AB}$=12.8, $\Delta v_{AB}$=34.0), 2.61-2.45 (m, 2H), 2.35-2.35(m, 2H), 2.09-1.87 (m, 6H), 1.80-1.60 (m, 10H), 1.40-1.18 (m, 12H, including two singlets at 1.35 and 1.33), 0.98-0.86 (m, 2H), 0.96 (d, 6H, J=6.0), 0.88 (d, 3H, J=7.6), 0.85 (d, 3H, J=7.6); HRMS(ES) m/z calcd for $C_{39}H_{57}NO_9SNa$ (M+Na) 738.3646, found 738.3664.

Example 47

Synthesis bis-trioxane ketone O-TMS cyanohydrin 44

To a solution of trimethylsilyl cyanide (0.003 mL, 0.023 mmol) in anhydrous tetrahydrofuran (0.8 mL) at room temperature was added lithium tertiary butoxide (1.0 M sol. in tetrahydrofuran, 0.002 mL, 0.002 mmol). The reaction was stirred for 10 mins at room temperature before slow addition of a solution of bis-trioxane ketone 7 (9.0 mg, 0.015 mmol) in anhydrous tetrahydrofuran (0.4 mL). After stirring for 30 mins, the reaction was quenched with distilled water (1.0 mL). The reaction mixture was then poured into a mixture of diethyl ether (20 mL) and 10% aqueous $NaHCO_3$ solution (20 mL) before the organic layer was separated, dried ($MgSO_4$) and concentrated in vacuo. Gradient column chromatography on silica eluting with 10% and then 15% ethyl acetate/hexanes isolated bis-trioxane ketone O-TMS cyanohdrin 44 as a sticky solid (9.8 mg, 0.014 mmol, 93%). $^1$H NMR (400 MHz, $CDCl_3$) δ 5.41 (s, 1H), 5.37 (s, 1H), 4.65-4.61 (m, 1H), 4.54-4.50 (m, 1H), 2.85-2.75 (m, 2H), 2.46-2.25 (m, 5H), 1.41 (s, 3H), 1.36 (s, 3H), 0.94 (apparent triplet, 6H, J=6.0), 0.89 (d, 3H, J=7.6),0.86 (d, 3H, J=7.6), 0.25 (s, 9H); 13C NMR (100 MHz, $CDCl_3$) δ 121.67, 103.40, 103.01, 88.14, 88.07, 80.92, 80.85, 72.73, 72.08, 70.25, 52.46, 44.68, 44.63, 38.81, 38.22, 37.23, 37.06, 36.66, 36.60, 34.51, 34.40, 30.58, 30.29, 30.23, 29.69, 26.11, 26.04, 24.56, 24.48, 24.38, 24.30, 20.24, 20.20, 13.59, 13.51, 1.31; HRMS(ES) m/z calcd for $C_{37}H_{59}NO_9Na$ (M+Na) 712.3851, found 712.3863.

Example 48

Synthesis of bis-trioxane tertiary alcohol nitrile 45

To a solution of acetonitrile (0.005 mL, 0.096 mmol) and anhydrous tetrahydrofuran (0.8 mL) at −78° C. was added LHMDS (1.0 M sol. in THF, 0.096 mL, 0.096 mmol). The reaction was then stirred for 30 mins at −78° C. before slow addition of a solution of bis-trioxane ketone 7 (9.5 mg, 0.016 mmol) in anhydrous tetrahydrofuran (0.5 mL). After stirring for 30 mins, the reaction was quenched with distilled water (1.0 mL). The reaction mixture was then poured into a mixture of diethyl ether (20 mL) and saturated aqueous $NH_4Cl$ solution (20 mL). The organic layer was separated, dried ($MgSO_4$) and concentrated in vacuo. Flash column chromatography on silica eluting with 25% ethyl acetate/hexanes isolated bis-trioxane tertiary alcohol nitrile 45 as a white solid (6.0 mg, 0.009 mmol, 59%).$^1$H NMR (400 MHz, $CDCl_3$) δ 5.38 (s, 1H), 5.34 (s, 1H), 4.74-4.70 (m, 1H), 4.60-4.55 (m, 1H), 4.44 (s, 1H), 2.94 (ABq, 2H, $J_{AB}$=16.8, $\Delta v_{AB}$=83.2), 2.05-1.86 (m, 8H), 1.82-1.62 (m, 6H), 1.45-1.19 (m, 18H, including two apparent singlets at 1.39 and 1.38), 0.97-0.80 (m, 2H), 0.96 (d, 6H, J=6.0), 0.89 (d, 3H, J=7.2), 0.88 (d, 3H, J=7.2); $^{13}$C NMR (100 MHz, $CDCl_3$) δ 118.55, 102.94, 102.69, 90.09, 89.54, 81.13, 81.07, 72.93, 70.07, 69.65, 52.01, 51.81, 43.69, 43.30, 38.87, 37.48, 37.45, 37.06, 36.53, 34.31, 34.24, 30.87, 30.69, 29.14, 25.97, 24.88, 24.81, 24.76, 24.71, 20.06, 20.00, 12.51, 12.13; HRMS(ES) m/z calcd for $C_{35}H_{53}NO_9Na$ (M+Na) 654.3613, found 654.3632.

Example 49

Synthesis of bis-trioxane methyl enol ether 46

To a slurry of (methoxymethyl)triphenylphosphonium chloride (400 mg, 1.2 mmol) in anhydrous tetrahydrofuran (10 mL) at 0° C. was added lithium bis(trimethylsilyl)amide (1.0 M solution in tetrahydrofuran, 1.3 mL, 1.3 mmol) resulting in a deep dark red color. The reaction mixture was allowed to warm to room temperature and was stirred for 30 minutes, before being cooled to −78° C. At this time, a solution of bis-trioxane ketone 7 (270 mg, 0.46 mmol) in anhydrous tetrahydrofuran (10 mL) was added dropwise. A color change to pale orange was observed immediately. The reaction was stirred at −78° C. for 3 hours, at which time complete consumption of starting material was observed by TLC analysis. The reaction mixture was quenched with distilled water (5 mL) and organics were extracted with methylene chloride (3×30 mL), dried ($MgSO_4$) and concentrated in vacuo to give a pale yellow oil. Flash column chromatography on silica eluting with 20% ethyl acetate/petroleum ether isolated bis-trioxane methyl enol ether 46 as a white solid (220 mg, 0.35 mmol, 76%). $^1$H NMR ($CDCl_3$) δ 5.86 (s,1H), 5.45 (s, 1H), 5.42 (s,1H), 4.10-4.00 (m, 2H), 3.53 (s, 3H), 2.78-2.76 (m, 2H), 2.45-2.22 (m, 4H), 2.02-1.95 (m, 2H), 1.90-1.70 (m, 4H), 1.60-1.50 (m, 6H), 1.40-1.15 (m, 14H including a singlet at 1.39), 1.00-0.85 (m, 14H); HRMS (ES) m/z calcd for $C_{35}H_{54}O_9Na$ (M+Na) 641.3660, found 641.3657.

Example 50

Synthesis of bis-trioxane aldehyde 47

A 50 mL round bottom flask was charged with bis-trioxane methyl enol ether 46 (190 mg, 0.31 mmol), formic acid (10 mL) and diethyl ether (15 mL). The reaction was stirred at room temperature for 8 hours until complete consumption of starting material was observed by TLC analysis. The reaction was then poured into a separatory funnel containing saturated $NaHCO_3$ (20 mL) and diethyl ether (20 mL). Organics were extracted with diethyl ether (3×30 mL), dried ($MgSO_4$) and concentrated in vacuo to give a pale yellow oil. Flash column chromatography on silica eluting with 20% ethyl acetate/ petroleum ether isolated bis-trioxane aldehyde 47 as a white solid (160 mg 0.27 mmol, 87%). $^1$H NMR (400 MHz, $CDCl_3$) δ 9.85 (d, 1H, J=1.2 Hz), 5.24 (s, 1H), 5.21 (s, 1H), 4.35-4.26 (m, 2H), 2.84-2.80 (m, 1H), 2.70-2.50 (m, 2H), 2.38-2.22 (m, 2H), 2.19-2.09 (m, 2H), 2.02-1.96 (m, 4H), 1.90-1.70 (m, 4H), 1.62-1.58 (m, 6H), 1.40-1.15 (m, 12H, including two singlets at 1.39 and 1.38), 0.98-0.82 (m, 14H); 13C NMR (100 MHz, $CDCl_3$) δ 205.6, 103.8, 103.1, 89.69, 89.15, 81.47, 81.43, 73.37, 70.94, 52.54, 52.58, 47.79, 44.48, 44.20, 37.72, 37.65, 36.85 (2), 34.70, 34.65, 30.68, 30.51, 29.97, 28.92, 26.30, 26.19, 25.13, 25.11, 25.02, 24.95, 20.43, 20.37, 13.30, 12.74; HRMS (ES) m/z calcd for $C_{34}H_{52}O_9Na$ (M+Na) 627.3504, found 627.3445; IR (film, $cm^{-1}$) 3100, 2800, 2250, 1650, 1400, 1300, 850, 600; Mp. 66-70° C.

Example 51

Synthesis of bis-trioxane aniline 48

A 10 mL round bottom flask was charged with bis-trioxane aldehyde 47 (25 mg, 0.041 mmol), tetrahydrofuran (1.5 mL), aniline (0.008 mL, 0.088 mmol) and finally sodium triacetoxy borohydride (18 mg, 0.086 mmol). The reaction was stirred at room temperature for 3 hours until complete consumption of starting material was observed by TLC analysis. The reaction was quenched with saturated $NaHCO_3$ solution (1.0 mL) and organics were extracted with diethyl ether (3×30 mL), dried ($MgSO_4$) and concentrated in vacuo to give a pale yellow oil. Flash column chromatography on silica eluting with 15% ethyl acetate/petroleum ether isolated bis-trioxane aniline 48 as a colorless oil (15 mg, 0.023 mmol, 56%). $^1$H NMR (400 MHz, CDCl$_3$) δ 7.16-7.11 (m, 2H), 6.70-6.60 (m, 3H), 5.34 (s, 1H), 5.31 (s, 1H), 4.46-4.26 (m, 2H), 3.29-3.15 (m, 2H), 2.72-2.56 (m, 2H), 2.36-2.27 (m, 2H), 2.22-2.16 (m, 1H), 2.10-1.99 (m, 2H), 1.93-1.86 (m, 2H), 1.79-1.71 (m, 5H), 1.65-1.55 (m, 5H), 1.50-1.21 (m, 14H including two singlets at 1.41 and 1.38), 0.96-0.84 (m, 14H); $^{13}$C NMR (100 MHz, CDCl$_3$) δ 149.1, 129.1, 116.3, 112.7, 103.2, 103.0, 89.37, 88.91, 81.17 (2), 73.90, 71.47, 52.32, 52.16, 47.34, 44.39, 44.21, 37.42, 37.28, 36.61, 36.58, 34.81, 34.42, 31.50, 31.13, 30.70, 30.54, 26.11, 26.02, 24.83, 24.77, 24.73, 24.67, 20.16, 20.13, 13.15, 12.76; HRMS (ES) m/z calcd for C$_{40}$H$_{59}$NO$_8$Na (M+Na) 704.4133, found 704.4136.

Thus, the present invention encompasses methods of treating cancer (including but not limited to leukemia, non-small cell lung cancer, colon cancer, central nervous system cancer, melanoma cancer, ovarian cancer, renal cancer, prostate cancer, and breast cancer) which include the step of administering to a patient suffering from cancer a compound or combination of compounds recited in claims 1-83 of PCT/US2003/030612. as published in WO 2004/028476 A2, and incorporated herein by this reference. The present invention further encompasses methods of treating malaria which include the step of administering an effective amount of a compound or combination of compounds recited in claims 1-83 of PCT/US2003/030612, as published in WO 2004/028476 A2.

What is claimed is:

1. A compound including resolved enantiomers, diastereomers, solvates and pharmaceutical acceptable salts thereof, said compound having the formula:

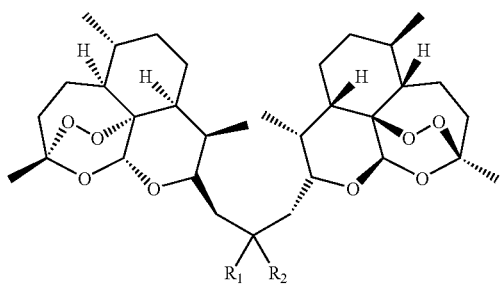

wherein if R$_1$ is hydrogen or —OH then R$_2$ is AX, and if R$_2$ is hydrogen or —OH then R$_1$ is AX, and A may be absent or A may be any alkyl or aryl group where X is hydrogen, a phosphate group, a phosphonic acid derivative group, an alcohol group, a carboxylic acid group, an ether group, an ester group, a nitrile group, a sulfone group, a sulfide group, an amino acid derivative group, an amine group, and amide group, an aldehyde group, or an aromatic group.

2. The compound of claim 1, wherein said alcohol group is represented by —R$^3$OH, wherein R$^3$ is a straight chained or branched alkyl group having 1 to 5 carbon atoms.

3. The compound of claim 1, wherein said carboxylic acid group comprises —R$^4$COOH wherein R$^4$ is at least one saturated or unsaturated alkyl group, an aryl group an ester group, an ether group or a combination thereof.

4. The compound of claim 3, wherein R$^4$ is an ester group represented by —R$^5$COO—, wherein R$^5$ is bonded to the carboxylic acid group and has 0 to 5 carbon atoms.

5. The compound of claim 3, wherein R$^4$ is an ether group represented by R$^6$—O—R$^7$ wherein R$^6$ and R$^7$ are, independently, an alkyl or allyl group having 0 to 5 carbon atoms.

6. The compound of claim 1, wherein said aromatic group comprises Ar—(R$^8$)$_m$, wherein Ar represents a benzene ring, and m is 1 or 2.

7. The compound of claim 6, wherein R8 is —CH=CH$_2$, or —COOH.

8. The compound of claim 1, wherein the ester group is represented by —CR$^9$, where R$^9$ is an ester of nicotinic acid, an ester of isonicotinic acid, or the ester group is represented by —CO(C=O)R$^{9a}$, where R$^{9a}$ is Ph(CY$_3$)$_o$, where o is 1 or 2, and Y may be, independently, H, F, Cl, Br, or I, or where R$^{9a}$ is a substituted heterocyclohexane compound.

9. The compound of claim 1, wherein the phosphonic acid derivative group is represented by —CO—P(R$^{10}$)(O)OH, where R$^{10}$ is an alkyl group having 0 to 5 carbon atoms.

10. The compound of claim 1, wherein the phosphate group is —COP(O)(OR$^{11}$)$_2$, where R$^{11}$ is an alkyl group having 0 to 5 carbon atoms, or a phenyl group.

11. The compound of claim 1, wherein the nitrile group is R$^{12}$CN, where R$^{12}$ is an alkyl group having 0 to 5 carbon atoms.

12. The compound of claim 1, wherein the sulfone group is —CS(=O)$_2$R$^{13}$, wherein R$^{13}$ is —N(CH$_3$)$_2$, —OR$^{14}$, or —Ph—COOR$^{14}$, where R$^{14}$ is H, CH$_3$, or —CH(CH$_3$)$_2$.

13. The compound of claim 1, wherein the sulfide group is —CSR$^{15}$, where R$^{15}$ is pyridine or —Ph—COOR$^{16}$, where R$^{16}$ is H or CH$_3$.

14. The compound of claim 1, wherein the amino acid derivative group is —COC(=O)CHR$^{21}$N(R$^{17}$)$_2$, where each R$^{17}$ group is, independently, H or CH$_3$ and R$^{21}$ is hydrogen or any other substituent.

15. The compound of claim 1, wherein the amine group is —CN(R$^{18}$)$_2$, where each R$^{18}$ group is, independently, H, an alkyl group, or a phenyl group.

16. The compound of claim 1, wherein the ether group is —C—O—CR$^{19}$, where R$^{19}$ is a substituted pyridine.

17. The compound of claim 1, wherein the amide group is —(C=O)N(R$^{20}$)$_2$, or —CH$_2$(C=O)N(R$^{20}$)$_2$ where each R$^{20}$ is, independently, H or —CH$_2$CH$_2$N(CH$_3$)$_2$.

18. A compound including resolved enantiomers, diastereomers, solvates and pharmaceutical acceptable salts thereof, said compound having the formula:

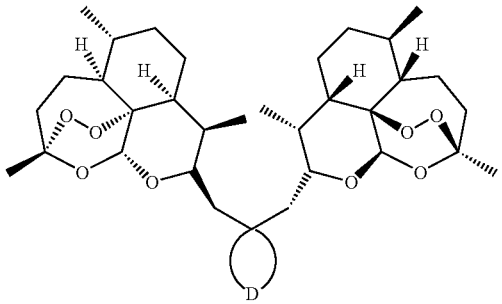

where D forms a heterocyclic ring having 3 to 5 atoms.

19. The compound of claim 18, wherein the heterocyclic ring is a 3-membered ring and one of the atoms in the ring is oxygen.

20. The compound of claim 18, wherein the heterocyclic ring is a 5-membered ring and two of the atoms in the ring are oxygen.

21. The compound of claim 20, wherein the heterocyclic ring is substituted with an oxygen atom.

22. The compound of claim 21, wherein another atom in the 5-membered ring is a sulfur or a phosporous atom.

23. The compound of claim 22, wherein the 5-membered ring is substituted with 1 or 2 oxygen atoms bonded to the sulfur atom.

24. A compound including resolved enantiomers, diastereomers, solvates and pharmaceutical acceptable salts thereof, said compound having the formula:

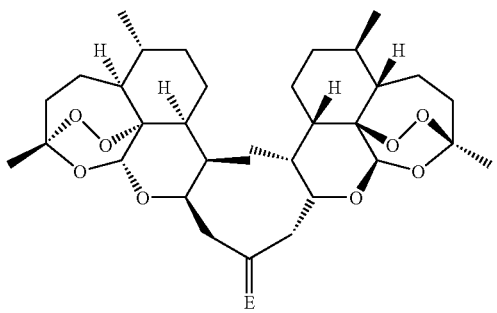

where E is H, O, NR, CH$_2$ or S wherein R may be hydrogen, alkyl, aryl or any other substituent.

25. The compound of claim 1 wherein if R$_1$ is H or —OH then R$_2$ is

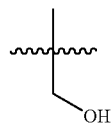

and if R$_2$ is OH or H then R$_1$ is

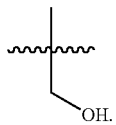

26. The compound of claim 1, wherein if R is H or —OH then R$_2$ is

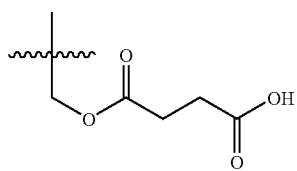

and if R$_2$ is OH or H then R$_1$ is

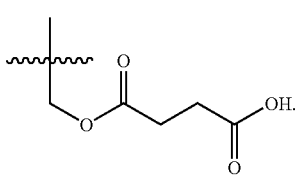

27. The compound of claim 1, wherein if R$_1$ is H or —OH then R$_2$ is

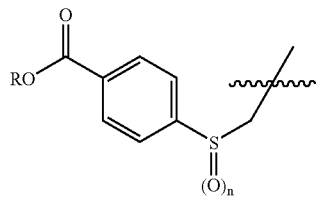

and if R$_2$ is —OH or H then R$_1$ is

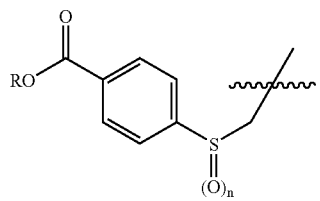

wherein R is hydrogen or a methyl group when n is 0 or 2.

28. The compound of claim 1, wherein if R$_1$ is H or —OH then R$_2$ is

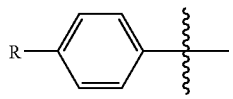

and if R$_2$ is —OH or H then R$_1$ is

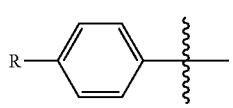

wherein R may be CH$_2$=CH or COOH.

29. The compound of claim 1, wherein if R$_1$ is H or —OH then R$_2$ is

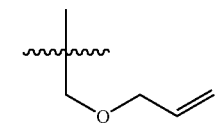

and if R$_2$ is —OH or H then R$_1$ is

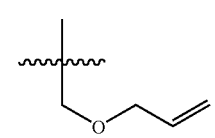

30. The compound of claim 1, wherein if $R_1$ is H or —OH then $R_2$ is

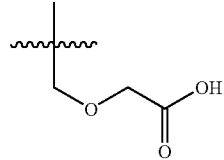

and if $R_2$ is —OH or H then $R_1$ is

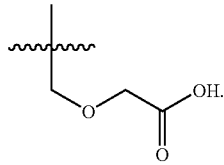

31. The compound of claim 1, wherein if $R_1$ is H or —OH then $R_2$ is

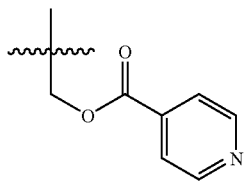

and if $R_2$ is —OH or H then $R_1$ is

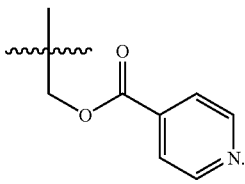

32. The compound of claim 1, wherein if $R_1$ is H or —OH then $R_2$ is

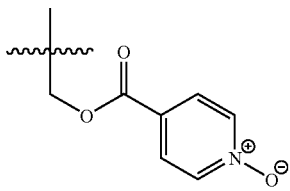

and if $R_2$ is —OH or H then $R_1$ is

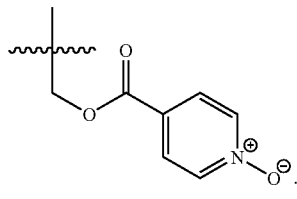

33. The compound of claim 1, wherein if $R_1$ is H or —OH then $R_2$ is

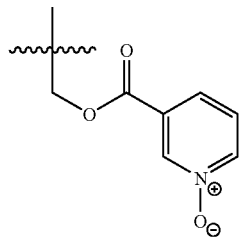

and if $R_2$ is —OH or H then $R_1$ is

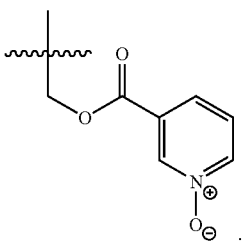

34. The compound of claim 1, wherein if $R_1$ is H or —OH then $R_2$ is

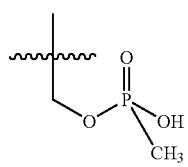

and if $R_2$ is —OH or H then $R_1$ is

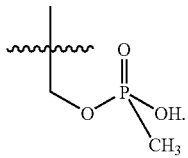

35. The compound of claim 1, wherein if $R_1$ is H or —OH then $R_2$ is

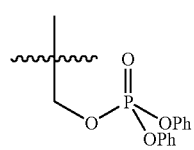

and if $R_2$ is —OH or H then $R_1$ is

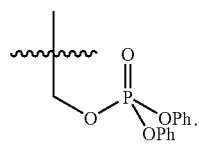

36. The compound of claim 1, wherein if $R_1$ is H then $R_2$ is —OH.

37. The compound of claim 1, wherein if $R_1$ is H or —OH then $R_2$ is

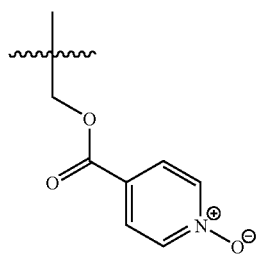

and if $R_2$ is —OH or H then $R_1$ is

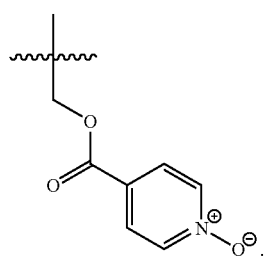

38. The compound of claim 1, wherein if $R_1$ is H then $R_2$ is carboxylic acid.

39. The compound of claim 1, wherein if $R_1$ is H or —OH then $R_2$ is

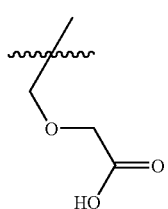

and if $R_2$ is —OH or H then $R_1$ is

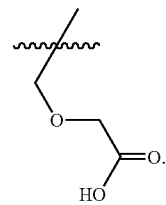

40. The compound of claim 1, wherein if $R_1$ is H or —OH then $R_2$ is

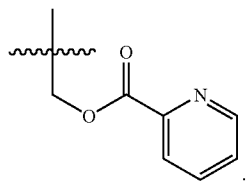

and if $R_2$ is —OH or H then $R_1$ is

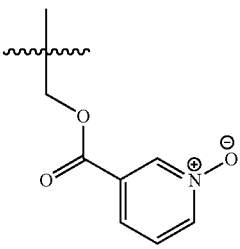

41. The compound of claim 1, wherein if $R_1$ is H or —OH then $R_2$ is

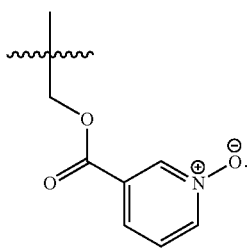

and if $R_2$ is —OH or H then $R_1$ is

42. The compound of claim 1, wherein if $R_1$ is H or —OH then $R_2$ is

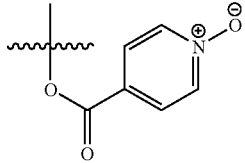

and if $R_2$ is —OH or H then $R_1$ is

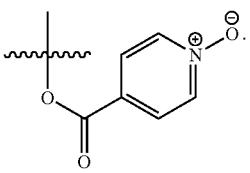

43. The compound of claim 1 wherein if $R_1$ is H or —OH then $R_2$ is

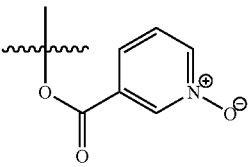

and if $R_2$ is —OH or H then $R_1$ is

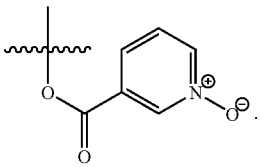

44. The compound of claim 1, wherein is $R_1$ is H or —OH then $R_2$ is

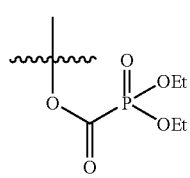

and if $R_2$ is —OH or H then $R_1$ is

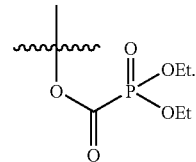

45. The compound of claim 1, wherein if $R_1$ is H or —OH then $R_2$ is

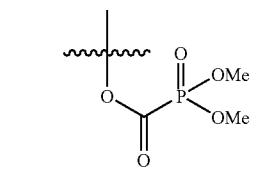

and if $R_2$ is —OH or H then $R_1$ is

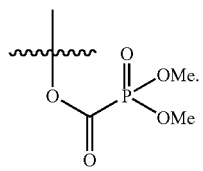

46. The compound of claim 1, wherein if $R_1$ is H or —OH then $R_2$ is

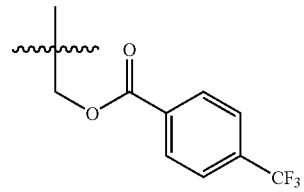

and if $R_2$ is —OH or H then $R_1$ is

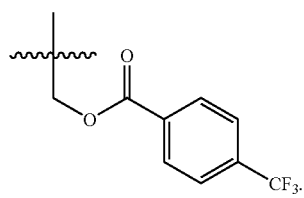

47. The compound of claim 1, wherein if $R_1$ is H or —OH then $R_2$ is

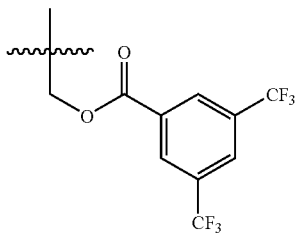

and if $R_2$ is —OH or H then $R_1$ is

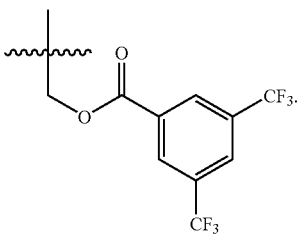

48. The compound of claim 1, wherein if $R_1$ is H or —OH then $R_2$ is

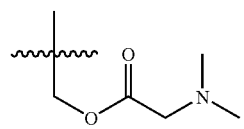

and if $R_2$ is —OH or H then $R_1$ is

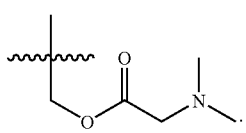

49. The compound of claim 1, wherein is $R_1$ is H or —OH then $R_2$ is

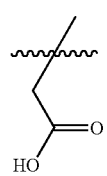

and if $R_2$ is —OH or H then $R_1$ is

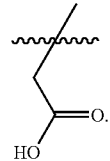

50. The compound of claim 1, wherein if $R_1$ is H or —OH then $R_2$ is

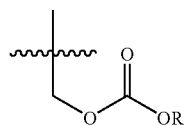

and if $R_2$ is —OH or H then $R_1$ is

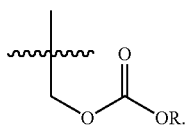

51. The compound of claim 50 wherein R is a methyl or ethyl group.

52. The compound of claim 1, wherein if $R_1$ is H or —OH then $R_2$ is

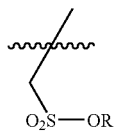

and if $R_2$ is —OH or H then $R_1$ is

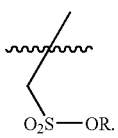

53. The compound of claim 52 wherein R is a methy group.

54. The compound of claim 52 wherein R is an iso-propyl group.

55. The compound of claim 1, wherein if $R_1$ is H or —OH then $R_2$ is

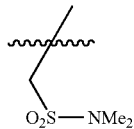

and if $R_2$ is —OH or H then $R_1$ is

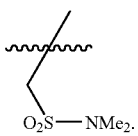

56. The compound of claim 1, wherein if $R_1$ is H or —OH then $R_2$ is

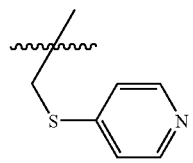

and if $R_2$ is —OH or H then $R_1$ is

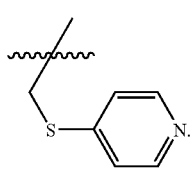

57. The compound of claim 1, wherein if $R_1$ is H or —OH then $R_2$ is

and if $R_2$ is —OH or H then $R_1$ is

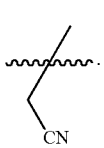

58. The compound of claim 1, wherein if $R_1$ is H or —OH then $R_2$ is

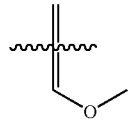

and if $R_2$ is —OH or H then $R_1$ is

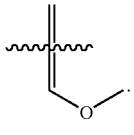

59. The compound of claim 1, wherein if $R_1$ is H or —OH then $R_2$ is

and if $R_2$ is —OH or H then $R_1$ is

60. The compound of claim 1, wherein if $R_1$ is H or —OH then $R_2$ is

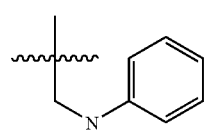

and if $R_2$ is —OH or H then $R_1$ is

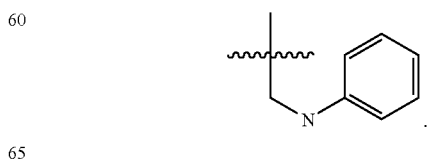

61. The compound of claim 1, wherein if $R_1$ is H or —OH then $R_2$ is

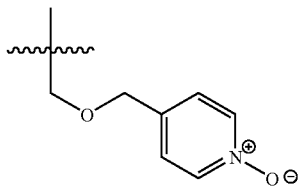

and if $R_2$ is —OH or H then $R_1$ is

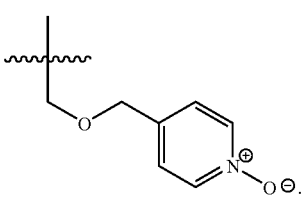

62. The compound of claim 1, wherein if $R_1$ is H or —OH then $R_2$ is

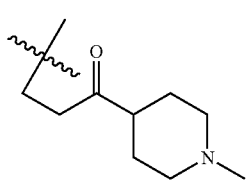

and if $R_2$ is —OH or H then $R_1$ is

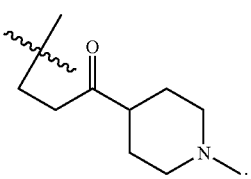

63. The compound of claim 1, wherein if $R_1$ is H or —OH then $R_2$ is

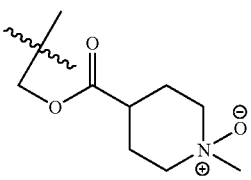

and if $R_2$ is —OH or H then $R_1$ is

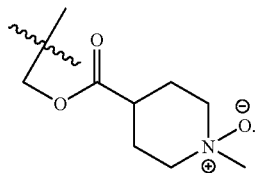

64. The compound of claim 1, wherein if $R_1$ is H or —OH then $R_2$ is

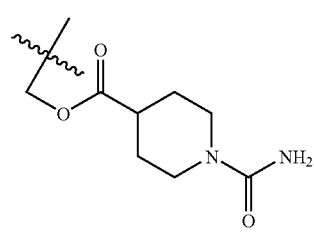

and if $R_2$ is —OH or H then $R_1$ is

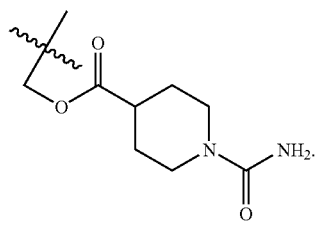

65. The compound of claim 1, wherein if $R_1$ is H or —OH then $R_2$ is

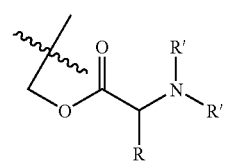

and if $R_2$ is —OH or H then $R_1$ is

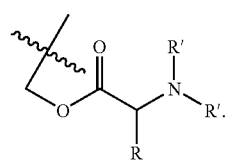

66. The compound of claim 65 wherein each R' and R independently can be any amino acid of all possible stereochemistries and with any degree and choice of protecting group.

67. The compound of claim 1, wherein if $R_1$ is H or —OH then $R_2$ is

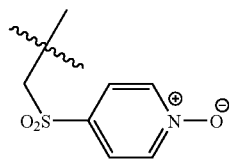

and if $R_2$ is —OH or H then $R_1$ is

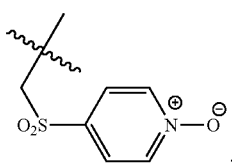

68. The compound of claim 1, wherein if $R_1$ is H or —OH then $R_2$ is

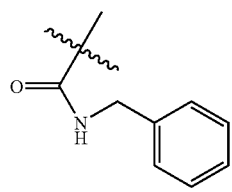

and if $R_2$ is —OH or H then $R_1$ is

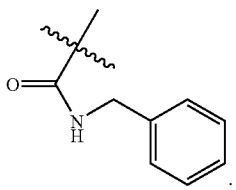

69. The compound of claim 1, wherein if $R_1$ is H or —OH then $R_2$ is

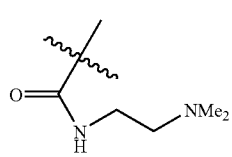

and if $R_2$ is —OH or H then $R_1$ is

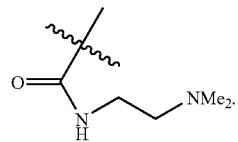

70. The compound of claim 1, wherein if $R_1$ is H or —OH then $R_2$ is

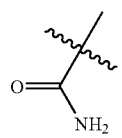

and if $R_2$ is —OH or H then $R_1$ is

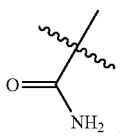

71. The compound of claim 1, wherein if $R_1$ is H or —OH then $R_2$ is

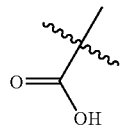

and if $R_2$ is —OH or H then $R_1$ is

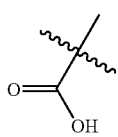

72. The compound of claim 1, wherein if $R_1$ is H or —OH then $R_2$ is

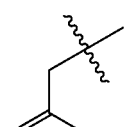

and if R₂ is —OH or H then R₁ is

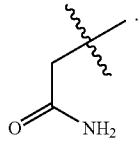

73. The compound of claim 1, wherein if R₁ is H or —OH then R₂ is

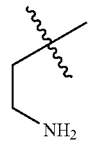

and if R₂ is —OH or H then R₁ is

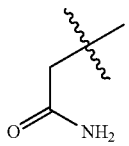

74. The compound of claim 1, wherein if R₁ is H or —OH then R₂ is

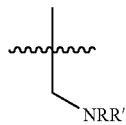

and if R₂ is —OH or H then R₁ is

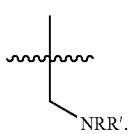

75. The compound of claim 74, wherein R and R' are independently of each other hydrogen, alkyl, aryl, or allyl.

76. The compound of claim 19 wherein said heterocyclic ring is

77. The compound of claim 21 wherein said heterocyclic ring is

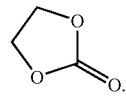

78. The compound of claim 22 wherein said heterocyclic ring is

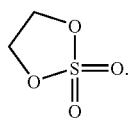

79. The compound of claim 21 wherein said heterocyclic ring is

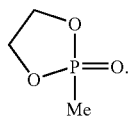

80. The compound of claim 22 wherein said heterocyclic ring is

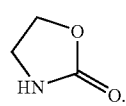

81. A compound including resolved enantiomers, diastereomers, solvates and pharmaceutical acceptable salts thereof, said compound having the formula:

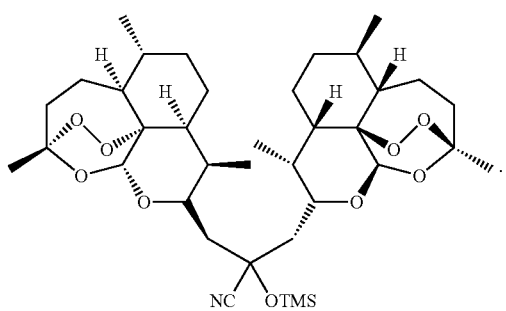

82. A compound including resolved enantiomers, diastereomers, solvates and pharmaceutical acceptable salts thereof, said compound having the formula:

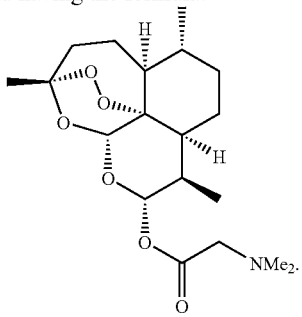

83. A method of treating cancer, which comprises administering to a patient suffering from said cancer the compound of claim 1.

84. A method according to claim 83 wherein said cancer is selected from the group of cancers consisting of leukemia, non-small cell lung cancer, colon cancer, central nervous system cancer, melanoma cancer, ovarian cancer, renal cancer, prostate cancer, and breast cancer.

85. A method for treating malaria comprising administering an effective amount of the compound of claim 1.

* * * * *